US012670416B2

(12) United States Patent
Ihsani et al.

(10) Patent No.: US 12,670,416 B2
(45) Date of Patent: Jun. 30, 2026

(54) PREPROCESSING DATA USING A NETWORK INTERFACE

(71) Applicant: NVIDIA Corporation, Santa Clara, CA (US)

(72) Inventors: Alvin Ihsani, Everett, MA (US); Shaul Arazi, Tel-Aviv (IL); Elena Agostini, Rome (IT); Penn Tasinga, Bellevue, WA (US); Carl Everett Lacey, Jr., Palo Alto, CA (US); Dana Groff, Seattle, WA (US); Dotan David Levi, Kiryat Motzkin (IL); Wojciech Wasko, Młynek (PL); Vishwesh Nath, Nashville, TN (US); Sachidanand Alle, Cambridge (GB)

(73) Assignee: NVIDIA CORPORATION, Santa Clara, CA (US)

( * ) Notice: Subject to any disclaimer, the term of this patent is extended or adjusted under 35 U.S.C. 154(b) by 452 days.

(21) Appl. No.: 18/076,221

(22) Filed: Dec. 6, 2022

(65) Prior Publication Data

US 2024/0185100 A1      Jun. 6, 2024

(51) Int. Cl.
*G06N 5/04*          (2023.01)
*G16H 30/20*          (2018.01)

(52) U.S. Cl.
CPC .............. *G06N 5/04* (2013.01); *G16H 30/20* (2018.01)

(58) Field of Classification Search
None
See application file for complete search history.

(56) References Cited

U.S. PATENT DOCUMENTS

| | | | |
|---|---|---|---|
| 5,347,514 A | 9/1994 | Davis et al. | |
| 5,448,558 A | 9/1995 | Gildea et al. | |
| 5,530,902 A | 6/1996 | McRoberts et al. | |
| 6,115,747 A | 9/2000 | Billings et al. | |
| 6,308,228 B1 | 10/2001 | Yocum et al. | |
| 6,466,550 B1 | 10/2002 | Foster et al. | |
| 6,697,870 B1 | 2/2004 | Cafarelli, III et al. | |
| 6,850,999 B1 | 2/2005 | Mak et al. | |
| 7,082,502 B2 | 7/2006 | Najam et al. | |
| 7,145,913 B2 | 12/2006 | Craig et al. | |
| 7,173,635 B2 * | 2/2007 | Amann .................. G09G 3/003 |
| | | | 345/503 |
| 7,324,112 B1 | 1/2008 | Lindholm et al. | |
| 7,406,567 B1 | 7/2008 | Nakil et al. | |
| 7,746,783 B1 | 6/2010 | Tripathi et al. | |
| 7,839,854 B2 | 11/2010 | Alexander | |
| 8,014,295 B2 | 9/2011 | Chang et al. | |
| 8,116,306 B2 | 2/2012 | Shimizu | |

(Continued)

OTHER PUBLICATIONS

Agostini et al., "DPDK Acceleration with GPU [Video]," DPDK Project, uploaded Nov. 21, 2019, https://youtu.be/-1WHhiX1BcQ, 2 pages.

(Continued)

*Primary Examiner* — Darryl V Dottin
(74) *Attorney, Agent, or Firm* — Davis Wright Tremaine LLP

(57) ABSTRACT

Methods and systems for obtaining data having a first format, converting the data to a second format, storing the converted data in memory accessible by at least one parallel processing unit, and processing the converted data stored in the memory using the at least one parallel processing unit.

28 Claims, 48 Drawing Sheets

(56) References Cited

U.S. PATENT DOCUMENTS

| | | | |
|---|---|---|---|
| 8,291,034 B1 | 10/2012 | Gopalan et al. | |
| 8,572,260 B2 | 10/2013 | Pyatkovskiy | |
| 8,635,387 B2 | 1/2014 | Liu et al. | |
| 8,645,634 B1 | 2/2014 | Cox et al. | |
| 8,654,643 B2 | 2/2014 | Chew | |
| 8,819,245 B2 | 8/2014 | Pyatkovskiy | |
| 9,288,101 B1 | 3/2016 | Dalal et al. | |
| 9,374,265 B1 | 6/2016 | Mok et al. | |
| 9,396,150 B2 | 7/2016 | Sato et al. | |
| 9,602,437 B1 | 3/2017 | Bernath | |
| 9,665,503 B2 | 5/2017 | Dalal | |
| 9,990,287 B2 | 6/2018 | Raikin et al. | |
| 10,332,235 B1 | 6/2019 | Amento et al. | |
| 10,521,389 B2 | 12/2019 | Cheng | |
| 10,691,612 B2 | 6/2020 | Baxter et al. | |
| 10,740,163 B2 | 8/2020 | Hamidouche et al. | |
| 10,885,880 B2 | 1/2021 | Boles et al. | |
| 10,887,238 B2 | 1/2021 | Ramey et al. | |
| 10,932,202 B2 | 2/2021 | Singh et al. | |
| 11,082,350 B2 | 8/2021 | Dalal | |
| 11,144,459 B2 | 10/2021 | Li et al. | |
| 11,165,720 B2 | 11/2021 | Pope et al. | |
| 11,216,308 B2 | 1/2022 | Zante et al. | |
| 11,226,780 B2* | 1/2022 | Tanaka | G06F 3/1231 |
| 11,321,256 B2 | 5/2022 | Amento et al. | |
| 11,444,877 B2 | 9/2022 | Zaifman et al. | |
| 11,544,121 B2 | 1/2023 | LeBeane et al. | |
| 11,636,569 B1 | 4/2023 | Xu et al. | |
| 11,687,460 B2 | 6/2023 | LeBeane et al. | |
| 11,861,758 B2 | 1/2024 | Agostini | |
| 11,876,880 B2 | 1/2024 | Pope et al. | |
| 11,961,619 B1* | 4/2024 | LaBorde | G06N 3/02 |
| 2002/0087710 A1 | 7/2002 | Aiken et al. | |
| 2002/0154636 A1 | 10/2002 | Thomas | |
| 2003/0187914 A1 | 10/2003 | Kaniyar et al. | |
| 2003/0195938 A1 | 10/2003 | Howard et al. | |
| 2005/0015625 A1 | 1/2005 | Inoue et al. | |
| 2005/0025151 A1 | 2/2005 | Marce et al. | |
| 2005/0080953 A1 | 4/2005 | Oner et al. | |
| 2005/0097226 A1 | 5/2005 | Tripathi | |
| 2006/0291506 A1* | 12/2006 | Cain | H04N 21/4623 |
| | | | 370/486 |
| 2008/0068458 A1* | 3/2008 | Carroll | H04N 7/181 |
| | | | 348/E7.086 |
| 2008/0228871 A1 | 9/2008 | Sano | |
| 2008/0240111 A1 | 10/2008 | Gadelrab | |
| 2008/0263315 A1 | 10/2008 | Zhang et al. | |
| 2009/0089475 A1 | 4/2009 | Chitlur et al. | |
| 2010/0293280 A1 | 11/2010 | Namihira | |
| 2011/0085464 A1 | 4/2011 | Nordmark et al. | |
| 2011/0087814 A1 | 4/2011 | Liu et al. | |
| 2011/0317713 A1 | 12/2011 | Assarpour et al. | |
| 2012/0030448 A1 | 2/2012 | Lieske | |
| 2012/0069035 A1 | 3/2012 | Bourd et al. | |
| 2014/0071866 A1 | 3/2014 | Maciocco et al. | |
| 2014/0310721 A1 | 10/2014 | Chew | |
| 2014/0317220 A1 | 10/2014 | Karlsson et al. | |
| 2015/0242722 A1 | 8/2015 | Watanabe | |
| 2015/0256645 A1 | 9/2015 | Sukonik et al. | |
| 2016/0071264 A1* | 3/2016 | Agam | G06V 10/774 |
| | | | 382/128 |
| 2017/0046306 A1 | 2/2017 | Li et al. | |
| 2017/0180272 A1 | 6/2017 | Bernath | |
| 2018/0004693 A1 | 1/2018 | MacNamara et al. | |
| 2018/0212885 A1 | 7/2018 | Contavalli et al. | |
| 2018/0227226 A1 | 8/2018 | Lu et al. | |
| 2018/0285105 A1 | 10/2018 | Wang et al. | |
| 2018/0336071 A1 | 11/2018 | Zaifman et al. | |
| 2019/0044890 A1 | 2/2019 | Underwood et al. | |
| 2019/0149480 A1 | 5/2019 | Singhvi et al. | |
| 2020/0136998 A1 | 4/2020 | Lu | |
| 2020/0151127 A1 | 5/2020 | Amento et al. | |
| 2020/0293367 A1 | 9/2020 | Andrei et al. | |
| 2021/0109888 A1 | 4/2021 | Vaidyanathan et al. | |
| 2021/0326176 A1 | 10/2021 | Maiyuran et al. | |
| 2021/0334933 A1 | 10/2021 | Strauss et al. | |
| 2021/0397559 A1 | 12/2021 | Chen et al. | |
| 2022/0116364 A1* | 4/2022 | Westin | H04L 63/0428 |
| 2022/0124051 A1 | 4/2022 | Brewer et al. | |
| 2022/0292626 A1 | 9/2022 | Agostini | |
| 2022/0413869 A1 | 12/2022 | Vembu et al. | |
| 2023/0013468 A1 | 1/2023 | Dai | |
| 2024/0337961 A1 | 10/2024 | Katagiri | |
| 2025/0165280 A1 | 5/2025 | Grant | |

OTHER PUBLICATIONS

Agostini et al., "DPDK Acceleration with GPU," DPDK Project Video Partial Transcription & Presentation Slides, Nov. 21, 2019, 12 pages.

Agostini et al., "DPDK Acceleration with GPU," retrieved from https://dpdkna2019.sched.com/event/WYB1/dpdk-acceleration-with-gpu-elena-agostini-nvidia-cliff-burdick-viasat-shahaf-shuler-mellanox, Nov. 12, 2019, 3 pages.

Agostini, "Boosting Inline Packet Processing Using DPDK and GPUdev with GPUs," Nvidia, retrieved from https://developer.nvidia.com/blog/optimizing-inline-packet-processing-using-dpdk-and-gpudev-with-gpus/, Apr. 28, 2022, 7 pages.

Github, "Project—MONAI / MONAI," Retrieved from https://github.com/Project-MONAI/MONAI/tree/dev/monai/transforms, Dec. 2020, 2 Pages.

IEEE, "IEEE Standard 754-2008 (Revision of IEEE Standard 754-1985): IEEE Standard for Floating-Point Arithmetic," Aug. 29, 2008, 70 pages.

IEEE, "IEEE Standard for 802.3," IEEE Standard for Ethernet, IEEE Computer Society, Dec. 28, 2012, 634 pages.

Mellanox, "Nv_Peer_Memory," retrieved from https://github.com/mellanox/nv_peer_memory, Jan. 28, 2021, 4 pages.

Nvidia, "Developing a Linux Kernel Module using RDMA for GPUDirect," retrieved from https://docs.nvidia.com/cuda/gpudirect-rdma/index.html, Mar. 10, 2021, 6 pages.

Nvidia, "GDRCopy," retrieved from https://github.com/NVIDIA/gdrcopy, Mar. 2, 2021, 10 pages.

Tekur et al., "Packet Processing on GPU at 100GbE Line Rater," retrieved from https://gputechconf2019.smarteventscloud.com/connect/sessionDetail.ww?SESSION_ID=272390, Mar. 21, 2019, 1 pages.

Wikipedia, "IEEE 802.11," Wikipedia the Free Encyclopedia, https://en.wikipedia.org/wiki/IEEE_802.11, most recent edit Sep. 20, 2020 [retrieved Sep. 22, 2020], 15 pages.

Wikipedia, "IEEE 802.5," Wikepedia The Free Encyclopedia, https://en.wikipedia.org/wiki/Token_Ring, Jan. 14, 2020, 12 pages.

Hirschmüller, "Accurate and Efficient Stereo Processing by Semi-Global Matching and Mutual Information," IEEE Conference on Computer Vision and Pattern Recognition, Jun. 2005, 8 pages.

Hirschmüller, "Stereo Processing by Semi-Global Matching and Mutual Information," IEEE Transactions on Pattern Analysis and Machine Intelligence, Apr. 16, 2007, 14 pages.

Extended European Search Report for Application No. 23195831.5, Jan. 29, 2024, 12 pages.

* cited by examiner

Figure 7:
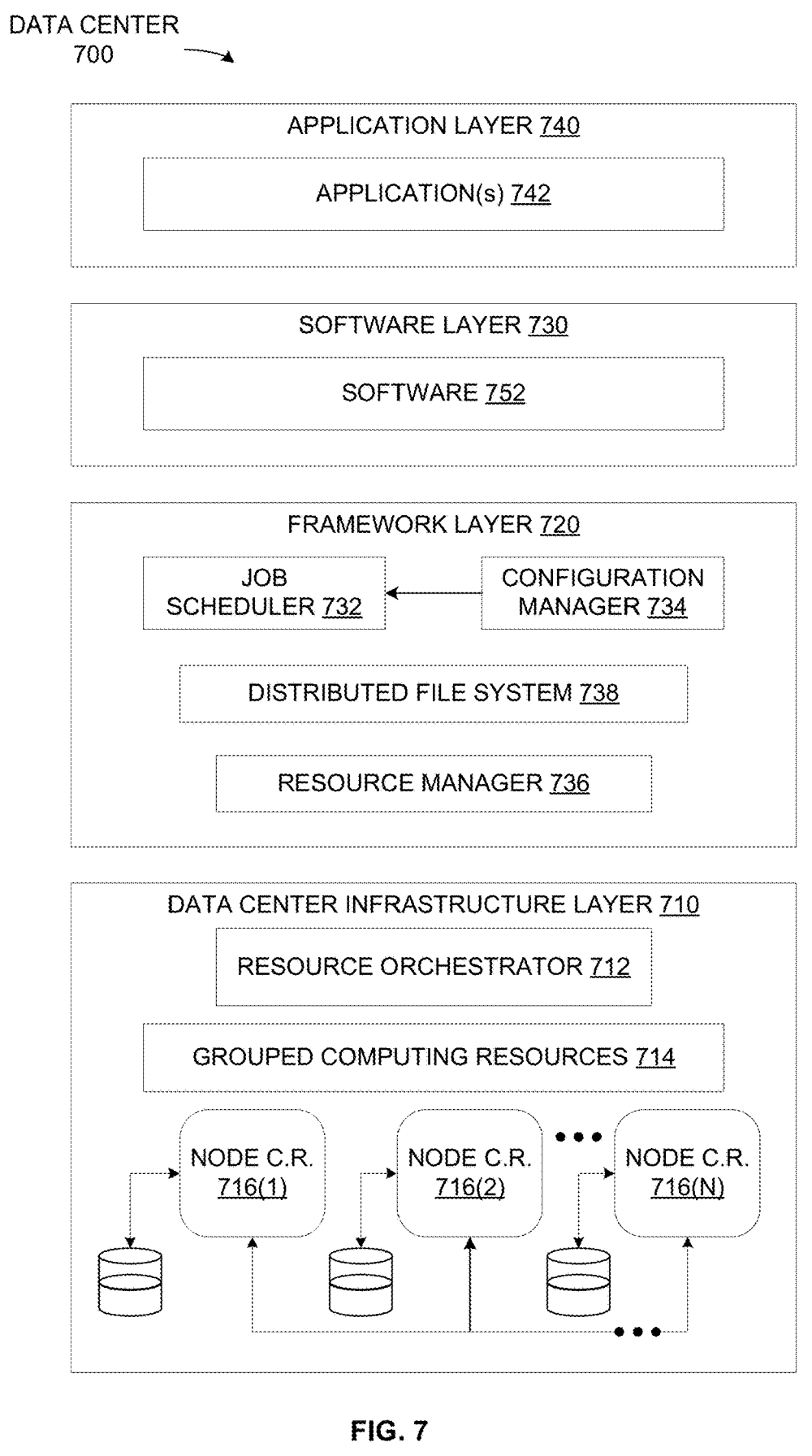

DATA CENTER
700

APPLICATION LAYER 740

APPLICATION(s) 742

SOFTWARE LAYER 730

SOFTWARE 752

FRAMEWORK LAYER 720

JOB
SCHEDULER 732    ◄    CONFIGURATION
MANAGER 734

DISTRIBUTED FILE SYSTEM 738

RESOURCE MANAGER 736

DATA CENTER INFRASTRUCTURE LAYER 710

RESOURCE ORCHESTRATOR 712

GROUPED COMPUTING RESOURCES 714

NODE C.R.
716(1)      NODE C.R.
716(2)    • • •    NODE C.R.
716(N)

Network Manager (NM)

Element Manager (EM)

NFC Orchestrator (NFVO)

VNF Manager (VNFM)

Virtualized Network Function (VNF)

Virtualized Network Function (VNF)

Virtualized Infrastructure (VIM)

Network Function Virtualization Infrastructure (NFVI)

INTEGRATED
CIRCUIT
2900

APPLICATION
PROCESSOR(S)
2905

GRAPHICS
PROCESSOR
2910

IMAGE
PROCESSOR
2915

VIDEO
PROCESSOR
2920

USB
2925

UART
2930

SPI/
SDIO
2935

I²S/I²C
2940

DISPLAY
2945

SECURITY
ENGINE
2970

MEMORY
2965

FLASH
2960

MIPI
2955

HDMI
2950

GRAPHICS PROCESSOR
3440

INTER-CORE TASK MANAGER
(e.g., THREAD DISPATCHER)
3445

SHADER CORE 3455A

SHADER CORE 3455C

SHADER CORE 3455E

- - -

SHADER CORE 3455N-1

SHADER CORE 3455B

SHADER CORE 3455D

SHADER CORE 3455F

- - -

SHADER CORE 3455N

TILING UNIT
3458

MMU
3420A

MMU
3420B

CACHE
3425A

CACHE
3425B

INTERCONNECT
3430A

INTERCONNECT
3430B

PREPROCESSING DATA USING A NETWORK INTERFACE

FIELD

At least one embodiment pertains to methods and/or systems for preprocessing data (e.g., medical imaging data) before providing the preprocessed data to one or more parallel processing units (e.g., for inferencing). In at least one embodiment, the data is obtained and preprocessed by a network interface. In at least one embodiment, the pre-processing converts the data from a first format (e.g., Digital Imaging and Communications in Medicine format) to a second format (e.g., a tensor format, a TensorFlow tensor format, a PyTorch tensor format, CuPy array format, and/or the like) for processing by the parallel processing unit(s). In at least one embodiment, the methods may be implemented within a data center that implements various novel techniques.

BACKGROUND

A typical medical inference system includes a network interface (e.g., a network interface card ("NIC")), at least one central processing unit ("CPU"), and at least one graphics processing unit ("GPU"). The network interface receives input data (e.g., imaging data and meta data) from at least one inference requestor device, such as a medical scanner, and supplies the input data to the CPU(s). The CPU(s) perform one or more pre-processing operations on the input data and supply processed input data the GPU(s). The pre-processing operation(s) prepare the input data for inference engine(s) implemented by the GPU(s) so that the inference engine(s) will provide a reliable result. By way of non-limiting example, the preprocessing operation(s) may include for example, alignment transformation operation(s) and/or data format conversion operation(s) (e.g., that convert the input data from a medical format (e.g., Digital Imaging and Communications in Medicine ("DICOM") format) to a GPU-friendly format (e.g., a tensor format, a TensorFlow tensor format, a PyTorch tensor format, CuPy array format, and/or the like).

The GPU(s) perform(s) one or more inference operations (e.g., tumor detection) with respect to the input data and return(s) output data to the CPU(s). The CPU(s) forward(s) the output data to the network interface, which sends the output data to at least one inference receiver device, such as the inference requestor device(s), a database, and/or the like. Before forwarding the output data to the network interface, the CPU(s) may perform one or more post-processing operations on the output data. Because the CPU(s) perform(s) the pre-processing operation(s) on the input data, the speed of the CPU(s) may determine at least in part an amount of time required to perform the inference. Additionally, time is consumed copying the input data from the network interface into the CPU memory and from the CPU memory to the GPU memory.

BRIEF DESCRIPTION OF THE DRAWINGS

FIG. 7 illustrates an exemplary data center, in accordance with at least one embodiment;

3

Figure 30:
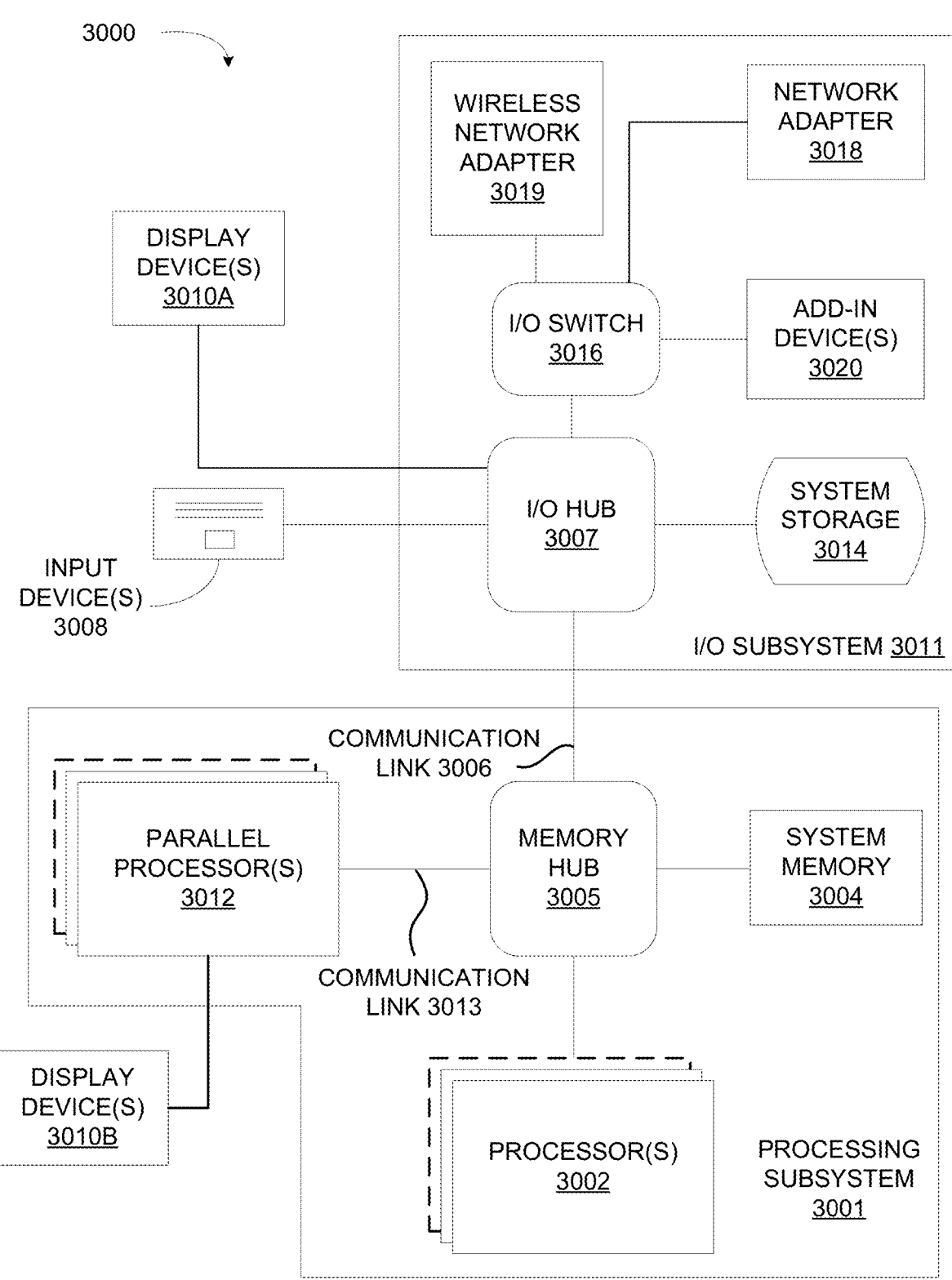
Figure 31:
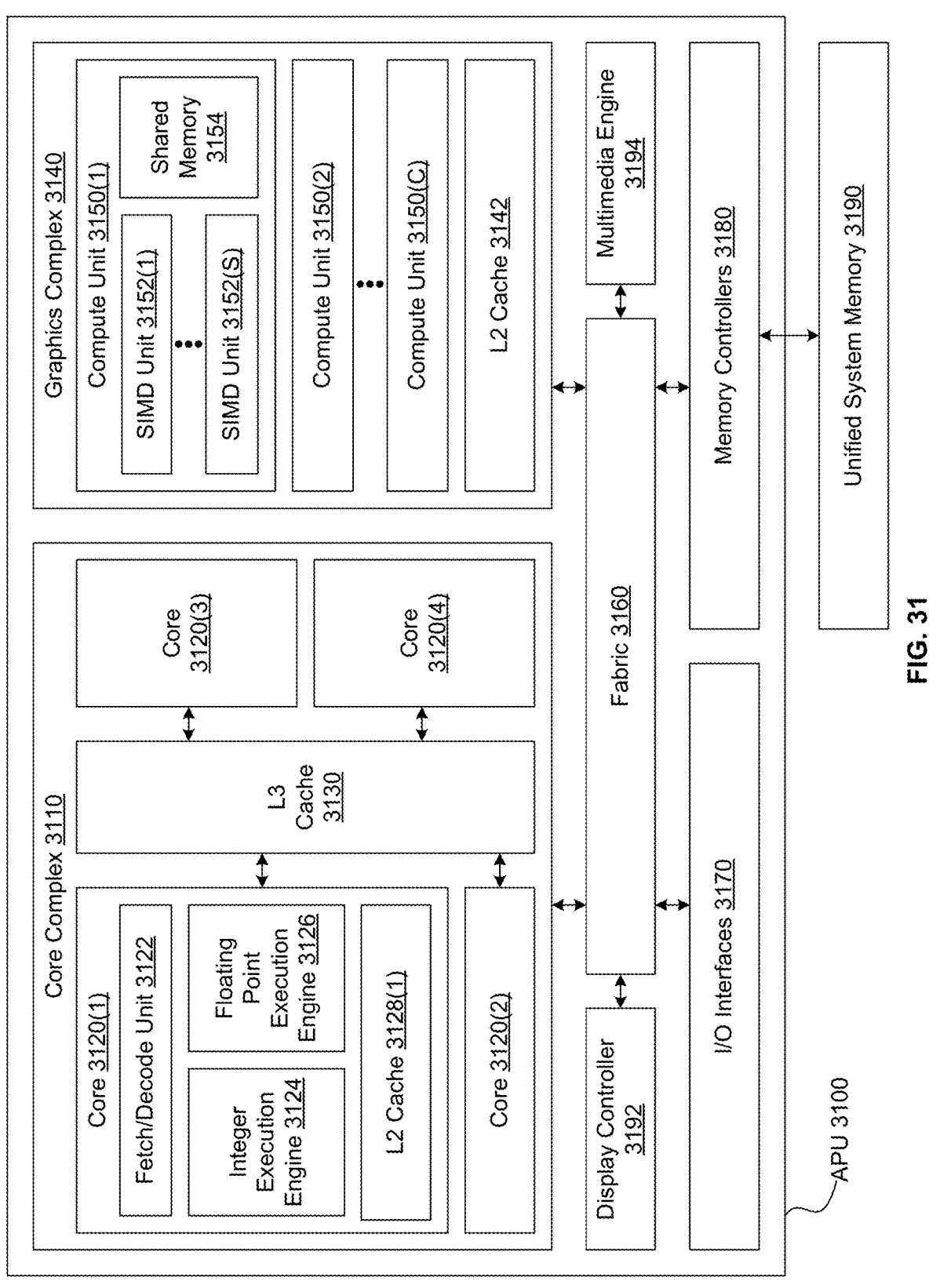
Figure 32:
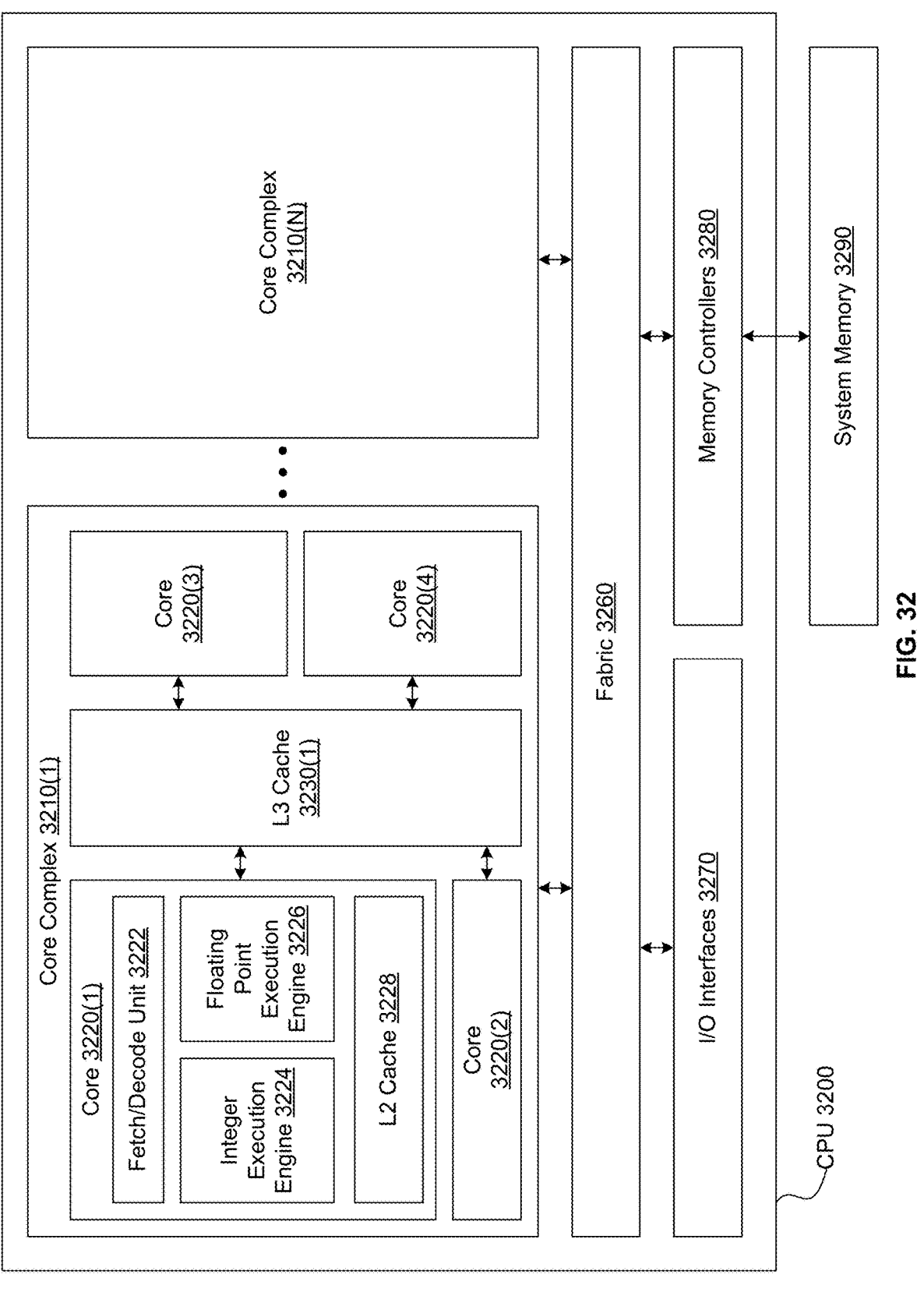
Figure 33:
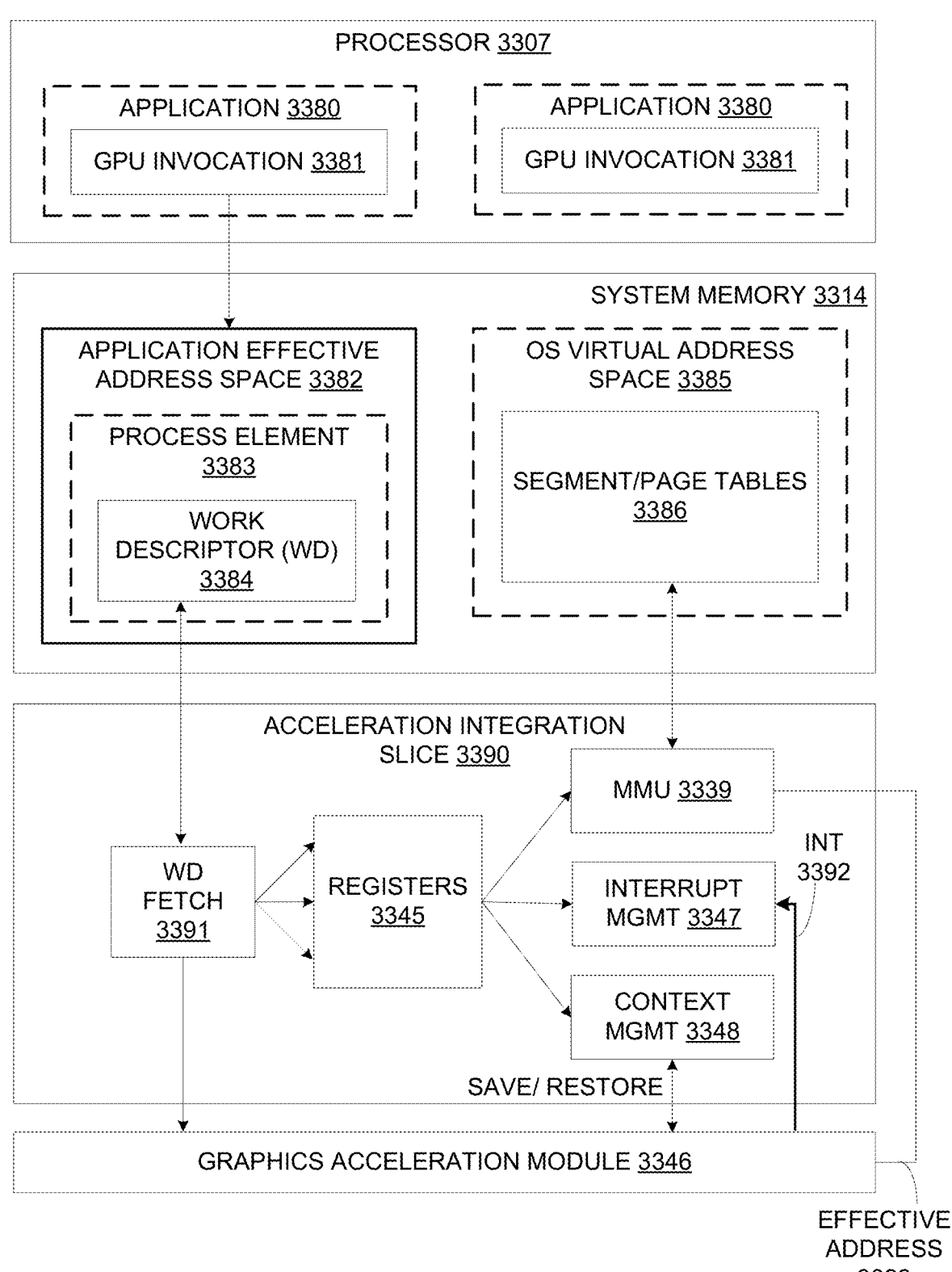
Figure 34A:
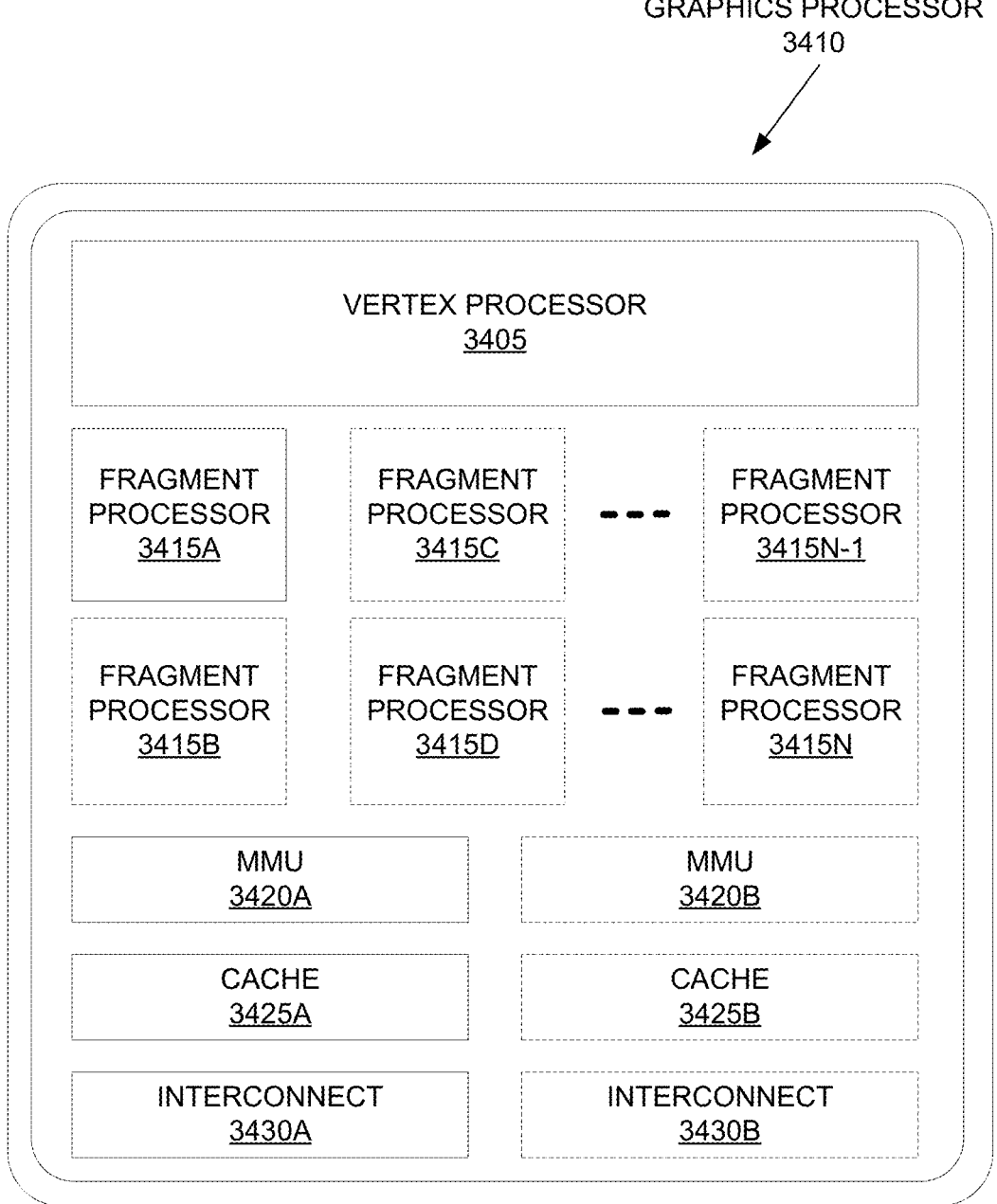
Figure 34B:
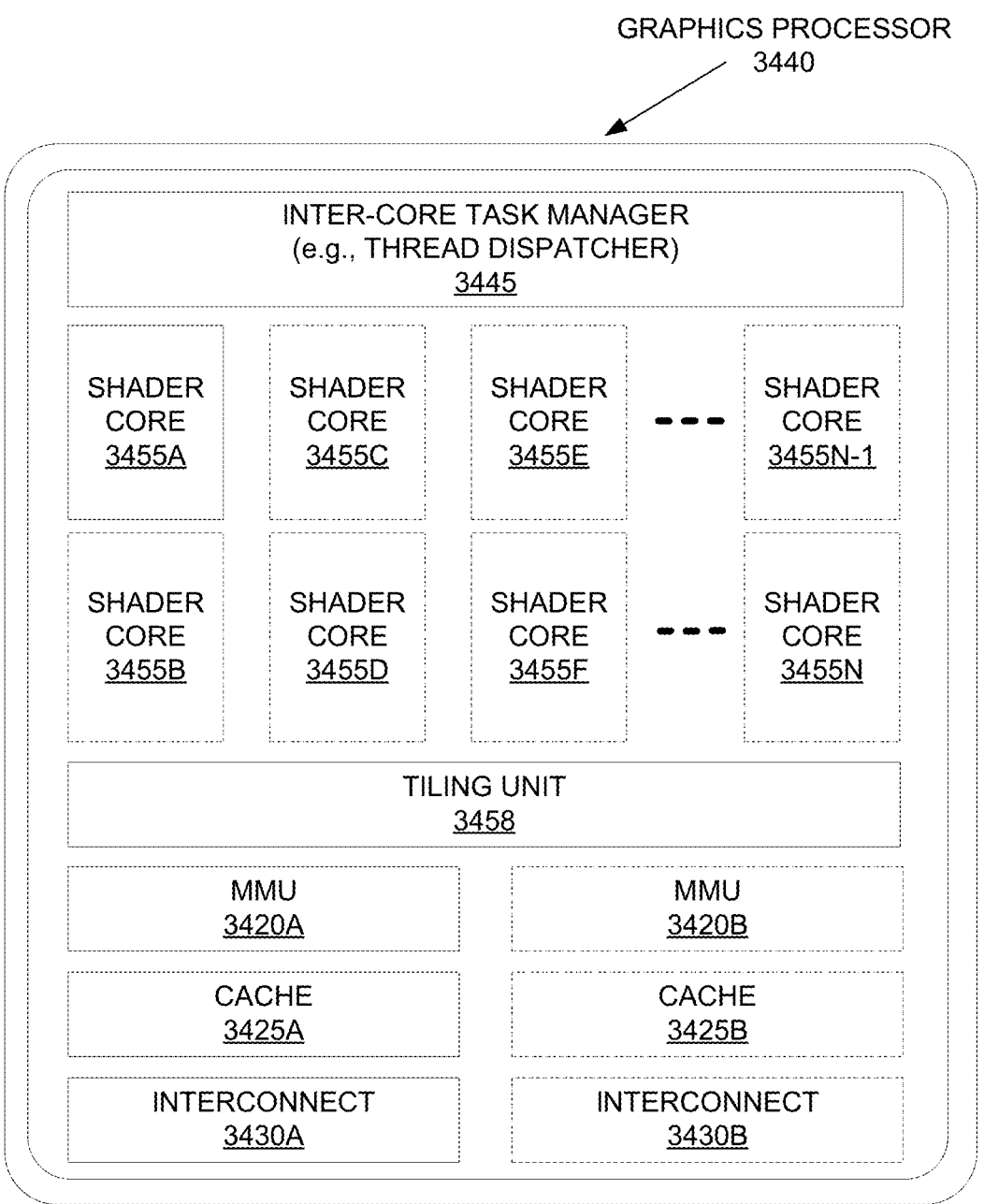
Figure 35A:
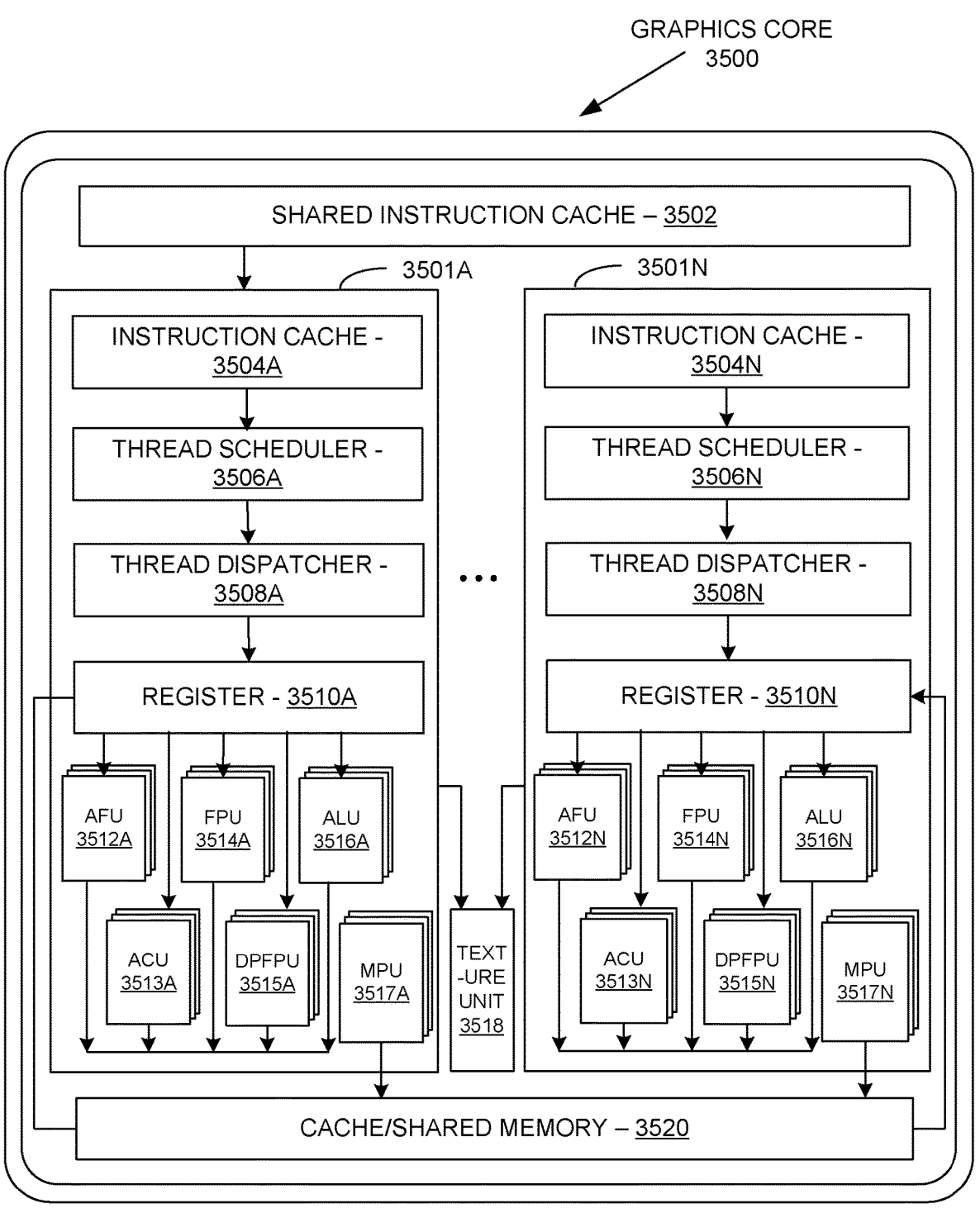
Figure 35B:
Figure 36A:
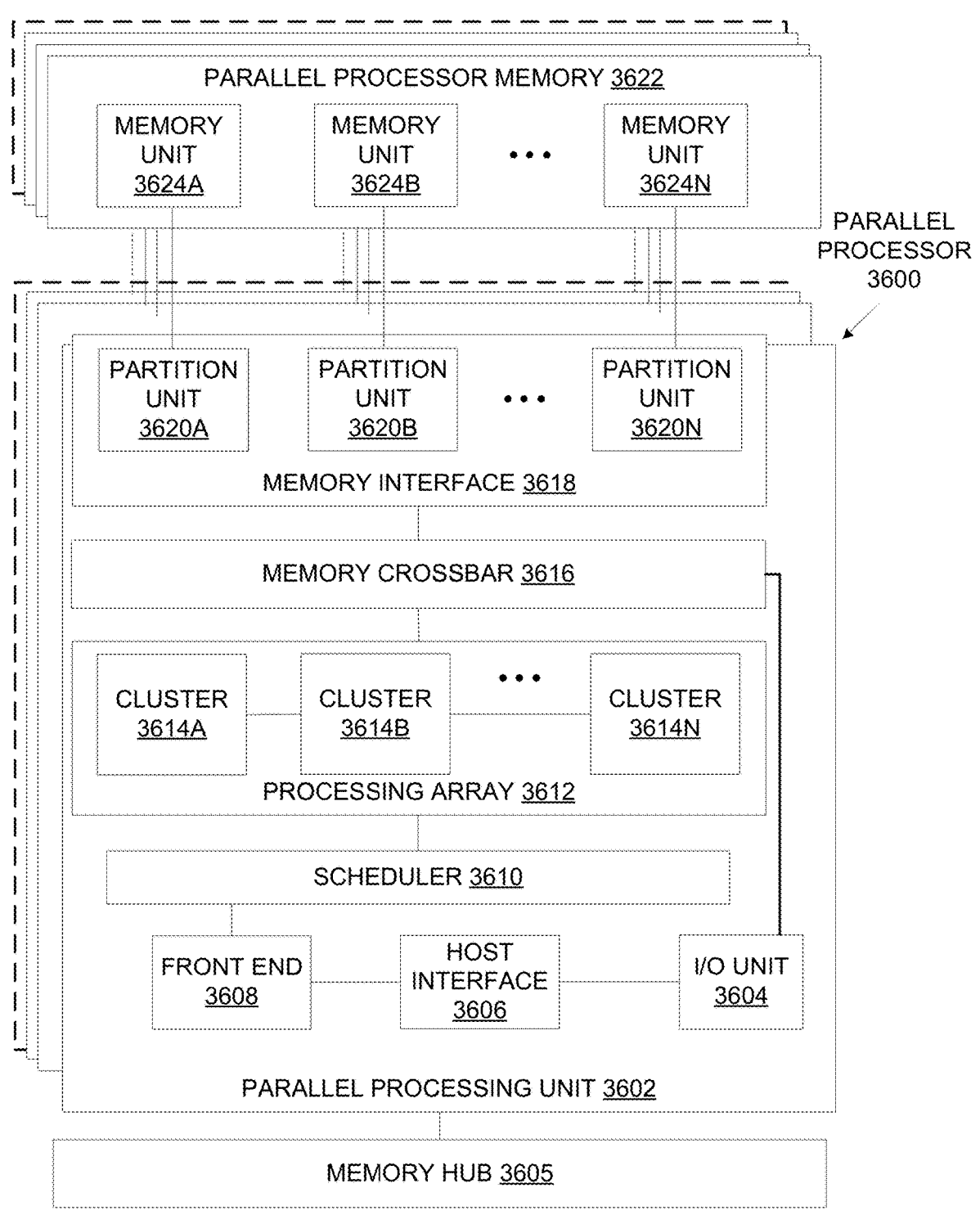
Figure 36B:
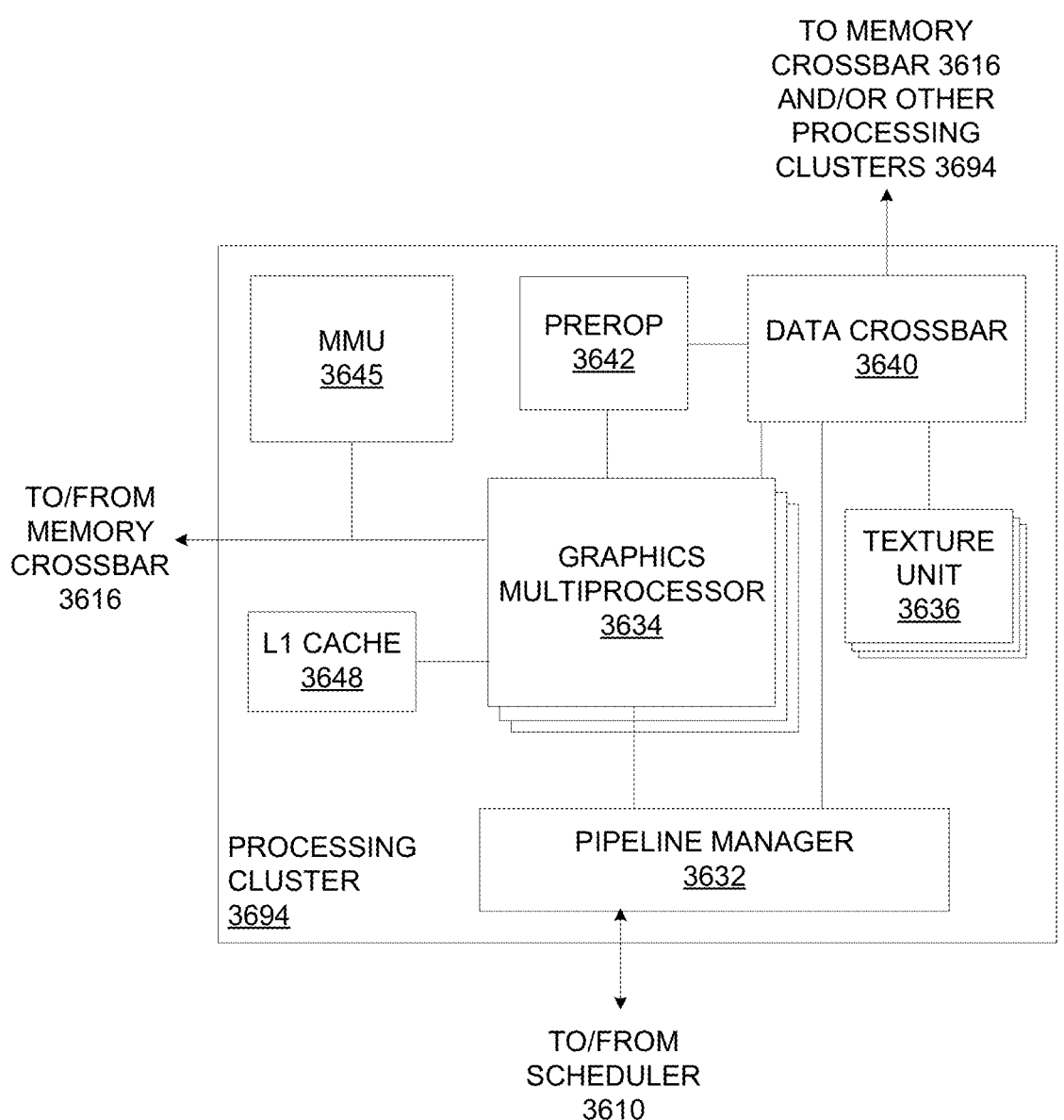
Figure 36C:
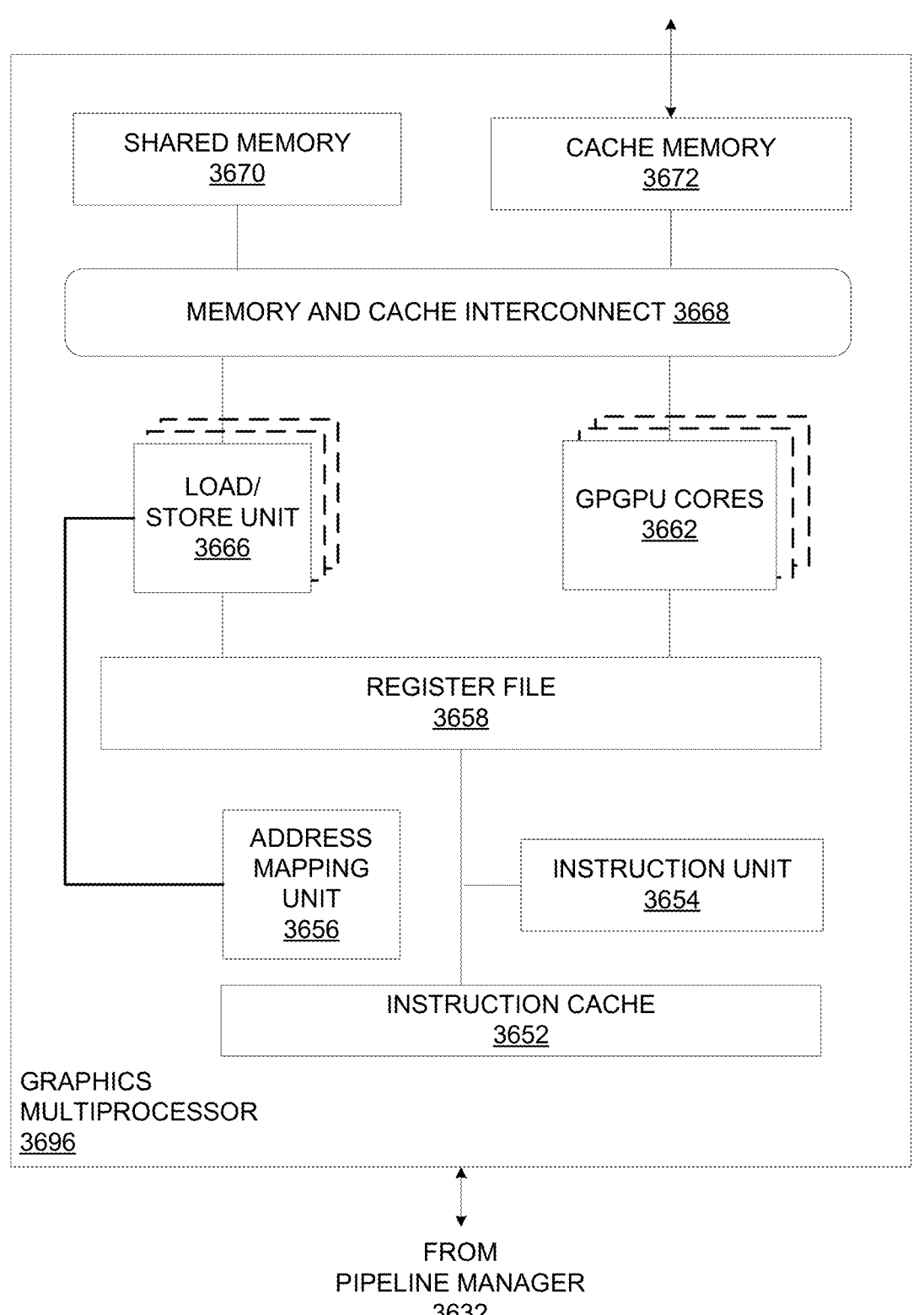
Figure 37:
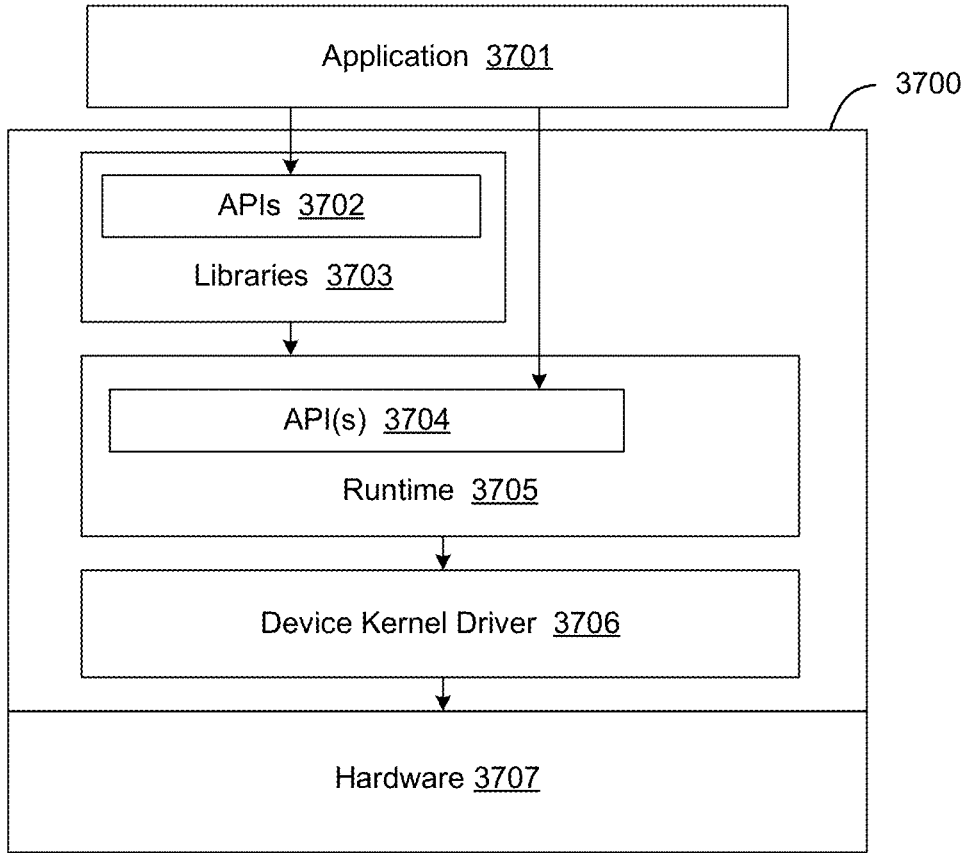
Figure 38:
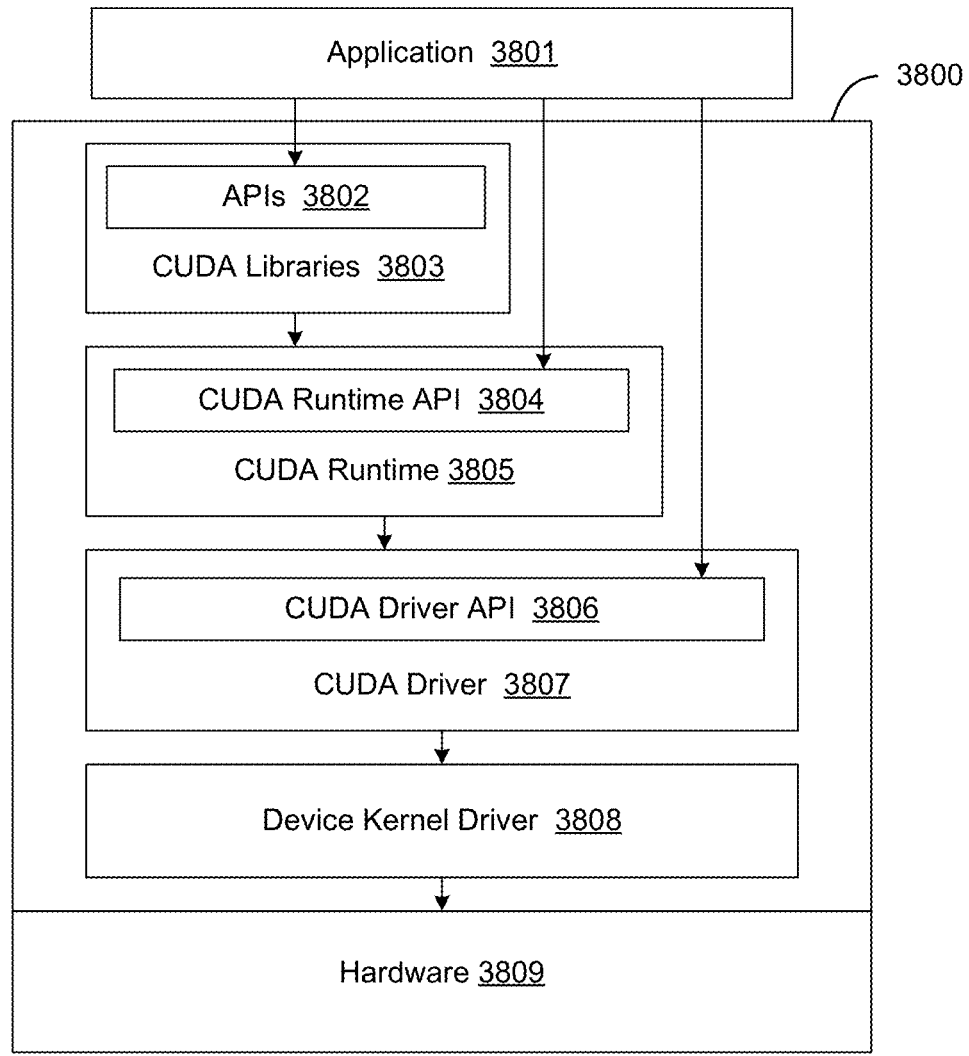
Figure 39:
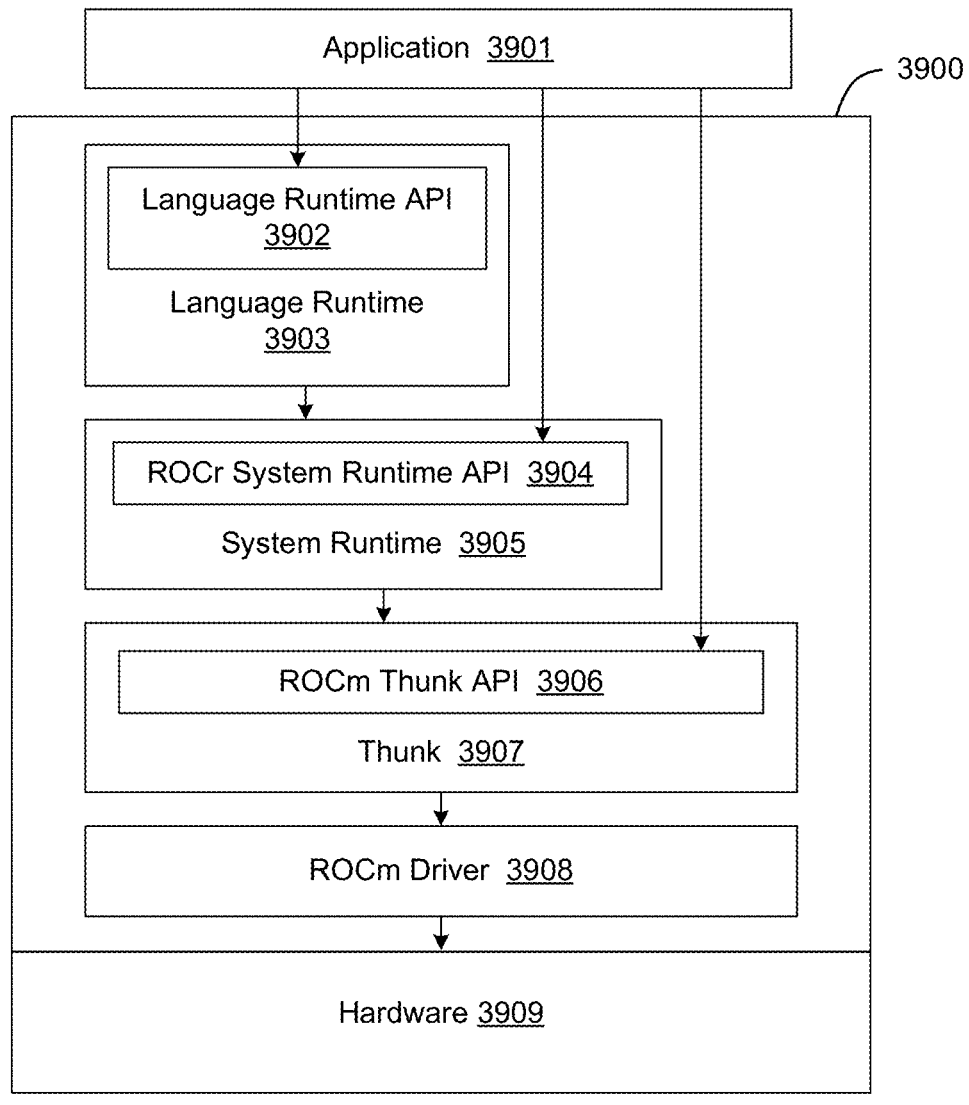
Figure 40:
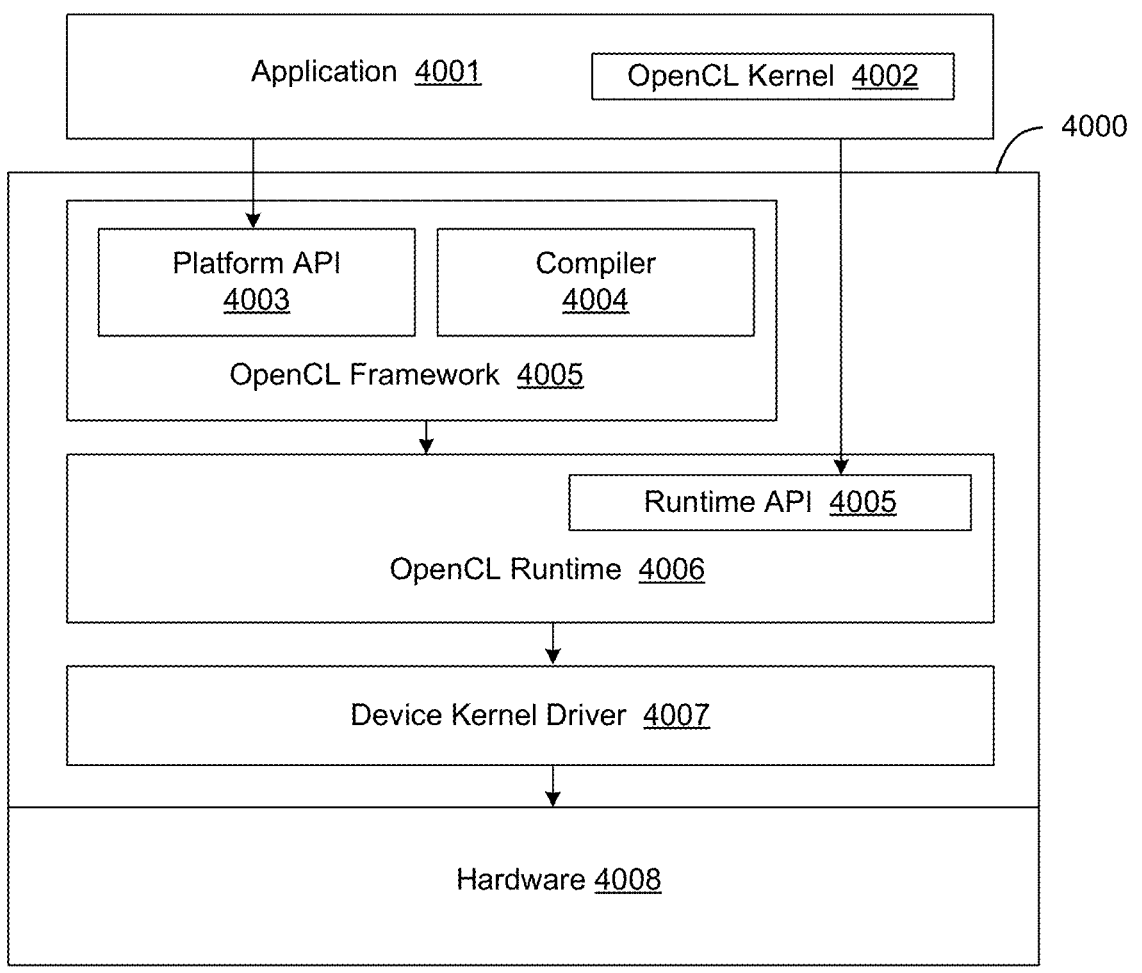
Figure 41:
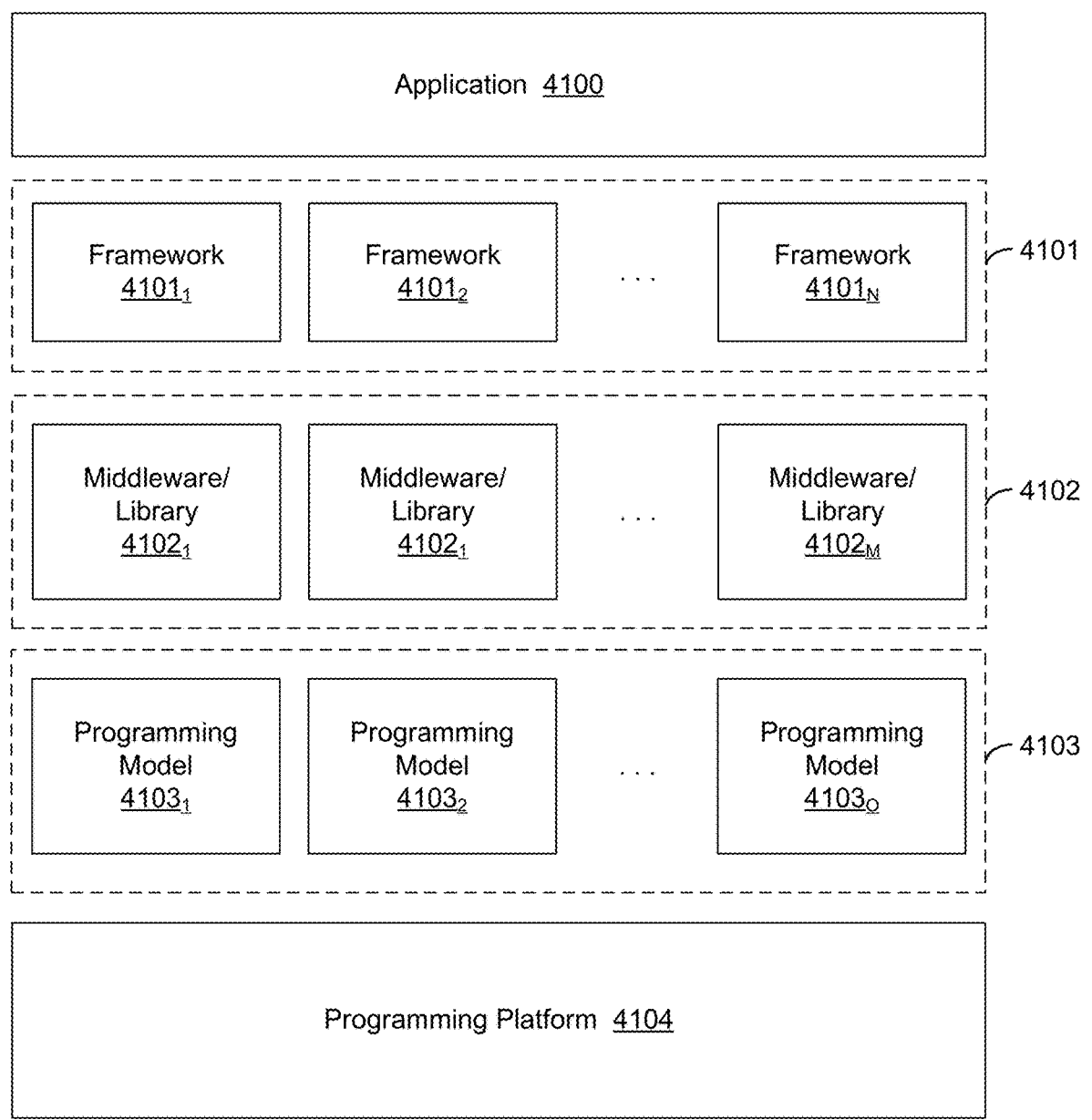
Figure 42:
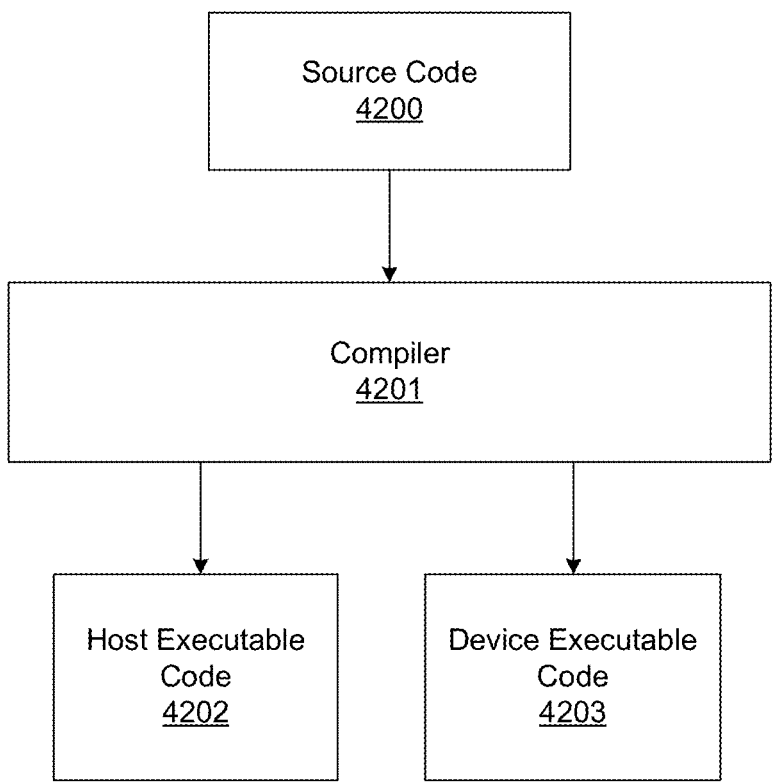

FIG. 30 illustrates a computing system, according to at least one embodiment;

FIG. 31 illustrates an APU, in accordance with at least one embodiment;

FIG. 32 illustrates a CPU, in accordance with at least one embodiment;

FIG. 33 illustrates an exemplary accelerator integration slice, in accordance with at least one embodiment;

FIGS. 34A-34B illustrate exemplary graphics processors, in accordance with at least one embodiment;

FIG. 35A illustrates a graphics core, in accordance with at least one embodiment;

FIG. 35B illustrates a GPGPU, in accordance with at least one embodiment;

FIG. 36A illustrates a parallel processor, in accordance with at least one embodiment;

FIG. 36B illustrates a processing cluster, in accordance with at least one embodiment;

FIG. 36C illustrates a graphics multiprocessor, in accordance with at least one embodiment;

FIG. 37 illustrates a software stack of a programming platform, in accordance with at least one embodiment;

FIG. 38 illustrates a CUDA implementation of a software stack of FIG. 37, in accordance with at least one embodiment;

FIG. 39 illustrates a ROCm implementation of a software stack of FIG. 37, in accordance with at least one embodiment;

FIG. 40 illustrates an OpenCL implementation of a software stack of FIG. 37, in accordance with at least one embodiment;

FIG. 41 illustrates software that is supported by a programming platform, in accordance with at least one embodiment; and FIG. 42 illustrates compiling code to execute on programming platforms of FIGS. 37-40, in accordance with at least one embodiment.

DETAILED DESCRIPTION

In the following description, numerous specific details are set forth to provide a more thorough understanding of at least one embodiment. However, it will be apparent to one skilled in the art that the inventive concepts may be practiced without one or more of these specific details.

Figure 1:
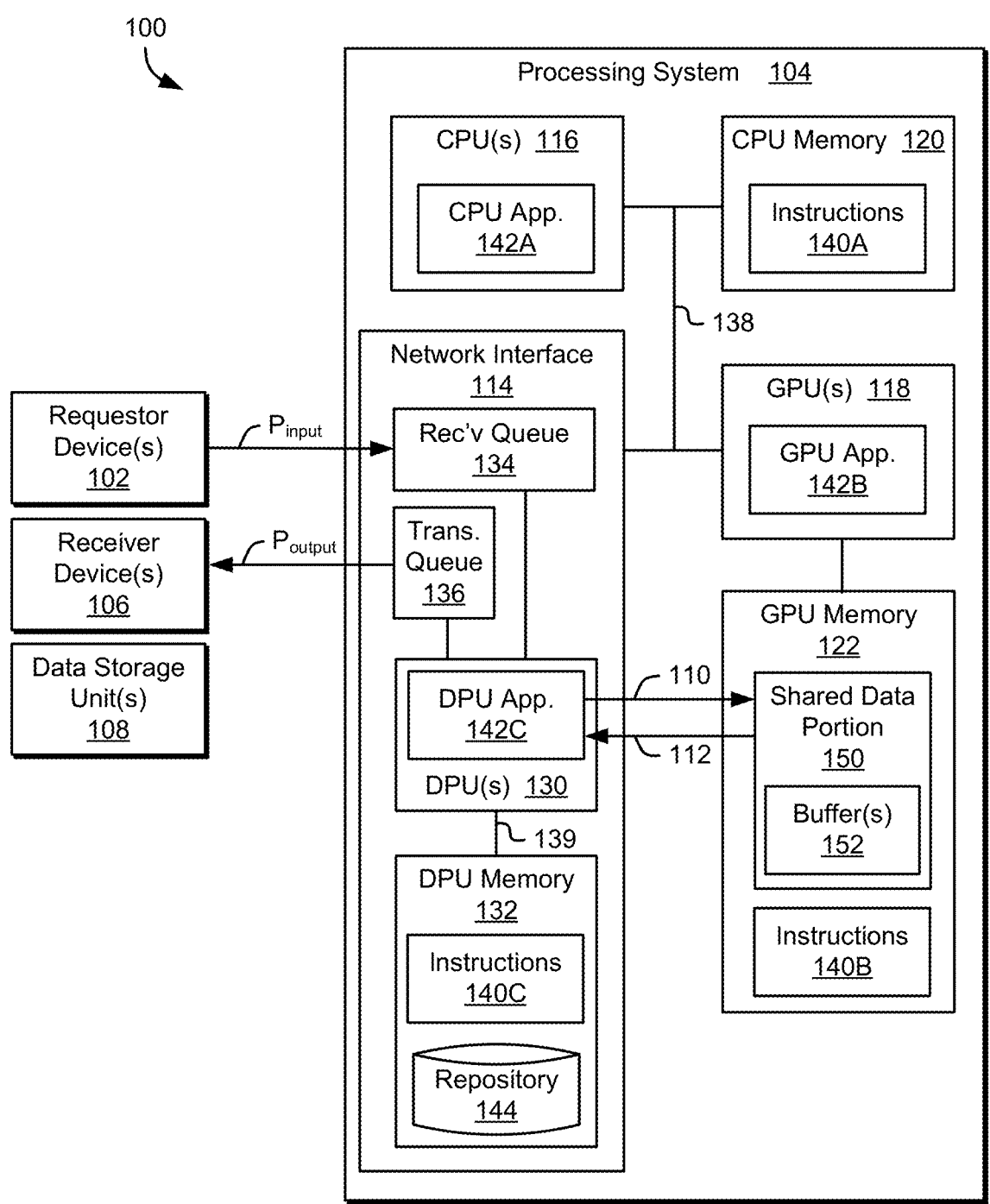
FIG. 1 illustrates a block diagram of an example system, in accordance with at least one embodiment.

FIG. 1 illustrates a block diagram of an example system 100, in accordance with at least one embodiment. The system 100 includes at least one requestor device 102, a processing system 104, at least one receiver device 106, and one or more optional data storage units 108. The requestor device(s) 102 may be implemented as one or more data collection device, such as one or more medical imaging devices, one or more medical scanners, and/or the like. By way of non-limiting examples, the requestor device(s) 102 may include one or more computed tomography ("CT") devices, one or more computerized axial tomography ("CAT") devices, one or more magnetic resonance imaging ("MRI") devices, one or more positron emission tomography ("PET") devices, one or more ultrasound devices, and/or the like. The requestor device(s) 102 may be implemented as a Picture Archiving and Communication System ("PACS"), a data store, a database, a computing system, and/or the like.

The processing system 104 may be implemented as a computing system (e.g., a computing cluster, such as Clara Deploy, NVIDIA Triton, and/or the like). The processing system 104 may perform one or more diagnostic tasks (e.g., detecting a disease condition, such as the presence of COVID-19, cancer, heart disease, and/or the like).

The receiver device(s) 106 may be implemented as the requestor device(s) 102, and/or one or more of any of the devices suitable for implementing the requestor device(s) 102. The optional data storage unit(s) 108 may be implemented as one or more computing devices, one or more databases, one or more memory devices, one or more data stores, and/or the like. One or more of the optional data storage unit(s) 108 may be implemented as an emulated storage device.

The requestor device(s) 102, the processing system 104, the receiver device(s) 106, and the optional data storage units 108 may be connected to one another by a network, such as an Ethernet network, an Infiniband network, and/or the like. The requestor device(s) 102 may send information (e.g., imaging data and meta data) to the processing system 104. In the embodiment illustrated, the information may be sent as packets $P_{input}$ that each include at least a portion of data being communicated by the requestor device(s) 102 to the processing system 104. This portion of the data will be referred to as payload data. The payload data of the packets $P_{input}$ may communicate a series (or stack) of images that the processing system 104 may assemble to create a volume. For examples, the payload data included in the packets $P_{input}$ may be assembled into a three-dimensional ("3D") volume, a four-dimensional ("4D") volume, and/or the like. By way of another non-limiting example, the payload data included in the packets $P_{input}$ may be assembled into a sinogram. In such embodiments, the payload data includes projections of a volume (e.g., 3D or 4D) instead of slices of (or images captured from) the volume. A sinogram may be performed, for example, to visualize any abnormal opening (sinus) in the body.

The payload data may be characterized as communicating a number of separate files, such as imaging files, projection files, and/or the like, to the processing system 104. The files may be sent separately to the processing system 104 by the requestor device(s) 102. When the payload data included in the packets $P_{input}$ has a format specified by the DICOM standard, the packets $P_{input}$ may be communicated between the processing system 104 and the requestor device(s) 102 using DICOM Message Service Element ("DIMSE") protocol, which is built on top of Transmission Control Protocol ("TCP"), and/or using DICOMWeb protocol, which sends the packets $P_{input}$ using Hypertext Transfer Protocol ("HTTP"). Using any of these protocols, the files may each be sent in a separate request within a single transaction.

The processing system 104 receives the packets $P_{input}$ from the requestor device(s) 102, obtains input data 110 from the packets $P_{input}$, and processes the input data 110 to obtain output data 112. The processing may include performing one or more inference operations (e.g., tumor detection) with respect to the input data 110. The inference operation(s) may be performed using machine learning (e.g., one or more neural networks, one or more classifiers, and/or the like), artificial intelligence, and/or the like. Then, the processing system 104 forwards the output data 112 (e.g., as packets $P_{output}$) to the receiver device(s) 106.

The processing system 104 includes a network interface 114 (e.g., a network interface card ("NIC")), at least one central processing unit ("CPU") 116, and at least one graphics processing unit ("GPU") 118. The CPU(s) 116 include and/or are connected to CPU memory 120. The GPU(s) 118 include and/or are connected to GPU memory 122. The network interface 114 includes at least one data processing unit ("DPU(s)") 130, DPU memory 132, one or more receive queues 134, and one or more transmit queues 136. The network interface 114 may be implemented as a NIC, a network interface card, a network adapter, a Local Area Network ("LAN") adapter, a physical network interface, a host channel adapter ("HCA"), an Ethernet NIC, one or more circuits, and/or the like. Each of the CPU(s) 116, the GPU(s) 118, and the DPU(s) 130 may be implemented, for example, using a main CPU complex, one or more microprocessors, one or more microcontrollers, one or more parallel processing units ("PPU(s)"), one or more GPUs, one or more DPUs, and/or the like. Each of the CPU memory 120, the GPU memory 122, and the DPU memory 132 may be implemented as one or more non-transitory processor-readable medium. Each of the CPU memory 120, the GPU memory 122, and the DPU memory 132 may be implemented, for example, using volatile memory (e.g., dynamic random-access memory ("DRAM")) and/or nonvolatile memory (e.g., a hard drive, a solid-state device ("SSD"), and/or the like).

The network interface 114 is connected to the GPU(s) 118, the CPU(s) 116, the CPU memory 120, and/or the GPU memory 122 by a connection 138, such as a bus, a serial computer expansion bus, a Peripheral Component Interconnect Express ("PCIe") bus, and the like. The DPU(s) 130 are connected to the DPU memory 132, the receive queue(s) 134, and the transmit queue(s) 136 by a connection 139, such as a bus, a serial computer expansion bus, and the like. The GPU(s) 118 and/or the CPU(s) 116 may be connected to the receive queue(s) 134 and/or the transmit queue(s) 136 by the connection 138.

The CPU memory 120 (e.g., one or more non-transitory processor-readable medium) may store instructions 140A that are executable by the CPU(s) 116. When executed by the CPU(s) 116, at least a portion of the instructions 140A may implement a CPU application 142A. The CPU application 142A may cause the GPU(s) 118 to execute a GPU application 142B (e.g., a Compute Unified Device Architecture ("CUDA") kernel) and/or the DPU(s) 130 to execute a DPU application 142C. The CPU application 142A may configure the GPU application 142B and/or the DPU application 142C. The applications 142A-142C may communicate with one another (e.g., over the connection 138). The GPU memory 122 (e.g., one or more non-transitory processor-readable medium) may store instructions 140B that when executed by the GPU(s) 118 implement the GPU application 142B. The DPU memory 132 (e.g., one or more non-transitory processor-readable medium) may store instructions 140C that when executed by the DPU(s) 130 implement the DPU application 142C. The DPU memory 132 may store a repository 144.

The CPU application 142A may instruct the GPU(s) 118 and/or the GPU application 142B to allocate a shared memory portion 150 of the GPU memory 122 for use by the DPU application 142C, the GPU application 142B, and/or the CPU application 142A. In response to this instruction, the GPU(s) 118 and/or the GPU application 142B may allocate the shared memory portion 150 and provide an address of the shared memory portion 150 to the CPU application 142A and/or the DPU application 142C for use thereby.

Figure 2:
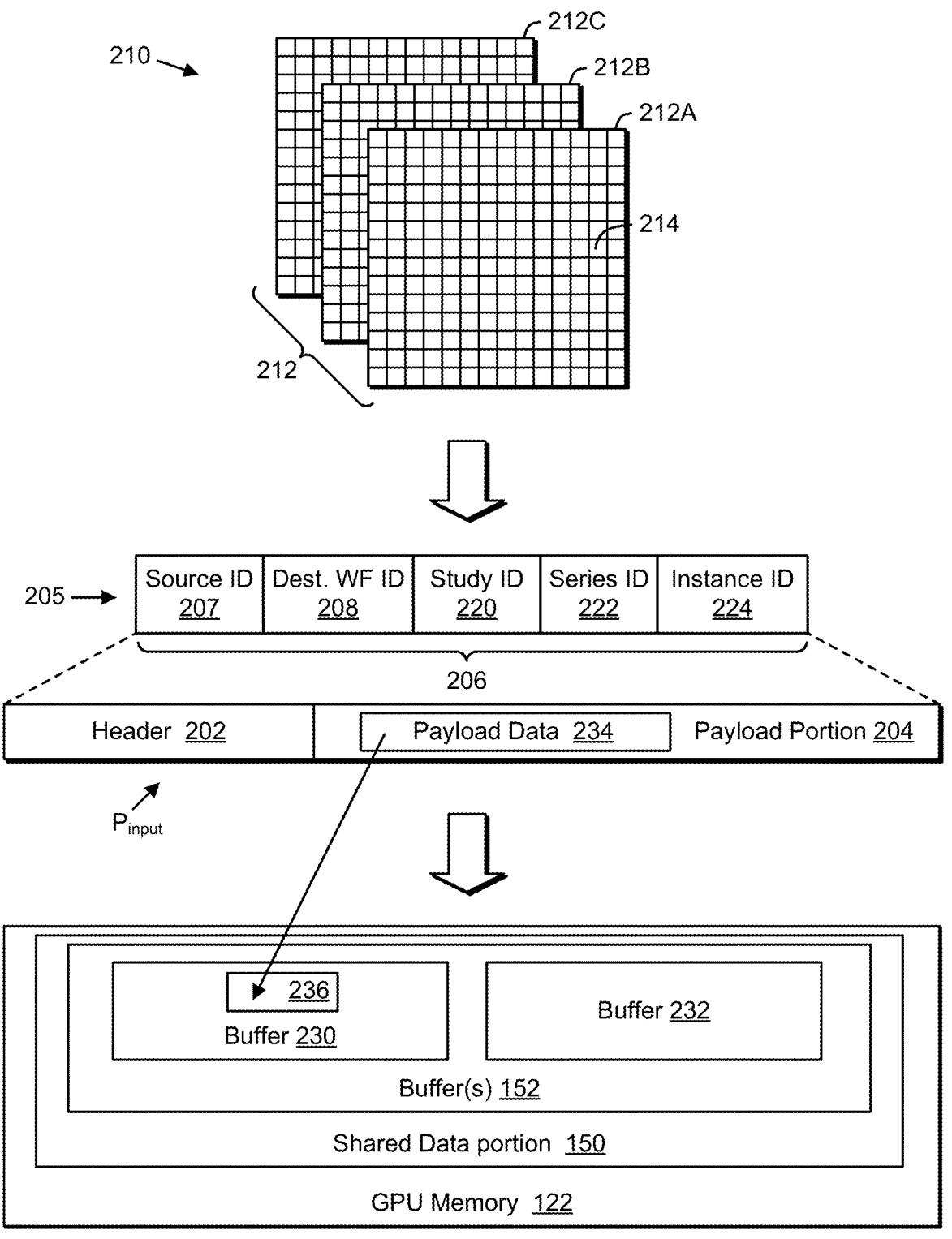
FIG. 2 illustrates a block diagram of a study transmitted in payload data of packets, and stored in GPU memory of the system of FIG. 1, in accordance with at least one embodiment.

The DPU application 142C may store the address in the repository 144 and associate the address with the requestor device(s) 102, at least a portion of the GPU application 142B, and/or a particular study (e.g., a study 210 illustrated in FIG. 2). Thus, the GPU and DPU applications 142B and 142C may both know the location of the shared memory portion 150 in the GPU memory 122. In at least one embodiment, the GPU(s) 118 and/or the GPU application 142B may provide an address of the shared memory portion 150 to the CPU application 142A for use thereby. In such embodiment(s), the CPU application 142A and the DPU application 142C and optionally the GPU application 142B may know the location of the shared memory portion 150 in the GPU memory 122.

The packets $P_{input}$ may be received by the receive queue(s) 134 (e.g., from the requestor device(s) 102). The DPU application 142C may poll the receive queue(s) 134 for new packets. When the DPU application 142C determines the packets $P_{input}$ have been received, the DPU application 142C may obtain the input data 110 and one or more parameter values (e.g., using deep packet inspection) from the packets $P_{input}$.

The DPU application 142C may use deep packet inspection to extract the parameter value(s) from the packets $P_{input}$. By way of non-limiting examples, the parameter value(s) may include a number (e.g., N) of columns in an imaging file, a number (e.g., K) of rows in the imaging file, a number (e.g., M) of imaging files belonging to the study, an identifier of a pixel format, an endian, an identifier of an imaging format, and/or the like. The parameter value(s) may include storage information, which may include a source identifier (e.g., an IP address) associated with the requestor device(s) 102, a source port associated with the requestor device(s) 102, and/or a destination workflow identifier (e.g., application entity title ("AET") in the DIMSE protocol) associated with at least a portion of the GPU application 142B. When the DICOMWeb protocol is used, the destination workflow identifier may be included in HTTP packet header information that was inserted by the requestor device(s) 102. By way of a non-limiting examples, the destination workflow identifier may identify an inference model implemented at least in part by the GPU application 142B.

The DPU application 142C may use the parameter value(s) to determine whether the input data 110 has a format (e.g., DICOM format) that is to be stored in the shared memory portion 150. By way of another non-limiting example, the DPU application 142C may use the storage information to determine whether the input data 110 is to be stored in the shared memory portion 150. For example, as mentioned above, the CPU application 142A may instruct the GPU(s) 118 and/or the GPU application 142B to allocate the shared memory portion 150, which may be used to process the payload data included in the packets $P_{input}$. After the GPU(s) 118 and/or the GPU application 142B allocate(s) the shared memory portion 150 and send(s) its address to the DPU application 142C, the DPU application 142C may store the address in the repository 144 and associate the address with the storage information (e.g., the source identifier, the source port, and/or the destination workflow identifier). Then, the DPU application 142C may look up the storage information in the repository 144 and determine the input data 110 is to be moved to the shared memory portion 150 when the storage information is associated with the address of the shared memory portion 150.

The shared memory portion 150 may include one or more different data blocks or buffers 152. Different ones of the buffer(s) 152 may be associated with different studies (e.g., the study 210 illustrated in FIG. 2). For example, the repository 144 may associate each of the buffer(s) 152 with a study identifier. The storage information may include a study identifier associated with one of the studies. The DPU application 142C may use the storage information to identify one or more of the buffer(s) 152 in which to store the input data 110. For example, the DPU application 142C may look up the storage information in the repository 144 and identify one or more of the buffer(s) 152 associated with the study identifier.

If the storage information is not associated with one or more of the buffer(s) 152, the DPU application 142C may send a request to the GPU application 142B and/or the GPU(s) 118 to allocate a new buffer in the shared memory portion 150. The request may include one or more of the parameter value(s) or information (e.g., a buffer size) obtained using the parameter value(s) that the GPU application 142B may use to allocate the new buffer. For example, the DPU application 142C may use at least some of the parameter value(s) to determine the buffer size, for example, by multiplying the number of columns, the number of rows, and the number of imaging files in the study together (e.g., N*K*M) and optionally performing one or more bit and/or precision conversions, if necessary. The DPU application 142C may send the buffer size (e.g., as metadata) to the GPU application 142B, which may allocate the new buffer for the input data 110 (e.g., a tensor, a TensorFlow tensor, a PyTorch tensor, CuPy array, and/or the like).

After the GPU application 142B and/or the GPU(s) 118 allocate(s) the new buffer in the shared memory portion 150, the GPU application 142B and/or the GPU(s) 118 send(s) an address of the new buffer to the DPU application 142C. The DPU application 142C may store the address in the repository 144 and associate the address with the storage information.

After one or more of the buffer(s) 152 is/are identified as being associated with the storage information, the DPU application 142C may optionally perform at least one pre-processing operation on the input data 110 (e.g., the DPU application 142C may convert and/or filter the input data 110) before storing the input data 110 in the identified buffer(s). The DPU application 142C may mark the packets P$_{input}$ in the receive queue(s) 134 as having been processed, which means the input data 110 has been stored in the identified buffer(s).

At this point, the input data 110 is awaiting processing by the GPU application 142B. Methods by which the GPU application 142B may detect or be notified that the input data 110 is awaiting processing are described in U.S. patent application Ser. No. 17/228,426 (NVIDIA Ref. 21-SC-0025US02), titled Packet Processing Acceleration Using Parallel Processing, filed on Apr. 12, 2021, and U.S. patent application Ser. No. 17/947,857, titled Using Parallel Processor(s) to Process Packets in Real-Time, filed on Sep. 19, 2022. Both of these U.S. patent applications are incorporated herein by reference in their entireties. The system 100 may use any of the methods described in the aforementioned patent applications to transfer the input data 110 to the GPU memory 122.

By way of a non-limiting example, the GPU application 142B may poll or query the receive queue(s) 134 for packets to determine when the network interface 114 has received the packets P$_{input}$ and stored the input data 110 in the shared memory portion 150. By way of another non-limiting example, the DPU application 142C may inform the GPU application 142B that the input data 110 has been stored in the shared memory portion 150. By way of yet another non-limiting example, the CPU application 142A may poll or query the receive queue(s) 134 for packets to determine when the network interface 114 has received the packets P$_{input}$ and stored the input data 110 in the shared memory portion 150. When the CPU application 142A determines stored the input data 110 has been stored in the shared memory portion 150, the CPU application 142A may inform the GPU application 142B that the input data 110 has been stored in the shared memory portion 150. For example, the CPU application 142A may launch the GPU application 142B. By way of yet another non-limiting example, when the GPU application 142B is already executing (e.g., as a persistent application, such as a persistent CUDA kernel), the CPU application 142A may set a ready flag (e.g., in a semaphore) in the shared memory portion 150 indicating the input data 110 is ready for processing. The GPU application 142B may poll or query the ready flag to determine when the input data 110 is ready for processing.

The GPU application 142B processes the input data 110 and obtains the output data 112. Then, the processing system 104 forwards the output data 112 (e.g., as the packets P$_{output}$) to the receiver device(s) 106.

In at least one embodiment, the network interface 114 may receive Electronic Medical Record ("EMR") data, for example, as packets from a computing device (not shown). The EMR data may include laboratory results, for example, stored as lightweight text data. The EMR data may be received using a Fast Healthcare Interoperability Resources ("FHIR") protocol (e.g., as a JSON formatted string stream), Health Level 7 ("HL7") protocol (e.g., as XML), and/or the like. The DPU application 142C may perform a deep packet inspection on the packets transmitting the EMR data and locate an identification value (e.g., associated with a hospital visit by a patient). The DPU application 142C may determine whether any imaging data is associated with the identification value. For example, the DPU application 142C may use a lookup table (e.g., stored in the repository 144) to determine whether imaging data is associated with the identification value. If the DPU application 142C determines imaging data is associated with the identification value, the DPU application 142C may request the imaging data from the from the requestor device(s) 102 (e.g., a potentially remote system). The requestor device(s) 102 may send the imaging data to the network interface 114 as the packets P$_{input}$. Thus, the DPU application 142C may process the EMR data and request the imaging data (e.g., from the requestor device(s) 102) if any is available. The EMR data and/or the imaging data may be used for inferencing.

FIG. 2 illustrates a block diagram of the study 210 transmitted in payload data of the packets P$_{input}$, and stored in the GPU memory 122, in accordance with at least one embodiment. Referring to FIG. 2, the packets P$_{input}$ may each include a header 202 and a payload portion 204. Each of the packets P$_{input}$ may include information that the DPU application 142C may extract using deep packet inspection. For example, the DPU application 142C may extract one or more parameter values 205 from the header 202 and/or the payload portion 204 of each of the packets P$_{input}$. By way of non-limiting examples, the parameter value(s) 205 may include the number (e.g., N) of columns in an imaging file, the number (e.g., K) of rows in the imaging file, the number (e.g., M) of imaging files belonging to the study, the identifier of the pixel format, the endian, the identifier of the imaging format, and/or the like. The parameter value(s) 205 may include storage information 206, which may include a source identifier 207 and/or a destination workflow identifier 208. Optionally, the storage information 206 may identify a source port. The source identifier 207 may identify the requestor device(s) 102 (see FIGS. 1 and 3) and/or a process being performed thereby. The destination workflow identifier 208 may identify the GPU application 142B (see FIGS. 1 and 3). As mentioned herein, referring to FIG. 1, the DPU application 142C may use the parameter value(s) 205 to determine whether the input data 110 has a format (e.g., DICOM format) that is to be stored in the shared memory portion 150. By way of another non-limiting example, the DPU application 142C may use the storage information 206 (see FIG. 2) to determine whether the input data 110 is to be stored in the shared memory portion 150. For example, the DPU application 142C may look up the storage information 206 in the repository 144 and determine the storage information 206 is associated with an address of the shared memory portion 150 or portion thereof.

Referring to FIG. 2, the storage information 206 may identify the study 210, an image in a series 212, and/or an instance 214 (or packet sequence number). By way of a non-limiting example, each time a study is performed with respect to a patient (e.g., the study 210), a study identifier is assigned to the study. In the example illustrated, a study identifier 220 has been associated with the study 210. The study 210 may include the series 212, which in the embodiment illustrated, includes images 212A-212C. However, the series 212 may include any number of images. Each image in the series 212 may be assigned a series identifier 222. The images 212A-212C may be characterized as being an imaging file. The packets P$_{input}$ may transmit many (e.g., hundreds of) imaging files (e.g., in the DICOM format), which may be part of the single study 210. Each of the packets P$_{input}$ may include the study identifier 220 for the study 210, the series identifier 222 identifying one of the images 212A-212C, and an instance identifier 224 that corresponds to a different location in the image identified by the series identifier 222 from which payload data 234 included in the payload portion 204 of the packet was obtained. The instance identifiers 224 may correspond to a packet sequence number and be used to order the packets P$_{input}$ so that the image(s) (e.g., the images 212A-212C) may be reassembled and/or used to construct a volume (e.g., a 3D volume, a 4D volume, and/or the like). The storage information 206 may include the study identifier 220 for the study 210, the series identifier 222 identifying one of the images 212A-212C, and/or the instance identifier 224. The storage information 206 may a packet size value and/or payload data size value.

The repository 144 (see FIG. 1) may associate the study identifier 220 with a particular one of the buffer(s) 152 (e.g., a buffer 230). In the example illustrated in FIG. 2, the buffer(s) 152 include buffers 230 and 232. However, the buffer(s) 152 may include any number of buffers, including a single buffer. Thus, the DPU application 142C (see FIGS. 1 and 3) may use the storage information 206 to identify one or more of the buffer(s) 152 in which to store the payload data 234 received in each of the packets P$_{input}$. For example, the DPU application 142C may look up the storage information 206 in the repository 144 and identify one or more of the buffer(s) 152 associated with the storage information 206 (e.g., the study identifier 220). In the example illustrated in FIG. 2, the storage information 206 is associated with a buffer 230.

Referring to FIG. 1, if the storage information 206 (see FIG. 2) is not associated with one or more of the buffer(s) 152, the DPU application 142C may send a request including the parameter value(s) 205 or information (e.g., a buffer size) obtained using the parameter value(s) 205 to the GPU application 142B and/or the GPU(s) 118 to allocate a new buffer in the shared memory portion 150. The GPU application 142B and/or the GPU(s) 118 may use the parameter value(s) 205 and/or the information obtained using the parameter value(s) 205 to allocate the new buffer in the shared memory portion 150 and send an address of the new buffer to the DPU application 142C, which may store the address in the repository 144 and associate the address with the storage information 206. Thus, if a subsequent packet having the same the study identifier 220 is received, the DPU application 142C may look up the storage information 206 in the repository 144 and identify the buffer 230 has being the location in which to store the payload data 234 included in the packet.

Each of at least a portion of the buffer(s) 152 may be associated with a different study (e.g., the study 210). Thus, the DPU application 142C (see FIGS. 1 and 3) may be used with multiple different studies each associated with a different buffer like the buffer 230. The DPU application 142C may perform deep packet inspection on the packets P$_{input}$ and locate the source identifier 207, the destination workflow identifier 208, the study identifier 220, the series identifier 222, and/or the instance identifier 224 in each of the packets P$_{input}$. If the packets P$_{input}$ are transmitting a series of images (e.g., the series 212) associated with the same study identifier, the images may be assembled into a volume and the series identifiers may be characterized as corresponding to an offset within that volume (e.g., along one or more axes). The instance identifiers may be characterized as corresponding to one or more memory locations 236 (e.g., a range of memory locations) in the buffer 230 (corresponding to the volume) where the payload data 234 in the payload portion 204 will be stored by the DPU application 142C. The range may be determined based at least in part on the instance identifiers and the payload data size values.

Figure 3:
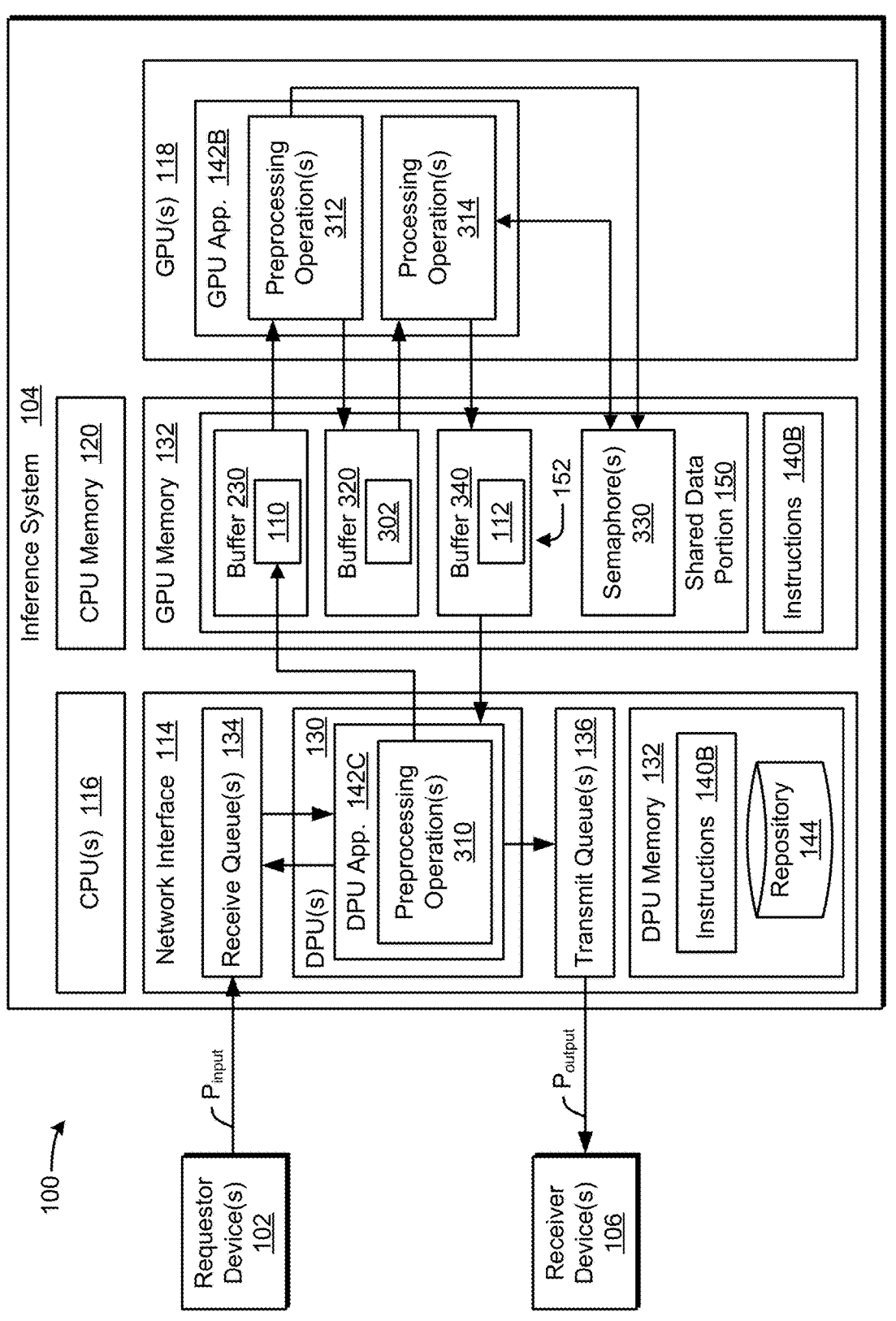
FIG. 3 illustrates the system of FIG. 1 receiving and processing packets, in accordance with at least one embodiment.

FIG. 3 illustrates the system 100 receiving and processing the packets P$_{input}$, in accordance with at least one embodiment. Referring to FIG. 3, instead of the CPU(s) 116 performing one or more preprocessing operations on the input data 110 and supplying processed input data to the GPU(s), one or more of the DPU(s) 130 and/or one or more of the GPU(s) 118 may perform the preprocessing operation(s) on the input data 110 to obtain processed input data 302 before the GPU(s) 118 perform processing operation(s) (e.g., inferencing operation(s)) on the processed input data 302. Thus, the GPU application 142B and/or the DPU application 142C may include one or more preprocessing operations. In the embodiment illustrated, the DPU application 142C includes preprocessing operation(s) 310 and the GPU application 142B includes preprocessing operation(s) 312. By way of non-limiting example, the preprocessing operation(s) 310 may include for example, alignment transformation operation(s) and/or data format conversion operation(s). The preprocessing operation(s) 310 may include for example, data format conversion operation(s) that convert data received in the packets P$_{input}$ to the input data 110 that the DPU application 144C stores in one or more of the buffer(s) 152 (e.g., in the buffer 230). By way of non-limiting example, the payload data 234 (see FIG. 2) received in the packets P$_{input}$ may have a medical format (e.g., DICOM format) and the preprocessing operation(s) 310 may convert the payload data 234 from the medical format to a GPU-friendly format (e.g., a tensor format, a TensorFlow tensor format, a PyTorch tensor format, CuPy array format, and/or the like). The preprocessing operation(s) 310 may remove the header 202, assemble the input data 110 from multiple different packets, perform defragmentation of the payload data 234 communicated by the packets P$_{input}$, and/or the like. The preprocessing operation(s) 310 may convert pixel representations (in the imaging files) in the payload data 234 to a floating point and/or integer representation. For example, the DICOM format may allow data (e.g., pixels) to be represented in one or more formats that are not supported by the GPU(s) 118 (e.g., 12-bit data, 10-bit data, and/or the like). The preprocessing operation(s) 310 may convert such data into a destination format that is compatible with the GPU(s) 118 (e.g., float32, int16, int32, etc.). Thus, incoming pixel data (e.g., represented in 12-bit) may be converted into a compatible pixel format (e.g., 32-bit floating point format) by the preprocessing operation(s) 310.

As mentioned herein, the DPU application 142C may extract the parameter value(s) 205 (see FIG. 2) from the packets P$_{input}$. The preprocessing operation(s) 310 may use the parameter value(s) 205 (e.g., imaging format) to convert the payload data 234 (see FIG. 2) into a format (e.g., a tensor, a TensorFlow tensor, a PyTorch tensor, CuPy array, and/or the like) upon which the preprocessing operation(s) 312 may be performed. For example, the preprocessing operation(s) 310 may convert those of the packets P$_{input}$ communicating the series 212 of the images 212A-212C into a data structure, such as a PyTorch Tensor (e.g., representing a two-dimensional (2D) image, a 3D volume, a 4D volume, a sinogram, and/or the like) that the GPU application 142B may process.

The GPU application 142B includes one or more processing operations 314. The preprocessing operation(s) 312 convert the input data 110 stored in the buffer 230 to the processed input data 302, which may be processed by the processing operation(s) 314. The preprocessing operation(s) 312 may store the processed input data 302 in a process buffer 320. The process buffer 320 may be separate from the buffer 230 and accessible by those of the GPU(s) 118 that will perform the processing operation(s) 314 on the processed input data 302.

The preprocessing operation(s) 312 may prepare the input data 110 for the processing operation(s) 314, so that the processing operation(s) 314 may provide a reliable result. By way of non-limiting example, the preprocessing operation(s) 312 may include for example, alignment transformation operation(s) and/or data format conversion operation(s). The preprocessing operation(s) 312 may include, for example, normalizing the intensity values, normalizing spatial dimensions, scaling pixel size from non-isotropic to isotropic, and/or performing histogram normalization. In some implementations, the preprocessing operation(s) 312 may be performed after all of the packets P$_{input}$ for a particular study (e.g., the study 210 illustrated in FIG. 2) have been received.

The preprocessing operation(s) 312 may notify the processing operation(s) 314 that the processed input data 302 is ready for processing. For example, a semaphore is a block of memory used to communicate information (e.g., status, address, data size, etc.) between different processors and/or processes. The shared memory portion 150 may store one or more semaphores 330 that may store information, such as one or more parameter values, that is to be shared between different processors and/or processes. The parameter value(s) may include a ready flag, a memory address of the corresponding buffer (e.g., of a first location in the corresponding buffer), and a data size value that may be used to identify a number of strides in a corresponding buffer (e.g., the process buffer 320). The preprocessing operation(s) 312 may set a ready flag (e.g., equal to TRUE) of one of the semaphore(s) 330 corresponding to the process buffer 320 after storing the processed input data 302 in the process buffer 320. The processing operation(s) 314 may poll the semaphore and determine when the ready flag indicates the processed input data 302 is available. The processing operation(s) 314 may also obtain the memory address and/or data size value from the semaphore and use this information to locate the processed input data 302.

The processing operation(s) 314 may include, for example, performing inferencing, performing one or more diagnostic tasks (e.g., detecting a disease condition, such as the presence of COVID-19, cancer, heart disease, and/or the like), and/or the like. The processing operation(s) 314 obtain the processed input data 302 from the process buffer 320, process the processed input data 302 to produce the output data 112, and optionally store the output data 112 in an output buffer 340. Alternatively or additionally, the processing operation(s) 314 may transmit the output data 112 to the transmit queue(s) 136 and/or the CPU memory 120.

Figure 4:
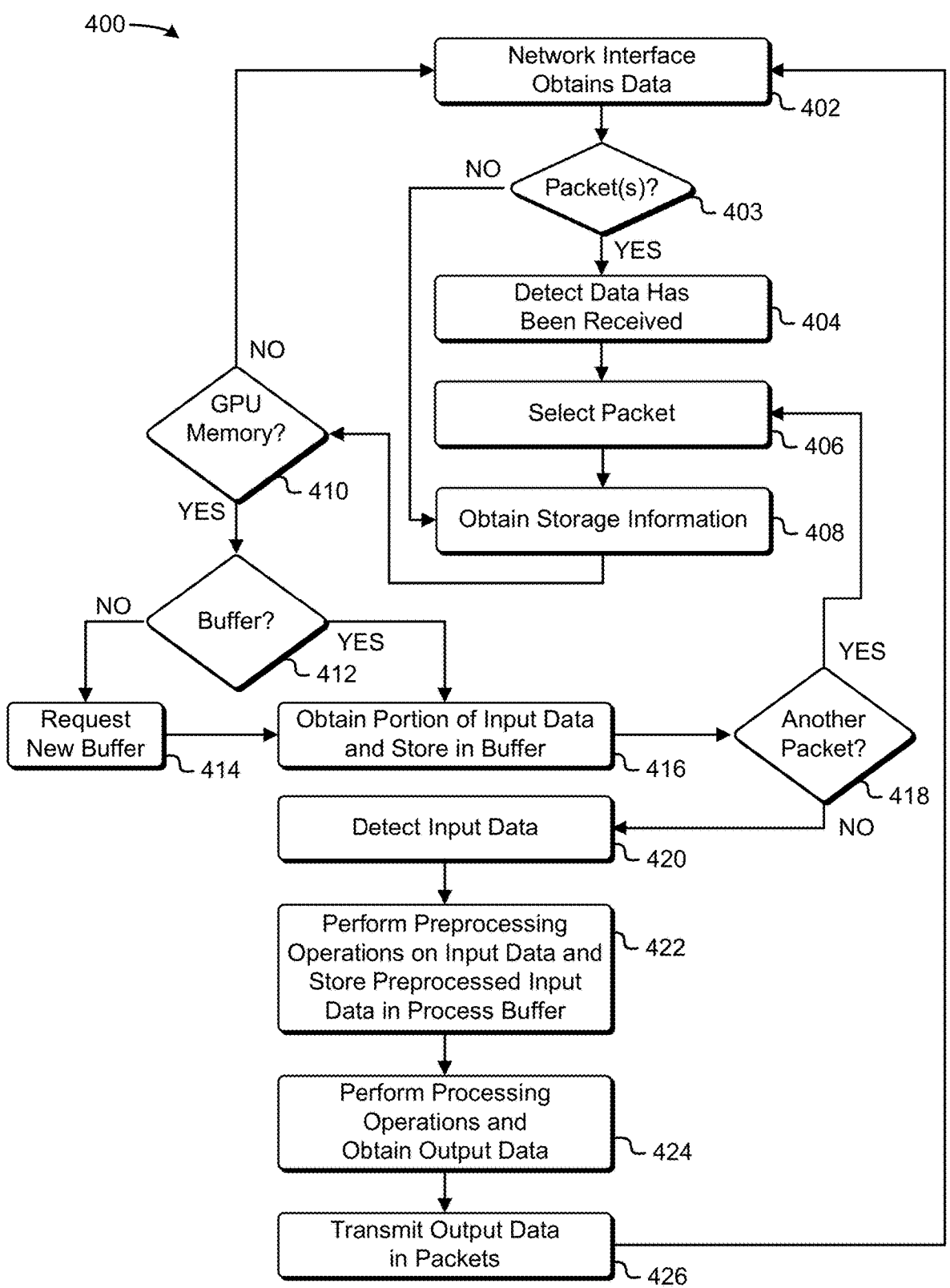
FIG. 4 illustrates a flow diagram of a method of processing data, in accordance with at least one embodiment.

FIG. 4 illustrates a flow diagram of a method 400 of processing data (e.g., the packets P$_{input}$), in accordance with at least one embodiment. The method 400 may be performed by the system 100. For example, at least a portion of the method 400 may be performed by the DPU application 142C and at least a portion of the method 400 may be performed by the GPU application 142B.

In first block 402, the system 100 obtains the data. For example, the data may be received from the requestor device(s) 102 as the packets P$_{input}$ and stored in the receive queue(s) 134. In at least one embodiment, instead of receiving the data from the requestor device(s) 102, the network interface 114 may load or read the input data 110 from memory (e.g., the CPU memory 120, one of the optional data storage unit(s) 108, an emulated storage device, and/or the like). In such embodiments, the network interface 114 may function as a DMA engine that may perform one or more in-flight transformation of the data. The network interface 114 may optionally store the data obtained from the memory in the receive queue(s) 134 as the packets P$_{input}$. Alternatively, the data may not be stored in the receive queue(s) 134. Thus, the data may be stored in the receive queue(s) 134 as the packets P$_{input}$ or obtained directly by the DPU(s) 130 (see FIGS. 1 and 3).

If the data was stored in the receive queue(s) 134 as the packets P$_{input}$ the decision in decision block 403 is "YES." Otherwise, the decision in decision block 403 is "NO." When the decision in decision block 403 is "YES," the DPU application 142C advances to block 404. On the other hand, when the decision in decision block 403 is "NO," the DPU application 142C advances to block 408.

In block 404, the DPU application 142C may detect that the receive queue(s) 134 has received the packets P$_{input}$. For example, the DPU application 142C may detect the packets P$_{input}$ have been received by polling the receive queue(s) 134 for new packets. Then, in block 406, the DPU application 142C selects one of the packets P$_{input}$ and advances to block 408.

In block 408, the DPU application 142C may obtain the parameter value(s) 205 (see FIG. 2), which include the storage information 206 (e.g., the source identifier 207, the destination workflow identifier 208, and/or the study identifier 220). If the decision in decision block 403 was "YES," the DPU application 142C may obtain the parameter value(s) 205 from the packet selected in block 406 (e.g., using deep packet inspection). Otherwise, the DPU application 142C may obtain the parameter value(s) 205 from the data obtained in block 402.

In decision block 410, the DPU application 142C determines whether the parameter value(s) 205 (e.g., the storage information 206) indicate that at least a portion of the data obtained in block 402 (e.g., the payload data 234 of the selected packet) is to be stored in the GPU memory 122. The decision in decision block 410 is "YES" when the DPU application 142C determines the parameter value(s) 205 indicate at least a portion of the data obtained in block 402 is to be stored in the GPU memory 122. Otherwise, the decision in decision block 410 is "NO." The DPU application 142C may make the determination in decision block 410 based on whether the parameter value(s) 205 indicate that at least a portion of the data obtained in block 402 (e.g., the payload data 234 of the selected packet) has a format (e.g., DICOM format) that is to be stored in the GPU memory 122. Alternatively or additionally, the DPU application 142C may make the determination in decision block 410 by looking up the storage information 206 (e.g., the source identifier 207 and/or the destination workflow identifier 208) in the repository 144 (see FIG. 1), which may indicate whether at least a portion of the data obtained in block 402 is to be stored in the GPU memory 122. For example, the repository 144 may associate the storage information 206 with an address of the shared memory portion 150 when at least a portion of the data obtained in block 402 is to be stored in the GPU memory 122.

When the decision in decision block 410 is "NO," the system 100 returns to block 402 to obtain new data (e.g., new packets). On the other hand, when the decision in decision block 410 is "YES," in decision block 412, the DPU application 142C determines whether the shared memory portion 150 includes a buffer to receive the data obtained in block 402 (e.g., in the selected packet). The decision in decision block 412 is "YES" when the DPU application 142C determines the shared memory portion 150 includes a buffer to receive the data. Otherwise, the decision in decision block 412 is "NO." The DPU application 142C may make the determination in decision block 412 by looking up the storage information 206 (e.g., the study identifier 220) in the repository 144 (see FIG. 1), which may identify one or more of the buffer(s) 152 in which to store the data.

When the decision in decision block 412 is "NO," in block 414, the DPU application 142C may send a request to the GPU(s) 118 and/or the GPU application 142B to allocate a new buffer. The request may include one or more of the parameter value(s) and/or information obtained using one or more of the parameter value(s) 205 that the GPU(s) 118 and/or the GPU application 142B may use to allocate the new buffer. The GPU(s) 118 and/or the GPU application 142B may allocate the new buffer in the shared memory portion 150 and send an address of the new buffer to the DPU application 142C. The DPU application 142C may store the address in the repository 144 and associate the address with the storage information 206. After the block 414, the DPU application 142C advances to block 416.

When the decision in decision block 412 is "YES," the DPU application 142C advances to block 416. In block 416, the DPU application 142C obtains at least a portion of the input data 110 by performing the preprocessing operation(s) 310 on the data (e.g., the data obtained in block 402 or the payload data 234 of the selected packet) and stores the portion of the input data 110 in the buffer (e.g., the buffer 230) identified in decision block 412 or block 414. In block 416, when the decision in decision block 403 was "YES," the DPU application 142C may mark the selected packet in the receive queue(s) 134 as having been processed (e.g., having its payload data 234 stored in the shared memory portion 150).

Then, in decision block 418, the DPU application 142C determines whether there is another packet to process. The decision in decision block 418 is "NO," when the decision in decision block 403 was "NO" or the DPU application 142C determines the packet is the last packet, which means all of the packets $P_{input}$ have been selected in block 406 and the input data 110 is stored in the buffer (e.g., the buffer 230) identified in decision block 412. Otherwise, the decision in decision block 418 is "YES." When the decision in decision block 418 is "YES," the DPU application 142C returns to block 406 and selects another one of the packets $P_{input}$.

On the other hand, when the decision in decision block 418 is "NO," in block 420, the GPU application 143B detects the input data 110 is stored in the buffer (e.g., the buffer 230) identified in decision block 412. In block 420, the GPU application 142B may detect the input data 110 by polling or querying the receive queue(s) 134 for packets and, when the GPU application 142B detects the packets $P_{input}$, determining the buffer (e.g., the buffer 230) identified in decision block 412 stores the input data 110 when the DPU application 142C has marked the packets $P_{input}$ as having been processed. By way of another non-limiting example, the DPU application 142C may inform the GPU application 142B that the input data 110 has been stored in the shared memory portion 150. For example, the DPU application 142C may set a ready flag (e.g., in a semaphore) in the shared memory portion 150 indicating the input data 110 is ready for processing (e.g., the ready flag may be set to TRUE when the buffer 230 is storing data awaiting processing). The GPU application 142B may poll or query the ready flag to determine when the input data 110 is ready for processing. In such embodiments, the GPU application 142B may locate and obtain the input data 110 using a memory address and a data size value stored in the semaphore.

By way of yet another non-limiting example, the CPU application 142A may poll or query the receive queue(s) 134 for packets to determine when the network interface 114 has received the packets $P_{input}$ and stored the input data 110 in the shared memory portion 150. When the CPU application 142A determines the input data 110 has been stored in the shared memory portion 150, the CPU application 142A may inform the GPU application 142B that the input data 110 has been stored in the shared memory portion 150. For example, the CPU application 142A may launch the GPU application 142B or otherwise cause the preprocessing operation(s) 312 to be performed on the input data 110. By way of yet another non-limiting example, when the GPU application 142B is already executing (e.g., as a persistent application, such as a persistent CUDA kernel), the CPU application 142A may set a ready flag (e.g., in a semaphore) in the shared memory portion 150 indicating the input data 110 is ready for processing (e.g., the ready flag may be set to TRUE when the buffer 230 is storing data awaiting processing). The GPU application 142B may poll or query the ready flag to determine when the input data 110 is ready for processing. In such embodiments, the GPU application 142B may locate and obtain the input data 110 using a memory address and a data size value stored in the semaphore.

In block 422, the GPU application 142B obtains the input data 110 from the buffer (e.g., the buffer 230) identified in decision block 412, performs the preprocessing operation(s) 312 on the input data 110, and stores the preprocessed input data 302 in a process buffer (e.g., the process buffer 320). After the GPU application 142B obtains the input data 110, the GPU application 142B may update the ready flag (e.g., the ready flag may be set to FALSE) to indicate that the corresponding buffer is not storing data or that the input data 110 is no longer awaiting processing.

Then, in block 424, the GPU application 142B obtains the processed input data 302 from the process buffer (e.g., the process buffer 320), performs the processing operation(s) 314 on the processed input data 302 to obtain the output data 112.

Next, in block 426, the system 100 transmits the output data 112 in the packets $P_{output}$ to the receiver device(s) 106. In block 426, the GPU application 142B may store the output data 112 in an output buffer (e.g., the output buffer 340) and/or update a semaphore associated with the output buffer 340. The DPU application 142C may poll the semaphore associated with the output buffer 340 to determine when the output data 112 is ready. When the DPU application 142C determines the output data 112 is ready, the DPU application 142C may copy the output data 112 to the transmit queue(s) 136. By way of another non-limiting example, the GPU application 142B may copy the output data 112 to the transmit queue(s) 136 on the network interface 114 and/or to the CPU memory 120 instead of or in addition to storing the output data 112 in the output buffer 340. Optionally, when the output data 112 is copied to the CPU memory 120, the CPU(s) 116 may perform post-processing operation(s) on the output data 112 before copying the output data 112 to the transmit queue(s) 136 of the network interface 114. Then, the network interface 114 may send the output data 112 (in the packets $P_{output}$) to the receiver device(s) 106.

While the method 400 has been described as processing the packets $P_{input}$ serially, the method 400 may process at least a portion of the packets $P_{input}$ parallelly.

Referring to FIG. 1, the DPU(s) 130 of the system 100 do/does not direct the input data 110 to the CPU memory 120. Instead, the DPU(s) 130 may direct the input data 110 to the GPU memory 122 after performing the preprocessing operation(s) 310 (see FIG. 3) on at least a portion of the payload data 234 (see FIG. 2) transmitted by the packets $P_{input}$. Then, the GPU application 142B may perform the preprocessing operation(s) 312 (see FIG. 3) on the input data 110 to prepare the processed input data 302 (see FIG. 3) for the processing operation(s) 314 (see FIG. 3). Thus, the processing system 104 may use one or more of the DPU(s) 130 and/or one or more of the GPU(s) 118, instead of the CPU(s) 116, to perform preprocessing operation(s) (e.g., the preprocessing operation(s) 310 and/or 312) on the payload data 234 received in the packets $P_{input}$ to produce the processed input data 302.

The preprocessing operation(s) 310 of the DPU application 142C may convert the payload data 234 in the packets $P_{input}$ from a first format (e.g., DICOM format) into the converted input data 110 having a second format (e.g., a tensor, a TensorFlow tensor, a PyTorch tensor, CuPy array, or the like) that may be preprocessed by the preprocessing operation(s) 312 (e.g., transformed, normalized, and/or the like) into the preprocessed input data 302 that has a third format that may be processed by the processing operation(s) 314, which may include a model-based algorithm (e.g., a machine learning algorithm, such as a neural network) that makes one or more inferences (e.g., detect a tumor) based on the preprocessed input data 302. By way of non-limiting examples, the preprocessing operation(s) 312 may include for example, normalizing the intensity values, normalizing spatial dimensions, scaling pixel size from non-isotropic to isotropic, and/or performing histogram normalization.

The DPU(s) 130 and/or the DPU application 142C may inspect the payload data 234 as it arrives (packet-by-packet) and the DPU application 142C and/or GPU application 142B may converts(s) the payload data 234 on the fly allowing the processing operation(s) 314 (e.g., one or more inference operations) to be performed on the preprocessed input data 302 as the payload data 234 is received.

Figure 5:
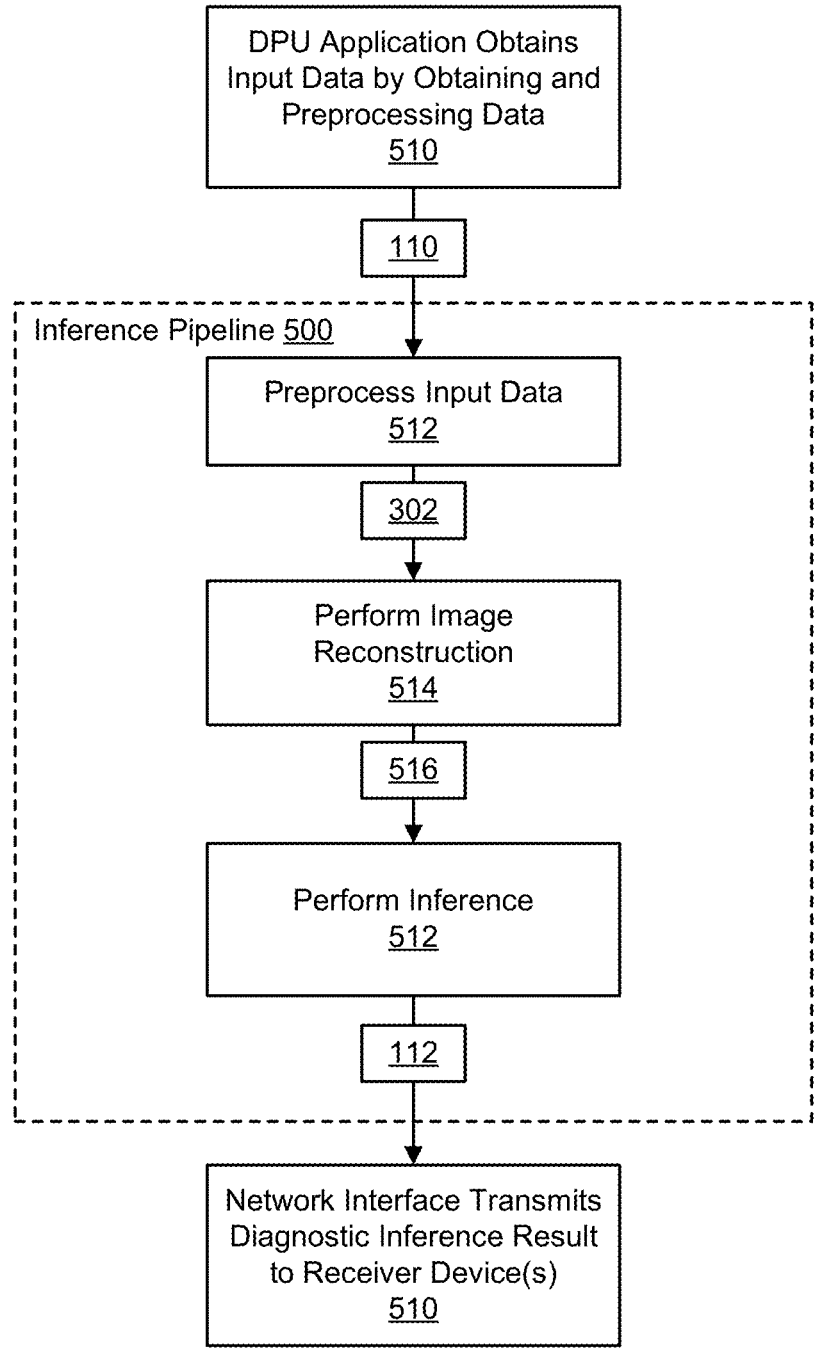
FIG. 5 is a block diagram illustrating an inference pipeline for processing imaging data, in accordance with at least one embodiment.

FIG. 5 is a block diagram illustrating an inference pipeline 500 for processing imaging data, in accordance with at least one embodiment. Referring to FIG. 5, the inference pipeline 500 may implemented by the GPU(s) 118 of the processing system 104 (see FIGS. 1 and 3). The payload data 234 included in the packets $P_{input}$ may include imaging data that, for example, may be assembled into at least one sinogram. Sinograms are projections of 3D images Thus, the payload data 234 may include projections of a volume (e.g., 3D or 4D) instead of slices of (or images captured from) the volume. By way of a non-limiting example, the imaging data (e.g., a sinogram) may be stored and/or transmitted as DICOM data to the processing system 104 for inference. The inference pipeline 500 may receive the input data 110 from the DPU application 142C. As described herein, in block 510, the DPU application 142C may obtain the imaging data, perform the preprocessing operation(s) 310 on the imaging data to obtain the input data 110, and store the input data 110 in the GPU memory 122. The DPU application 142C may obtain the imaging data by receiving the packets $P_{input}$ and/or loading the imaging data from memory (e.g., the CPU memory 120, one of the optional data storage unit(s) 108, an emulated storage device, and/or the like).

Then, at block 512, the GPU application 142B may obtain the input data 110 from the GPU memory 122 and perform the preprocessing operation(s) 312 on the input data 110 to obtain the processed input data 302. For example, the preprocessing operation(s) 312 may include sinogram normalization, scatter correction, and/or the like.

Next, at block 514, the GPU application 142B may perform the processing operation(s) 314 on the processed input data 302. The processing operation(s) 314 may include performing an image reconstruction using the processed input data 302 to obtain a (e.g., 3D or 4D) volume 516. The processing operation(s) 314 may also include performing at least one inference on the volume 516 to obtain the output data 112 (e.g., one or more diagnostic results). In at least one embodiment, the processing operation(s) 314 may omit reconstructing the volume 516. In such embodiments, the processing operation(s) 314 may perform at least one inference on the processed input data 302 to obtain the output data 112.

The GPU application 142B may provide the output data 112 (e.g., as the packets $P_{output}$) to the network interface 114, which may transmit the output data 112 (e.g., as the packets $P_{output}$) to the receiver device(s) 106.

Servers and Data Centers

The following figures set forth, without limitation, exemplary network server and data center based systems that can be used to implement at least one embodiment.

Figure 6:
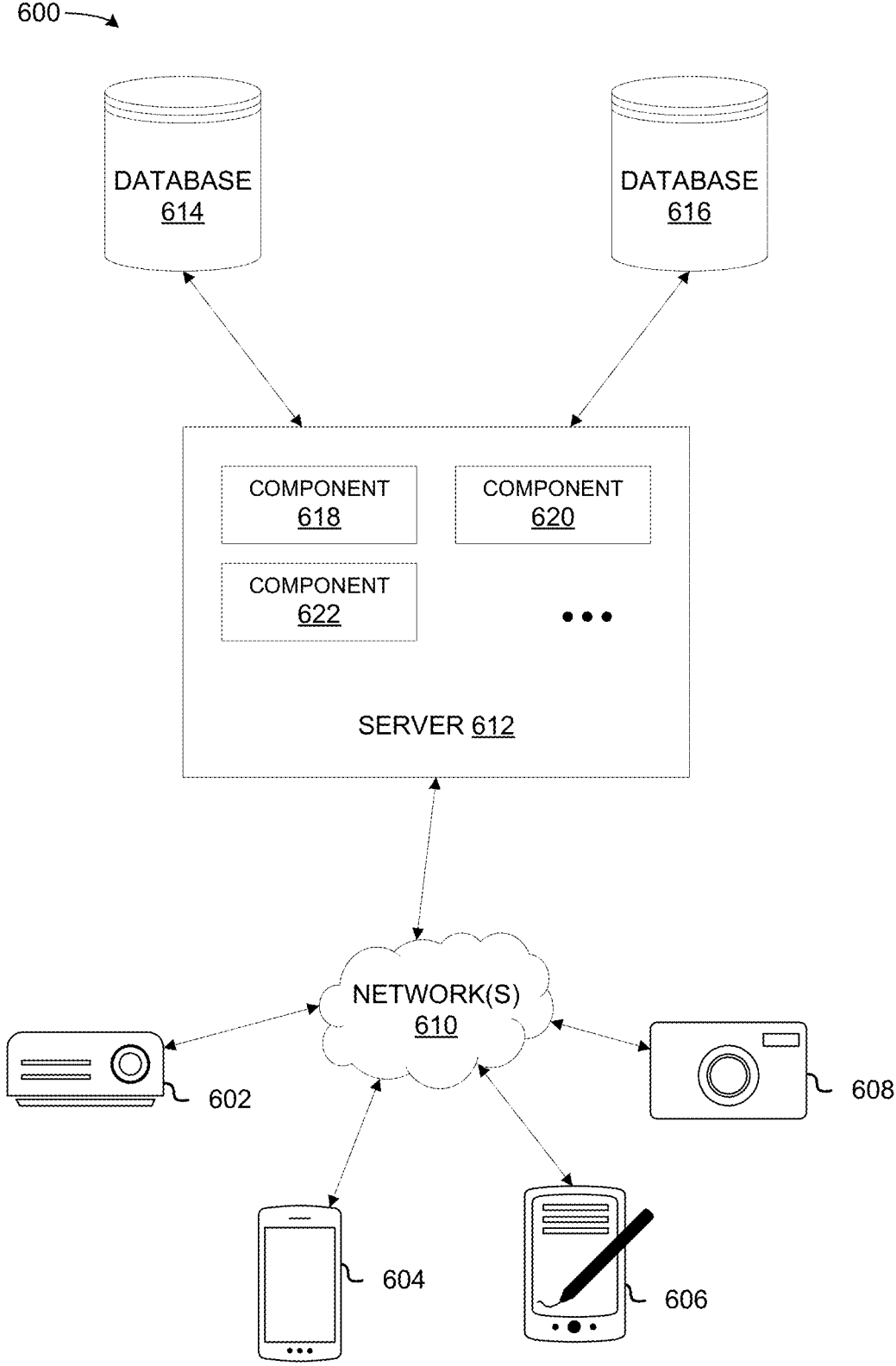
FIG. 6 illustrates a distributed system, in accordance with at least one embodiment.

FIG. 6 illustrates a distributed system 600, in accordance with at least one embodiment. In at least one embodiment, distributed system 600 includes one or more client computing devices 602, 604, 606, and 608, which are configured to execute and operate a client application such as a web browser, proprietary client, and/or variations thereof over one or more network(s) 610. In at least one embodiment, server 612 may be communicatively coupled with remote client computing devices 602, 604, 606, and 608 via network 610.

In at least one embodiment, server 612 may be adapted to run one or more services or software applications such as services and applications that may manage session activity of single sign-on (SSO) access across multiple data centers. In at least one embodiment, server 612 may also provide other services or software applications can include non-virtual and virtual environments. In at least one embodiment, these services may be offered as web-based or cloud services or under a Software as a Service (SaaS) model to users of client computing devices 602, 604, 606, and/or 608. In at least one embodiment, users operating client computing devices 602, 604, 606, and/or 608 may in turn utilize one or more client applications to interact with server 612 to utilize services provided by these components.

In at least one embodiment, software components 618, 620 and 622 of system 600 are implemented on server 612. In at least one embodiment, one or more components of system 600 and/or services provided by these components may also be implemented by one or more of client computing devices 602, 604, 606, and/or 608. In at least one embodiment, users operating client computing devices may then utilize one or more client applications to use services provided by these components. In at least one embodiment, these components may be implemented in hardware, firmware, software, or combinations thereof. It should be appreciated that various different system configurations are possible, which may be different from distributed system 600. The embodiment shown in FIG. 6 is thus one example of a distributed system for implementing an embodiment system and is not intended to be limiting.

In at least one embodiment, client computing devices 602, 604, 606, and/or 608 may include various types of computing systems. In at least one embodiment, a client computing device may include portable handheld devices (e.g., an iPhone®, cellular telephone, an iPad®, computing tablet, a personal digital assistant (PDA)) or wearable devices (e.g., a Google Glass® head mounted display), running software such as Microsoft Windows Mobile®, and/or a variety of mobile operating systems such as iOS, Windows Phone, Android, BlackBerry 10, Palm OS, and/or variations thereof. In at least one embodiment, devices may support various applications such as various Internet-related apps, e-mail, short message service (SMS) applications, and may use various other communication protocols. In at least one embodiment, client computing devices may also include general purpose personal computers including, by way of example, personal computers and/or laptop computers running various versions of Microsoft Windows®, Apple Macintosh®, and/or Linux operating systems. In at least one embodiment, client computing devices can be workstation computers running any of a variety of commercially-available UNIX® or UNIX-like operating systems, including without limitation a variety of GNU/Linux operating systems, such as Google Chrome OS. In at least one embodiment, client computing devices may also include electronic devices such as a thin-client computer, an Internet-enabled gaming system (e.g., a Microsoft Xbox gaming console with or without a Kinect® gesture input device), and/or a personal messaging device, capable of communicating over network(s) 610. Although distributed system 600 in FIG. 6 is shown with four client computing devices, any number of client computing devices may be supported. Other devices, such as devices with sensors, etc., may interact with server 612.

In at least one embodiment, network(s) 610 in distributed system 600 may be any type of network that can support data communications using any of a variety of available protocols, including without limitation TCP/IP (transmission control protocol/Internet protocol), SNA (systems network architecture), IPX (Internet packet exchange), AppleTalk, and/or variations thereof. In at least one embodiment, network(s) 610 can be a local area network (LAN), networks based on Ethernet, Token-Ring, a wide-area network, Internet, a virtual network, a virtual private network (VPN), an intranet, an extranet, a public switched telephone network (PSTN), an infra-red network, a wireless network (e.g., a network operating under any of the Institute of Electrical and Electronics (IEEE) 802.11 suite of protocols, Bluetooth®, and/or any other wireless protocol), and/or any combination of these and/or other networks.

In at least one embodiment, server 612 may be composed of one or more general purpose computers, specialized server computers (including, by way of example, PC (personal computer) servers, UNIX® servers, mid-range servers, mainframe computers, rack-mounted servers, etc.), server farms, server clusters, or any other appropriate arrangement and/or combination. In at least one embodiment, server 612 can include one or more virtual machines running virtual operating systems, or other computing architectures involving virtualization. In at least one embodiment, one or more flexible pools of logical storage devices can be virtualized to maintain virtual storage devices for a server. In at least one embodiment, virtual networks can be controlled by server 612 using software defined networking. In at least one embodiment, server 612 may be adapted to run one or more services or software applications.

In at least one embodiment, server 612 may run any operating system, as well as any commercially available server operating system. In at least one embodiment, server 612 may also run any of a variety of additional server applications and/or mid-tier applications, including HTTP (hypertext transport protocol) servers, FTP (file transfer protocol) servers, CGI (common gateway interface) servers, JAVA® servers, database servers, and/or variations thereof. In at least one embodiment, exemplary database servers include without limitation those commercially available from Oracle, Microsoft, Sybase, IBM (International Business Machines), and/or variations thereof.

In at least one embodiment, server 612 may include one or more applications to analyze and consolidate data feeds and/or event updates received from users of client computing devices 602, 604, 606, and 608. In at least one embodiment, data feeds and/or event updates may include, but are not limited to, Twitter® feeds, Facebook® updates or real-time updates received from one or more third party information sources and continuous data streams, which may include real-time events related to sensor data applications, financial tickers, network performance measuring tools (e.g., network monitoring and traffic management applications), clickstream analysis tools, automobile traffic monitoring, and/or variations thereof. In at least one embodiment, server 612 may also include one or more applications to display data feeds and/or real-time events via one or more display devices of client computing devices 602, 604, 606, and 608.

In at least one embodiment, distributed system 600 may also include one or more databases 614 and 616. In at least one embodiment, databases may provide a mechanism for storing information such as user interactions information, usage patterns information, adaptation rules information, and other information. In at least one embodiment, databases 614 and 616 may reside in a variety of locations. In at least one embodiment, one or more of databases 614 and 616 may reside on a non-transitory storage medium local to (and/or resident in) server 612. In at least one embodiment, databases 614 and 616 may be remote from server 612 and in communication with server 612 via a network-based or dedicated connection. In at least one embodiment, databases 614 and 616 may reside in a storage-area network (SAN). In at least one embodiment, any necessary files for performing functions attributed to server 612 may be stored locally on server 612 and/or remotely, as appropriate. In at least one embodiment, databases 614 and 616 may include relational databases, such as databases that are adapted to store, update, and retrieve data in response to SQL-formatted commands.

In at least one embodiment, the distributed system 600 may be used to implement the system 100 (see FIG. 1) and/or the inference pipeline 500 (see FIG. 5). In at least one embodiment, the server 612 may be used to implement the processing system 104. In at least one embodiment, at least one of the client computing devices 602, 604, 606, and 608 may be used to implement the requestor device(s) 102, the receiver device(s) 106, and/or the optional data storage units 108. In at least one embodiment, at least one of the databases 614 and 616 may be used to implement the requestor device(s) 102, the receiver device(s) 106, and/or the optional data storage units 108. In at least one embodiment, at least a portion of the system(s) depicted in FIG. 6 is used to implement one or more systems, techniques, functions, and/or processes described in connection with FIGS. 1-5. For example, in at least one embodiment, at least one component shown or described with respect to FIG. 6 is used to process data (e.g., data having a DICOM format) in accordance with one or more techniques, functions, and/or processes described with respect to any of FIGS. 1-5.

FIG. 7 illustrates an exemplary data center 700, in accordance with at least one embodiment. In at least one embodiment, data center 700 includes, without limitation, a data center infrastructure layer 710, a framework layer 720, a software layer 730 and an application layer 740.

In at least one embodiment, as shown in FIG. 7, data center infrastructure layer 710 may include a resource orchestrator 712, grouped computing resources 714, and node computing resources ("node C.R.s") 716(1)-716(N), where "N" represents any whole, positive integer. In at least one embodiment, node C.R.s 716(1)-716(N) may include, but are not limited to, any number of central processing units ("CPUs") or other processors (including accelerators, field programmable gate arrays ("FPGAs"), graphics processors, etc.), memory devices (e.g., dynamic read-only memory), storage devices (e.g., solid state or disk drives), network input/output ("NW I/O") devices, network switches, virtual machines ("VMs"), power modules, and cooling modules, etc. In at least one embodiment, one or more node C.R.s from among node C.R.s 716(1)-716(N) may be a server having one or more of above-mentioned computing resources.

In at least one embodiment, grouped computing resources 714 may include separate groupings of node C.R.s housed within one or more racks (not shown), or many racks housed in data centers at various geographical locations (also not shown). Separate groupings of node C.R.s within grouped computing resources 714 may include grouped compute, network, memory or storage resources that may be configured or allocated to support one or more workloads. In at least one embodiment, several node C.R.s including CPUs or processors may grouped within one or more racks to provide compute resources to support one or more workloads. In at least one embodiment, one or more racks may also include any number of power modules, cooling modules, and network switches, in any combination.

In at least one embodiment, resource orchestrator 712 may configure or otherwise control one or more node C.R.s 716(1)-716(N) and/or grouped computing resources 714. In at least one embodiment, resource orchestrator 712 may include a software design infrastructure ("SDI") management entity for data center 700. In at least one embodiment, resource orchestrator 712 may include hardware, software or some combination thereof.

In at least one embodiment, as shown in FIG. 7, framework layer 720 includes, without limitation, a job scheduler 732, a configuration manager 734, a resource manager 736 and a distributed file system 738. In at least one embodiment, framework layer 720 may include a framework to support software 752 of software layer 730 and/or one or more application(s) 742 of application layer 740. In at least one embodiment, software 752 or application(s) 742 may respectively include web-based service software or applications, such as those provided by Amazon Web Services, Google Cloud and Microsoft Azure. In at least one embodiment, framework layer 720 may be, but is not limited to, a type of free and open-source software web application framework such as Apache Spark™ (hereinafter "Spark") that may utilize distributed file system 738 for large-scale data processing (e.g., "big data"). In at least one embodiment, job scheduler 732 may include a Spark driver to facilitate scheduling of workloads supported by various layers of data center 700. In at least one embodiment, configuration manager 734 may be capable of configuring different layers such as software layer 730 and framework layer 720, including Spark and distributed file system 738 for supporting large-scale data processing. In at least one embodiment, resource manager 736 may be capable of managing clustered or grouped computing resources mapped to or allocated for support of distributed file system 738 and job scheduler 732. In at least one embodiment, clustered or grouped computing resources may include grouped computing resource 714 at data center infrastructure layer 710. In at least one embodiment, resource manager 736 may coordinate with resource orchestrator 712 to manage these mapped or allocated computing resources.

In at least one embodiment, software 752 included in software layer 730 may include software used by at least portions of node C.R.s 716(1)-716(N), grouped computing resources 714, and/or distributed file system 738 of framework layer 720. One or more types of software may include, but are not limited to, Internet web page search software, e-mail virus scan software, database software, and streaming video content software.

In at least one embodiment, application(s) 742 included in application layer 740 may include one or more types of applications used by at least portions of node C.R.s 716(1)-716(N), grouped computing resources 714, and/or distributed file system 738 of framework layer 720. In at least one or more types of applications may include, without limitation, CUDA applications, 5G network applications, artificial intelligence application, data center applications, and/or variations thereof.

In at least one embodiment, any of configuration manager 734, resource manager 736, and resource orchestrator 712 may implement any number and type of self-modifying actions based on any amount and type of data acquired in any technically feasible fashion. In at least one embodiment, self-modifying actions may relieve a data center operator of data center 700 from making possibly bad configuration decisions and possibly avoiding underutilized and/or poor performing portions of a data center.

In at least one embodiment, the data center 700 may be used to implement the system 100 (see FIG. 1) and/or the inference pipeline 500 (see FIG. 5). In at least one embodiment, the grouped computing resources 714 and/or one or more of the node C.R.s 716(1)-716(N) may be used to implement the processing system 104, the requestor device(s) 102, the receiver device(s) 106, and/or the optional data storage units 108. In at least one embodiment, the software layer 730 and/or the application layer 740 may include at least a portion of one or more of the CPU application 142A, the GPU application 142B, and/or the DPU application 142C. In at least one embodiment, at least a portion of the system(s) depicted in FIG. 7 is used to implement one or more systems, techniques, functions, and/or processes described in connection with FIGS. 1-5. For example, in at least one embodiment, at least one component shown or described with respect to FIG. 7 is used to process data (e.g., data having a DICOM format) in accordance with one or more techniques, functions, and/or processes described with respect to any of FIGS. 1-5.

Figure 8:
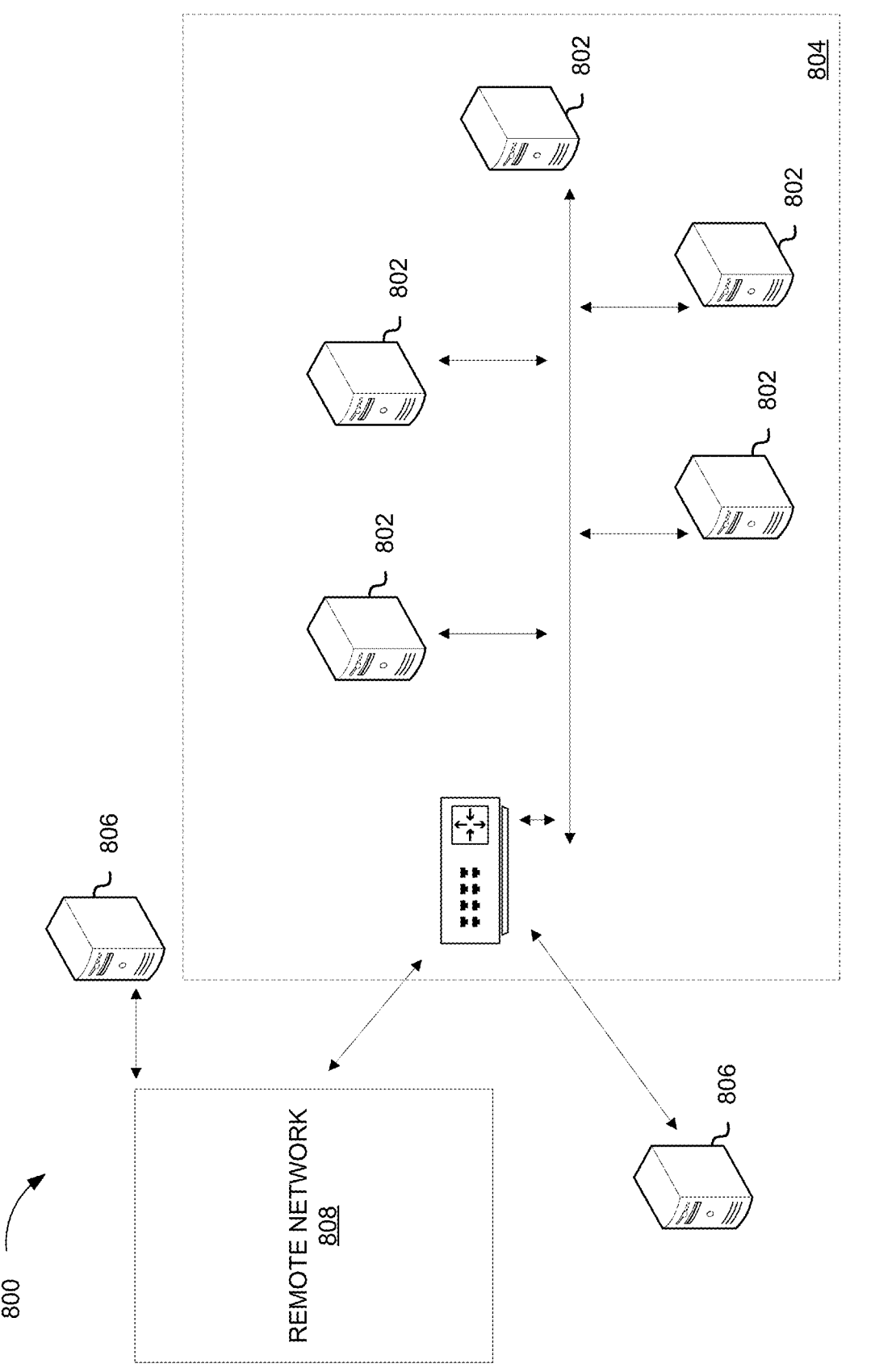
FIG. 8 illustrates a client-server network, in accordance with at least one embodiment.

FIG. 8 illustrates a client-server network 804 formed by a plurality of network server computers 802 which are interlinked, in accordance with at least one embodiment. In at least one embodiment, in a system 800, each network server computer 802 stores data accessible to other network server computers 802 and to client computers 806 and networks 808 which link into a wide area network 804. In at least one embodiment, configuration of a client-server network 804 may change over time as client computers 806 and one or more networks 808 connect and disconnect from a network 804, and as one or more trunk line server computers 802 are added or removed from a network 804. In at least one embodiment, when a client computer 806 and a network 808 are connected with network server computers 802, client-server network includes such client computer 806 and network 808. In at least one embodiment, the term computer includes any device or machine capable of accepting data, applying prescribed processes to data, and supplying results of processes.

In at least one embodiment, client-server network 804 stores information which is accessible to network server computers 802, remote networks 808 and client computers 806. In at least one embodiment, network server computers 802 are formed by main frame computers minicomputers, and/or microcomputers having one or more processors each. In at least one embodiment, server computers 802 are linked together by wired and/or wireless transfer media, such as conductive wire, fiber optic cable, and/or microwave transmission media, satellite transmission media or other conductive, optic or electromagnetic wave transmission media. In at least one embodiment, client computers 806 access a network server computer 802 by a similar wired or a wireless transfer medium. In at least one embodiment, a client computer 806 may link into a client-server network 804 using a modem and a standard telephone communication network. In at least one embodiment, alternative carrier systems such as cable and satellite communication systems also may be used to link into client-server network 804. In at least one embodiment, other private or time-shared carrier systems may be used. In at least one embodiment, network 804 is a global information network, such as the Internet. In at least one embodiment, network is a private intranet using similar protocols as the Internet, but with added security measures and restricted access controls. In at least one embodiment, network 804 is a private, or semi-private network using proprietary communication protocols.

In at least one embodiment, client computer 806 is any end user computer, and may also be a mainframe computer, mini-computer or microcomputer having one or more microprocessors. In at least one embodiment, server computer 802 may at times function as a client computer accessing another server computer 802. In at least one embodiment, remote network 808 may be a local area network, a network added into a wide area network through an independent service provider (ISP) for the Internet, or another group of computers interconnected by wired or wireless transfer media having a configuration which is either fixed or changing over time. In at least one embodiment, client computers 806 may link into and access a network 804 independently or through a remote network 808.

In at least one embodiment, the system 800 may be used to implement the system 100 (see FIG. 1) and/or the inference pipeline 500 (see FIG. 5). In at least one embodiment, at least one of the plurality of network server computers 802 may be used to implement the processing system 104, the requestor device(s) 102, the receiver device(s) 106, and/or the optional data storage units 108. In at least one embodiment, at least a portion of the system(s) depicted in FIG. 8 is used to implement one or more systems, techniques, functions, and/or processes described in connection with FIGS. 1-5. For example, in at least one embodiment, at least one component shown or described with respect to FIG. 8 is used to process data (e.g., data having a DICOM format) in accordance with one or more techniques, functions, and/or processes described with respect to any of FIGS. 1-5.

Figure 9:
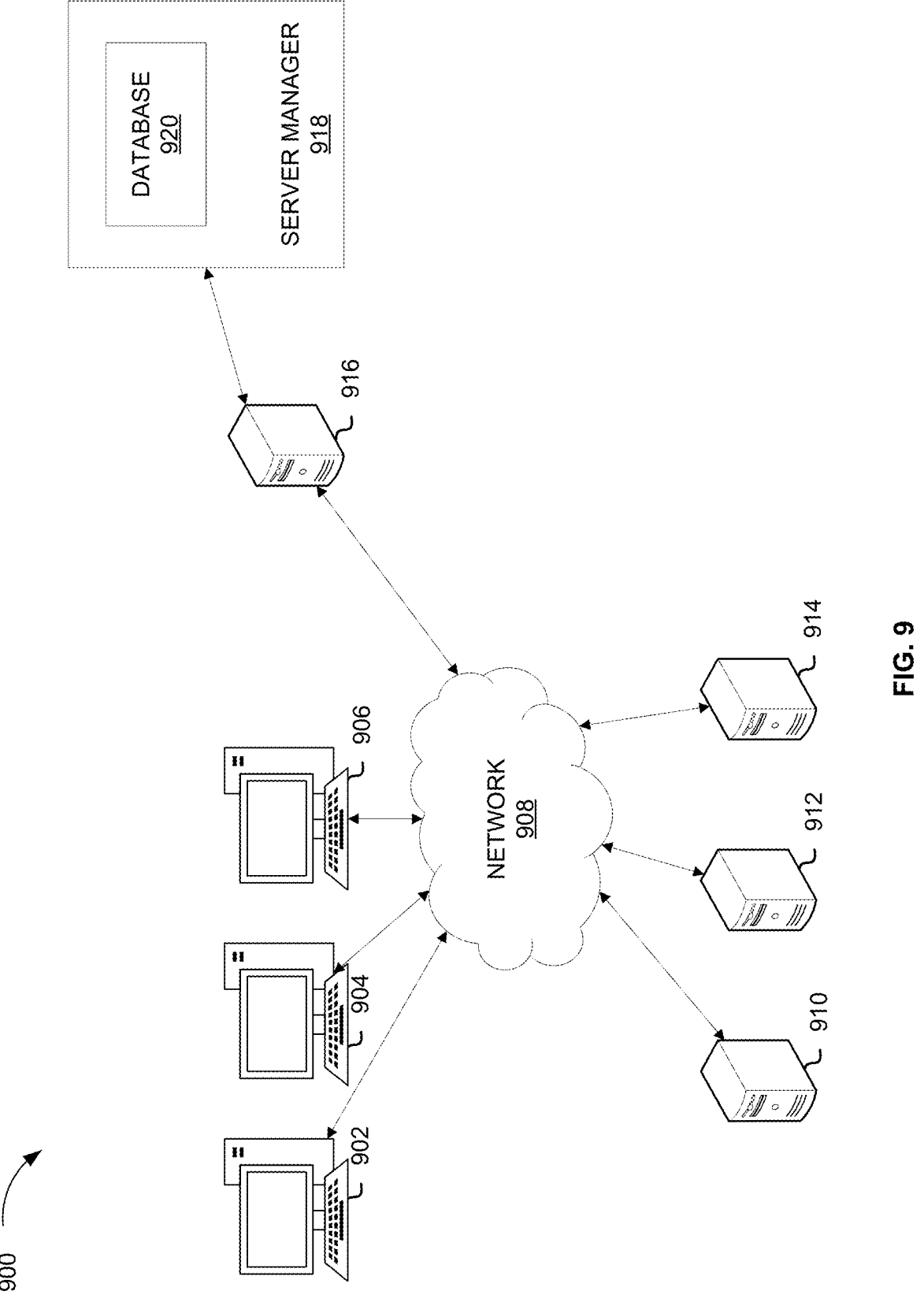
FIG. 9 illustrates an example system that includes a computer network, in accordance with at least one embodiment.

FIG. 9 illustrates an example system 900 that includes a computer network 908 connecting one or more computing machines, in accordance with at least one embodiment. In at least one embodiment, network 908 may be any type of electronically connected group of computers including, for instance, the following networks: Internet, Intranet, Local Area Networks (LAN), Wide Area Networks (WAN) or an interconnected combination of these network types. In at least one embodiment, connectivity within a network 908 may be a remote modem, Ethernet (IEEE 802.3), Token Ring (IEEE 802.5), Fiber Distributed Datalink Interface (FDDI), Asynchronous Transfer Mode (ATM), or any other communication protocol. In at least one embodiment, computing devices linked to a network may be desktop, server, portable, handheld, set-top box, personal digital assistant (PDA), a terminal, or any other desired type or configuration. In at least one embodiment, depending on their functionality, network connected devices may vary widely in processing power, internal memory, and other performance aspects. In at least one embodiment, communications within a network and to or from computing devices connected to a network may be either wired or wireless. In at least one embodiment, network 908 may include, at least in part, the world-wide public Internet which generally connects a plurality of users in accordance with a client-server model in accordance with a transmission control protocol/internet protocol (TCP/IP) specification. In at least one embodiment, client-server network is a dominant model for communicating between two computers. In at least one embodiment, a client computer ("client") issues one or more commands to a server computer ("server"). In at least one embodiment, server fulfills client commands by accessing available network resources and returning information to a client pursuant to client commands. In at least one embodiment, client computer systems and network resources resident on network servers are assigned a network address for identification during communications between elements of a network. In at least one embodiment, communications from other network connected systems to servers will include a network address of a relevant server/network resource as part of communication so that an appropriate destination of a data/request is identified as a recipient. In at least one embodiment, when a network 908 includes the global Internet, a network address is an IP address in a TCP/IP format which may, at least in part, route data to an e-mail account, a website, or other Internet tool resident on a server. In at least one embodiment, information and services which are resident on network servers may be available to a web browser of a client computer through a domain name (e.g. www.site.com) which maps to an IP address of a network server.

In at least one embodiment, a plurality of clients 902, 904, and 906 are connected to a network 908 via respective communication links. In at least one embodiment, each of these clients may access a network 908 via any desired form of communication, such as via a dial-up modem connection, cable link, a digital subscriber line (DSL), wireless or satellite link, or any other form of communication. In at least one embodiment, each client may communicate using any machine that is compatible with a network 908, such as a personal computer (PC), work station, dedicated terminal, personal data assistant (PDA), or other similar equipment. In at least one embodiment, clients 902, 904, and 906 may or may not be located in a same geographical area.

In at least one embodiment, a plurality of servers 910, 912, and 914 are connected to a network 908 to serve clients that are in communication with a network 908. In at least one embodiment, each server is typically a powerful computer or device that manages network resources and responds to client commands. In at least one embodiment, servers include computer readable data storage media such as hard disk drives and RAM memory that store program instructions and data. In at least one embodiment, servers 910, 912, 914 run application programs that respond to client commands. In at least one embodiment, server 910 may run a web server application for responding to client requests for HTML pages and may also run a mail server application for receiving and routing electronic mail. In at least one embodiment, other application programs, such as an FTP server or a media server for streaming audio/video data to clients may also be running on a server 910. In at least one embodiment, different servers may be dedicated to performing different tasks. In at least one embodiment, server 910 may be a dedicated web server that manages resources relating to web sites for various users, whereas a server 912 may be dedicated to provide electronic mail (email) management. In at least one embodiment, other servers may be dedicated for media (audio, video, etc.), file transfer protocol (FTP), or a combination of any two or more services that are typically available or provided over a network. In at least one embodiment, each server may be in a location that is the same as or different from that of other servers. In at least one embodiment, there may be multiple servers that perform mirrored tasks for users, thereby relieving congestion or minimizing traffic directed to and from a single server. In at least one embodiment, servers 910, 912, 914 are under control of a web hosting provider in a business of maintaining and delivering third party content over a network 908.

In at least one embodiment, web hosting providers deliver services to two different types of clients. In at least one embodiment, one type, which may be referred to as a browser, requests content from servers 910, 912, 914 such as web pages, email messages, video clips, etc. In at least one embodiment, a second type, which may be referred to as a user, hires a web hosting provider to maintain a network resource such as a web site, and to make it available to browsers. In at least one embodiment, users contract with a web hosting provider to make memory space, processor capacity, and communication bandwidth available for their desired network resource in accordance with an amount of server resources a user desires to utilize.

In at least one embodiment, in order for a web hosting provider to provide services for both of these clients, application programs which manage a network resources hosted by servers must be properly configured. In at least one embodiment, program configuration process involves defining a set of parameters which control, at least in part, an application program's response to browser requests and which also define, at least in part, a server resources available to a particular user.

In one embodiment, an intranet server 916 is in communication with a network 908 via a communication link. In at least one embodiment, intranet server 916 is in communication with a server manager 918. In at least one embodiment, server manager 918 includes a database of an application program configuration parameters which are being utilized in servers 910, 912, 914. In at least one embodiment, users modify a database 920 via an intranet 916, and a server manager 918 interacts with servers 910, 912, 914 to modify application program parameters so that they match a content of a database. In at least one embodiment, a user logs onto an intranet server 916 by connecting to an intranet 916 via computer 902 and entering authentication information, such as a username and password.

In at least one embodiment, when a user wishes to sign up for new service or modify an existing service, an intranet server 916 authenticates a user and provides a user with an interactive screen display/control panel that allows a user to access configuration parameters for a particular application program. In at least one embodiment, a user is presented with a number of modifiable text boxes that describe aspects of a configuration of a user's web site or other network resource. In at least one embodiment, if a user desires to increase memory space reserved on a server for its web site, a user is provided with a field in which a user specifies a desired memory space. In at least one embodiment, in response to receiving this information, an intranet server 916 updates a database 920. In at least one embodiment, server manager 918 forwards this information to an appropriate server, and a new parameter is used during application program operation. In at least one embodiment, an intranet server 916 is configured to provide users with access to configuration parameters of hosted network resources (e.g., web pages, email, FTP sites, media sites, etc.), for which a user has contracted with a web hosting service provider.

In at least one embodiment, the system 900 may be used to implement the system 100 (see FIG. 1) and/or the inference pipeline 500 (see FIG. 5). In at least one embodiment, at least one of the servers 910, 912, 914 may be used to implement the processing system 104, the requestor device(s) 102, the receiver device(s) 106, and/or the optional data storage units 108. Alternatively or additionally, the intranet server 916 and/or the server manager 918 may be used to implement the processing system 104, the requestor device(s) 102, the receiver device(s) 106, and/or the optional data storage units 108. In at least one embodiment, at least a portion of the system(s) depicted in FIG. 9 is used to implement one or more systems, techniques, functions, and/or processes described in connection with FIGS. 1-5. For example, in at least one embodiment, at least one component shown or described with respect to FIG. 9 is used to process data (e.g., data having a DICOM format) in accordance with one or more techniques, functions, and/or processes described with respect to any of FIGS. 1-5.

Figure 10A:
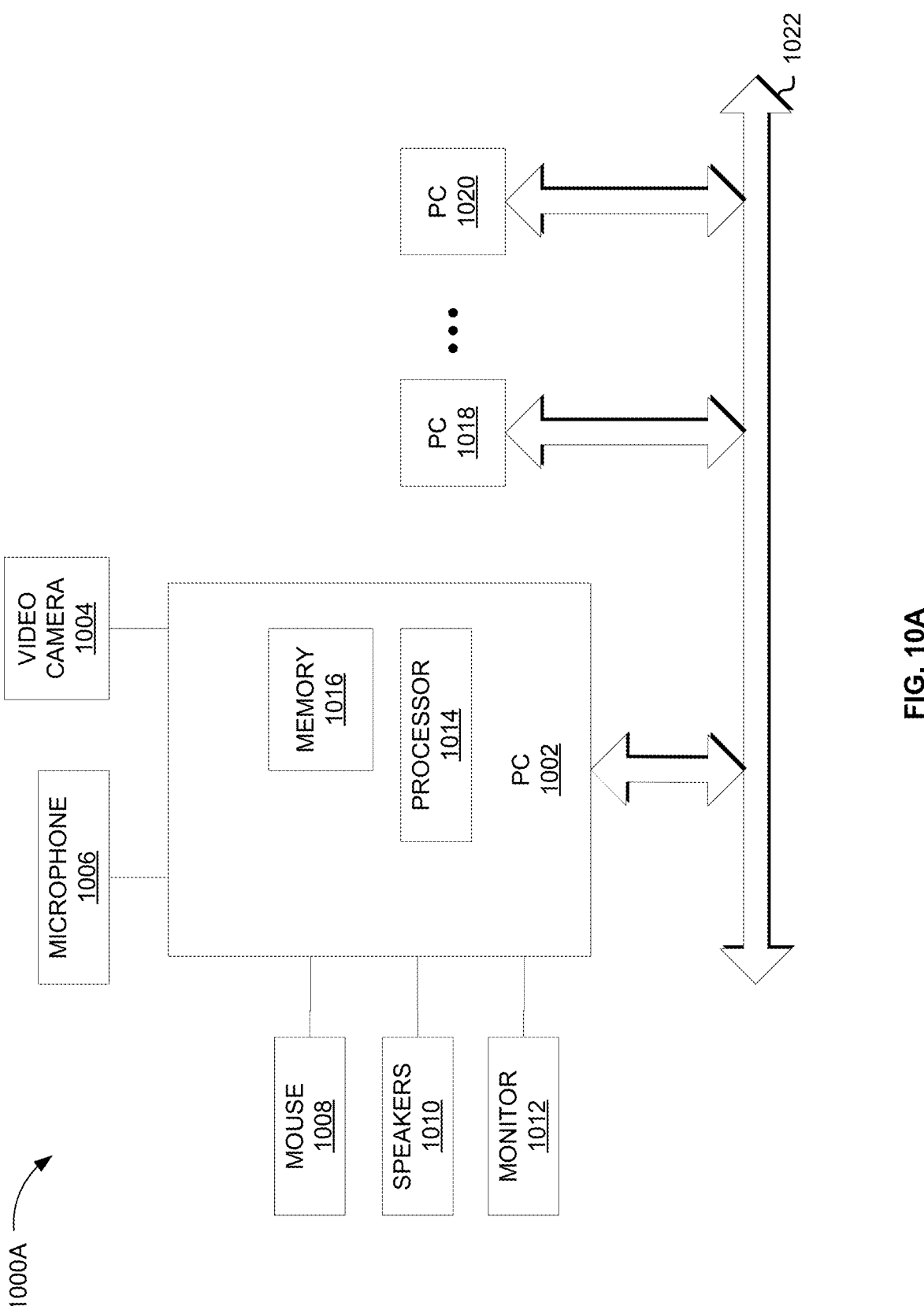
FIG. 10A illustrates a networked computer system, in accordance with at least one embodiment.

FIG. 10A illustrates a networked computer system 1000A, in accordance with at least one embodiment. In at least one embodiment, networked computer system 1000A includes a plurality of nodes or personal computers ("PCs") 1002, 1018, 1020. In at least one embodiment, personal computer or node 1002 includes a processor 1014, memory 1016, video camera 1004, microphone 1006, mouse 1008, speakers 1010, and monitor 1012. In at least one embodiment, PCs 1002, 1018, 1020 may each run one or more desktop servers of an internal network within a given company, for instance, or may be servers of a general network not limited to a specific environment. In at least one embodiment, there is one server per PC node of a network, so that each PC node of a network represents a particular network server, having a particular network URL address. In at least one embodiment, each server defaults to a default web page for that server's user, which may itself contain embedded URLs pointing to further subpages of that user on that server, or to other servers or pages on other servers on a network.

In at least one embodiment, nodes 1002, 1018, 1020 and other nodes of a network are interconnected via medium 1022. In at least one embodiment, medium 1022 may be, a communication channel such as an Integrated Services Digital Network ("ISDN"). In at least one embodiment, various nodes of a networked computer system may be connected through a variety of communication media, including local area networks ("LANs"), plain-old telephone lines ("POTS"), sometimes referred to as public switched telephone networks ("PSTN"), and/or variations thereof. In at least one embodiment, various nodes of a network may also constitute computer system users inter-connected via a network such as the Internet. In at least one embodiment, each server on a network (running from a particular node of a network at a given instance) has a unique address or identification within a network, which may be specifiable in terms of an URL.

In at least one embodiment, a plurality of multi-point conferencing units ("MCUs") may thus be utilized to transmit data to and from various nodes or "endpoints" of a conferencing system. In at least one embodiment, nodes and/or MCUs may be interconnected via an ISDN link or through a local area network ("LAN"), in addition to various other communications media such as nodes connected through the Internet. In at least one embodiment, nodes of a conferencing system may, in general, be connected directly to a communications medium such as a LAN or through an MCU, and that a conferencing system may include other nodes or elements such as routers, servers, and/or variations thereof.

In at least one embodiment, processor 1014 is a general-purpose programmable processor. In at least one embodiment, processors of nodes of networked computer system 1000A may also be special-purpose video processors. In at least one embodiment, various peripherals and components of a node such as those of node 1002 may vary from those of other nodes. In at least one embodiment, node 1018 and node 1020 may be configured identically to or differently than node 1002. In at least one embodiment, a node may be implemented on any suitable computer system in addition to PC systems.

Figure 10B:
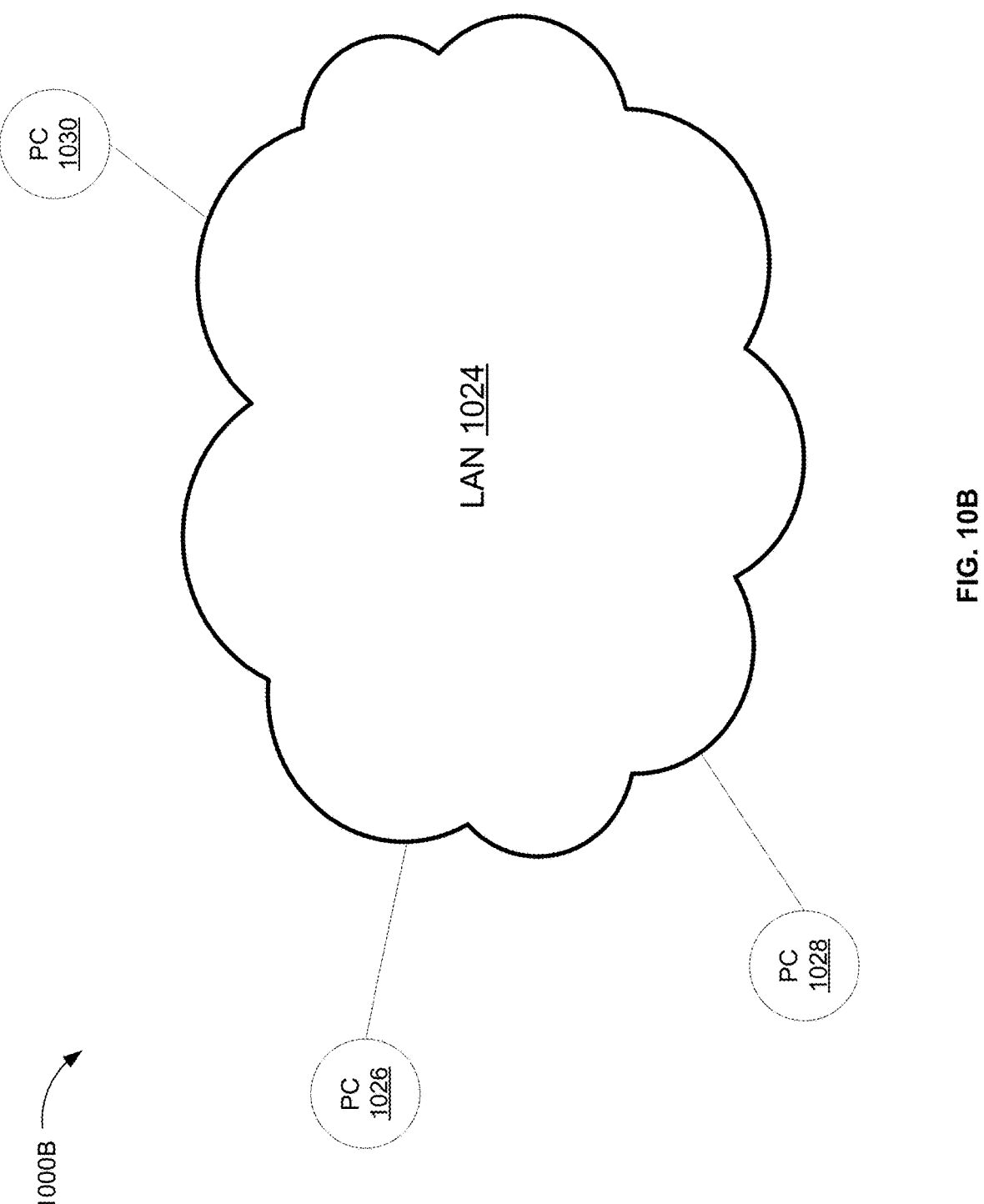
FIG. 10B illustrates a networked computer system, in accordance with at least one embodiment.

FIG. 10B illustrates a networked computer system 1000B, in accordance with at least one embodiment. In at least one embodiment, system 1000B illustrates a network such as LAN 1024, which may be used to interconnect a variety of nodes that may communicate with each other. In at least one embodiment, attached to LAN 1024 are a plurality of nodes such as PC nodes 1026, 1028, 1030. In at least one embodiment, a node may also be connected to the LAN via a network server or other means. In at least one embodiment, system 1000B includes other types of nodes or elements, for example including routers, servers, and nodes.

Figure 10C:
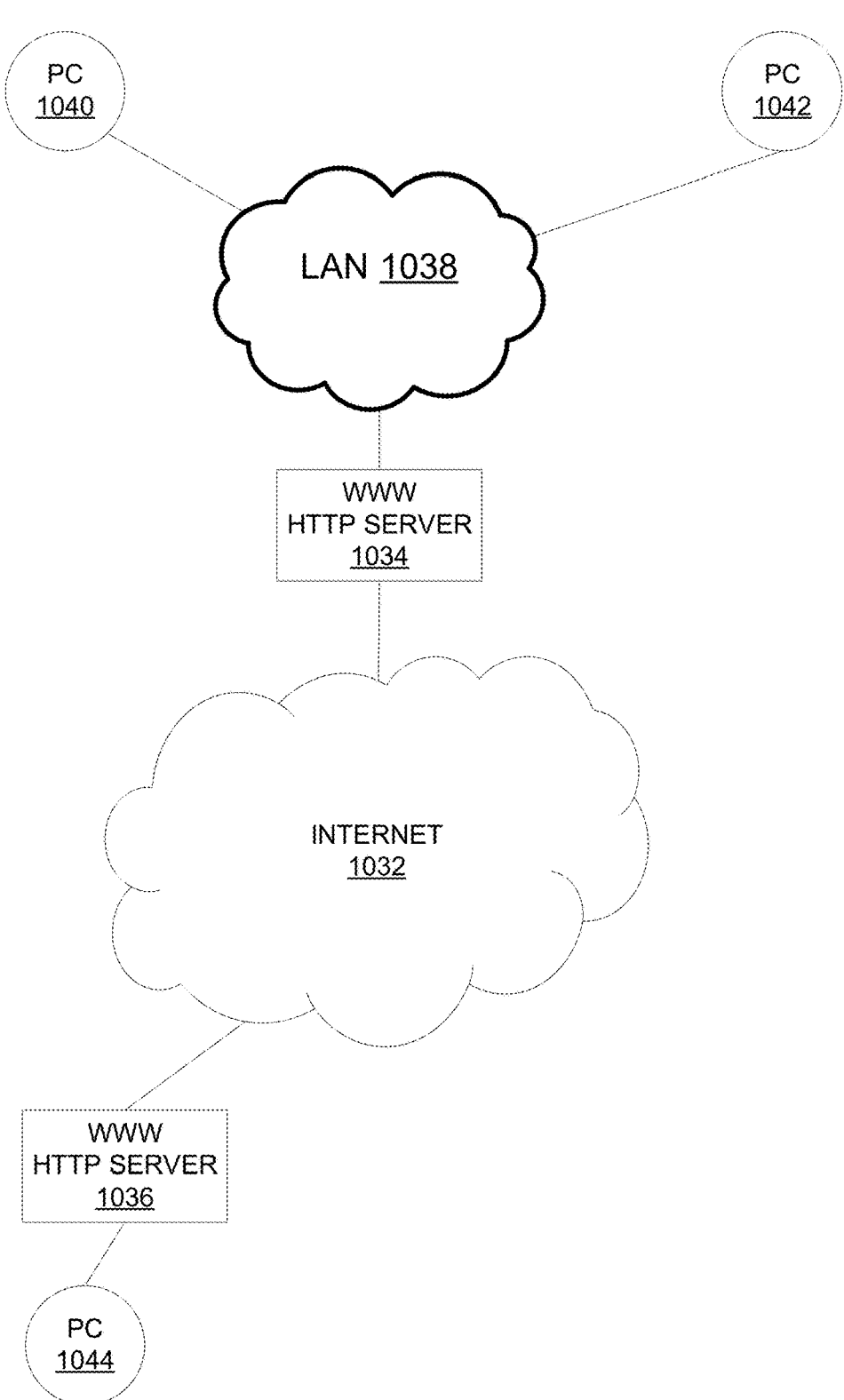
FIG. 10C illustrates a networked computer system, in accordance with at least one embodiment.

FIG. 10C illustrates a networked computer system 1000C, in accordance with at least one embodiment. In at least one embodiment, system 1000C illustrates a WWW system having communications across a backbone communications network such as Internet 1032, which may be used to interconnect a variety of nodes of a network. In at least one embodiment, WWW is a set of protocols operating on top of the Internet, and allows a graphical interface system to operate thereon for accessing information through the Internet. In at least one embodiment, attached to Internet 1032 in WWW are a plurality of nodes such as PCs 1040, 1042, 1044. In at least one embodiment, a node is interfaced to other nodes of WWW through a WWW HTTP server such as servers 1034, 1036. In at least one embodiment, PC 1044 may be a PC forming a node of network 1032 and itself running its server 1036, although PC 1044 and server 1036 are illustrated separately in FIG. 10C for illustrative purposes.

In at least one embodiment, WWW is a distributed type of application, characterized by WWW HTTP, WWW's protocol, which runs on top of the Internet's transmission control protocol/Internet protocol ("TCP/IP"). In at least one embodiment, WWW may thus be characterized by a set of protocols (i.e., HTTP) running on the Internet as its "backbone."

In at least one embodiment, a web browser is an application running on a node of a network that, in WWW-compatible type network systems, allows users of a particular server or node to view such information and thus allows a user to search graphical and text-based files that are linked together using hypertext links that are embedded in documents or files available from servers on a network that understand HTTP. In at least one embodiment, when a given web page of a first server associated with a first node is retrieved by a user using another server on a network such as the Internet, a document retrieved may have various hypertext links embedded therein and a local copy of a page is created local to a retrieving user. In at least one embodiment, when a user clicks on a hypertext link, locally-stored information related to a selected hypertext link is typically sufficient to allow a user's machine to open a connection across the Internet to a server indicated by a hypertext link.

In at least one embodiment, more than one user may be coupled to each HTTP server, for example through a LAN such as LAN 1038 as illustrated with respect to WWW HTTP server 1034. In at least one embodiment, system 1000C may also include other types of nodes or elements. In at least one embodiment, a WWW HTTP server is an application running on a machine, such as a PC. In at least one embodiment, each user may be considered to have a unique "server," as illustrated with respect to PC 1044. In at least one embodiment, a server may be considered to be a server such as WWW HTTP server 1034, which provides access to a network for a LAN or plurality of nodes or plurality of LANs. In at least one embodiment, there are a plurality of users, each having a desktop PC or node of a network, each desktop PC potentially establishing a server for a user thereof. In at least one embodiment, each server is associated with a particular network address or URL, which, when accessed, provides a default web page for that user. In at least one embodiment, a web page may contain further links (embedded URLs) pointing to further subpages of that user on that server, or to other servers on a network or to pages on other servers on a network.

In at least one embodiment, the system 1000 may be used to implement the system 100 (see FIG. 1) and/or the inference pipeline 500 (see FIG. 5). In at least one embodiment, at least one of the PC nodes 1026, 1028, 1030 and/or at least one of the PCs 1002, 1018, 1020, 1040, 1042 may be used to implement the processing system 104, the requestor device(s) 102, the receiver device(s) 106, and/or the optional data storage units 108. In at least one embodiment, the processor 1014 may be used to implement at least one of the CPU(s) 116, at least one of the GPU(s) 118, and/or at least one of the DPU(s) 130. In at least one embodiment, the memory 1016 may be used to implement the CPU memory 120, the GPU memory 122, and/or the DPU memory 132. In at least one embodiment, at least a portion of the system(s) depicted in FIGS. 10A-10C is used to implement one or more systems, techniques, functions, and/or processes described in connection with FIGS. 1-5. For example, in at least one embodiment, at least one component shown or described with respect to FIGS. 10A-10C is used to process data (e.g., data having a DICOM format) in accordance with one or more techniques, functions, and/or processes described with respect to any of FIGS. 1-5.

Cloud Computing and Services

The following figures set forth, without limitation, exemplary cloud-based systems that can be used to implement at least one embodiment.

In at least one embodiment, cloud computing is a style of computing in which dynamically scalable and often virtualized resources are provided as a service over the Internet. In at least one embodiment, users need not have knowledge of, expertise in, or control over technology infrastructure, which can be referred to as "in the cloud," that supports them. In at least one embodiment, cloud computing incorporates infrastructure as a service, platform as a service, software as a service, and other variations that have a common theme of reliance on the Internet for satisfying computing needs of users. In at least one embodiment, a typical cloud deployment, such as in a private cloud (e.g., enterprise network), or a data center (DC) in a public cloud (e.g., Internet) can consist of thousands of servers (or alternatively, VMs), hundreds of Ethernet, Fiber Channel or Fiber Channel over Ethernet (FCOE) ports, switching and storage infrastructure, etc. In at least one embodiment, cloud can also consist of network services infrastructure like IPsec VPN hubs, firewalls, load balancers, wide area network (WAN) optimizers etc. In at least one embodiment, remote subscribers can access cloud applications and services securely by connecting via a VPN tunnel, such as an IPsec VPN tunnel.

In at least one embodiment, cloud computing is a model for enabling convenient, on-demand network access to a shared pool of configurable computing resources (e.g., networks, servers, storage, applications, and services) that can be rapidly provisioned and released with minimal management effort or service provider interaction.

In at least one embodiment, cloud computing is characterized by on-demand self-service, in which a consumer can unilaterally provision computing capabilities, such as server time and network storage, as needed automatically without requiring human inter-action with each service's provider. In at least one embodiment, cloud computing is characterized by broad network access, in which capabilities are available over a network and accessed through standard mechanisms that promote use by heterogeneous thin or thick client platforms (e.g., mobile phones, laptops, and PDAs). In at least one embodiment, cloud computing is characterized by resource pooling, in which a provider's computing resources are pooled to serve multiple consumers using a multi-tenant model, with different physical and virtual resources dynamically as-signed and reassigned according to consumer demand. In at least one embodiment, there is a sense of location independence in that a customer generally has no control or knowledge over an exact location of provided resources, but may be able to specify location at a higher level of abstraction (e.g., country, state, or datacenter). In at least one embodiment, examples of resources include storage, processing, memory, network bandwidth, and virtual machines. In at least one embodiment, cloud computing is characterized by rapid elasticity, in which capabilities can be rapidly and elastically provisioned, in some cases automatically, to quickly scale out and rapidly released to quickly scale in. In at least one embodiment, to a consumer, capabilities available for provisioning often appear to be unlimited and can be purchased in any quantity at any time. In at least one embodiment, cloud computing is characterized by measured service, in which cloud systems automatically control and optimize resource use by leveraging a metering capability at some level of abstraction appropriate to a type of service (e.g., storage, processing, bandwidth, and active user accounts). In at least one embodiment, resource usage can be monitored, controlled, and reported providing transparency for both a provider and consumer of a utilized service.

In at least one embodiment, cloud computing may be associated with various services. In at least one embodiment, cloud Software as a Service (SaaS) may refer to as service in which a capability provided to a consumer is to use a provider's applications running on a cloud infrastructure. In at least one embodiment, applications are accessible from various client devices through a thin client interface such as a web browser (e.g., web-based email). In at least one embodiment, consumer does not manage or control underlying cloud infrastructure including network, servers, operating systems, storage, or even individual application capabilities, with a possible exception of limited user-specific application configuration settings.

In at least one embodiment, cloud Platform as a Service (PaaS) may refer to a service in which a capability provided to a consumer is to deploy onto cloud infrastructure consumer-created or acquired applications created using programming languages and tools supported by a provider. In at least one embodiment, consumer does not manage or control underlying cloud infrastructure including networks, servers, operating systems, or storage, but has control over deployed applications and possibly application hosting environment configurations.

In at least one embodiment, cloud Infrastructure as a Service (IaaS) may refer to a service in which a capability provided to a consumer is to provision processing, storage, networks, and other fundamental computing resources where a consumer is able to deploy and run arbitrary software, which can include operating systems and applications. In at least one embodiment, consumer does not manage or control underlying cloud infrastructure, but has control over operating systems, storage, deployed applications, and possibly limited control of select networking components (e.g., host firewalls).

In at least one embodiment, cloud computing may be deployed in various ways. In at least one embodiment, a private cloud may refer to a cloud infrastructure that is operated solely for an organization. In at least one embodiment, a private cloud may be managed by an organization or a third party and may exist on-premises or off-premises. In at least one embodiment, a community cloud may refer to a cloud infrastructure that is shared by several organizations and supports a specific community that has shared concerns (e.g., mission, security requirements, policy, and compliance considerations). In at least one embodiment, a community cloud may be managed by organizations or a third party and may exist on-premises or off-premises. In at least one embodiment, a public cloud may refer to a cloud infrastructure that is made available to a general public or a large industry group and is owned by an organization providing cloud services. In at least one embodiment, a hybrid cloud may refer to a cloud infrastructure is a composition of two or more clouds (private, community, or public) that remain unique entities, but are bound together by standardized or proprietary technology that enables data and application portability (e.g., cloud bursting for load-balancing between clouds). In at least one embodiment, a cloud computing environment is service oriented with a focus on statelessness, low coupling, modularity, and semantic interoperability.

Figure 11:
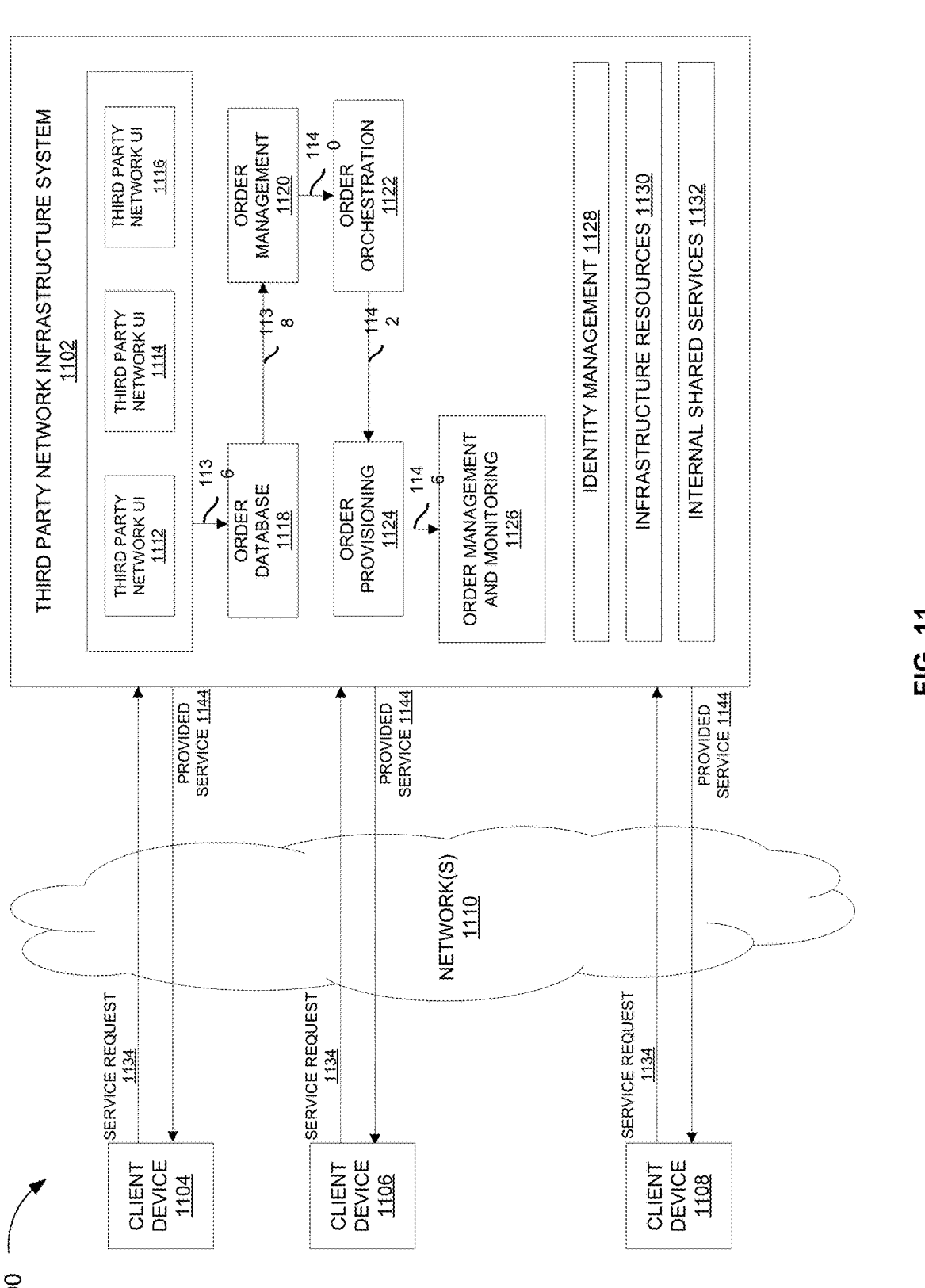
FIG. 11 illustrates one or more components of a system environment in which services may be offered as third party network services, in accordance with at least one embodiment.

FIG. 11 illustrates one or more components of a system environment 1100 in which services may be offered as third party network services, in accordance with at least one embodiment. In at least one embodiment, a third party network may be referred to as a cloud, cloud network, cloud computing network, and/or variations thereof. In at least one embodiment, system environment 1100 includes one or more client computing devices 1104, 1106, and 1108 that may be used by users to interact with a third party network infrastructure system 1102 that provides third party network services, which may be referred to as cloud computing services. In at least one embodiment, third party network infrastructure system 1102 may include one or more computers and/or servers.

It should be appreciated that third party network infrastructure system 1102 depicted in FIG. 11 may have other components than those depicted. Further, FIG. 11 depicts an embodiment of a third party network infrastructure system. In at least one embodiment, third party network infrastructure system 1102 may have more or fewer components than depicted in FIG. 11, may combine two or more components, or may have a different configuration or arrangement of components.

In at least one embodiment, client computing devices 1104, 1106, and 1108 may be configured to operate a client application such as a web browser, a proprietary client application, or some other application, which may be used by a user of a client computing device to interact with third party network infrastructure system 1102 to use services provided by third party network infrastructure system 1102. Although exemplary system environment 1100 is shown with three client computing devices, any number of client computing devices may be supported. In at least one embodiment, other devices such as devices with sensors, etc. may interact with third party network infrastructure system 1102. In at least one embodiment, network(s) 1110 may facilitate communications and exchange of data between client computing devices 1104, 1106, and 1108 and third party network infrastructure system 1102.

In at least one embodiment, services provided by third party network infrastructure system 1102 may include a host of services that are made available to users of a third party network infrastructure system on demand. In at least one embodiment, various services may also be offered including without limitation online data storage and backup solutions, Web-based e-mail services, hosted office suites and document collaboration services, database management and processing, managed technical support services, and/or variations thereof. In at least one embodiment, services provided by a third party network infrastructure system can dynamically scale to meet needs of its users.

In at least one embodiment, a specific instantiation of a service provided by third party network infrastructure system 1102 may be referred to as a "service instance." In at least one embodiment, in general, any service made available to a user via a communication network, such as the Internet, from a third party network service provider's system is referred to as a "third party network service." In at least one embodiment, in a public third party network environment, servers and systems that make up a third party network service provider's system are different from a customer's own on-premises servers and systems. In at least one embodiment, a third party network service provider's system may host an application, and a user may, via a communication network such as the Internet, on demand, order and use an application.

In at least one embodiment, a service in a computer network third party network infrastructure may include protected computer network access to storage, a hosted database, a hosted web server, a software application, or other service provided by a third party network vendor to a user. In at least one embodiment, a service can include password-protected access to remote storage on a third party network through the Internet. In at least one embodiment, a service can include a web service-based hosted relational database and a script-language middleware engine for private use by a networked developer. In at least one embodiment, a service can include access to an email software application hosted on a third party network vendor's web site.

In at least one embodiment, third party network infrastructure system 1102 may include a suite of applications, middleware, and database service offerings that are delivered to a customer in a self-service, subscription-based, elastically scalable, reliable, highly available, and secure manner. In at least one embodiment, third party network infrastructure system 1102 may also provide "big data" related computation and analysis services. In at least one embodiment, term "big data" is generally used to refer to extremely large data sets that can be stored and manipulated by analysts and researchers to visualize large amounts of data, detect trends, and/or otherwise interact with data. In at least one embodiment, big data and related applications can be hosted and/or manipulated by an infrastructure system on many levels and at different scales. In at least one embodiment, tens, hundreds, or thousands of processors linked in parallel can act upon such data in order to present it or simulate external forces on data or what it represents. In at least one embodiment, these data sets can involve structured data, such as that organized in a database or otherwise according to a structured model, and/or unstructured data (e.g., emails, images, data blobs (binary large objects), web pages, complex event processing). In at least one embodiment, by leveraging an ability of an embodiment to relatively quickly focus more (or fewer) computing resources upon an objective, a third party network infrastructure system may be better available to carry out tasks on large data sets based on demand from a business, government agency, research organization, private individual, group of like-minded individuals or organizations, or other entity.

In at least one embodiment, third party network infrastructure system 1102 may be adapted to automatically provision, manage and track a customer's subscription to services offered by third party network infrastructure system 1102. In at least one embodiment, third party network infrastructure system 1102 may provide third party network services via different deployment models. In at least one embodiment, services may be provided under a public third party network model in which third party network infrastructure system 1102 is owned by an organization selling third party network services and services are made available to a general public or different industry enterprises. In at least one embodiment, services may be provided under a private third party network model in which third party network infrastructure system 1102 is operated solely for a single organization and may provide services for one or more entities within an organization. In at least one embodiment, third party network services may also be provided under a community third party network model in which third party network infrastructure system 1102 and services provided by third party network infrastructure system 1102 are shared by several organizations in a related community. In at least one embodiment, third party network services may also be provided under a hybrid third party network model, which is a combination of two or more different models.

In at least one embodiment, services provided by third party network infrastructure system 1102 may include one or more services provided under Software as a Service (Saas) category, Platform as a Service (PaaS) category, Infrastructure as a Service (IaaS) category, or other categories of services including hybrid services. In at least one embodiment, a customer, via a subscription order, may order one or more services provided by third party network infrastructure system 1102. In at least one embodiment, third party network infrastructure system 1102 then performs processing to provide services in a customer's subscription order.

In at least one embodiment, services provided by third party network infrastructure system 1102 may include, without limitation, application services, platform services and infrastructure services. In at least one embodiment, application services may be provided by a third party network infrastructure system via a SaaS platform. In at least one embodiment, SaaS platform may be configured to provide third party network services that fall under a SaaS category. In at least one embodiment, SaaS platform may provide capabilities to build and deliver a suite of on-demand applications on an integrated development and deployment platform. In at least one embodiment, SaaS platform may manage and control underlying software and infrastructure for providing SaaS services. In at least one embodiment, by utilizing services provided by a SaaS platform, customers can utilize applications executing on a third party network infrastructure system. In at least one embodiment, customers can acquire an application services without a need for customers to purchase separate licenses and support. In at least one embodiment, various different SaaS services may be provided. In at least one embodiment, examples include, without limitation, services that provide solutions for sales performance management, enterprise integration, and business flexibility for large organizations.

In at least one embodiment, platform services may be provided by third party network infrastructure system 1102 via a PaaS platform. In at least one embodiment, PaaS platform may be configured to provide third party network services that fall under a PaaS category. In at least one embodiment, examples of platform services may include without limitation services that enable organizations to consolidate existing applications on a shared, common architecture, as well as an ability to build new applications that leverage shared services provided by a platform. In at least one embodiment, PaaS platform may manage and control underlying software and infrastructure for providing PaaS services. In at least one embodiment, customers can acquire PaaS services provided by third party network infrastructure system 1102 without a need for customers to purchase separate licenses and support.

In at least one embodiment, by utilizing services provided by a PaaS platform, customers can employ programming languages and tools supported by a third party network infrastructure system and also control deployed services. In at least one embodiment, platform services provided by a third party network infrastructure system may include database third party network services, middleware third party network services and third party network services. In at least one embodiment, database third party network services may support shared service deployment models that enable organizations to pool database resources and offer customers a Database as a Service in a form of a database third party network. In at least one embodiment, middleware third party network services may provide a platform for customers to develop and deploy various business applications, and third party network services may provide a platform for customers to deploy applications, in a third party network infrastructure system.

In at least one embodiment, various different infrastructure services may be provided by an IaaS platform in a third party network infrastructure system. In at least one embodiment, infrastructure services facilitate management and control of underlying computing resources, such as storage, networks, and other fundamental computing resources for customers utilizing services provided by a SaaS platform and a PaaS platform.

In at least one embodiment, third party network infrastructure system 1102 may also include infrastructure resources 1130 for providing resources used to provide various services to customers of a third party network infrastructure system. In at least one embodiment, infrastructure resources 1130 may include pre-integrated and optimized combinations of hardware, such as servers, storage, and networking resources to execute services provided by a Paas platform and a Saas platform, and other resources.

In at least one embodiment, resources in third party network infrastructure system 1102 may be shared by multiple users and dynamically re-allocated per demand. In at least one embodiment, resources may be allocated to users in different time zones. In at least one embodiment, third party network infrastructure system 1102 may enable a first set of users in a first time zone to utilize resources of a third party network infrastructure system for a specified number of hours and then enable a re-allocation of same resources to another set of users located in a different time zone, thereby maximizing utilization of resources.

In at least one embodiment, a number of internal shared services 1132 may be provided that are shared by different components or modules of third party network infrastructure system 1102 to enable provision of services by third party network infrastructure system 1102. In at least one embodiment, these internal shared services may include, without limitation, a security and identity service, an integration service, an enterprise repository service, an enterprise manager service, a virus scanning and white list service, a high availability, backup and recovery service, service for enabling third party network support, an email service, a notification service, a file transfer service, and/or variations thereof.

In at least one embodiment, third party network infrastructure system 1102 may provide comprehensive management of third party network services (e.g., SaaS, PaaS, and IaaS services) in a third party network infrastructure system. In at least one embodiment, third party network management functionality may include capabilities for provisioning, managing and tracking a customer's subscription received by third party network infrastructure system 1102, and/or variations thereof.

In at least one embodiment, as depicted in FIG. 11, third party network management functionality may be provided by one or more modules, such as an order management module 1120, an order orchestration module 1122, an order provisioning module 1124, an order management and monitoring module 1126, and an identity management module 1128. In at least one embodiment, these modules may include or be provided using one or more computers and/or servers, which may be general purpose computers, specialized server computers, server farms, server clusters, or any other appropriate arrangement and/or combination.

In at least one embodiment, at step 1134, a customer using a client device, such as client computing devices 1104, 1106 or 1108, may interact with third party network infrastructure system 1102 by requesting one or more services provided by third party network infrastructure system 1102 and placing an order for a subscription for one or more services offered by third party network infrastructure system 1102. In at least one embodiment, a customer may access a third party network User Interface (UI) such as third party network UI 1112, third party network UI 1114 and/or third party network UI 1116 and place a subscription order via these UIs. In at least one embodiment, order information received by third party network infrastructure system 1102 in response to a customer placing an order may include information identifying a customer and one or more services offered by a third party network infrastructure system 1102 that a customer intends to subscribe to.

In at least one embodiment, at step 1136, an order information received from a customer may be stored in an order database 1118. In at least one embodiment, if this is a new order, a new record may be created for an order. In at least one embodiment, order database 1118 can be one of several databases operated by third party network infrastructure system 1118 and operated in conjunction with other system elements.

In at least one embodiment, at step 1138, an order information may be forwarded to an order management module 1120 that may be configured to perform billing and accounting functions related to an order, such as verifying an order, and upon verification, booking an order.

In at least one embodiment, at step 1140, information regarding an order may be communicated to an order orchestration module 1122 that is configured to orchestrate provisioning of services and resources for an order placed by a customer. In at least one embodiment, order orchestration module 1122 may use services of order provisioning module 1124 for provisioning. In at least one embodiment, order orchestration module 1122 enables management of business processes associated with each order and applies business logic to determine whether an order should proceed to provisioning.

In at least one embodiment, at step 1142, upon receiving an order for a new subscription, order orchestration module 1122 sends a request to order provisioning module 1124 to allocate resources and configure resources needed to fulfill a subscription order. In at least one embodiment, order provisioning module 1124 enables an allocation of resources for services ordered by a customer. In at least one embodiment, order provisioning module 1124 provides a level of abstraction between third party network services provided by third party network infrastructure system 1100 and a physical implementation layer that is used to provision resources for providing requested services. In at least one embodiment, this enables order orchestration module 1122 to be isolated from implementation details, such as whether or not services and resources are actually provisioned in real-time or pre-provisioned and only allocated/assigned upon request.

In at least one embodiment, at step 1144, once services and resources are provisioned, a notification may be sent to subscribing customers indicating that a requested service is now ready for use. In at least one embodiment, information (e.g. a link) may be sent to a customer that enables a customer to start using requested services.

In at least one embodiment, at step 1146, a customer's subscription order may be managed and tracked by an order management and monitoring module 1126. In at least one embodiment, order management and monitoring module 1126 may be configured to collect usage statistics regarding a customer use of subscribed services. In at least one embodiment, statistics may be collected for an amount of storage used, an amount data transferred, a number of users, and an amount of system up time and system down time, and/or variations thereof.

In at least one embodiment, third party network infrastructure system 1100 may include an identity management module 1128 that is configured to provide identity services, such as access management and authorization services in third party network infrastructure system 1100. In at least one embodiment, identity management module 1128 may control information about customers who wish to utilize services provided by third party network infrastructure system 1102. In at least one embodiment, such information can include information that authenticates identities of such customers and information that describes which actions those customers are authorized to perform relative to various system resources (e.g., files, directories, applications, communication ports, memory segments, etc.). In at least one embodiment, identity management module 1128 may also include management of descriptive information about each customer and about how and by whom that descriptive information can be accessed and modified.

In at least one embodiment, the system environment 1100 may be used to implement the system 100 (see FIG. 1) and/or the inference pipeline 500 (see FIG. 5). In at least one embodiment, the third party network infrastructure system 1002 may be used to implement the system 100 (see FIG. 1) and/or the inference pipeline 500 (see FIG. 5). In at least one embodiment, at least one of the client computing devices 1104, 1106, and 1108 may implement the processing system 104, the requestor device(s) 102, the receiver device(s) 106, and/or the optional data storage units 108. In at least one embodiment, at least a portion of the system(s) depicted in FIG. 11 is used to implement one or more systems, techniques, functions, and/or processes described in connection with FIGS. 1-5. For example, in at least one embodiment, at least one component shown or described with respect to FIG. 11 is used to process data (e.g., data having a DICOM format) in accordance with one or more techniques, functions, and/or processes described with respect to any of FIGS. 1-5.

Figure 12:
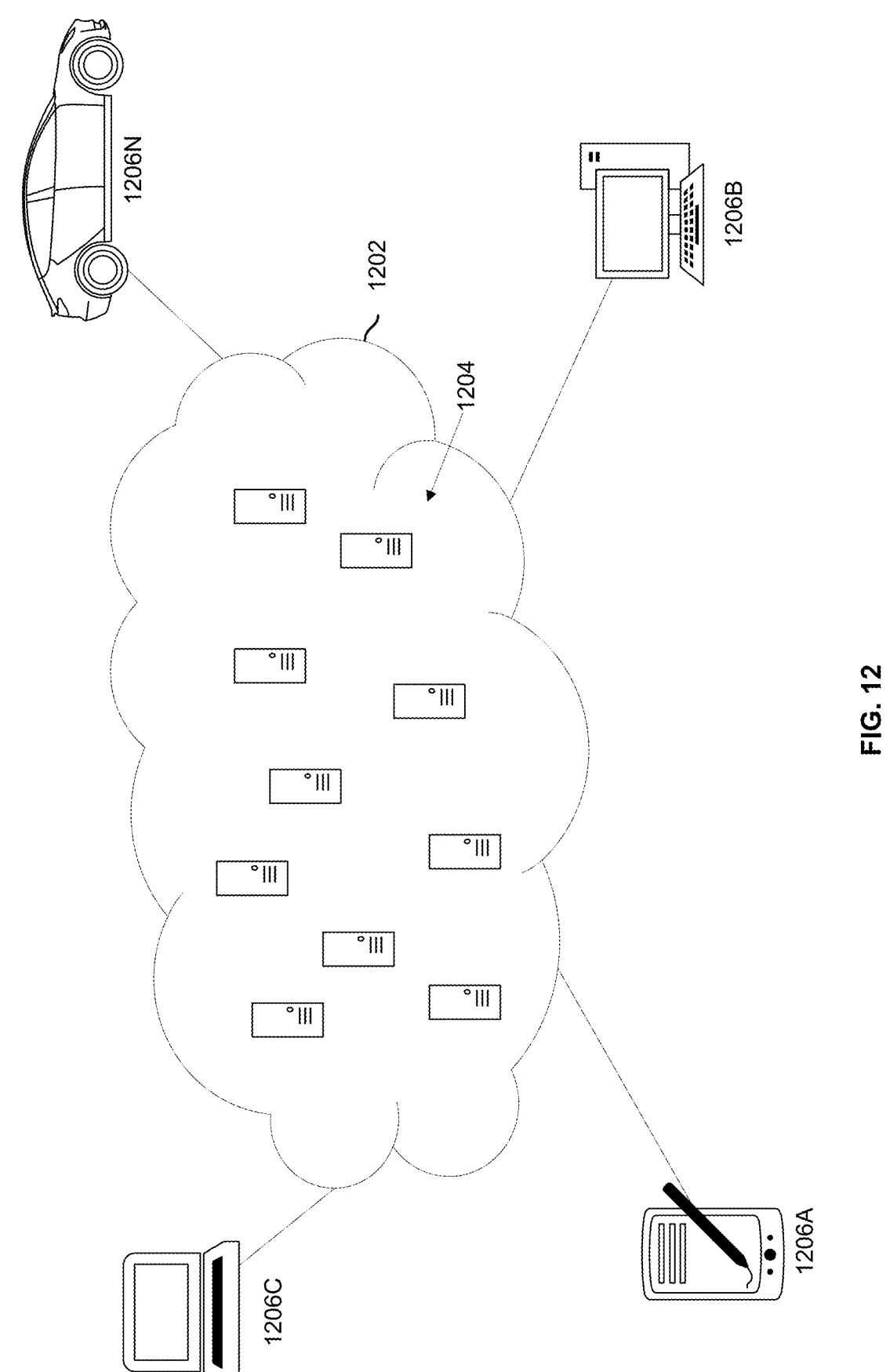
FIG. 12 illustrates a cloud computing environment, in accordance with at least one embodiment.

FIG. 12 illustrates a cloud computing environment 1202, in accordance with at least one embodiment. In at least one embodiment, cloud computing environment 1202 includes one or more computer system/servers 1204 with which computing devices such as, personal digital assistant (PDA) or cellular telephone 1206A, desktop computer 1206B, laptop computer 1206C, and/or automobile computer system 1206N communicate. In at least one embodiment, this allows for infrastructure, platforms and/or software to be offered as services from cloud computing environment 1202, so as to not require each client to separately maintain such resources. It is understood that types of computing devices 1206A-N shown in FIG. 12 are intended to be illustrative only and that cloud computing environment 1202 can communicate with any type of computerized device over any type of network and/or network/addressable connection (e.g., using a web browser).

In at least one embodiment, a computer system/server 1204, which can be denoted as a cloud computing node, is operational with numerous other general purpose or special purpose computing system environments or configurations. In at least one embodiment, examples of computing systems, environments, and/or configurations that may be suitable for use with computer system/server 1204 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and/or variations thereof.

In at least one embodiment, computer system/server 1204 may be described in a general context of computer system-executable instructions, such as program modules, being executed by a computer system. In at least one embodiment, program modules include routines, programs, objects, components, logic, data structures, and so on, that perform particular tasks or implement particular abstract data types. In at least one embodiment, exemplary computer system/server 1204 may be practiced in distributed loud computing environments where tasks are performed by remote processing devices that are linked through a communications network. In at least one embodiment, in a distributed cloud computing environment, program modules may be located in both local and remote computer system storage media including memory storage devices.

In at least one embodiment, the cloud computing environment 1202 may be used to implement the system 100 (see FIG. 1) and/or the workload analysis pipeline 500 (see FIG. 5). In at least one embodiment, at least one of the computer system/servers 1204 may be used to implement the processing system 104, the requestor device(s) 102, the receiver device(s) 106, and/or the optional data storage units 108. In at least one embodiment, at least one of the computing devices 1206A-N may implement the processing system 104, the requestor device(s) 102, the receiver device(s) 106, and/or the optional data storage units 108. In at least one embodiment, at least a portion of the system(s) depicted in FIG. 12 is used to implement one or more systems, techniques, functions, and/or processes described in connection with FIGS. 1-5. For example, in at least one embodiment, at least one component shown or described with respect to FIG. 12 is used to process data (e.g., data having a DICOM format) in accordance with one or more techniques, functions, and/or processes described with respect to any of FIGS. 1-5.

Figure 13:
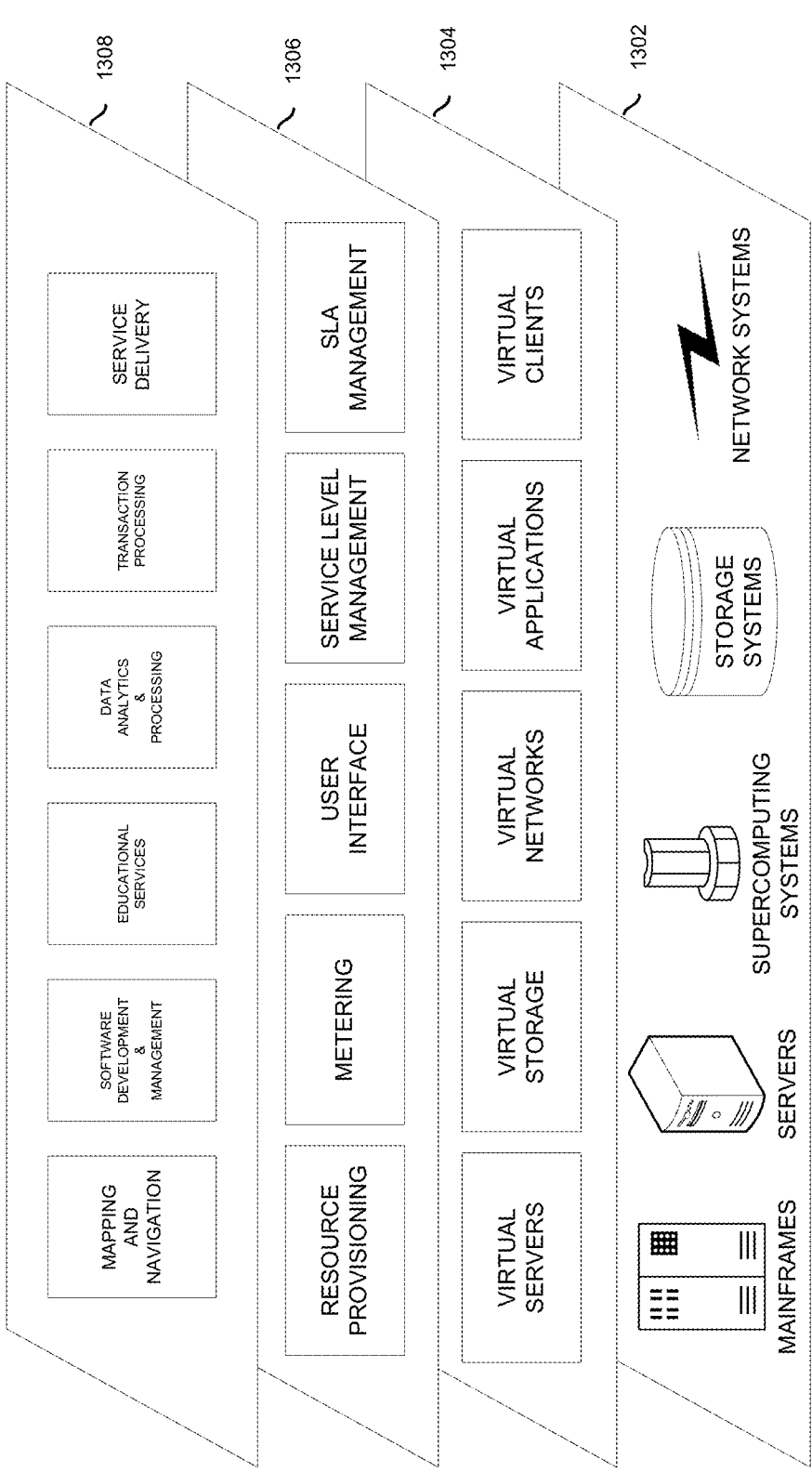
FIG. 13 illustrates a set of functional abstraction layers provided by a cloud computing environment, in accordance with at least one embodiment.

FIG. 13 illustrates a set of functional abstraction layers provided by cloud computing environment 1202 (FIG. 12), in accordance with at least one embodiment. It should be understood in advance that components, layers, and functions shown in FIG. 13 are intended to be illustrative only, and components, layers, and functions may vary.

In at least one embodiment, hardware and software layer 1302 includes hardware and software components. In at least one embodiment, examples of hardware components include mainframes, various RISC (Reduced Instruction Set Computer) architecture based servers, various computing systems, supercomputing systems, storage devices, networks, networking components, and/or variations thereof. In at least one embodiment, examples of software components include network application server software, various application server software, various database software, and/or variations thereof.

In at least one embodiment, virtualization layer 1304 provides an abstraction layer from which following exemplary virtual entities may be provided: virtual servers, virtual storage, virtual networks, including virtual private networks, virtual applications, virtual clients, and/or variations thereof.

In at least one embodiment, management layer 1306 provides various functions. In at least one embodiment, resource provisioning provides dynamic procurement of computing resources and other resources that are utilized to perform tasks within a cloud computing environment. In at least one embodiment, metering provides usage tracking as resources are utilized within a cloud computing environment, and billing or invoicing for consumption of these resources. In at least one embodiment, resources may include application software licenses. In at least one embodiment, security provides identity verification for users and tasks, as well as protection for data and other resources. In at least one embodiment, user interface provides access to a cloud computing environment for both users and system administrators. In at least one embodiment, service level management provides cloud computing resource allocation and management such that required service levels are met. In at least one embodiment, Service Level Agreement (SLA) management provides pre-arrangement for, and procurement of, cloud computing resources for which a future requirement is anticipated in accordance with an SLA.

In at least one embodiment, workloads layer 1308 provides functionality for which a cloud computing environment is utilized. In at least one embodiment, examples of workloads and functions which may be provided from this layer include: mapping and navigation, software development and management, educational services, data analytics and processing, transaction processing, and service delivery.

Supercomputing

The following figures set forth, without limitation, exemplary supercomputer-based systems that can be used to implement at least one embodiment.

In at least one embodiment, a supercomputer may refer to a hardware system exhibiting substantial parallelism and including at least one chip, where chips in a system are interconnected by a network and are placed in hierarchically organized enclosures. In at least one embodiment, a large hardware system filling a machine room, with several racks, each containing several boards/rack modules, each containing several chips, all interconnected by a scalable network, is one particular example of a supercomputer. In at least one embodiment, a single rack of such a large hardware system is another example of a supercomputer. In at least one embodiment, a single chip exhibiting substantial parallelism and containing several hardware components can equally be considered to be a supercomputer, since as feature sizes may decrease, an amount of hardware that can be incorporated in a single chip may also increase.

Figure 14:
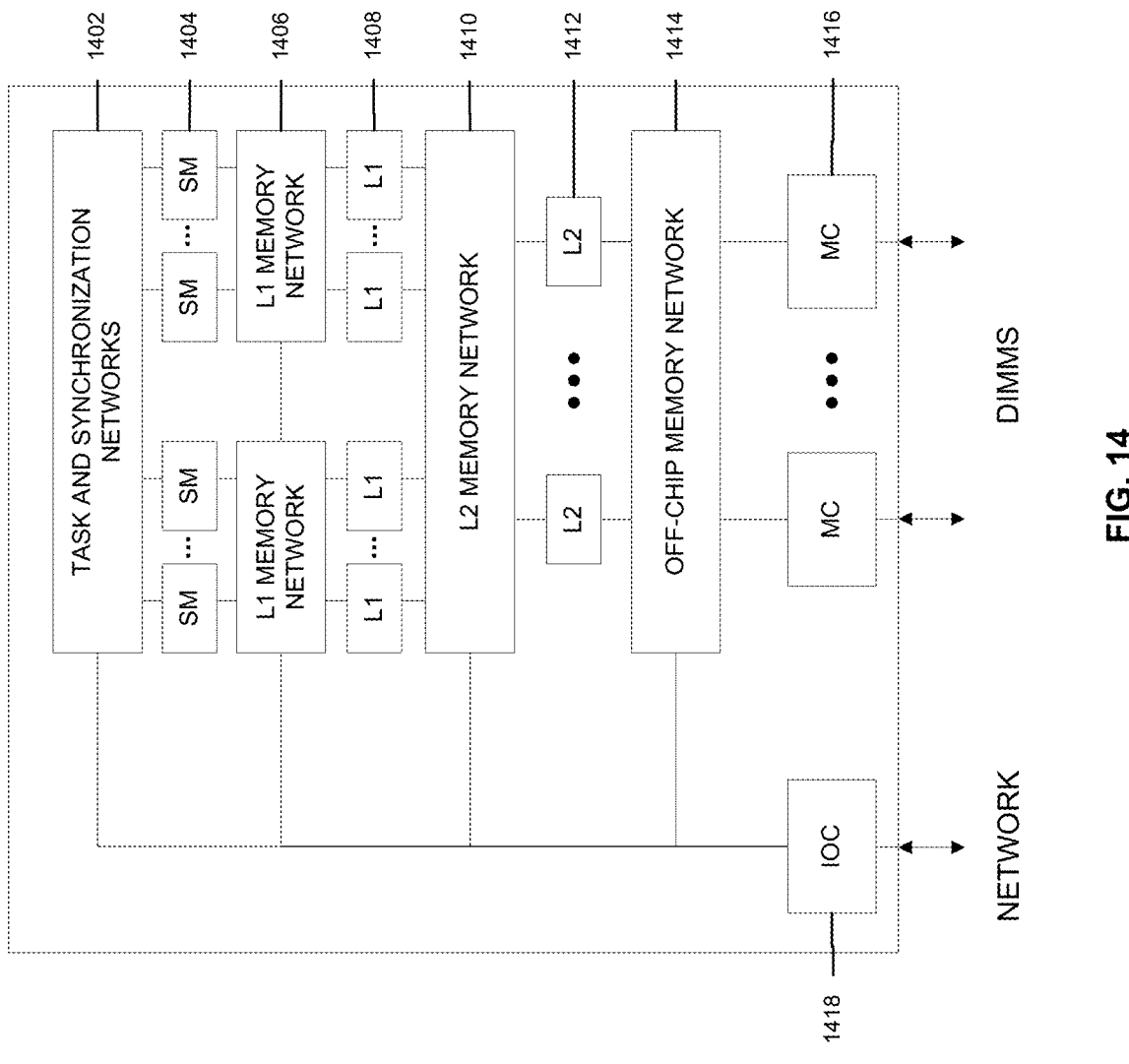
FIG. 14 illustrates a supercomputer at a chip level, in accordance with at least one embodiment.

FIG. 14 illustrates a supercomputer at a chip level, in accordance with at least one embodiment. In at least one embodiment, inside an FPGA or ASIC chip, main computation is performed within finite state machines (1404) called thread units. In at least one embodiment, task and synchronization networks (1402) connect finite state machines and are used to dispatch threads and execute operations in correct order. In at least one embodiment, a multi-level partitioned on-chip cache hierarchy (1408, 1412) is accessed using memory networks (1406, 1410). In at least one embodiment, off-chip memory is accessed using memory controllers (1416) and an off-chip memory network (1414). In at least one embodiment, I/O controller (1418) is used for cross-chip communication when a design does not fit in a single logic chip.

Figure 15:
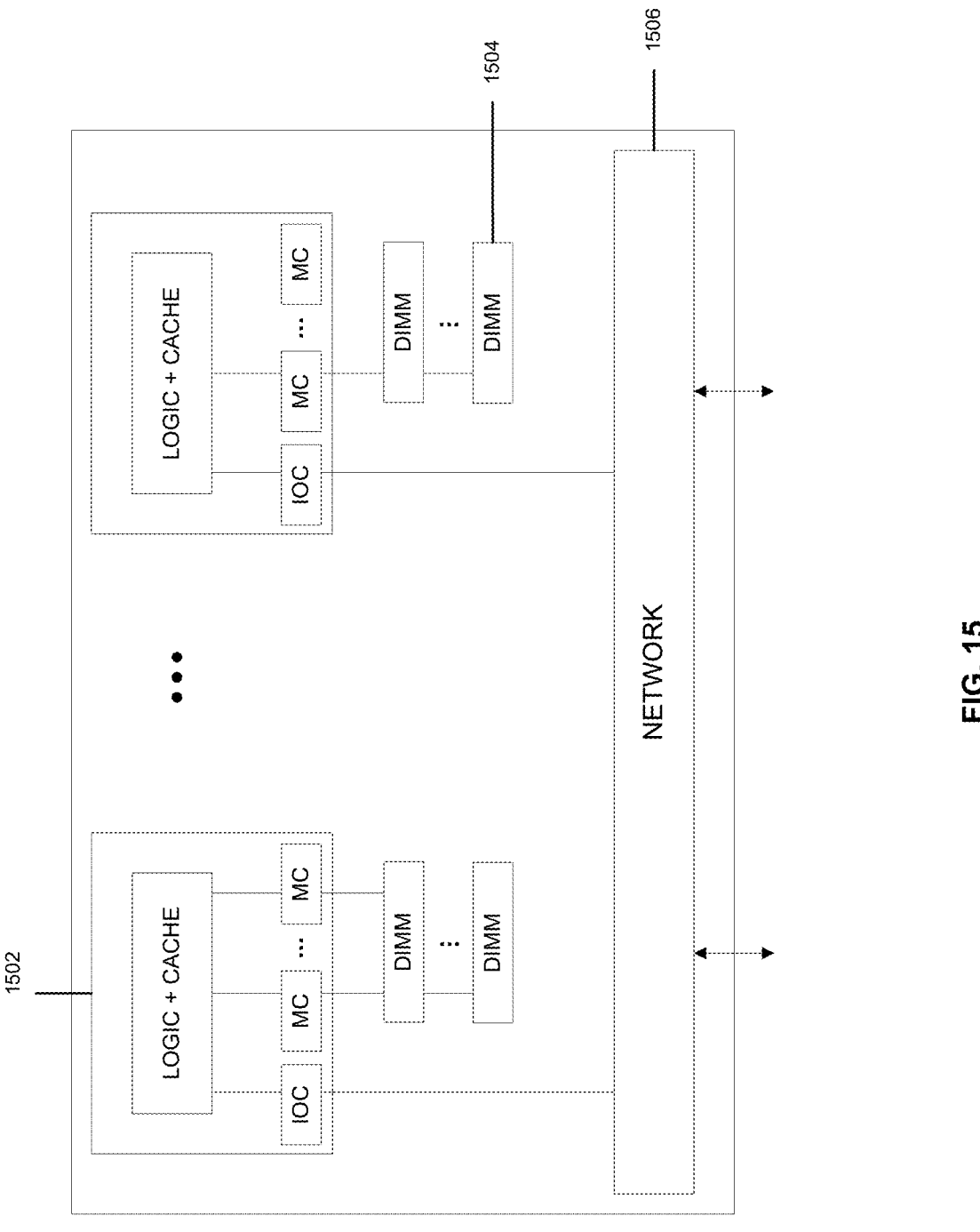
FIG. 15 illustrates a supercomputer at a rack module level, in accordance with at least one embodiment.

FIG. 15 illustrates a supercomputer at a rock module level, in accordance with at least one embodiment. In at least one embodiment, within a rack module, there are multiple FPGA or ASIC chips (1502) that are connected to one or more DRAM units (1504) which constitute main accelerator memory. In at least one embodiment, each FPGA/ASIC chip is connected to its neighbor FPGA/ASIC chip using wide busses on a board, with differential high speed signaling (1506). In at least one embodiment, each FPGA/ASIC chip is also connected to at least one high-speed serial communication cable.

Figure 16:
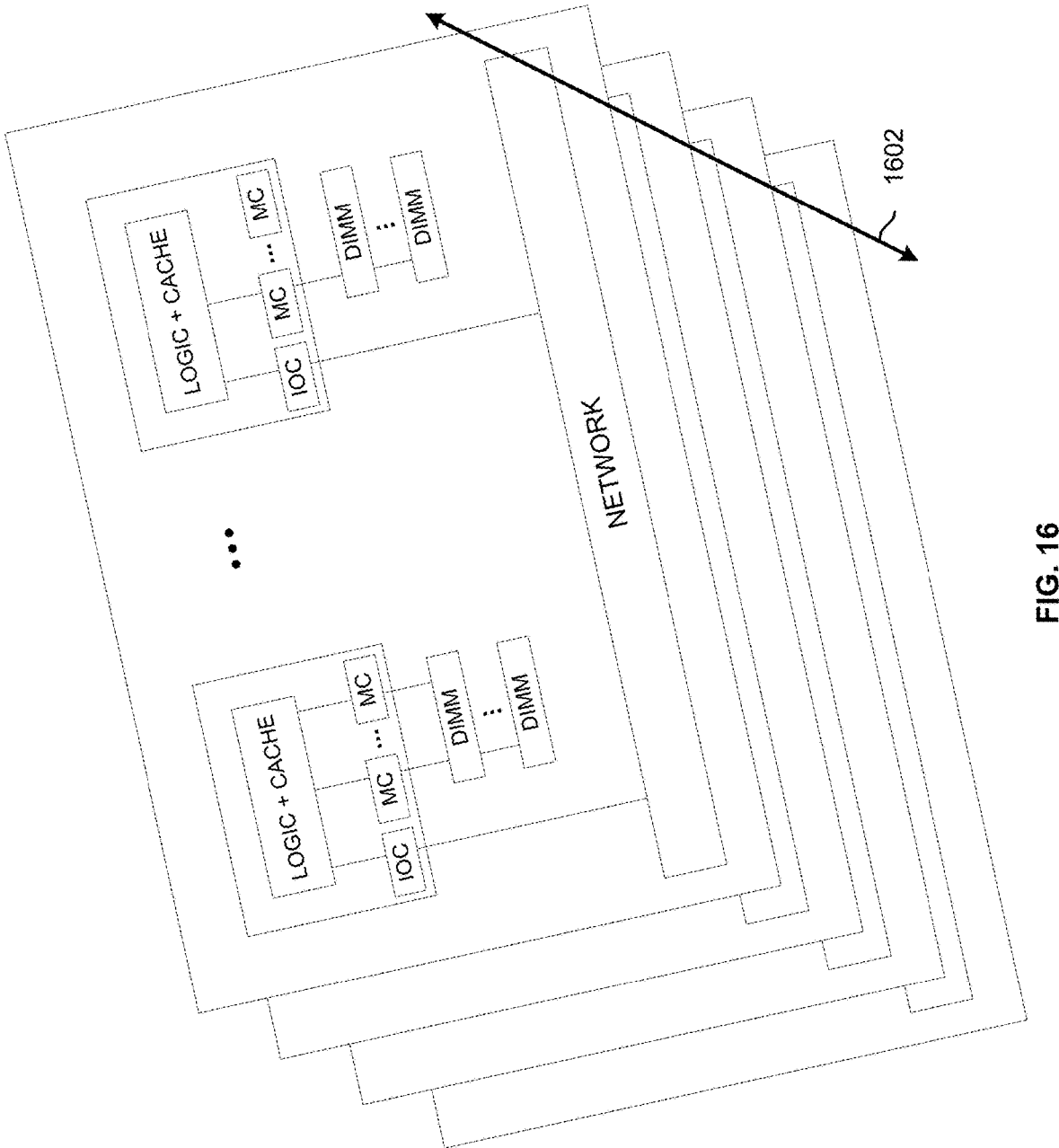
FIG. 16 illustrates a supercomputer at a rack level, in accordance with at least one embodiment.
Figure 17:
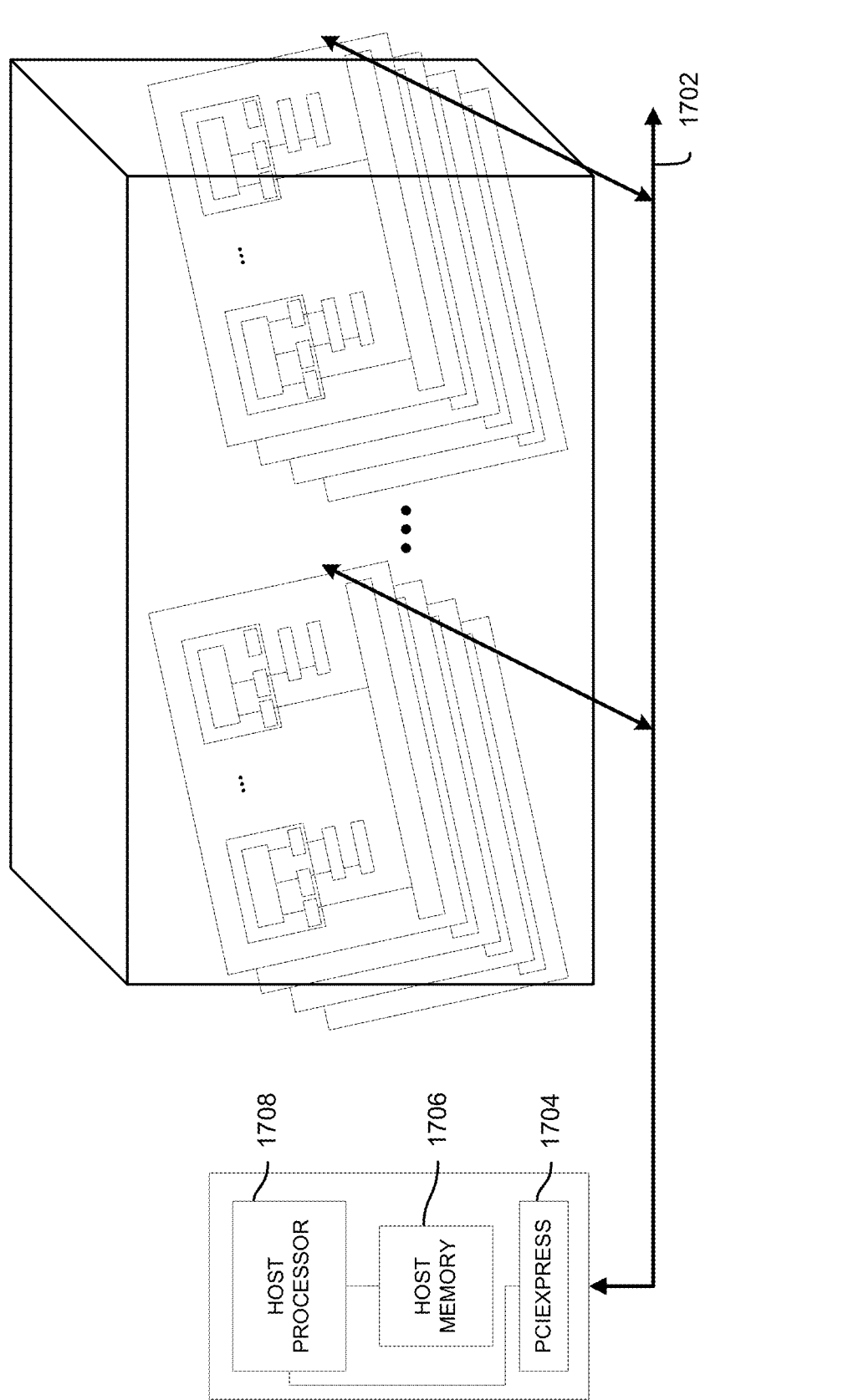
FIG. 17 illustrates a supercomputer at a whole system level, in accordance with at least one embodiment.

FIG. 16 illustrates a supercomputer at a rack level, in accordance with at least one embodiment. FIG. 17 illustrates a supercomputer at a whole system level, in accordance with at least one embodiment. In at least one embodiment, referring to FIG. 16 and FIG. 17, between rack modules in a rack and across racks throughout an entire system, high-speed serial optical or copper cables (1602, 1702) are used to realize a scalable, possibly incomplete hypercube network. In at least one embodiment, one of FPGA/ASIC chips of an accelerator is connected to a host system through a PCI-Express connection (1704). In at least one embodiment, host system includes a host microprocessor (1708) that a software part of an application runs on and a memory consisting of one or more host memory DRAM units (1706) that is kept coherent with memory on an accelerator. In at least one embodiment, host system can be a separate module on one of racks, or can be integrated with one of a supercomputer's modules. In at least one embodiment, cube-connected cycles topology provide communication links to create a hypercube network for a large supercomputer. In at least one embodiment, a small group of FPGA/ASIC chips on a rack module can act as a single hypercube node, such that a total number of external links of each group is increased, compared to a single chip. In at least one embodiment, a group contains chips A, B, C and D on a rack module with internal wide differential busses connecting A, B, C and D in a torus organization. In at least one embodiment, there are 12 serial communication cables connecting a rack module to an outside world. In at least one embodiment, chip A on a rack module connects to serial communication cables 0, 1, 2. In at least one embodiment, chip B connects to cables 3, 4, 5. In at least one embodiment, chip C connects to 6, 7, 8. In at least one embodiment, chip D connects to 9, 10, 11. In at least one embodiment, an entire group {A, B, C, D} constituting a rack module can form a hypercube node within a supercomputer system, with up to 212=4096 rack modules (16384 FPGA/ASIC chips). In at least one embodiment, for chip A to send a message out on link 4 of group {A, B, C, D}, a message has to be routed first to chip B with an on-board differential wide bus connection. In at least one embodiment, a message arriving into a group {A, B, C, D} on link 4 (i.e., arriving at B) destined to chip A, also has to be routed first to a correct destination chip (A) internally within a group {A, B, C, D}. In at least one embodiment, parallel supercomputer systems of other sizes may also be implemented.

In at least one embodiment, at least one of the supercomputers illustrated in FIGS. 14-17 may be used to implement the system 100 (see FIG. 1) and/or the inference pipeline 500 (see FIG. 5). For example, at least one of the supercomputers illustrated in FIGS. 14-17 may be used to implement the processing system 104, the requestor device(s) 102, the receiver device(s) 106, and/or the optional data storage units 108. In at least one embodiment, at least one of the supercomputers illustrated in FIGS. 14-17 may be used to implement the at least one of the CPU(s) 116, at least one of the GPU(s) 118, and/or at least one of the DPU(s) 130. In at least one embodiment, at least a portion of the system(s) depicted in FIGS. 14-17 is used to implement one or more systems, techniques, functions, and/or processes described in connection with FIGS. 1-5. For example, in at least one embodiment, at least one component shown or described with respect to FIGS. 14-17 is used to process data (e.g., data having a DICOM format) in accordance with one or more techniques, functions, and/or processes described with respect to any of FIGS. 1-5.

Artificial Intelligence

The following figures set forth, without limitation, exemplary artificial intelligence-based systems that can be used to implement at least one embodiment.

Figure 18A:
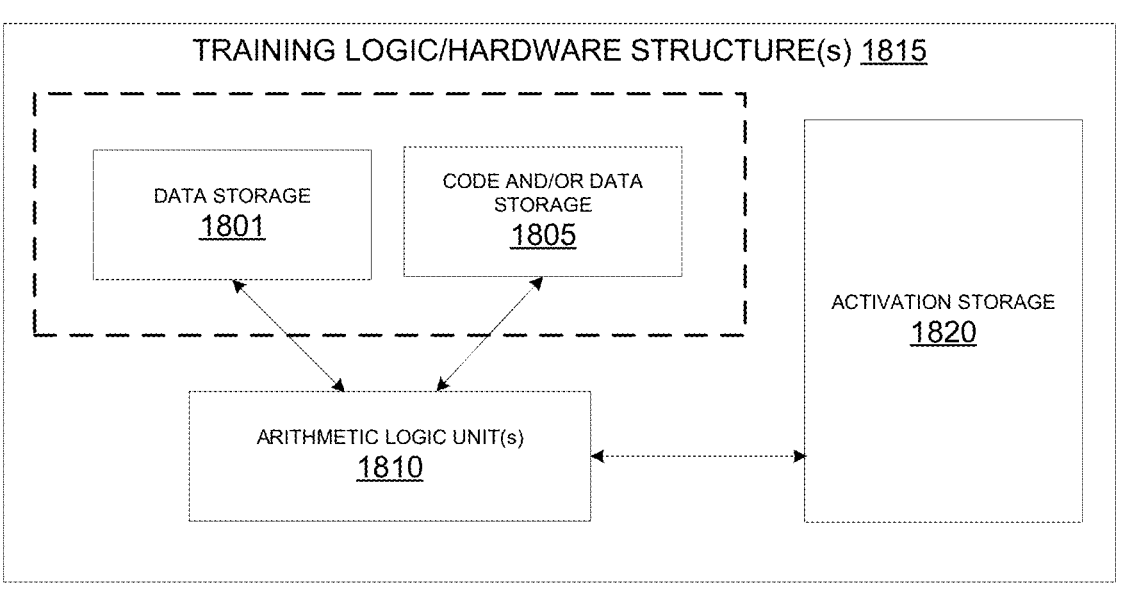
FIG. 18A illustrates inference and/or training logic, in accordance with at least one embodiment.

FIG. 18A illustrates inference and/or training logic 1815 used to perform inferencing and/or training operations associated with one or more embodiments. Details regarding inference and/or training logic 1815 are provided below in conjunction with FIGS. 18A and/or 18B.

In at least one embodiment, inference and/or training logic 1815 may include, without limitation, code and/or data storage 1801 to store forward and/or output weight and/or input/output data, and/or other parameters to configure neurons or layers of a neural network trained and/or used for inferencing in aspects of one or more embodiments. In at least one embodiment, training logic 1815 may include, or be coupled to code and/or data storage 1801 to store graph code or other software to control timing and/or order, in which weight and/or other parameter information is to be loaded to configure, logic, including integer and/or floating point units (collectively, arithmetic logic units (ALUs). In at least one embodiment, code, such as graph code, loads weight or other parameter information into processor ALUs based on an architecture of a neural network to which such code corresponds. In at least one embodiment code and/or data storage 1801 stores weight parameters and/or input/output data of each layer of a neural network trained or used in conjunction with one or more embodiments during forward propagation of input/output data and/or weight parameters during training and/or inferencing using aspects of one or more embodiments. In at least one embodiment, any portion of code and/or data storage 1801 may be included with other on-chip or off-chip data storage, including a processor's L1, L2, or L3 cache or system memory.

In at least one embodiment, any portion of code and/or data storage 1801 may be internal or external to one or more processors or other hardware logic devices or circuits. In at least one embodiment, code and/or code and/or data storage 1801 may be cache memory, dynamic randomly addressable memory ("DRAM"), static randomly addressable memory ("SRAM"), non-volatile memory (e.g., flash memory), or other storage. In at least one embodiment, a choice of whether code and/or code and/or data storage 1801 is internal or external to a processor, for example, or including DRAM, SRAM, flash or some other storage type may depend on available storage on-chip versus off-chip, latency requirements of training and/or inferencing functions being performed, batch size of data used in inferencing and/or training of a neural network, or some combination of these factors.

In at least one embodiment, inference and/or training logic 1815 may include, without limitation, a code and/or data storage 1805 to store backward and/or output weight and/or input/output data corresponding to neurons or layers of a neural network trained and/or used for inferencing in aspects of one or more embodiments. In at least one embodiment, code and/or data storage 1805 stores weight parameters and/or input/output data of each layer of a neural network trained or used in conjunction with one or more embodiments during backward propagation of input/output data and/or weight parameters during training and/or inferencing using aspects of one or more embodiments. In at least one embodiment, training logic 1815 may include, or be coupled to code and/or data storage 1805 to store graph code or other software to control timing and/or order, in which weight and/or other parameter information is to be loaded to configure, logic, including integer and/or floating point units (collectively, arithmetic logic units (ALUs).

In at least one embodiment, code, such as graph code, causes loading of weight or other parameter information into processor ALUs based on an architecture of a neural network to which such code corresponds. In at least one embodiment, any portion of code and/or data storage 1805 may be included with other on-chip or off-chip data storage, including a processor's L1, L2, or L3 cache or system memory. In at least one embodiment, any portion of code and/or data storage 1805 may be internal or external to one or more processors or other hardware logic devices or circuits. In at least one embodiment, code and/or data storage 1805 may be cache memory, DRAM, SRAM, non-volatile memory (e.g., flash memory), or other storage. In at least one embodiment, a choice of whether code and/or data storage 1805 is internal or external to a processor, for example, or including DRAM, SRAM, flash memory or some other storage type may depend on available storage on-chip versus off-chip, latency requirements of training and/or inferencing functions being performed, batch size of data used in inferencing and/or training of a neural network, or some combination of these factors.

In at least one embodiment, code and/or data storage 1801 and code and/or data storage 1805 may be separate storage structures. In at least one embodiment, code and/or data storage 1801 and code and/or data storage 1805 may be a combined storage structure. In at least one embodiment, code and/or data storage 1801 and code and/or data storage 1805 may be partially combined and partially separate. In at least one embodiment, any portion of code and/or data storage 1801 and code and/or data storage 1805 may be included with other on-chip or off-chip data storage, including a processor's L1, L2, or L3 cache or system memory.

In at least one embodiment, inference and/or training logic 1815 may include, without limitation, one or more arithmetic logic unit(s) ("ALU(s)") 1810, including integer and/or floating point units, to perform logical and/or mathematical operations based, at least in part on, or indicated by, training and/or inference code (e.g., graph code), a result of which may produce activations (e.g., output values from layers or neurons within a neural network) stored in an activation storage 1820 that are functions of input/output and/or weight parameter data stored in code and/or data storage 1801 and/or code and/or data storage 1805. In at least one embodiment, activations stored in activation storage 1820 are generated according to linear algebraic and or matrix-based mathematics performed by ALU(s) 1810 in response to performing instructions or other code, wherein weight values stored in code and/or data storage 1805 and/or data storage 1801 are used as operands along with other values, such as bias values, gradient information, momentum values, or other parameters or hyperparameters, any or all of which may be stored in code and/or data storage 1805 or code and/or data storage 1801 or another storage on or off-chip.

In at least one embodiment, ALU(s) 1810 are included within one or more processors or other hardware logic devices or circuits, whereas in another embodiment, ALU(s) 1810 may be external to a processor or other hardware logic device or circuit that uses them (e.g., a co-processor). In at least one embodiment, ALUs 1810 may be included within a processor's execution units or otherwise within a bank of ALUs accessible by a processor's execution units either within same processor or distributed between different processors of different types (e.g., central processing units, graphics processing units, fixed function units, etc.). In at least one embodiment, code and/or data storage 1801, code and/or data storage 1805, and activation storage 1820 may share a processor or other hardware logic device or circuit, whereas in another embodiment, they may be in different processors or other hardware logic devices or circuits, or some combination of same and different processors or other hardware logic devices or circuits. In at least one embodiment, any portion of activation storage 1820 may be included with other on-chip or off-chip data storage, including a processor's L1, L2, or L3 cache or system memory. Furthermore, inferencing and/or training code may be stored with other code accessible to a processor or other hardware logic or circuit and fetched and/or processed using a processor's fetch, decode, scheduling, execution, retirement and/or other logical circuits.

In at least one embodiment, activation storage 1820 may be cache memory, DRAM, SRAM, non-volatile memory (e.g., flash memory), or other storage. In at least one embodiment, activation storage 1820 may be completely or partially within or external to one or more processors or other logical circuits. In at least one embodiment, a choice of whether activation storage 1820 is internal or external to a processor, for example, or including DRAM, SRAM, flash memory or some other storage type may depend on available storage on-chip versus off-chip, latency requirements of training and/or inferencing functions being performed, batch size of data used in inferencing and/or training of a neural network, or some combination of these factors.

In at least one embodiment, inference and/or training logic 1815 illustrated in FIG. 18A may be used in conjunction with an application-specific integrated circuit ("ASIC"), such as a TensorFlow® Processing Unit from Google, an inference processing unit (IPU) from Graphcore™, or a Nervana® (e.g., "Lake Crest") processor from Intel Corp. In at least one embodiment, inference and/or training logic 1815 illustrated in FIG. 18A may be used in conjunction with central processing unit ("CPU") hardware, graphics processing unit ("GPU") hardware or other hardware, such as field programmable gate arrays ("FPGAs").

Figure 18B:
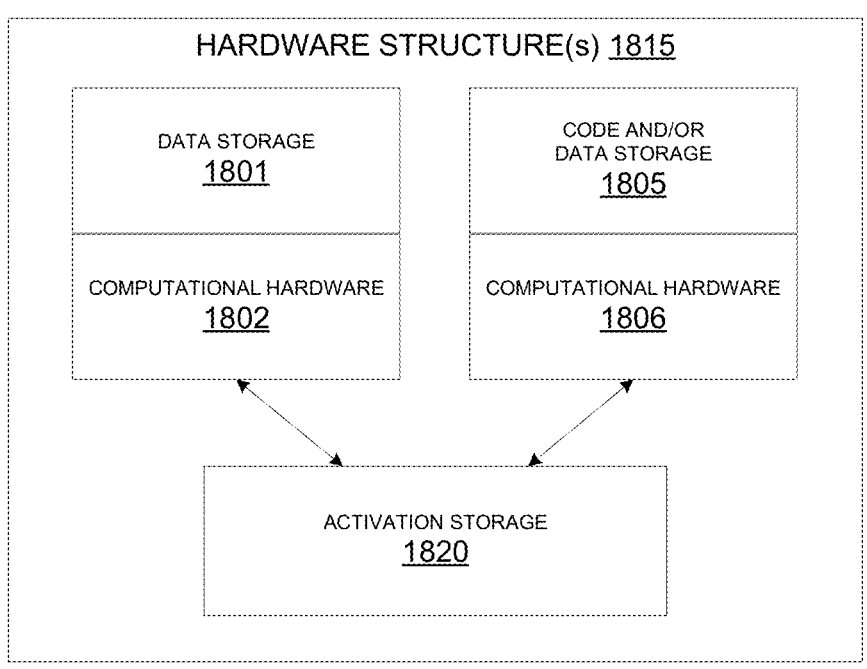
FIG. 18B illustrates inference and/or training logic, in accordance with at least one embodiment.

FIG. 18B illustrates inference and/or training logic 1815, according to at least one embodiment. In at least one embodiment, inference and/or training logic 1815 may include, without limitation, hardware logic in which computational resources are dedicated or otherwise exclusively used in conjunction with weight values or other information corresponding to one or more layers of neurons within a neural network. In at least one embodiment, inference and/or training logic 1815 illustrated in FIG. 18B may be used in conjunction with an application-specific integrated circuit (ASIC), such as TensorFlow® Processing Unit from Google, an inference processing unit (IPU) from Graphcore™, or a Nervana® (e.g., "Lake Crest") processor from Intel Corp. In at least one embodiment, inference and/or training logic 1815 illustrated in FIG. 18B may be used in conjunction with central processing unit (CPU) hardware, graphics processing unit (GPU) hardware or other hardware, such as field programmable gate arrays (FPGAs). In at least one embodiment, inference and/or training logic 1815 includes, without limitation, code and/or data storage 1801 and code and/or data storage 1805, which may be used to store code (e.g., graph code), weight values and/or other information, including bias values, gradient information, momentum values, and/or other parameter or hyperparameter information. In at least one embodiment illustrated in FIG. 18B, each of code and/or data storage 1801 and code and/or data storage 1805 is associated with a dedicated computational resource, such as computational hardware 1802 and computational hardware 1806, respectively. In at least one embodiment, each of computational hardware 1802 and computational hardware 1806 includes one or more ALUs that perform mathematical functions, such as linear algebraic functions, only on information stored in code and/or data storage 1801 and code and/or data storage 1805, respectively, result of which is stored in activation storage 1820.

In at least one embodiment, each of code and/or data storage 1801 and 1805 and corresponding computational hardware 1802 and 1806, respectively, correspond to different layers of a neural network, such that resulting activation from one storage/computational pair 1801/1802 of code and/or data storage 1801 and computational hardware 1802 is provided as an input to a next storage/computational pair 1805/1806 of code and/or data storage 1805 and computational hardware 1806, in order to mirror a conceptual organization of a neural network. In at least one embodiment, each of storage/computational pairs 1801/1802 and 1805/1806 may correspond to more than one neural network layer. In at least one embodiment, additional storage/computation pairs (not shown) subsequent to or in parallel with storage/computation pairs 1801/1802 and 1805/1806 may be included in inference and/or training logic 1815.

In at least one embodiment, the inference and/or training logic 1815 may be used to implement the system 100 (see FIG. 1) and/or the inference pipeline 500 (see FIG. 5). For example, the inference and/or training logic 1815 may be used to implement at least a portion of the GPU application 142B (e.g., any inferencing performed by the processing operation(s) 314). In at least one embodiment, the inference and/or training logic 1815 may be implemented by the processing system 104. In at least one embodiment, at least a portion of the system(s) depicted in FIGS. 18A and 18B is used to implement one or more systems, techniques, functions, and/or processes described in connection with FIGS. 1-5. For example, in at least one embodiment, at least one component shown or described with respect to FIGS. 18A and 18B is used to process data (e.g., data having a DICOM format) in accordance with one or more techniques, functions, and/or processes described with respect to any of FIGS. 1-5.

Figure 19:
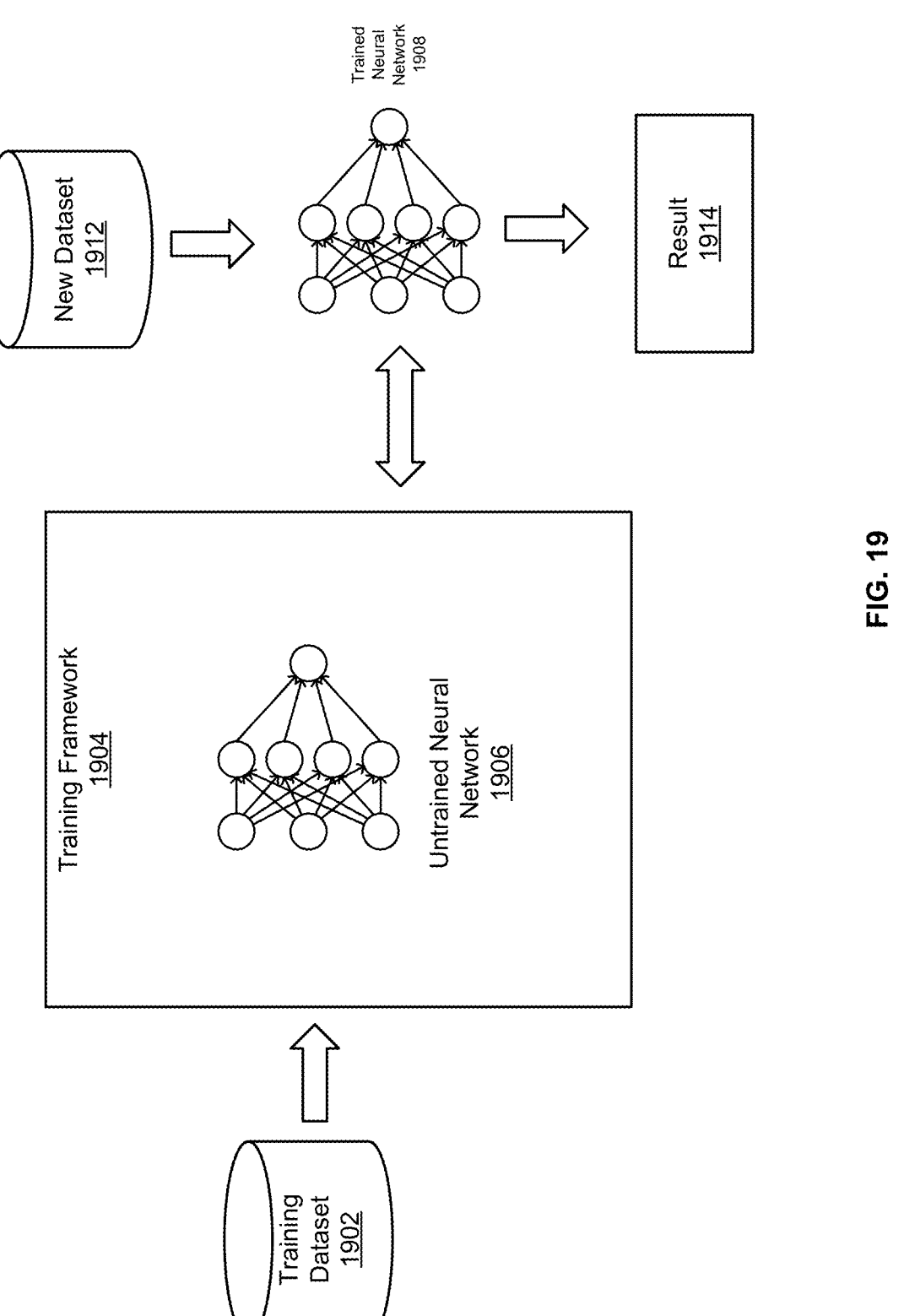
FIG. 19 illustrates training and deployment of a neural network, in accordance with at least one embodiment.

FIG. 19 illustrates training and deployment of a deep neural network, according to at least one embodiment. In at least one embodiment, untrained neural network 1906 is trained using a training dataset 1902. In at least one embodiment, training framework 1904 is a PyTorch framework, whereas in other embodiments, training framework 1904 is a TensorFlow, Boost, Caffe, Microsoft Cognitive Toolkit/CNTK, MXNet, Chainer, Keras, Deeplearning4j, or other training framework. In at least one embodiment, training framework 1904 trains an untrained neural network 1906 and enables it to be trained using processing resources described herein to generate a trained neural network 1908. In at least one embodiment, weights may be chosen randomly or by pre-training using a deep belief network. In at least one embodiment, training may be performed in either a supervised, partially supervised, or unsupervised manner.

In at least one embodiment, untrained neural network 1906 is trained using supervised learning, wherein training dataset 1902 includes an input paired with a desired output for an input, or where training dataset 1902 includes input having a known output and an output of neural network 1906 is manually graded. In at least one embodiment, untrained neural network 1906 is trained in a supervised manner and processes inputs from training dataset 1902 and compares resulting outputs against a set of expected or desired outputs. In at least one embodiment, errors are then propagated back through untrained neural network 1906. In at least one embodiment, training framework 1904 adjusts weights that control untrained neural network 1906. In at least one embodiment, training framework 1904 includes tools to monitor how well untrained neural network 1906 is converging towards a model, such as trained neural network 1908, suitable to generating correct answers, such as in result 1914, based on input data such as a new dataset 1912. In at least one embodiment, training framework 1904 trains untrained neural network 1906 repeatedly while adjust weights to refine an output of untrained neural network 1906 using a loss function and adjustment algorithm, such as stochastic gradient descent. In at least one embodiment, training framework 1904 trains untrained neural network 1906 until untrained neural network 1906 achieves a desired accuracy. In at least one embodiment, trained neural network 1908 can then be deployed to implement any number of machine learning operations.

In at least one embodiment, untrained neural network 1906 is trained using unsupervised learning, wherein untrained neural network 1906 attempts to train itself using unlabeled data. In at least one embodiment, unsupervised learning training dataset 1902 will include input data without any associated output data or "ground truth" data. In at least one embodiment, untrained neural network 1906 can learn groupings within training dataset 1902 and can determine how individual inputs are related to untrained dataset 1902. In at least one embodiment, unsupervised training can be used to generate a self-organizing map in trained neural network 1908 capable of performing operations useful in reducing dimensionality of new dataset 1912. In at least one embodiment, unsupervised training can also be used to perform anomaly detection, which allows identification of data points in new dataset 1912 that deviate from normal patterns of new dataset 1912.

In at least one embodiment, semi-supervised learning may be used, which is a technique in which in training dataset 1902 includes a mix of labeled and unlabeled data. In at least one embodiment, training framework 1904 may be used to perform incremental learning, such as through transferred learning techniques. In at least one embodiment, incremental learning enables trained neural network 1908 to adapt to new dataset 1912 without forgetting knowledge instilled within trained neural network 1908 during initial training.

In at least one embodiment, the training and deployment illustrated in FIG. 19 of the deep neural network may be used to implement the system 100 (see FIG. 1) and/or the inference pipeline 500 (see FIG. 5). For example, the training and deployment may be used to implement at least a portion of the GPU application 142B (e.g., any inferencing performed by the processing operation(s) 314). In at least one embodiment, the training and deployment may be implemented by the processing system 104. In at least one embodiment, at least a portion of the system(s) depicted in FIG. 19 is used to implement one or more systems, techniques, functions, and/or processes described in connection with FIGS. 1-5. For example, in at least one embodiment, at least one component shown or described with respect to FIG. 19 is used to process data (e.g., data having a DICOM format) in accordance with one or more techniques, functions, and/or processes described with respect to any of FIGS. 1-5.

5G Networks

The following figures set forth, without limitation, exemplary 5G network-based systems that can be used to implement at least one embodiment.

Figure 20:
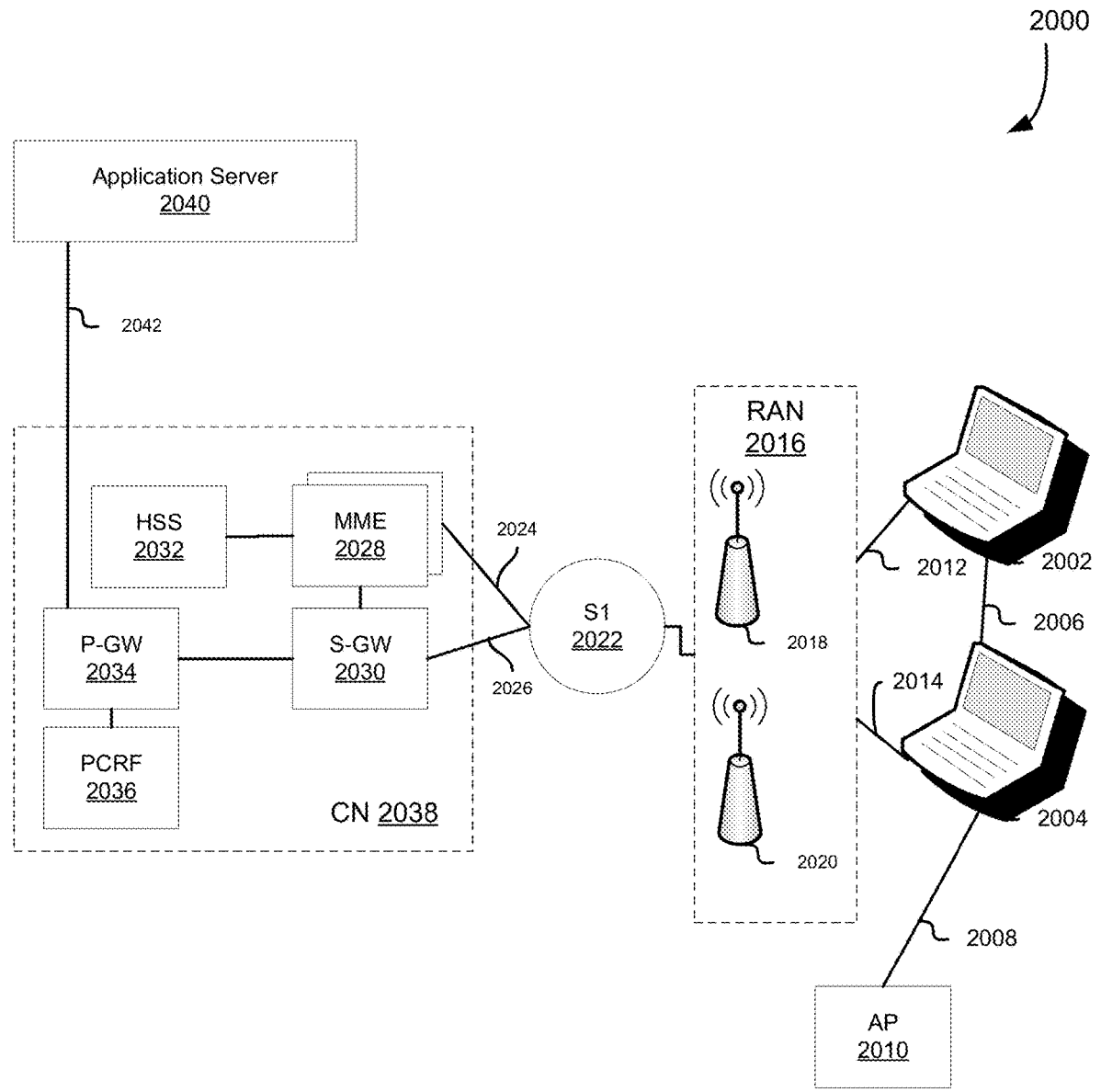
FIG. 20 illustrates an architecture of a system of a network, in accordance with at least one embodiment.

FIG. 20 illustrates an architecture of a system 2000 of a network, in accordance with at least one embodiment. In at least one embodiment, system 2000 is shown to include a user equipment (UE) 2002 and a UE 2004. In at least one embodiment, UEs 2002 and 2004 are illustrated as smartphones (e.g., handheld touchscreen mobile computing devices connectable to one or more cellular networks) but may also include any mobile or non-mobile computing device, such as Personal Data Assistants (PDAs), pagers, laptop computers, desktop computers, wireless handsets, or any computing device including a wireless communications interface.

In at least one embodiment, any of UEs 2002 and 2004 can include an Internet of Things (IoT) UE, which can include a network access layer designed for low-power IoT applications utilizing short-lived UE connections. In at least one embodiment, an IoT UE can utilize technologies such as machine-to-machine (M2M) or machine-type communications (MTC) for exchanging data with an MTC server or device via a public land mobile network (PLMN), Proximity-Based Service (ProSe) or device-to-device (D2D) communication, sensor networks, or IoT networks. In at least one embodiment, a M2M or MTC exchange of data may be a machine-initiated exchange of data. In at least one embodiment, an IoT network describes interconnecting IoT UEs, which may include uniquely identifiable embedded computing devices (within Internet infrastructure), with short-lived connections. In at least one embodiment, an IoT UEs may execute background applications (e.g., keep alive messages, status updates, etc.) to facilitate connections of an IoT network.

In at least one embodiment, UEs 2002 and 2004 may be configured to connect, e.g., communicatively couple, with a radio access network (RAN) 2016. In at least one embodiment, RAN 2016 may be, for example, an Evolved Universal Mobile Telecommunications System (UMTS) Terrestrial Radio Access Network (E-UTRAN), a NextGen RAN (NG RAN), or some other type of RAN. In at least one embodiment, UEs 2002 and 2004 utilize connections 2012 and 2014, respectively, each of which includes a physical communications interface or layer. In at least one embodiment, connections 2012 and 2014 are illustrated as an air interface to enable communicative coupling, and can be consistent with cellular communications protocols, such as a Global System for Mobile Communications (GSM) protocol, a code-division multiple access (CDMA) network protocol, a Push-to-Talk (PTT) protocol, a PTT over Cellular (POC) protocol, a Universal Mobile Telecommunications System (UMTS) protocol, a 3GPP Long Term Evolution (LTE) protocol, a fifth generation (5G) protocol, a New Radio (NR) protocol, and variations thereof.

In at least one embodiment, UEs 2002 and 2004 may further directly exchange communication data via a ProSe interface 2006. In at least one embodiment, ProSe interface 2006 may alternatively be referred to as a sidelink interface including one or more logical channels, including but not limited to a Physical Sidelink Control Channel (PSCCH), a Physical Sidelink Shared Channel (PSSCH), a Physical Sidelink Discovery Channel (PSDCH), and a Physical Sidelink Broadcast Channel (PSBCH).

In at least one embodiment, UE 2004 is shown to be configured to access an access point (AP) 2010 via connection 2008. In at least one embodiment, connection 2008 can include a local wireless connection, such as a connection consistent with any IEEE 802.11 protocol, wherein AP 2010 would include a wireless fidelity (WiFi®) router. In at least one embodiment, AP 2010 is shown to be connected to an Internet without connecting to a core network of a wireless system.

In at least one embodiment, RAN 2016 can include one or more access nodes that enable connections 2012 and 2014. In at least one embodiment, these access nodes (ANs) can be referred to as base stations (BSs), NodeBs, evolved NodeBs (eNBs), next Generation NodeBs (gNB), RAN nodes, and so forth, and can include ground stations (e.g., terrestrial access points) or satellite stations providing coverage within a geographic area (e.g., a cell). In at least one embodiment, RAN 2016 may include one or more RAN nodes for providing macrocells, e.g., macro RAN node 2018, and one or more RAN nodes for providing femtocells or picocells (e.g., cells having smaller coverage areas, smaller user capacity, or higher bandwidth compared to macrocells), e.g., low power (LP) RAN node 2020.

In at least one embodiment, any of RAN nodes 2018 and 2020 can terminate an air interface protocol and can be a first point of contact for UEs 2002 and 2004. In at least one embodiment, any of RAN nodes 2018 and 2020 can fulfill various logical functions for RAN 2016 including, but not limited to, radio network controller (RNC) functions such as radio bearer management, uplink and downlink dynamic radio resource management and data packet scheduling, and mobility management.

In at least one embodiment, UEs 2002 and 2004 can be configured to communicate using Orthogonal Frequency-Division Multiplexing (OFDM) communication signals with each other or with any of RAN nodes 2018 and 2020 over a multi-carrier communication channel in accordance various communication techniques, such as, but not limited to, an Orthogonal Frequency Division Multiple Access (OFDMA) communication technique (e.g., for downlink communications) or a Single Carrier Frequency Division Multiple Access (SC-FDMA) communication technique (e.g., for uplink and ProSe or sidelink communications), and/or variations thereof. In at least one embodiment, OFDM signals can include a plurality of orthogonal subcarriers.

In at least one embodiment, a downlink resource grid can be used for downlink transmissions from any of RAN nodes 2018 and 2020 to UEs 2002 and 2004, while uplink transmissions can utilize similar techniques. In at least one embodiment, a grid can be a time frequency grid, called a resource grid or time-frequency resource grid, which is a physical resource in a downlink in each slot. In at least one embodiment, such a time frequency plane representation is a common practice for OFDM systems, which makes it intuitive for radio resource allocation. In at least one embodiment, each column and each row of a resource grid corresponds to one OFDM symbol and one OFDM subcarrier, respectively. In at least one embodiment, a duration of a resource grid in a time domain corresponds to one slot in a radio frame. In at least one embodiment, a smallest time-frequency unit in a resource grid is denoted as a resource element. In at least one embodiment, each resource grid includes a number of resource blocks, which describe a mapping of certain physical channels to resource elements. In at least one embodiment, each resource block includes a collection of resource elements. In at least one embodiment, in a frequency domain, this may represent a smallest quantity of resources that currently can be allocated. In at least one embodiment, there are several different physical downlink channels that are conveyed using such resource blocks.

In at least one embodiment, a physical downlink shared channel (PDSCH) may carry user data and higher-layer signaling to UEs 2002 and 2004. In at least one embodiment, a physical downlink control channel (PDCCH) may carry information about a transport format and resource allocations related to PDSCH channel, among other things. In at least one embodiment, it may also inform UEs 2002 and 2004 about a transport format, resource allocation, and HARQ (Hybrid Automatic Repeat Request) information related to an uplink shared channel. In at least one embodiment, typically, downlink scheduling (assigning control and shared channel resource blocks to UE 2002 within a cell) may be performed at any of RAN nodes 2018 and 2020 based on channel quality information fed back from any of UEs 2002 and 2004. In at least one embodiment, downlink resource assignment information may be sent on a PDCCH used for (e.g., assigned to) each of UEs 2002 and 2004.

In at least one embodiment, a PDCCH may use control channel elements (CCEs) to convey control information. In at least one embodiment, before being mapped to resource elements, PDCCH complex valued symbols may first be organized into quadruplets, which may then be permuted using a sub-block interleaver for rate matching. In at least one embodiment, each PDCCH may be transmitted using one or more of these CCEs, where each CCE may correspond to nine sets of four physical resource elements known as resource element groups (REGs). In at least one embodiment, four Quadrature Phase Shift Keying (QPSK) symbols may be mapped to each REG. In at least one embodiment, PDCCH can be transmitted using one or more CCEs, depending on a size of a downlink control information (DCI) and a channel condition. In at least one embodiment, there can be four or more different PDCCH formats defined in LTE with different numbers of CCEs (e.g., aggregation level, L=1, 2, 4, or 8).

In at least one embodiment, an enhanced physical downlink control channel (EPDCCH) that uses PDSCH resources may be utilized for control information transmission. In at least one embodiment, EPDCCH may be transmitted using one or more enhanced control channel elements (ECCEs). In at least one embodiment, each ECCE may correspond to nine sets of four physical resource elements known as an enhanced resource element groups (EREGs). In at least one embodiment, an ECCE may have other numbers of EREGs in some situations.

In at least one embodiment, RAN 2016 is shown to be communicatively coupled to a core network (CN) 2038 via an S1 interface 2022. In at least one embodiment, CN 2038 may be an evolved packet core (EPC) network, a NextGen Packet Core (NPC) network, or some other type of CN. In at least one embodiment, S1 interface 2022 is split into two parts: S1-U interface 2026, which carries traffic data between RAN nodes 2018 and 2020 and serving gateway (S-GW) 2030, and a S1-mobility management entity (MME) interface 2024, which is a signaling interface between RAN nodes 2018 and 2020 and MMEs 2028.

In at least one embodiment, CN 2038 includes MMEs 2028, S-GW 2030, Packet Data Network (PDN) Gateway (P-GW) 2034, and a home subscriber server (HSS) 2032. In at least one embodiment, MMEs 2028 may be similar in function to a control plane of legacy Serving General Packet Radio Service (GPRS) Support Nodes (SGSN). In at least one embodiment, MMEs 2028 may manage mobility aspects in access such as gateway selection and tracking area list management. In at least one embodiment, HSS 2032 may include a database for network users, including subscription related information to support a network entities' handling of communication sessions. In at least one embodiment, CN 2038 may include one or several HSSs 2032, depending on a number of mobile subscribers, on a capacity of an equipment, on an organization of a network, etc. In at least one embodiment, HSS 2032 can provide support for routing/ roaming, authentication, authorization, naming/addressing resolution, location dependencies, etc.

In at least one embodiment, S-GW 2030 may terminate a S1 interface 2022 towards RAN 2016, and routes data packets between RAN 2016 and CN 2038. In at least one embodiment, S-GW 2030 may be a local mobility anchor point for inter-RAN node handovers and also may provide an anchor for inter-3GPP mobility. In at least one embodiment, other responsibilities may include lawful intercept, charging, and some policy enforcement.

In at least one embodiment, P-GW 2034 may terminate an SGi interface toward a PDN. In at least one embodiment, P-GW 2034 may route data packets between an EPC network 2038 and external networks such as a network including application server 2040 (alternatively referred to as application function (AF)) via an Internet Protocol (IP) interface 2042. In at least one embodiment, application server 2040 may be an element offering applications that use IP bearer resources with a core network (e.g., UMTS Packet Services (PS) domain, LTE PS data services, etc.). In at least one embodiment, P-GW 2034 is shown to be communicatively coupled to an application server 2040 via an IP communications interface 2042. In at least one embodiment, application server 2040 can also be configured to support one or more communication services (e.g., Voice-over-Internet Protocol (VOIP) sessions, PTT sessions, group communication sessions, social networking services, etc.) for UEs 2002 and 2004 via CN 2038.

In at least one embodiment, P-GW 2034 may further be a node for policy enforcement and charging data collection. In at least one embodiment, policy and Charging Enforcement Function (PCRF) 2036 is a policy and charging control element of CN 2038. In at least one embodiment, in a non-roaming scenario, there may be a single PCRF in a Home Public Land Mobile Network (HPLMN) associated with a UE's Internet Protocol Connectivity Access Network (IP-CAN) session. In at least one embodiment, in a roaming scenario with local breakout of traffic, there may be two PCRFs associated with a UE's IP-CAN session: a Home PCRF (H-PCRF) within a HPLMN and a Visited PCRF (V-PCRF) within a Visited Public Land Mobile Network (VPLMN). In at least one embodiment, PCRF 2036 may be communicatively coupled to application server 2040 via P-GW 2034. In at least one embodiment, application server 2040 may signal PCRF 2036 to indicate a new service flow and select an appropriate Quality of Service (QOS) and charging parameters. In at least one embodiment, PCRF 2036 may provision this rule into a Policy and Charging Enforcement Function (PCEF) (not shown) with an appropriate traffic flow template (TFT) and QoS class of identifier (QCI), which commences a QoS and charging as specified by application server 2040.

In at least one embodiment, the system 2000 may be used to implement the system 100 (see FIG. 1) and/or the inference pipeline 500 (see FIG. 5). For example, the application server 2040 may be used to implement the processing system 104, the requestor device(s) 102, the receiver device(s) 106, and/or the optional data storage units 108. In at least one embodiment, at least a portion of the system(s) depicted in FIG. 20 is used to implement one or more systems, techniques, functions, and/or processes described in connection with FIGS. 1-5. For example, in at least one embodiment, at least one component shown or described with respect to FIG. 20 is used to process data (e.g., data having a DICOM format) in accordance with one or more techniques, functions, and/or processes described with respect to any of FIGS. 1-5.

Figure 21:
FIG. 21 illustrates an architecture of a system of a network, in accordance with at least one embodiment.
Figure 21:
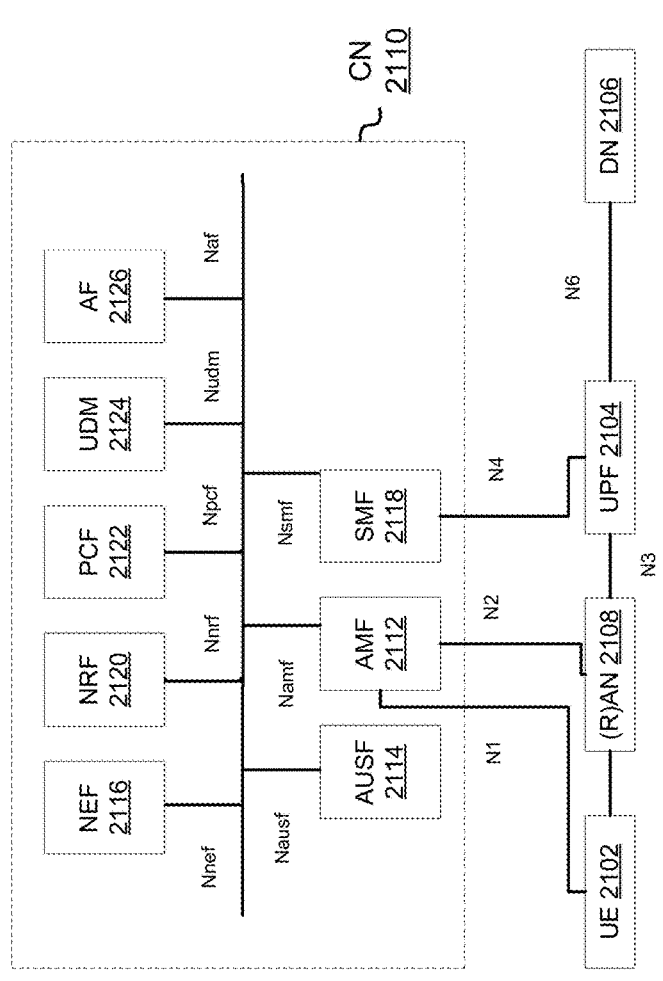

FIG. 21 illustrates an architecture of a system 2100 of a network in accordance with some embodiments. In at least one embodiment, system 2100 is shown to include a UE 2102, a 5G access node or RAN node (shown as (R)AN node 2108), a User Plane Function (shown as UPF 2104), a Data Network (DN 2106), which may be, for example, operator services, Internet access or 3rd party services, and a 5G Core Network (5GC) (shown as CN 2110).

In at least one embodiment, CN 2110 includes an Authentication Server Function (AUSF 2114); a Core Access and Mobility Management Function (AMF 2112); a Session Management Function (SMF 2118); a Network Exposure Function (NEF 2116); a Policy Control Function (PCF 2122); a Network Function (NF) Repository Function (NRF 2120); a Unified Data Management (UDM 2124); and an Application Function (AF 2126). In at least one embodiment, CN 2110 may also include other elements that are not shown, such as a Structured Data Storage network function (SDSF), an Unstructured Data Storage network function (UDSF), and variations thereof.

In at least one embodiment, UPF 2104 may act as an anchor point for intra-RAT and inter-RAT mobility, an external PDU session point of interconnect to DN 2106, and a branching point to support multi-homed PDU session. In at least one embodiment, UPF 2104 may also perform packet routing and forwarding, packet inspection, enforce user plane part of policy rules, lawfully intercept packets (UP collection); traffic usage reporting, perform QoS handling for user plane (e.g. packet filtering, gating, UL/DL rate enforcement), perform Uplink Traffic verification (e.g., SDF to QoS flow mapping), transport level packet marking in uplink and downlink, and downlink packet buffering and downlink data notification triggering. In at least one embodiment, UPF 2104 may include an uplink classifier to support routing traffic flows to a data network. In at least one embodiment, DN 2106 may represent various network operator services, Internet access, or third party services.

In at least one embodiment, AUSF 2114 may store data for authentication of UE 2102 and handle authentication related functionality. In at least one embodiment, AUSF 2114 may facilitate a common authentication framework for various access types.

In at least one embodiment, AMF 2112 may be responsible for registration management (e.g., for registering UE 2102, etc.), connection management, reachability management, mobility management, and lawful interception of AMF-related events, and access authentication and authorization. In at least one embodiment, AMF 2112 may provide transport for SM messages for SMF 2118, and act as a transparent proxy for routing SM messages. In at least one embodiment, AMF 2112 may also provide transport for short message service (SMS) messages between UE 2102 and an SMS function (SMSF) (not shown by FIG. 21). In at least one embodiment, AMF 2112 may act as Security Anchor Function (SEA), which may include interaction with AUSF 2114 and UE 2102 and receipt of an intermediate key that was established as a result of UE 2102 authentication process. In at least one embodiment, where USIM based authentication is used, AMF 2112 may retrieve security material from AUSF 2114. In at least one embodiment, AMF 2112 may also include a Security Context Management (SCM) function, which receives a key from SEA that it uses to derive access-network specific keys. In at least one embodiment, furthermore, AMF 2112 may be a termination point of RAN CP interface (N2 reference point), a termination point of NAS (NI) signaling, and perform NAS ciphering and integrity protection.

In at least one embodiment, AMF 2112 may also support NAS signaling with a UE 2102 over an N3 interworking-function (IWF) interface. In at least one embodiment, N3IWF may be used to provide access to untrusted entities. In at least one embodiment, N3IWF may be a termination point for N2 and N3 interfaces for control plane and user plane, respectively, and as such, may handle N2 signaling from SMF and AMF for PDU sessions and QoS, encapsulate/de-encapsulate packets for IPSec and N3 tunneling, mark N3 user-plane packets in uplink, and enforce QoS corresponding to N3 packet marking taking into account QoS requirements associated to such marking received over N2. In at least one embodiment, N3IWF may also relay uplink and downlink control-plane NAS (NI) signaling between UE 2102 and AMF 2112, and relay uplink and downlink user-plane packets between UE 2102 and UPF 2104. In at least one embodiment, N3IWF also provides mechanisms for IPsec tunnel establishment with UE 2102.

In at least one embodiment, SMF 2118 may be responsible for session management (e.g., session establishment, modify and release, including tunnel maintain between UPF and AN node); UE IP address allocation & management (including optional Authorization); Selection and control of UP function; Configures traffic steering at UPF to route traffic to proper destination; termination of interfaces towards Policy control functions; control part of policy enforcement and QoS; lawful intercept (for SM events and interface to LI System); termination of SM parts of NAS messages; downlink Data Notification; initiator of AN specific SM information, sent via AMF over N2 to AN; determine SSC mode of a session. In at least one embodiment, SMF 2118 may include following roaming functionality: handle local enforcement to apply QOS SLAB (VPLMN); charging data collection and charging interface (VPLMN); lawful intercept (in VPLMN for SM events and interface to LI System); support for interaction with external DN for transport of signaling for PDU session authorization/authentication by external DN.

In at least one embodiment, NEF 2116 may provide means for securely exposing services and capabilities provided by 3GPP network functions for third party, internal exposure/re-exposure, Application Functions (e.g., AF 2126), edge computing or fog computing systems, etc. In at least one embodiment, NEF 2116 may authenticate, authorize, and/or throttle AFs. In at least one embodiment, NEF 2116 may also translate information exchanged with AF 2126 and information exchanged with internal network functions. In at least one embodiment, NEF 2116 may translate between an AF-Service-Identifier and an internal 5GC information. In at least one embodiment, NEF 2116 may also receive information from other network functions (NFs) based on exposed capabilities of other network functions. In at least one embodiment, this information may be stored at NEF 2116 as structured data, or at a data storage NF using a standardized interfaces. In at least one embodiment, stored information can then be re-exposed by NEF 2116 to other NFs and AFs, and/or used for other purposes such as analytics.

In at least one embodiment, NRF 2120 may support service discovery functions, receive NF Discovery Requests from NF instances, and provide information of discovered NF instances to NF instances. In at least one embodiment, NRF 2120 also maintains information of available NF instances and their supported services.

In at least one embodiment, PCF 2122 may provide policy rules to control plane function(s) to enforce them, and may also support unified policy framework to govern network behavior. In at least one embodiment, PCF 2122 may also implement a front end (FE) to access subscription information relevant for policy decisions in a UDR of UDM 2124.

In at least one embodiment, UDM 2124 may handle subscription-related information to support a network entities' handling of communication sessions, and may store subscription data of UE 2102. In at least one embodiment, UDM 2124 may include two parts, an application FE and a User Data Repository (UDR). In at least one embodiment, UDM may include a UDM FE, which is in charge of processing of credentials, location management, subscription management and so on. In at least one embodiment, several different front ends may serve a same user in different transactions. In at least one embodiment, UDM-FE accesses subscription information stored in an UDR and performs authentication credential processing; user identification handling; access authorization; registration/mobility management; and subscription management. In at least one embodiment, UDR may interact with PCF 2122. In at least one embodiment, UDM 2124 may also support SMS management, wherein an SMS-FE implements a similar application logic as discussed previously.

In at least one embodiment, AF 2126 may provide application influence on traffic routing, access to a Network Capability Exposure (NCE), and interact with a policy framework for policy control. In at least one embodiment, NCE may be a mechanism that allows a 5GC and AF 2126 to provide information to each other via NEF 2116, which may be used for edge computing implementations. In at least one embodiment, network operator and third party services may be hosted close to UE 2102 access point of attachment to achieve an efficient service delivery through a reduced end-to-end latency and load on a transport network. In at least one embodiment, for edge computing implementations, 5GC may select a UPF 2104 close to UE 2102 and execute traffic steering from UPF 2104 to DN 2106 via N6 interface. In at least one embodiment, this may be based on UE subscription data, UE location, and information provided by AF 2126. In at least one embodiment, AF 2126 may influence UPF (re)selection and traffic routing. In at least one embodiment, based on operator deployment, when AF 2126 is considered to be a trusted entity, a network operator may permit AF 2126 to interact directly with relevant NFs.

In at least one embodiment, CN 2110 may include an SMSF, which may be responsible for SMS subscription checking and verification, and relaying SM messages to/from UE 2102 to/from other entities, such as an SMS-GMSC/IWMSC/SMS-router. In at least one embodiment, SMS may also interact with AMF 2112 and UDM 2124 for notification procedure that UE 2102 is available for SMS transfer (e.g., set a UE not reachable flag, and notifying UDM 2124 when UE 2102 is available for SMS).

In at least one embodiment, system 2100 may include following service-based interfaces: Namf: Service-based interface exhibited by AMF; Nsmf: Service-based interface exhibited by SMF; Nnef: Service-based interface exhibited by NEF; Npcf: Service-based interface exhibited by PCF; Nudm: Service-based interface exhibited by UDM; Naf: Service-based interface exhibited by AF; Nnrf: Service-based interface exhibited by NRF; and Nausf: Service-based interface exhibited by AUSF.

In at least one embodiment, system 2100 may include following reference points: N1: Reference point between UE and AMF; N2: Reference point between (R)AN and AMF; N3: Reference point between (R)AN and UPF; N4: Reference point between SMF and UPF; and N6: Reference point between UPF and a Data Network. In at least one embodiment, there may be many more reference points and/or service-based interfaces between a NF services in NFs, however, these interfaces and reference points have been omitted for clarity. In at least one embodiment, an NS reference point may be between a PCF and AF; an N7 reference point may be between PCF and SMF; an N11 reference point between AMF and SMF; etc. In at least one embodiment, CN 2110 may include an Nx interface, which is an inter-CN interface between MME and AMF 2112 in order to enable interworking between CN 2110 and CN 7221.

In at least one embodiment, system 2100 may include multiple RAN nodes (such as (R)AN node 2108) wherein an Xn interface is defined between two or more (R)AN node 2108 (e.g., gNBs) that connecting to 5GC 410, between a (R)AN node 2108 (e.g., gNB) connecting to CN 2110 and an eNB (e.g., a macro RAN node), and/or between two eNBs connecting to CN 2110.

In at least one embodiment, Xn interface may include an Xn user plane (Xn-U) interface and an Xn control plane (Xn-C) interface. In at least one embodiment, Xn-U may provide non-guaranteed delivery of user plane PDUs and support/provide data forwarding and flow control functionality. In at least one embodiment, Xn-C may provide management and error handling functionality, functionality to manage a Xn-C interface; mobility support for UE 2102 in a connected mode (e.g., CM-CONNECTED) including functionality to manage UE mobility for connected mode between one or more (R)AN node 2108. In at least one embodiment, mobility support may include context transfer from an old (source) serving (R)AN node 2108 to new (target) serving (R)AN node 2108; and control of user plane tunnels between old (source) serving (R)AN node 2108 to new (target) serving (R)AN node 2108.

In at least one embodiment, a protocol stack of a Xn-U may include a transport network layer built on Internet Protocol (IP) transport layer, and a GTP-U layer on top of a UDP and/or IP layer(s) to carry user plane PDUs. In at least one embodiment, Xn-C protocol stack may include an application layer signaling protocol (referred to as Xn Application Protocol (Xn-AP)) and a transport network layer that is built on an SCTP layer. In at least one embodiment, SCTP layer may be on top of an IP layer. In at least one embodiment, SCTP layer provides a guaranteed delivery of application layer messages. In at least one embodiment, in a transport IP layer point-to-point transmission is used to deliver signaling PDUs. In at least one embodiment, Xn-U protocol stack and/or a Xn-C protocol stack may be same or similar to an user plane and/or control plane protocol stack(s) shown and described herein.

In at least one embodiment, the network implemented by the system 2100 may be used to implement the system 100 (see FIG. 1) and/or the inference pipeline 500 (see FIG. 5). In at least one embodiment, at least a portion of the system(s) depicted in FIG. 21 is used to implement one or more systems, techniques, functions, and/or processes described in connection with FIGS. 1-5. For example, in at least one embodiment, at least one component shown or described with respect to FIG. 21 is used to process data (e.g., data having a DICOM format) in accordance with one or more techniques, functions, and/or processes described with respect to any of FIGS. 1-5.

Figure 22:
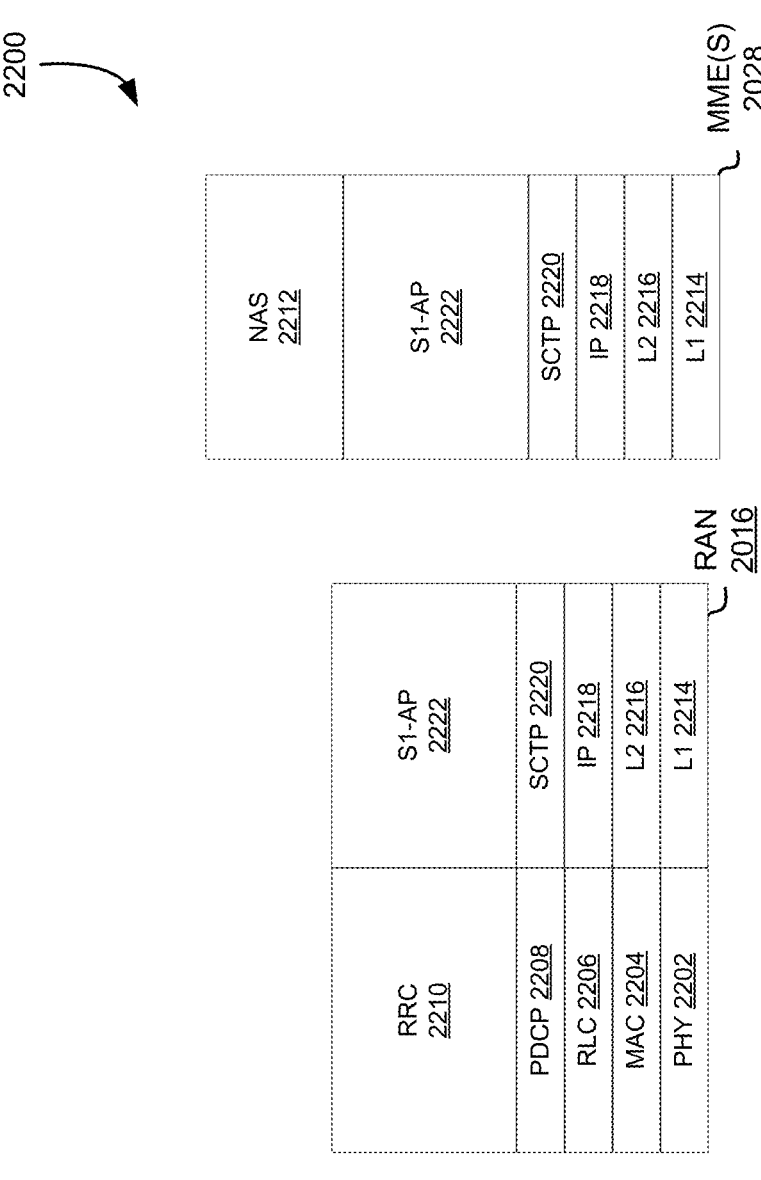
FIG. 22 illustrates a control plane protocol stack, in accordance with at least one embodiment.

FIG. 22 is an illustration of a control plane protocol stack in accordance with some embodiments. In at least one embodiment, a control plane 2200 is shown as a communications protocol stack between UE 2002 (or alternatively, UE 2004), RAN 2016, and MME(s) 2028.

In at least one embodiment, PHY layer 2202 may transmit or receive information used by MAC layer 2204 over one or more air interfaces. In at least one embodiment, PHY layer 2202 may further perform link adaptation or adaptive modulation and coding (AMC), power control, cell search (e.g., for initial synchronization and handover purposes), and other measurements used by higher layers, such as an RRC layer 2210. In at least one embodiment, PHY layer 2202 may still further perform error detection on transport channels, forward error correction (FEC) coding/de-coding of transport channels, modulation/demodulation of physical channels, interleaving, rate matching, mapping onto physical channels, and Multiple Input Multiple Output (MIMO) antenna processing.

In at least one embodiment, MAC layer 2204 may perform mapping between logical channels and transport channels, multiplexing of MAC service data units (SDUs) from one or more logical channels onto transport blocks (TB) to be delivered to PHY via transport channels, de-multiplexing MAC SDUs to one or more logical channels from transport blocks (TB) delivered from PHY via transport channels, multiplexing MAC SDUs onto TBs, scheduling information reporting, error correction through hybrid automatic repeat request (HARD), and logical channel prioritization.

In at least one embodiment, RLC layer 2206 may operate in a plurality of modes of operation, including: Transparent Mode (TM), Unacknowledged Mode (UM), and Acknowledged Mode (AM). In at least one embodiment, RLC layer 2206 may execute transfer of upper layer protocol data units (PDUs), error correction through automatic repeat request (ARQ) for AM data transfers, and concatenation, segmentation and reassembly of RLC SDUs for UM and AM data transfers. In at least one embodiment, RLC layer 2206 may also execute re-segmentation of RLC data PDUs for AM data transfers, reorder RLC data PDUs for UM and AM data transfers, detect duplicate data for UM and AM data transfers, discard RLC SDUs for UM and AM data transfers, detect protocol errors for AM data transfers, and perform RLC re-establishment.

In at least one embodiment, PDCP layer 2208 may execute header compression and decompression of IP data, maintain PDCP Sequence Numbers (SNs), perform in-sequence delivery of upper layer PDUs at re-establishment of lower layers, eliminate duplicates of lower layer SDUs at re-establishment of lower layers for radio bearers mapped on RLC AM, cipher and decipher control plane data, perform integrity protection and integrity verification of control plane data, control timer-based discard of data, and perform security operations (e.g., ciphering, deciphering, integrity protection, integrity verification, etc.).

In at least one embodiment, main services and functions of a RRC layer 2210 may include broadcast of system information (e.g., included in Master Information Blocks (MIBs) or System Information Blocks (SIBs) related to a non-access stratum (NAS)), broadcast of system information related to an access stratum (AS), paging, establishment, maintenance and release of an RRC connection between an UE and E-UTRAN (e.g., RRC connection paging, RRC connection establishment, RRC connection modification, and RRC connection release), establishment, configuration, maintenance and release of point-to-point radio bearers, security functions including key management, inter radio access technology (RAT) mobility, and measurement configuration for UE measurement reporting. In at least one embodiment, said MIBs and SIBs may include one or more information elements (IEs), which may each include individual data fields or data structures.

In at least one embodiment, UE 2002 and RAN 2016 may utilize a Uu interface (e.g., an LTE-Uu interface) to exchange control plane data via a protocol stack including PHY layer 2202, MAC layer 2204, RLC layer 2206, PDCP layer 2208, and RRC layer 2210.

In at least one embodiment, non-access stratum (NAS) protocols (NAS protocols 2212) form a highest stratum of a control plane between UE 2002 and MME(s) 2028. In at least one embodiment, NAS protocols 2212 support mobility of UE 2002 and session management procedures to establish and maintain IP connectivity between UE 2002 and P-GW 2034.

In at least one embodiment, Si Application Protocol (S1-AP) layer (Si-AP layer 2222) may support functions of a Si interface and include Elementary Procedures (EPs). In at least one embodiment, an EP is a unit of interaction between RAN 2016 and CN 2028. In at least one embodiment, S1-AP layer services may include two groups: UE-associated services and non UE-associated services. In at least one embodiment, these services perform functions including, but not limited to: E-UTRAN Radio Access Bearer (E-RAB) management, UE capability indication, mobility, NAS signaling transport, RAN Information Management (RIM), and configuration transfer.

In at least one embodiment, Stream Control Transmission Protocol (SCTP) layer (alternatively referred to as a stream control transmission protocol/internet protocol (SCTP/IP) layer) (SCTP layer 2220) may ensure reliable delivery of signaling messages between RAN 2016 and MME(s) 2028 based, in part, on an IP protocol, supported by an IP layer 2218. In at least one embodiment, L2 layer 2216 and an L1 layer 2214 may refer to communication links (e.g., wired or wireless) used by a RAN node and MME to exchange information.

In at least one embodiment, RAN 2016 and MME(s) 2028 may utilize an S1-MME interface to exchange control plane data via a protocol stack including a L1 layer 2214, L2 layer 2216, IP layer 2218, SCTP layer 2220, and Si-AP layer 2222.

Figure 23:
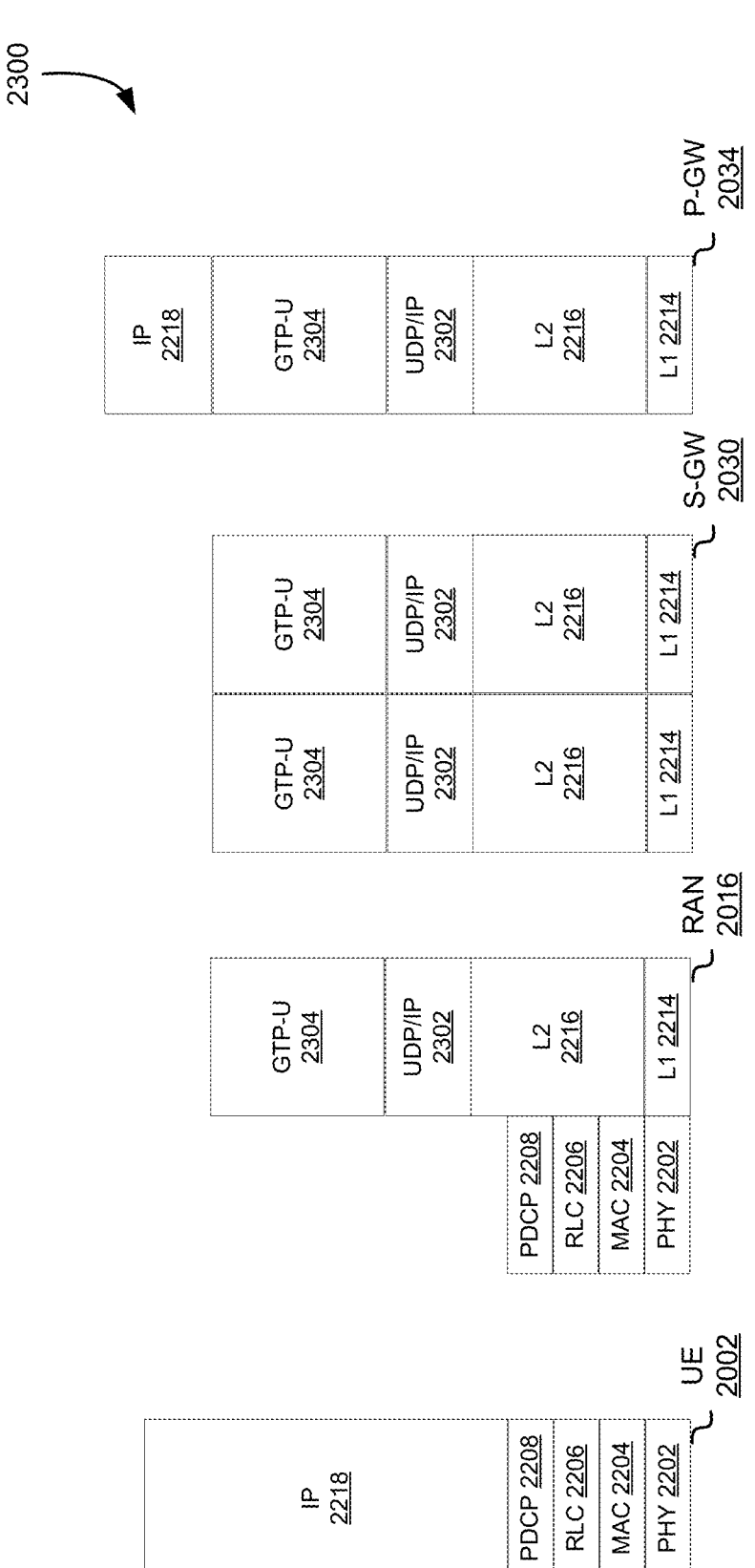
FIG. 23 illustrates a user plane protocol stack, in accordance with at least one embodiment.

FIG. 23 is an illustration of a user plane protocol stack in accordance with at least one embodiment. In at least one embodiment, a user plane 2300 is shown as a communications protocol stack between a UE 2002, RAN 2016, S-GW 2030, and P-GW 2034. In at least one embodiment, user plane 2300 may utilize a same protocol layers as control plane 2200. In at least one embodiment, for example, UE 2002 and RAN 2016 may utilize a Uu interface (e.g., an LTE-Uu interface) to exchange user plane data via a protocol stack including PHY layer 2202, MAC layer 2204, RLC layer 2206, PDCP layer 2208.

In at least one embodiment, General Packet Radio Service (GPRS) Tunneling Protocol for a user plane (GTP-U) layer (GTP-U layer 2304) may be used for carrying user data within a GPRS core network and between a radio access network and a core network. In at least one embodiment, user data transported can be packets in any of IPV4, IPV6, or PPP formats, for example. In at least one embodiment, UDP and IP security (UDP/IP) layer (UDP/IP layer 2302) may provide checksums for data integrity, port numbers for addressing different functions at a source and destination, and encryption and authentication on selected data flows. In at least one embodiment, RAN 2016 and S-GW 2030 may utilize an S1-U interface to exchange user plane data via a protocol stack including L1 layer 2214, L2 layer 2216, UDP/IP layer 2302, and GTP-U layer 2304. In at least one embodiment, S-GW 2030 and P-GW 2034 may utilize an S5/S8a interface to exchange user plane data via a protocol stack including L1 layer 2214, L2 layer 2216, UDP/IP layer 2302, and GTP-U layer 2304. In at least one embodiment, as discussed above with respect to FIG. 22, NAS protocols support a mobility of UE 2002 and session management procedures to establish and maintain IP connectivity between UE 2002 and P-GW 2034.

Figure 24:
FIG. 24 illustrates components of a core network, in accordance with at least one embodiment.
Figure 24:
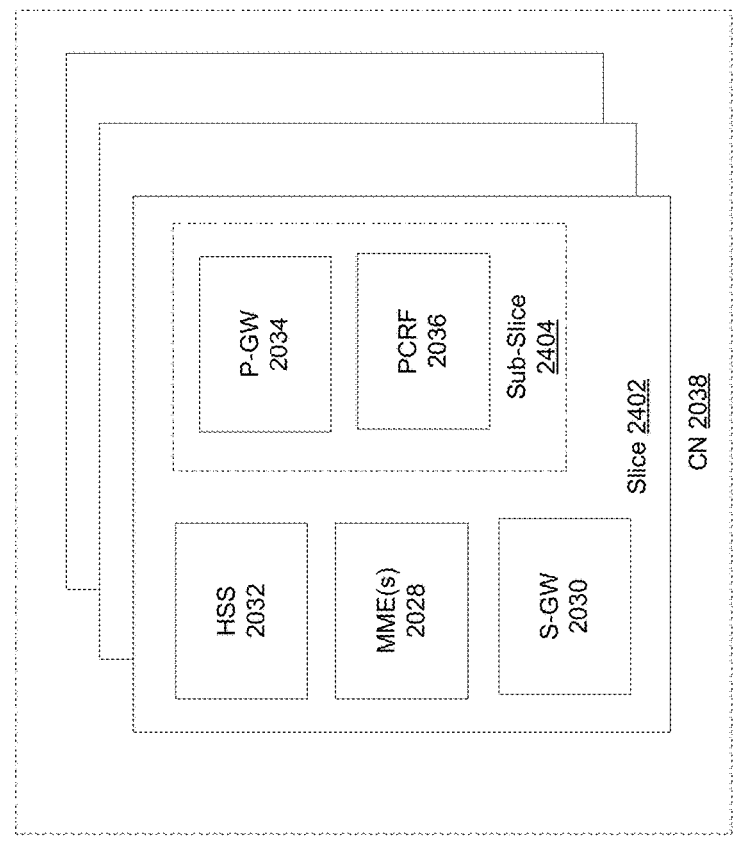

FIG. 24 illustrates components 2400 of a core network in accordance with at least one embodiment. In at least one embodiment, components of CN 2038 may be implemented in one physical node or separate physical nodes including components to read and execute instructions from a machine-readable or computer-readable medium (e.g., a non-transitory machine-readable storage medium). In at least one embodiment, Network Functions Virtualization (NFV) is utilized to virtualize any or all of above described network node functions via executable instructions stored in one or more computer readable storage mediums (described in further detail below). In at least one embodiment, a logical instantiation of CN 2038 may be referred to as a network slice 2402 (e.g., network slice 2402 is shown to include HSS 2032, MME(s) 2028, and S-GW 2030). In at least one embodiment, a logical instantiation of a portion of CN 2038 may be referred to as a network sub-slice 2404 (e.g., network sub-slice 2404 is shown to include P-GW 2034 and PCRF 2036).

In at least one embodiment, NFV architectures and infrastructures may be used to virtualize one or more network functions, alternatively performed by proprietary hardware, onto physical resources including a combination of industry-standard server hardware, storage hardware, or switches. In at least one embodiment, NFV systems can be used to execute virtual or reconfigurable implementations of one or more EPC components/functions.

Figure 25:
FIG. 25 illustrates components of a system to support network function virtualization (NFV), in accordance with at least one embodiment.
Figure 25:
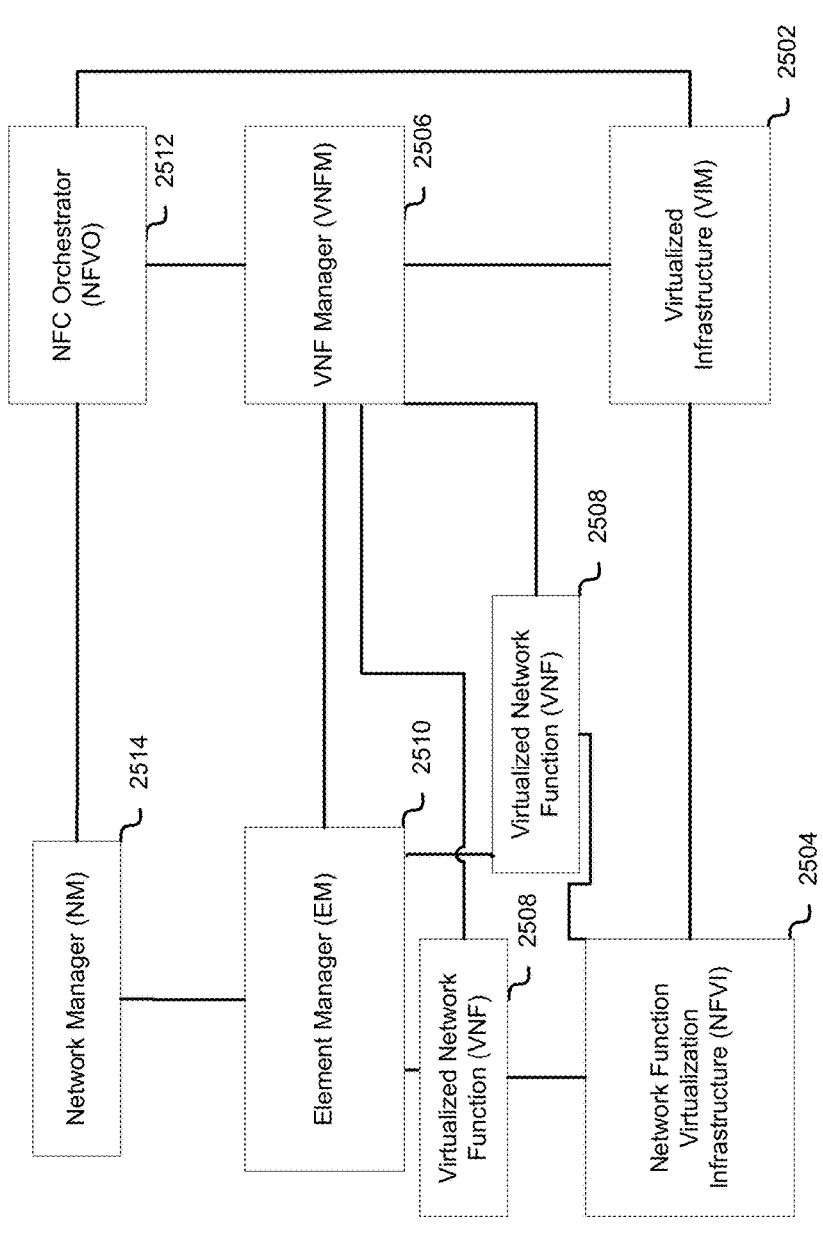

FIG. 25 is a block diagram illustrating components, according to at least one embodiment, of a system 2500 to support network function virtualization (NFV). In at least one embodiment, system 2500 is illustrated as including a virtualized infrastructure manager (shown as VIM 2502), a network function virtualization infrastructure (shown as NFVI 2504), a VNF manager (shown as VNFM 2506), virtualized network functions (shown as VNF 2508), an element manager (shown as EM 2510), an NFV Orchestrator (shown as NFVO 2512), and a network manager (shown as NM 2514).

In at least one embodiment, VIM 2502 manages resources of NFVI 2504. In at least one embodiment, NFVI 2504 can include physical or virtual resources and applications (including hypervisors) used to execute system 2500. In at least one embodiment, VIM 2502 may manage a life cycle of virtual resources with NFVI 2504 (e.g., creation, maintenance, and tear down of virtual machines (VMs) associated with one or more physical resources), track VM instances, track performance, fault and security of VM instances and associated physical resources, and expose VM instances and associated physical resources to other management systems.

In at least one embodiment, VNFM 2506 may manage VNF 2508. In at least one embodiment, VNF 2508 may be used to execute EPC components/functions. In at least one embodiment, VNFM 2506 may manage a life cycle of VNF 2508 and track performance, fault and security of virtual aspects of VNF 2508. In at least one embodiment, EM 2510 may track performance, fault and security of functional aspects of VNF 2508. In at least one embodiment, tracking data from VNFM 2506 and EM 2510 may include, for example, performance measurement (PM) data used by VIM 2502 or NFVI 2504. In at least one embodiment, both VNFM 2506 and EM 2510 can scale up/down a quantity of VNFs of system 2500.

In at least one embodiment, NFVO 2512 may coordinate, authorize, release and engage resources of NFVI 2504 in order to provide a requested service (e.g., to execute an EPC function, component, or slice). In at least one embodiment, NM 2514 may provide a package of end-user functions with responsibility for a management of a network, which may include network elements with VNFs, non-virtualized network functions, or both (management of VNFs may occur via an EM 2510).

In at least one embodiment, the system 2500 may be used to implement the system 100 (see FIG. 1) and/or the inference pipeline 500 (see FIG. 5). In at least one embodiment, at least a portion of the system(s) depicted in FIGS. 22-25 is used to implement one or more systems, techniques, functions, and/or processes described in connection with FIGS. 1-5. For example, in at least one embodiment, at least one component shown or described with respect to FIGS. 22-25 is used to process data (e.g., data having a DICOM format) in accordance with one or more techniques, functions, and/or processes described with respect to any of FIGS. 1-5.

Computer-Based Systems

The following figures set forth, without limitation, exemplary computer-based systems that can be used to implement at least one embodiment.

Figure 26:
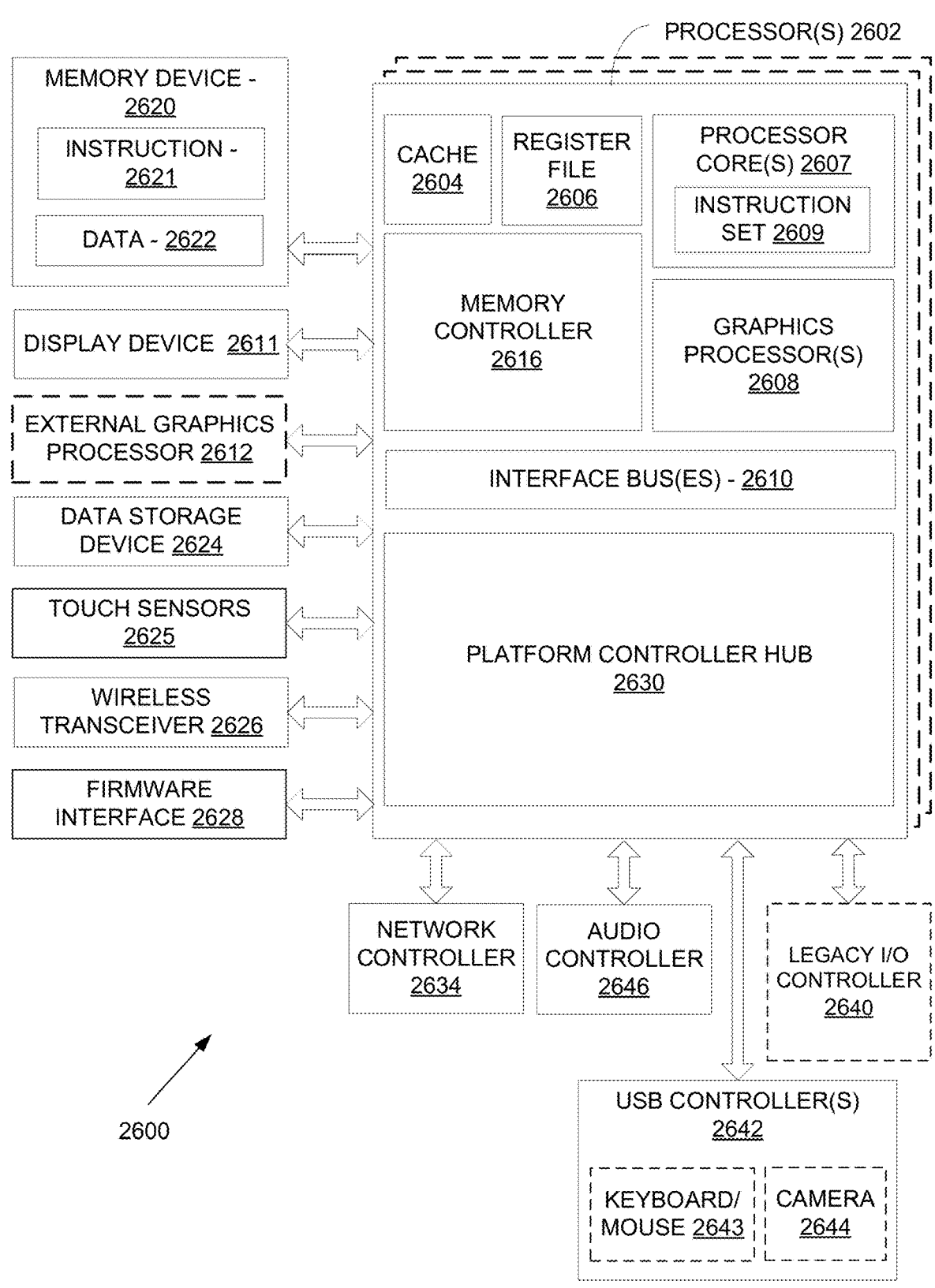
FIG. 26 illustrates a processing system, in accordance with at least one embodiment.

FIG. 26 illustrates a processing system 2600, in accordance with at least one embodiment. In at least one embodiment, processing system 2600 includes one or more processors 2602 and one or more graphics processors 2608, and may be a single processor desktop system, a multiprocessor workstation system, or a server system having a large number of processors 2602 or processor cores 2607. In at least one embodiment, processing system 2600 is a processing platform incorporated within a system-on-a-chip ("SoC") integrated circuit for use in mobile, handheld, or embedded devices.

In at least one embodiment, processing system 2600 can include, or be incorporated within a server-based gaming platform, a game console, a media console, a mobile gaming console, a handheld game console, or an online game console. In at least one embodiment, processing system 2600 is a mobile phone, smart phone, tablet computing device or mobile Internet device. In at least one embodiment, processing system 2600 can also include, couple with, or be integrated within a wearable device, such as a smart watch wearable device, smart eyewear device, augmented reality device, or virtual reality device. In at least one embodiment, processing system 2600 is a television or set top box device having one or more processors 2602 and a graphical interface generated by one or more graphics processors 2608.

In at least one embodiment, one or more processors 2602 each include one or more processor cores 2607 to process instructions which, when executed, perform operations for system and user software. In at least one embodiment, each of one or more processor cores 2607 is configured to process a specific instruction set 2609. In at least one embodiment, instruction set 2609 may facilitate Complex Instruction Set Computing ("CISC"), Reduced Instruction Set Computing ("RISC"), or computing via a Very Long Instruction Word ("VLIW"). In at least one embodiment, processor cores 2607 may each process a different instruction set 2609, which may include instructions to facilitate emulation of other instruction sets. In at least one embodiment, processor core 2607 may also include other processing devices, such as a digital signal processor ("DSP").

In at least one embodiment, processor 2602 includes cache memory ("cache") 2604. In at least one embodiment, processor 2602 can have a single internal cache or multiple levels of internal cache. In at least one embodiment, cache memory is shared among various components of processor 2602. In at least one embodiment, processor 2602 also uses an external cache (e.g., a Level 3 ("L3") cache or Last Level Cache ("LLC")) (not shown), which may be shared among processor cores 2607 using known cache coherency techniques. In at least one embodiment, register file 2606 is additionally included in processor 2602 which may include different types of registers for storing different types of data (e.g., integer registers, floating point registers, status registers, and an instruction pointer register). In at least one embodiment, register file 2606 may include general-purpose registers or other registers.

In at least one embodiment, one or more processor(s) 2602 are coupled with one or more interface bus(es) 2610 to transmit communication signals such as address, data, or control signals between processor 2602 and other components in processing system 2600. In at least one embodiment interface bus 2610, in one embodiment, can be a processor bus, such as a version of a Direct Media Interface ("DMI") bus. In at least one embodiment, interface bus 2610 is not limited to a DMI bus, and may include one or more Peripheral Component Interconnect buses (e.g., "PCI," PCI Express ("PCIe")), memory buses, or other types of interface buses. In at least one embodiment processor(s) 2602 include an integrated memory controller 2616 and a platform controller hub 2630. In at least one embodiment, memory controller 2616 facilitates communication between a memory device and other components of processing system 2600, while platform controller hub ("PCH") 2630 provides connections to Input/Output ("I/O") devices via a local I/O bus.

In at least one embodiment, memory device 2620 can be a dynamic random access memory ("DRAM") device, a static random access memory ("SRAM") device, flash memory device, phase-change memory device, or some other memory device having suitable performance to serve as processor memory. In at least one embodiment memory device 2620 can operate as system memory for processing system 2600, to store data 2622 and instructions 2621 for use when one or more processors 2602 executes an application or process. In at least one embodiment, memory controller 2616 also couples with an optional external graphics processor 2612, which may communicate with one or more graphics processors 2608 in processors 2602 to perform graphics and media operations. In at least one embodiment, a display device 2611 can connect to processor(s) 2602. In at least one embodiment display device 2611 can include one or more of an internal display device, as in a mobile electronic device or a laptop device or an external display device attached via a display interface (e.g., DisplayPort, etc.). In at least one embodiment, display device 2611 can include a head mounted display ("HMD") such as a stereoscopic display device for use in virtual reality ("VR") applications or augmented reality ("AR") applications.

In at least one embodiment, platform controller hub 2630 enables peripherals to connect to memory device 2620 and processor 2602 via a high-speed I/O bus. In at least one embodiment, I/O peripherals include, but are not limited to, an audio controller 2646, a network controller 2634, a firmware interface 2628, a wireless transceiver 2626, touch sensors 2625, a data storage device 2624 (e.g., hard disk drive, flash memory, etc.). In at least one embodiment, data storage device 2624 can connect via a storage interface (e.g., SATA) or via a peripheral bus, such as PCI, or PCIe. In at least one embodiment, touch sensors 2625 can include touch screen sensors, pressure sensors, or fingerprint sensors. In at least one embodiment, wireless transceiver 2626 can be a Wi-Fi transceiver, a Bluetooth transceiver, or a mobile network transceiver such as a 3G, 4G, or Long Term Evolution ("LTE") transceiver. In at least one embodiment, firmware interface 2628 enables communication with system firmware, and can be, for example, a unified extensible firmware interface ("UEFI"). In at least one embodiment, network controller 2634 can enable a network connection to a wired network. In at least one embodiment, a high-performance network controller (not shown) couples with interface bus 2610. In at least one embodiment, audio controller 2646 is a multi-channel high definition audio controller. In at least one embodiment, processing system 2600 includes an optional legacy I/O controller 2640 for coupling legacy (e.g., Personal System 2 ("PS/2")) devices to processing system 2600. In at least one embodiment, platform controller hub 2630 can also connect to one or more Universal Serial Bus ("USB") controllers 2642 connect input devices, such as keyboard and mouse 2643 combinations, a camera 2644, or other USB input devices.

In at least one embodiment, an instance of memory controller 2616 and platform controller hub 2630 may be integrated into a discreet external graphics processor, such as external graphics processor 2612. In at least one embodiment, platform controller hub 2630 and/or memory controller 2616 may be external to one or more processor(s) 2602. For example, in at least one embodiment, processing system 2600 can include an external memory controller 2616 and platform controller hub 2630, which may be configured as a memory controller hub and peripheral controller hub within a system chipset that is in communication with processor(s) 2602.

In at least one embodiment, the processing system 2600 may be used to implement the system 100 (see FIG. 1) and/or the inference pipeline 500 (see FIG. 5). For example, the processing system 2600 may be used to implement the processing system 104, the requestor device(s) 102, the receiver device(s) 106, and/or the optional data storage units 108. In at least one embodiment, at least one of the processor(s) 2602, the graphics processor(s) 2608, the processor core(s) 2607, and/or the external graphics processor 2612 may be used to implement at least one of the CPU(s)

116, at least one of the GPU(s) 118, and/or at least one of the DPU(s) 130. In at least one embodiment, the instruction set 2609 and/or the instructions 2621 may include the instructions 140A, 140B, and/or 140C. In at least one embodiment, the memory device 2620, the data storage device 2624, and/or the cache 2604 may be used to implement the CPU memory 120, the GPU memory 122, the DPU memory 132, and/or the optional data storage units 108. In at least one embodiment, the network controller 2634 may be used to implement the network controller 114. In at least one embodiment, at least a portion of the system(s) depicted in FIG. 26 is used to implement one or more systems, techniques, functions, and/or processes described in connection with FIGS. 1-5. For example, in at least one embodiment, at least one component shown or described with respect to FIG. 26 is used to process data (e.g., data having a DICOM format) in accordance with one or more techniques, functions, and/or processes described with respect to any of FIGS. 1-5.

Figure 27:
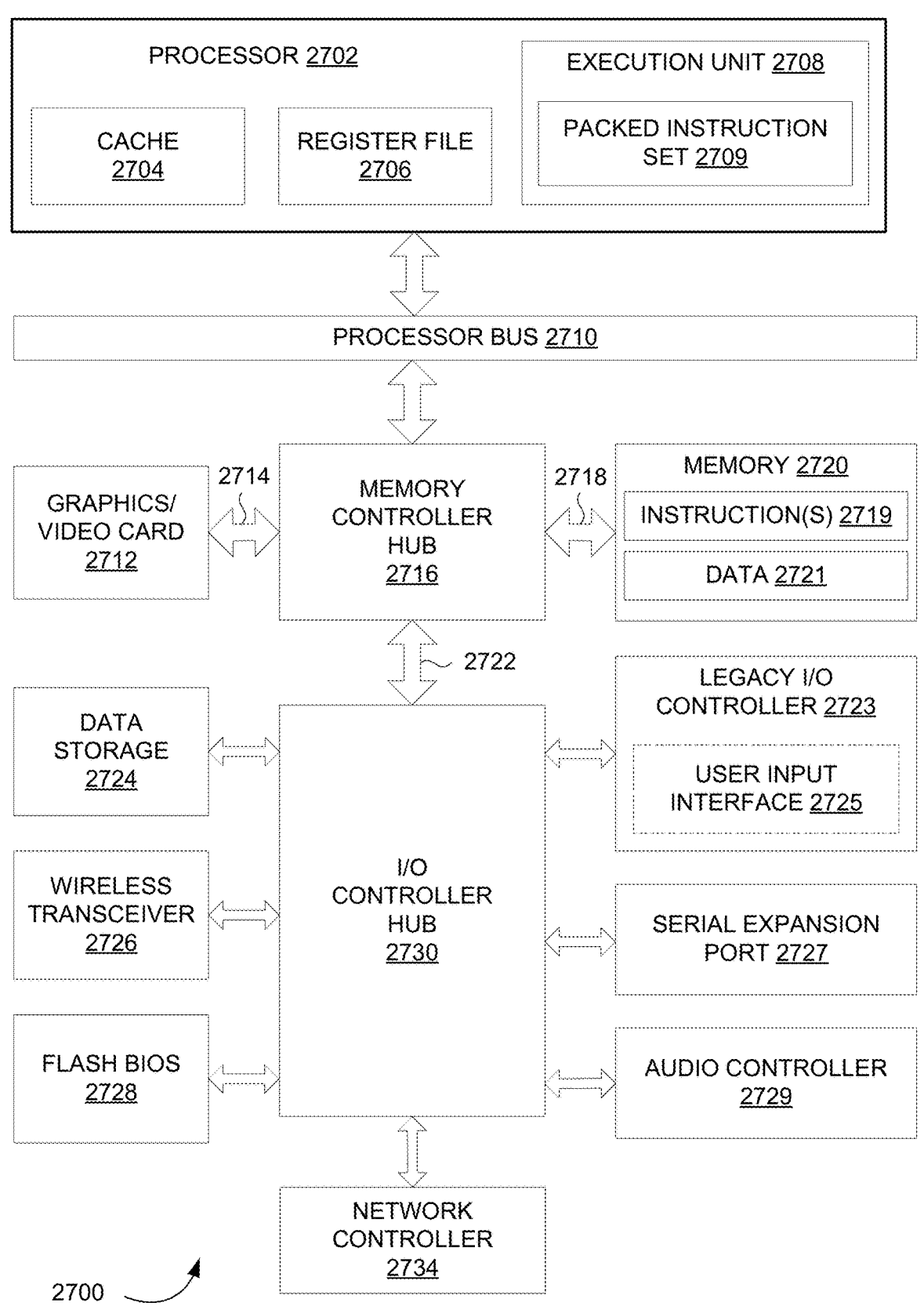
FIG. 27 illustrates a computer system, in accordance with at least one embodiment.

FIG. 27 illustrates a computer system 2700, in accordance with at least one embodiment. In at least one embodiment, computer system 2700 may be a system with interconnected devices and components, an SOC, or some combination. In at least on embodiment, computer system 2700 is formed with a processor 2702 that may include execution units to execute an instruction. In at least one embodiment, computer system 2700 may include, without limitation, a component, such as processor 2702 to employ execution units including logic to perform algorithms for processing data. In at least one embodiment, computer system 2700 may include processors, such as PENTIUM® Processor family, Xeon™, Itanium®, XScale™ and/or StrongARM™, Intel® Core™, or Intel® Nervana™ microprocessors available from Intel Corporation of Santa Clara, California, although other systems (including PCs having other microprocessors, engineering workstations, set-top boxes and like) may also be used. In at least one embodiment, computer system 2700 may execute a version of WINDOWS' operating system available from Microsoft Corporation of Redmond, Wash., although other operating systems (UNIX and Linux for example), embedded software, and/or graphical user interfaces, may also be used.

In at least one embodiment, computer system 2700 may be used in other devices such as handheld devices and embedded applications. Some examples of handheld devices include cellular phones, Internet Protocol devices, digital cameras, personal digital assistants ("PDAs"), and handheld PCs. In at least one embodiment, embedded applications may include a microcontroller, a digital signal processor (DSP), an SoC, network computers ("NetPCs"), set-top boxes, network hubs, wide area network ("WAN") switches, or any other system that may perform one or more instructions.

In at least one embodiment, computer system 2700 may include, without limitation, processor 2702 that may include, without limitation, one or more execution units 2708 that may be configured to execute a Compute Unified Device Architecture ("CUDA") (CUDA® is developed by NVIDIA Corporation of Santa Clara, CA) program. In at least one embodiment, a CUDA program is at least a portion of a software application written in a CUDA programming language. In at least one embodiment, computer system 2700 is a single processor desktop or server system. In at least one embodiment, computer system 2700 may be a multiprocessor system. In at least one embodiment, processor 2702 may include, without limitation, a CISC microprocessor, a RISC microprocessor, a VLIW microprocessor, a processor implementing a combination of instruction sets, or any other processor device, such as a digital signal processor, for example. In at least one embodiment, processor 2702 may be coupled to a processor bus 2710 that may transmit data signals between processor 2702 and other components in computer system 2700.

In at least one embodiment, processor 2702 may include, without limitation, a Level 1 ("L1") internal cache memory ("cache") 2704. In at least one embodiment, processor 2702 may have a single internal cache or multiple levels of internal cache. In at least one embodiment, cache memory may reside external to processor 2702. In at least one embodiment, processor 2702 may also include a combination of both internal and external caches. In at least one embodiment, a register file 2706 may store different types of data in various registers including, without limitation, integer registers, floating point registers, status registers, and instruction pointer register.

In at least one embodiment, execution unit 2708, including, without limitation, logic to perform integer and floating point operations, also resides in processor 2702. Processor 2702 may also include a microcode ("ucode") read only memory ("ROM") that stores microcode for certain macro instructions. In at least one embodiment, execution unit 2708 may include logic to handle a packed instruction set 2709. In at least one embodiment, by including packed instruction set 2709 in an instruction set of a general-purpose processor 2702, along with associated circuitry to execute instructions, operations used by many multimedia applications may be performed using packed data in a general-purpose processor 2702. In at least one embodiment, many multimedia applications may be accelerated and executed more efficiently by using full width of a processor's data bus for performing operations on packed data, which may eliminate a need to transfer smaller units of data across a processor's data bus to perform one or more operations one data element at a time.

In at least one embodiment, execution unit 2708 may also be used in microcontrollers, embedded processors, graphics devices, DSPs, and other types of logic circuits. In at least one embodiment, computer system 2700 may include, without limitation, a memory 2720. In at least one embodiment, memory 2720 may be implemented as a DRAM device, an SRAM device, flash memory device, or other memory device. Memory 2720 may store instruction(s) 2719 and/or data 2721 represented by data signals that may be executed by processor 2702.

In at least one embodiment, a system logic chip may be coupled to processor bus 2710 and memory 2720. In at least one embodiment, a system logic chip may include, without limitation, a memory controller hub ("MCH") 2716, and processor 2702 may communicate with MCH 2716 via processor bus 2710. In at least one embodiment, MCH 2716 may provide a high bandwidth memory path 2718 to memory 2720 for instruction and data storage and for storage of graphics commands, data and textures. In at least one embodiment, MCH 2716 may direct data signals between processor 2702, memory 2720, and other components in computer system 2700 and to bridge data signals between processor bus 2710, memory 2720, and a system I/O 2722. In at least one embodiment, system logic chip may provide a graphics port for coupling to a graphics controller. In at least one embodiment, MCH 2716 may be coupled to memory 2720 through high bandwidth memory path 2718 and graphics/video card 2712 may be coupled to MCH 2716 through an Accelerated Graphics Port ("AGP") interconnect 2714.

In at least one embodiment, computer system 2700 may use system I/O 2722 that is a proprietary hub interface bus to couple MCH 2716 to I/O controller hub ("ICH") 2730. In at least one embodiment, ICH 2730 may provide direct connections to some I/O devices via a local I/O bus. In at least one embodiment, local I/O bus may include, without limitation, a high-speed I/O bus for connecting peripherals to memory 2720, a chipset, and processor 2702. Examples may include, without limitation, an audio controller 2729, a firmware hub ("flash BIOS") 2728, a wireless transceiver 2726, a data storage 2724, a legacy I/O controller 2723 containing a user input interface 2725 and a keyboard interface, a serial expansion port 2727, such as a USB, and a network controller 2734. Data storage 2724 may include a hard disk drive, a floppy disk drive, a CD-ROM device, a flash memory device, or other mass storage device.

In at least one embodiment, FIG. 27 illustrates a system, which includes interconnected hardware devices or "chips." In at least one embodiment, FIG. 27 may illustrate an exemplary SoC. In at least one embodiment, devices illustrated in FIG. 27 may be interconnected with proprietary interconnects, standardized interconnects (e.g., PCIe), or some combination thereof. In at least one embodiment, one or more components of system 2700 are interconnected using compute express link ("CXL") interconnects.

In at least one embodiment, the computer system 2700 may be used to implement the system 100 (see FIG. 1) and/or the inference pipeline 500 (see FIG. 5). For example, the computer system 2700 may be used to implement the processing system 104, the requestor device(s) 102, the receiver device(s) 106, and/or the optional data storage units 108. In at least one embodiment, the processor 2702 may be used to implement at least one of the CPU(s) 116, at least one of the GPU(s) 118, and/or at least one of the DPU(s) 130. In at least one embodiment, the instruction set 2719 may include the instructions 140A, 140B, and/or 140C. In at least one embodiment, the memory 2720, the data storage 2724, and/or the cache 2704 may be used to implement the CPU memory 120, the GPU memory 122, the DPU memory 132, and/or the optional data storage units 108. In at least one embodiment, the network controller 2734 may be used to implement the network controller 114. In at least one embodiment, at least a portion of the system(s) depicted in FIG. 27 is used to implement one or more systems, techniques, functions, and/or processes described in connection with FIGS. 1-5. For example, in at least one embodiment, at least one component shown or described with respect to FIG. 27 is used to process data (e.g., data having a DICOM format) in accordance with one or more techniques, functions, and/or processes described with respect to any of FIGS. 1-5.

Figure 28:
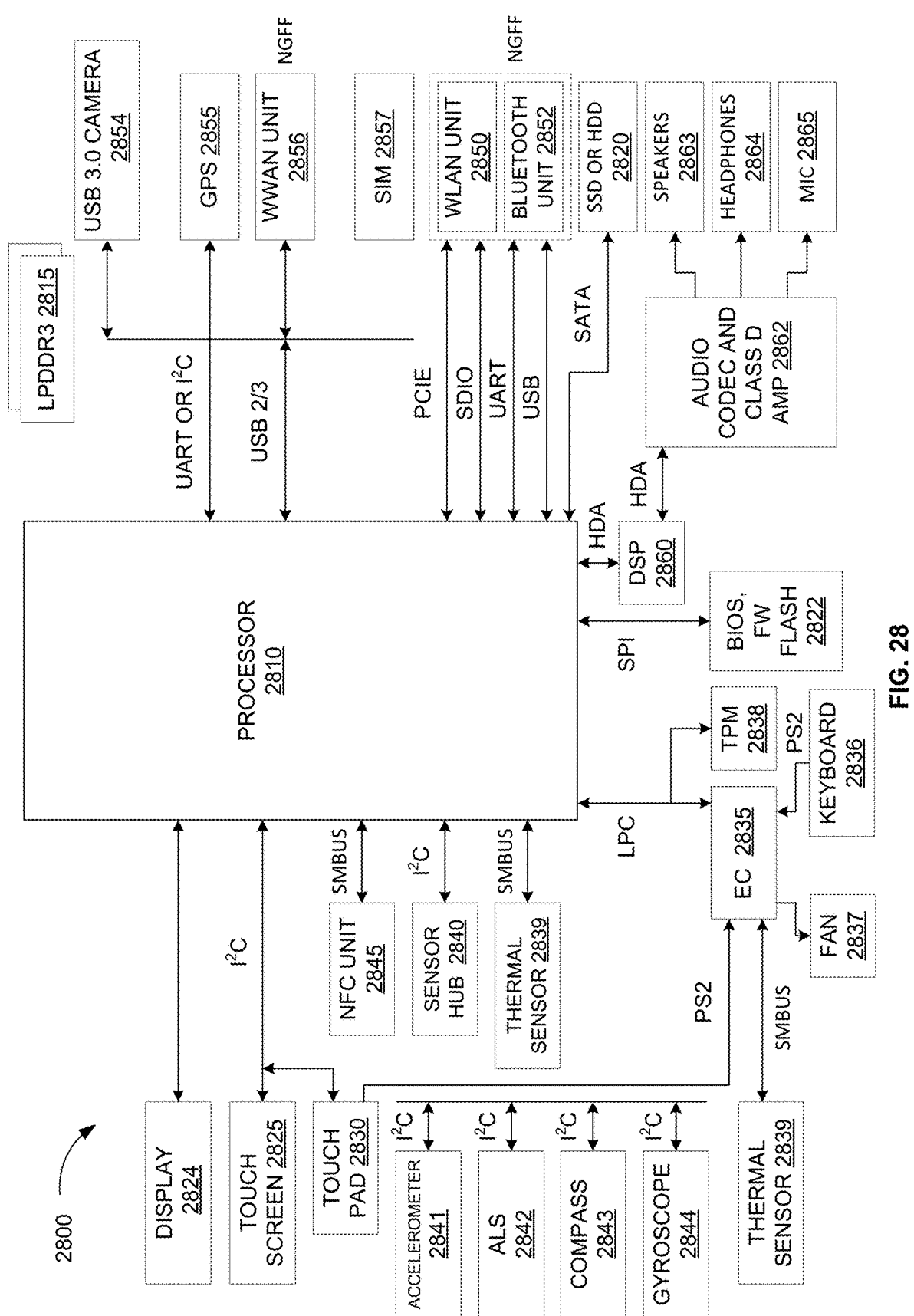
FIG. 28 illustrates a system, in accordance with at least one embodiment.

FIG. 28 illustrates a system 2800, in accordance with at least one embodiment. In at least one embodiment, system 2800 is an electronic device that utilizes a processor 2810. In at least one embodiment, system 2800 may be, for example and without limitation, a notebook, a tower server, a rack server, a blade server, a laptop, a desktop, a tablet, a mobile device, a phone, an embedded computer, or any other suitable electronic device.

In at least one embodiment, system 2800 may include, without limitation, processor 2810 communicatively coupled to any suitable number or kind of components, peripherals, modules, or devices. In at least one embodiment, processor 2810 is coupled using a bus or interface, such as an I2C bus, a System Management Bus ("SMBus"), a Low Pin Count ("LPC") bus, a Serial Peripheral Interface ("SPI"), a High Definition Audio ("HDA") bus, a Serial Advance Technology Attachment ("SATA") bus, a USB (versions 1, 2, 3), or a Universal Asynchronous Receiver/ Transmitter ("UART") bus. In at least one embodiment, FIG. 28 illustrates a system which includes interconnected hardware devices or "chips." In at least one embodiment, FIG. 28 may illustrate an exemplary SoC. In at least one embodiment, devices illustrated in FIG. 28 may be interconnected with proprietary interconnects, standardized interconnects (e.g., PCIe) or some combination thereof. In at least one embodiment, one or more components of FIG. 28 are interconnected using CXL interconnects.

In at least one embodiment, FIG. 28 may include a display 2824, a touch screen 2825, a touch pad 2830, a Near Field Communications unit ("NFC") 2845, a sensor hub 2840, a thermal sensor 2846, an Express Chipset ("EC") 2835, a Trusted Platform Module ("TPM") 2838, BIOS/firmware/ flash memory ("BIOS, FW Flash") 2822, a DSP 2860, a Solid State Disk ("SSD") or Hard Disk Drive ("HDD") 2820, a wireless local area network unit ("WLAN") 2850, a Bluetooth unit 2852, a Wireless Wide Area Network unit ("WWAN") 2856, a Global Positioning System ("GPS") 2855, a camera ("USB 3.0 camera") 2854 such as a USB 3.0 camera, or a Low Power Double Data Rate ("LPDDR") memory unit ("LPDDR3") 2815 implemented in, for example, LPDDR3 standard. These components may each be implemented in any suitable manner.

In at least one embodiment, other components may be communicatively coupled to processor 2810 through components discussed above. In at least one embodiment, an accelerometer 2841, an Ambient Light Sensor ("ALS") 2842, a compass 2843, and a gyroscope 2844 may be communicatively coupled to sensor hub 2840. In at least one embodiment, a thermal sensor 2839, a fan 2837, a keyboard 2846, and a touch pad 2830 may be communicatively coupled to EC 2835. In at least one embodiment, a speaker 2863, a headphones 2864, and a microphone ("mic") 2865 may be communicatively coupled to an audio unit ("audio codec and class d amp") 2864, which may in turn be communicatively coupled to DSP 2860. In at least one embodiment, audio unit 2864 may include, for example and without limitation, an audio coder/decoder ("codec") and a class D amplifier. In at least one embodiment, a SIM card ("SIM") 2857 may be communicatively coupled to WWAN unit 2856. In at least one embodiment, components such as WLAN unit 2850 and Bluetooth unit 2852, as well as WWAN unit 2856 may be implemented in a Next Generation Form Factor ("NGFF").

In at least one embodiment, the system 2800 may be used to implement the system 100 (see FIG. 1) and/or the inference pipeline 500 (see FIG. 5). For example, the system 2800 may be used to implement the processing system 104, the requestor device(s) 102, the receiver device(s) 106, and/or the optional data storage units 108. In at least one embodiment, the processor 2810 may be used to implement at least one of the CPU(s) 116, at least one of the GPU(s) 118, and/or at least one of the DPU(s) 130. In at least one embodiment, at least a portion of the system(s) depicted in FIG. 28 is used to implement one or more systems, techniques, functions, and/or processes described in connection with FIGS. 1-5. For example, in at least one embodiment, at least one component shown or described with respect to FIG. 28 is used to process data (e.g., data having a DICOM format) in accordance with one or more techniques, functions, and/or processes described with respect to any of FIGS. 1-5.

Figure 29:
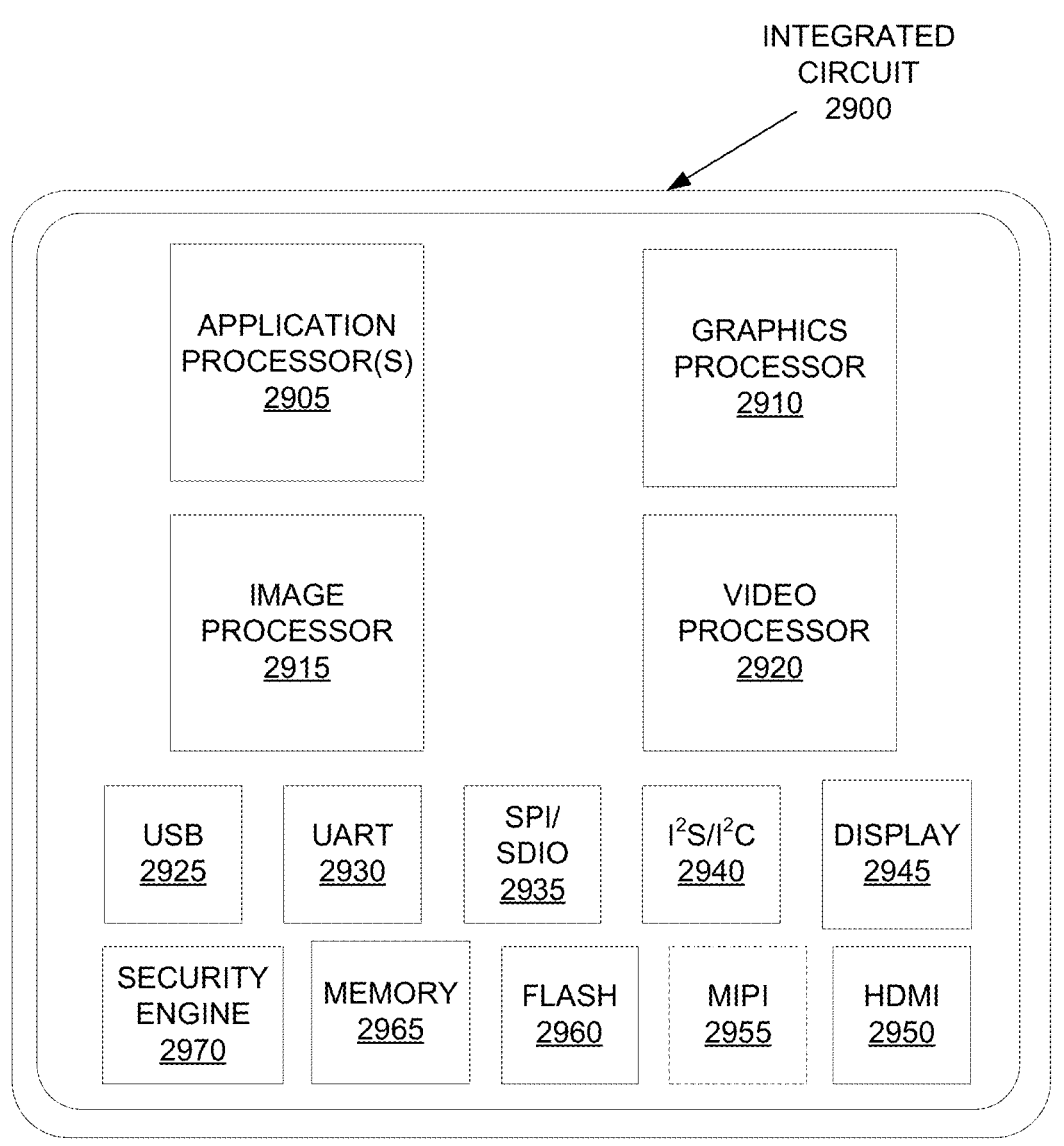
FIG. 29 illustrates an exemplary integrated circuit, in accordance with at least one embodiment.

FIG. 29 illustrates an exemplary integrated circuit 2900, in accordance with at least one embodiment. In at least one embodiment, exemplary integrated circuit 2900 is an SoC that may be fabricated using one or more IP cores. In at least one embodiment, integrated circuit 2900 includes one or more application processor(s) 2905 (e.g., CPUs), at least one graphics processor 2910, and may additionally include an image processor 2915 and/or a video processor 2920, any of which may be a modular IP core. In at least one embodiment, integrated circuit 2900 includes peripheral or bus logic including a USB controller 2925, a UART controller 2930, an SPI/SDIO controller 2935, and an I²S/I²C controller 2940. In at least one embodiment, integrated circuit 2900 can include a display device 2945 coupled to one or more of a high-definition multimedia interface ("HDMI") controller 2950 and a mobile industry processor interface ("MIPI") display interface 2955. In at least one embodiment, storage may be provided by a flash memory subsystem 2960 including flash memory and a flash memory controller. In at least one embodiment, a memory interface may be provided via a memory controller 2965 for access to SDRAM or SRAM memory devices. In at least one embodiment, some integrated circuits additionally include an embedded security engine 2970.

In at least one embodiment, the integrated circuit 2900 may be used to implement the system 100 (see FIG. 1) and/or the inference pipeline 500 (see FIG. 5). For example, the integrated circuit 2900 may be used to implement the processing system 104, the requestor device(s) 102, the receiver device(s) 106, and/or the optional data storage units 108. In at least one embodiment, the integrated circuit 2900 may be used to implement at least one of the CPU(s) 116, at least one of the GPU(s) 118, and/or at least one of the DPU(s) 130. In at least one embodiment, the application processor(s) 2905, the graphics processor(s) 2910, the image processor 2915, and/or the video processor 2920 may be used to implement at least one of the CPU(s) 116, at least one of the GPU(s) 118, and/or at least one of the DPU(s) 130. In at least one embodiment, the flash memory subsystem 2960 may be used to implement the CPU memory 120, the GPU memory 122, the DPU memory 132, and/or the optional data storage units 108. In at least one embodiment, at least a portion of the system(s) depicted in FIG. 29 is used to implement one or more systems, techniques, functions, and/or processes described in connection with FIGS. 1-5. For example, in at least one embodiment, at least one component shown or described with respect to FIG. 29 is used to process data (e.g., data having a DICOM format) in accordance with one or more techniques, functions, and/or processes described with respect to any of FIGS. 1-5.

FIG. 30 illustrates a computing system 3000, according to at least one embodiment; In at least one embodiment, computing system 3000 includes a processing subsystem 3001 having one or more processor(s) 3002 and a system memory 3004 communicating via an interconnection path that may include a memory hub 3005. In at least one embodiment, memory hub 3005 may be a separate component within a chipset component or may be integrated within one or more processor(s) 3002. In at least one embodiment, memory hub 3005 couples with an I/O subsystem 3011 via a communication link 3006. In at least one embodiment, I/O subsystem 3011 includes an I/O hub 3007 that can enable computing system 3000 to receive input from one or more input device(s) 3008. In at least one embodiment, I/O hub 3007 can enable a display controller, which may be included in one or more processor(s) 3002, to provide outputs to one or more display device(s) 3010A. In at least one embodiment, one or more display device(s) 3010A coupled with I/O hub 3007 can include a local, internal, or embedded display device.

In at least one embodiment, processing subsystem 3001 includes one or more parallel processor(s) 3012 coupled to memory hub 3005 via a bus or other communication link 3013. In at least one embodiment, communication link 3013 may be one of any number of standards based communication link technologies or protocols, such as, but not limited to PCIe, or may be a vendor specific communications interface or communications fabric. In at least one embodiment, one or more parallel processor(s) 3012 form a computationally focused parallel or vector processing system that can include a large number of processing cores and/or processing clusters, such as a many integrated core processor. In at least one embodiment, one or more parallel processor(s) 3012 form a graphics processing subsystem that can output pixels to one of one or more display device(s) 3010A coupled via I/O Hub 3007. In at least one embodiment, one or more parallel processor(s) 3012 can also include a display controller and display interface (not shown) to enable a direct connection to one or more display device(s) 3010B.

In at least one embodiment, a system storage unit 3014 can connect to I/O hub 3007 to provide a storage mechanism for computing system 3000. In at least one embodiment, an I/O switch 3016 can be used to provide an interface mechanism to enable connections between I/O hub 3007 and other components, such as a network adapter 3018 and/or wireless network adapter 3019 that may be integrated into a platform, and various other devices that can be added via one or more add-in device(s) 3020. In at least one embodiment, network adapter 3018 can be an Ethernet adapter or another wired network adapter. In at least one embodiment, wireless network adapter 3019 can include one or more of a Wi-Fi, Bluetooth, NFC, or other network device that includes one or more wireless radios.

In at least one embodiment, computing system 3000 can include other components not explicitly shown, including USB or other port connections, optical storage drives, video capture devices, and/or variations thereof, that may also be connected to I/O hub 3007. In at least one embodiment, communication paths interconnecting various components in FIG. 30 may be implemented using any suitable protocols, such as PCI based protocols (e.g., PCIe), or other bus or point-to-point communication interfaces and/or protocol(s), such as NVLink high-speed interconnect, or interconnect protocols.

In at least one embodiment, one or more parallel processor(s) 3012 incorporate circuitry optimized for graphics and video processing, including, for example, video output circuitry, and constitutes a graphics processing unit ("GPU"). In at least one embodiment, one or more parallel processor(s) 3012 incorporate circuitry optimized for general purpose processing. In at least embodiment, components of computing system 3000 may be integrated with one or more other system elements on a single integrated circuit. For example, in at least one embodiment, one or more parallel processor(s) 3012, memory hub 3005, processor(s) 3002, and I/O hub 3007 can be integrated into a SoC integrated circuit. In at least one embodiment, components of computing system 3000 can be integrated into a single package to form a system in package ("SIP") configuration. In at least one embodiment, at least a portion of components of computing system 3000 can be integrated into a multi-chip module ("MCM"), which can be interconnected with other multi-chip modules into a modular computing system.

In at least one embodiment, I/O subsystem 3011 and display devices 3010B are omitted from computing system 3000.

In at least one embodiment, the computing system 3000 may be used to implement the system 100 (see FIG. 1) and/or the inference pipeline 500 (see FIG. 5). For example, the computing system 3000 may be used to implement the processing system 104, the requestor device(s) 102, the receiver device(s) 106, and/or the optional data storage units 108. In at least one embodiment, the processor(s) 3002, and/or the parallel processor(s) 3012 may be used to implement at least one of the CPU(s) 116, at least one of the GPU(s) 118, and/or at least one of the DPU(s) 130. In at least one embodiment, the system memory 3004 may be used to implement the CPU memory 120, the GPU memory 122, the DPU memory 132, and/or the optional data storage units 108. In at least one embodiment, the network adapter 3018 and/or the wireless network adapter 3019 may be used to implement the network interface 114. In at least one embodiment, at least a portion of the system(s) depicted in FIG. 30 is used to implement one or more systems, techniques, functions, and/or processes described in connection with FIGS. 1-5. For example, in at least one embodiment, at least one component shown or described with respect to FIG. 30 is used to process data (e.g., data having a DICOM format) in accordance with one or more techniques, functions, and/or processes described with respect to any of FIGS. 1-5.

Processing Systems

The following figures set forth, without limitation, exemplary processing systems that can be used to implement at least one embodiment.

FIG. 31 illustrates an accelerated processing unit ("APU") 3100, in accordance with at least one embodiment. In at least one embodiment, APU 3100 is developed by AMD Corporation of Santa Clara, CA. In at least one embodiment, APU 3100 can be configured to execute an application program, such as a CUDA program. In at least one embodiment, APU 3100 includes, without limitation, a core complex 3110, a graphics complex 3140, fabric 3160, I/O interfaces 3170, memory controllers 3180, a display controller 3192, and a multimedia engine 3194. In at least one embodiment, APU 3100 may include, without limitation, any number of core complexes 3110, any number of graphics complexes 3140, any number of display controllers 3192, and any number of multimedia engines 3194 in any combination. For explanatory purposes, multiple instances of like objects are denoted herein with reference numbers identifying an object and parenthetical numbers identifying an instance where needed.

In at least one embodiment, core complex 3110 is a CPU, graphics complex 3140 is a GPU, and APU 3100 is a processing unit that integrates, without limitation, 3110 and 3140 onto a single chip. In at least one embodiment, some tasks may be assigned to core complex 3110 and other tasks may be assigned to graphics complex 3140. In at least one embodiment, core complex 3110 is configured to execute main control software associated with APU 3100, such as an operating system. In at least one embodiment, core complex 3110 is a master processor of APU 3100, controlling and coordinating operations of other processors. In at least one embodiment, core complex 3110 issues commands that control an operation of graphics complex 3140. In at least one embodiment, core complex 3110 can be configured to execute host executable code derived from CUDA source code, and graphics complex 3140 can be configured to execute device executable code derived from CUDA source code.

In at least one embodiment, core complex 3110 includes, without limitation, cores 3120(1)-3120(4) and an L3 cache

3130. In at least one embodiment, core complex 3110 may include, without limitation, any number of cores 3120 and any number and type of caches in any combination. In at least one embodiment, cores 3120 are configured to execute instructions of a particular instruction set architecture ("ISA"). In at least one embodiment, each core 3120 is a CPU core.

In at least one embodiment, each core 3120 includes, without limitation, a fetch/decode unit 3122, an integer execution engine 3124, a floating point execution engine 3126, and an L2 cache 3128. In at least one embodiment, fetch/decode unit 3122 fetches instructions, decodes such instructions, generates micro-operations, and dispatches separate micro-instructions to integer execution engine 3124 and floating point execution engine 3126. In at least one embodiment, fetch/decode unit 3122 can concurrently dispatch one micro-instruction to integer execution engine 3124 and another micro-instruction to floating point execution engine 3126. In at least one embodiment, integer execution engine 3124 executes, without limitation, integer and memory operations. In at least one embodiment, floating point engine 3126 executes, without limitation, floating point and vector operations. In at least one embodiment, fetch-decode unit 3122 dispatches micro-instructions to a single execution engine that replaces both integer execution engine 3124 and floating point execution engine 3126.

In at least one embodiment, each core 3120($i$), where i is an integer representing a particular instance of core 3120, may access L2 cache 3128($i$) included in core 3120($i$). In at least one embodiment, each core 3120 included in core complex 3110($j$), where j is an integer representing a particular instance of core complex 3110, is connected to other cores 3120 included in core complex 3110($j$) via L3 cache 3130($j$) included in core complex 3110($j$). In at least one embodiment, cores 3120 included in core complex 3110($j$), where j is an integer representing a particular instance of core complex 3110, can access all of L3 cache 3130($j$) included in core complex 3110($j$). In at least one embodiment, L3 cache 3130 may include, without limitation, any number of slices.

In at least one embodiment, graphics complex 3140 can be configured to perform compute operations in a highly-parallel fashion. In at least one embodiment, graphics complex 3140 is configured to execute graphics pipeline operations such as draw commands, pixel operations, geometric computations, and other operations associated with rendering an image to a display. In at least one embodiment, graphics complex 3140 is configured to execute operations unrelated to graphics. In at least one embodiment, graphics complex 3140 is configured to execute both operations related to graphics and operations unrelated to graphics.

In at least one embodiment, graphics complex 3140 includes, without limitation, any number of compute units 3150 and an L2 cache 3142. In at least one embodiment, compute units 3150 share L2 cache 3142. In at least one embodiment, L2 cache 3142 is partitioned. In at least one embodiment, graphics complex 3140 includes, without limitation, any number of compute units 3150 and any number (including zero) and type of caches. In at least one embodiment, graphics complex 3140 includes, without limitation, any amount of dedicated graphics hardware.

In at least one embodiment, each compute unit 3150 includes, without limitation, any number of SIMD units 3152 and a shared memory 3154. In at least one embodiment, each SIMD unit 3152 implements a SIMD architecture and is configured to perform operations in parallel. In at least one embodiment, each compute unit 3150 may execute any number of thread blocks, but each thread block executes on a single compute unit 3150. In at least one embodiment, a thread block includes, without limitation, any number of threads of execution. In at least one embodiment, a work-group is a thread block. In at least one embodiment, each SIMD unit 3152 executes a different warp. In at least one embodiment, a warp is a group of threads (e.g., 16 threads), where each thread in a warp belongs to a single thread block and is configured to process a different set of data based on a single set of instructions. In at least one embodiment, predication can be used to disable one or more threads in a warp. In at least one embodiment, a lane is a thread. In at least one embodiment, a work item is a thread. In at least one embodiment, a wavefront is a warp. In at least one embodiment, different wavefronts in a thread block may synchronize together and communicate via shared memory 3154.

In at least one embodiment, fabric 3160 is a system interconnect that facilitates data and control transmissions across core complex 3110, graphics complex 3140, I/O interfaces 3170, memory controllers 3180, display controller 3192, and multimedia engine 3194. In at least one embodiment, APU 3100 may include, without limitation, any amount and type of system interconnect in addition to or instead of fabric 3160 that facilitates data and control transmissions across any number and type of directly or indirectly linked components that may be internal or external to APU 3100. In at least one embodiment, I/O interfaces 3170 are representative of any number and type of I/O interfaces (e.g., PCI, PCI-Extended ("PCI-X"), PCIe, gigabit Ethernet ("GBE"), USB, etc.). In at least one embodiment, various types of peripheral devices are coupled to I/O interfaces 3170. In at least one embodiment, peripheral devices that are coupled to I/O interfaces 3170 may include, without limitation, keyboards, mice, printers, scanners, joysticks or other types of game controllers, media recording devices, external storage devices, network interface cards, and so forth.

In at least one embodiment, display controller AMD92 displays images on one or more display device(s), such as a liquid crystal display ("LCD") device. In at least one embodiment, multimedia engine 3194 includes, without limitation, any amount and type of circuitry that is related to multimedia, such as a video decoder, a video encoder, an image signal processor, etc. In at least one embodiment, memory controllers 3180 facilitate data transfers between APU 3100 and a unified system memory 3190. In at least one embodiment, core complex 3110 and graphics complex 3140 share unified system memory 3190.

In at least one embodiment, APU 3100 implements a memory subsystem that includes, without limitation, any amount and type of memory controllers 3180 and memory devices (e.g., shared memory 3154) that may be dedicated to one component or shared among multiple components. In at least one embodiment, APU 3100 implements a cache subsystem that includes, without limitation, one or more cache memories (e.g., L2 caches 3128, L3 cache 3130, and L2 cache 3142) that may each be private to or shared between any number of components (e.g., cores 3120, core complex 3110, SIMD units 3152, compute units 3150, and graphics complex 3140).

In at least one embodiment, the APU 3100 may be used to implement the system 100 (see FIG. 1) and/or the inference pipeline 500 (see FIG. 5). For example, the APU 3100 may be used to implement one or more of the processing system 104, the requestor device(s) 102, the receiver device(s) 106, and/or the optional data storage units 108. In at least one embodiment, the APU 3100 may be used to implement at least one of the CPU(s) 116, at least one of the GPU(s) 118, and/or at least one of the DPU(s) 130. In at least one embodiment, the unified system memory 3190 may be used to implement the CPU memory 120, the GPU memory 122, the DPU memory 132, and/or the optional data storage units 108.

FIG. 32 illustrates a CPU 3200, in accordance with at least one embodiment. In at least one embodiment, CPU 3200 is developed by AMD Corporation of Santa Clara, CA. In at least one embodiment, CPU 3200 can be configured to execute an application program. In at least one embodiment, CPU 3200 is configured to execute main control software, such as an operating system. In at least one embodiment, CPU 3200 issues commands that control an operation of an external GPU (not shown). In at least one embodiment, CPU 3200 can be configured to execute host executable code derived from CUDA source code, and an external GPU can be configured to execute device executable code derived from such CUDA source code. In at least one embodiment, CPU 3200 includes, without limitation, any number of core complexes 3210, fabric 3260, I/O interfaces 3270, and memory controllers 3280.

In at least one embodiment, core complex 3210 includes, without limitation, cores 3220(1)-3220(4) and an L3 cache 3230. In at least one embodiment, core complex 3210 may include, without limitation, any number of cores 3220 and any number and type of caches in any combination. In at least one embodiment, cores 3220 are configured to execute instructions of a particular ISA. In at least one embodiment, each core 3220 is a CPU core.

In at least one embodiment, each core 3220 includes, without limitation, a fetch/decode unit 3222, an integer execution engine 3224, a floating point execution engine 3226, and an L2 cache 3228. In at least one embodiment, fetch/decode unit 3222 fetches instructions, decodes such instructions, generates micro-operations, and dispatches separate micro-instructions to integer execution engine 3224 and floating point execution engine 3226. In at least one embodiment, fetch/decode unit 3222 can concurrently dispatch one micro-instruction to integer execution engine 3224 and another micro-instruction to floating point execution engine 3226. In at least one embodiment, integer execution engine 3224 executes, without limitation, integer and memory operations. In at least one embodiment, floating point engine 3226 executes, without limitation, floating point and vector operations. In at least one embodiment, fetch-decode unit 3222 dispatches micro-instructions to a single execution engine that replaces both integer execution engine 3224 and floating point execution engine 3226.

In at least one embodiment, each core 3220($i$), where i is an integer representing a particular instance of core 3220, may access L2 cache 3228($i$) included in core 3220($i$). In at least one embodiment, each core 3220 included in core complex 3210($j$), where j is an integer representing a particular instance of core complex 3210, is connected to other cores 3220 in core complex 3210($j$) via L3 cache 3230($j$) included in core complex 3210($j$). In at least one embodiment, cores 3220 included in core complex 3210($j$), where j is an integer representing a particular instance of core complex 3210, can access all of L3 cache 3230($j$) included in core complex 3210($j$). In at least one embodiment, L3 cache 3230 may include, without limitation, any number of slices.

In at least one embodiment, fabric 3260 is a system interconnect that facilitates data and control transmissions across core complexes 3210(1)-3210(N) (where N is an integer greater than zero), I/O interfaces 3270, and memory controllers 3280. In at least one embodiment, CPU 3200 may include, without limitation, any amount and type of system interconnect in addition to or instead of fabric 3260 that facilitates data and control transmissions across any number and type of directly or indirectly linked components that may be internal or external to CPU 3200. In at least one embodiment, I/O interfaces 3270 are representative of any number and type of I/O interfaces (e.g., PCI, PCI-X, PCIe, GBE, USB, etc.). In at least one embodiment, various types of peripheral devices are coupled to I/O interfaces 3270. In at least one embodiment, peripheral devices that are coupled to I/O interfaces 3270 may include, without limitation, displays, keyboards, mice, printers, scanners, joysticks or other types of game controllers, media recording devices, external storage devices, network interface cards, and so forth.

In at least one embodiment, memory controllers 3280 facilitate data transfers between CPU 3200 and a system memory 3290. In at least one embodiment, core complex 3210 and graphics complex 3240 share system memory 3290. In at least one embodiment, CPU 3200 implements a memory subsystem that includes, without limitation, any amount and type of memory controllers 3280 and memory devices that may be dedicated to one component or shared among multiple components. In at least one embodiment, CPU 3200 implements a cache subsystem that includes, without limitation, one or more cache memories (e.g., L2 caches 3228 and L3 caches 3230) that may each be private to or shared between any number of components (e.g., cores 3220 and core complexes 3210).

In at least one embodiment, the CPU 3200 may be used to implement the system 100 (see FIG. 1) and/or the inference pipeline 500 (see FIG. 5). For example, the CPU 3200 may be used to implement the processing system 104, the requestor device(s) 102, the receiver device(s) 106, and/or the optional data storage units 108. In at least one embodiment, the CPU 3200 may be used to implement at least one of the CPU(s) 116, at least one of the GPU(s) 118, and/or at least one of the DPU(s) 130. In at least one embodiment, the system memory 3290 may be used to implement the CPU memory 120, the GPU memory 122, the DPU memory 132, and/or the optional data storage units 108. In at least one embodiment, at least a portion of the system(s) depicted in FIG. 32 is used to implement one or more systems, techniques, functions, and/or processes described in connection with FIGS. 1-5. For example, in at least one embodiment, at least one component shown or described with respect to FIG. 32 is used to process data (e.g., data having a DICOM format) in accordance with one or more techniques, functions, and/or processes described with respect to any of FIGS. 1-5.

FIG. 33 illustrates an exemplary accelerator integration slice 3390, in accordance with at least one embodiment. As used herein, a "slice" includes a specified portion of processing resources of an accelerator integration circuit. In at least one embodiment, an accelerator integration circuit provides cache management, memory access, context management, and interrupt management services on behalf of multiple graphics processing engines included in a graphics acceleration module. Graphics processing engines may each include a separate GPU. Alternatively, graphics processing engines may include different types of graphics processing engines within a GPU such as graphics execution units, media processing engines (e.g., video encoders/decoders), samplers, and blit engines. In at least one embodiment, a graphics acceleration module may be a GPU with multiple graphics processing engines. In at least one embodiment, graphics processing engines may be individual GPUs integrated on a common package, line card, or chip.

An application effective address space 3382 within system memory 3314 stores process elements 3383. In one embodiment, process elements 3383 are stored in response to GPU invocations 3381 from applications 3380 executed on processor 3307. A process element 3383 contains process state for corresponding application 3380. A work descriptor ("WD") 3384 contained in process element 3383 can be a single job requested by an application or may contain a pointer to a queue of jobs. In at least one embodiment, WD 3384 is a pointer to a job request queue in application effective address space 3382.

Graphics acceleration module 3346 and/or individual graphics processing engines can be shared by all or a subset of processes in a system. In at least one embodiment, an infrastructure for setting up process state and sending WD 3384 to graphics acceleration module 3346 to start a job in a virtualized environment may be included.

In at least one embodiment, a dedicated-process programming model is implementation-specific. In this model, a single process owns graphics acceleration module 3346 or an individual graphics processing engine. Because graphics acceleration module 3346 is owned by a single process, a hypervisor initializes an accelerator integration circuit for an owning partition and an operating system initializes accelerator integration circuit for an owning process when graphics acceleration module 3346 is assigned.

In operation, a WD fetch unit 3391 in accelerator integration slice 3390 fetches next WD 3384 which includes an indication of work to be done by one or more graphics processing engines of graphics acceleration module 3346. Data from WD 3384 may be stored in registers 3345 and used by a memory management unit ("MMU") 3339, interrupt management circuit 3347 and/or context management circuit 3348 as illustrated. For example, one embodiment of MMU 3339 includes segment/page walk circuitry for accessing segment/page tables 3386 within OS virtual address space 3385. Interrupt management circuit 3347 may process interrupt events ("INT") 3392 received from graphics acceleration module 3346. When performing graphics operations, an effective address 3393 generated by a graphics processing engine is translated to a real address by MMU 3339.

In one embodiment, a same set of registers 3345 are duplicated for each graphics processing engine and/or graphics acceleration module 3346 and may be initialized by a hypervisor or operating system. Each of these duplicated registers may be included in accelerator integration slice 3390. Exemplary registers that may be initialized by a hypervisor are shown in Table 1.

TABLE 1

| | Hypervisor Initialized Registers |
|---|---|
| 1 | Slice Control Register |
| 2 | Real Address (RA) Scheduled Processes Area Pointer |
| 3 | Authority Mask Override Register |
| 4 | Interrupt Vector Table Entry Offset |
| 5 | Interrupt Vector Table Entry Limit |
| 6 | State Register |
| 7 | Logical Partition ID |
| 8 | Real address (RA) Hypervisor Accelerator Utilization Record Pointer |
| 9 | Storage Description Register |

Exemplary registers that may be initialized by an operating system are shown in Table 2.

TABLE 2

| Operating System Initialized Registers |
| --- |
| 1 | Process and Thread Identification |
| 2 | Effective Address (EA) Context Save/Restore Pointer |
| 3 | Virtual Address (VA) Accelerator Utilization Record Pointer |
| 4 | Virtual Address (VA) Storage Segment Table Pointer |
| 5 | Authority Mask |
| 6 | Work descriptor |

In one embodiment, each WD 3384 is specific to a particular graphics acceleration module 3346 and/or a particular graphics processing engine. It contains all information required by a graphics processing engine to do work or it can be a pointer to a memory location where an application has set up a command queue of work to be completed.

In at least one embodiment, the system of FIG. 33 may be used to implement the system 100 (see FIG. 1) and/or the inference pipeline 500 (see FIG. 5). For example, the system of FIG. 33 may be used to implement the processing system 104, the requestor device(s) 102, the receiver device(s) 106, and/or the optional data storage units 108. In at least one embodiment, the processor 3307, the graphics acceleration module 3346, and/or the accelerator integration slice 3390 may be used to implement at least one of the CPU(s) 116, at least one of the GPU(s) 118, and/or at least one of the DPU(s) 130. In at least one embodiment, the system memory 3314 may be used to implement the CPU memory 120, the GPU memory 122, the DPU memory 132, and/or the optional data storage units 108. In at least one embodiment, at least a portion of the system(s) depicted in FIG. 33 is used to implement one or more systems, techniques, functions, and/or processes described in connection with FIGS. 1-5. For example, in at least one embodiment, at least one component shown or described with respect to FIG. 33 is used to process data (e.g., data having a DICOM format) in accordance with one or more techniques, functions, and/or processes described with respect to any of FIGS. 1-5.

FIGS. 34A-34B illustrate exemplary graphics processors, in accordance with at least one embodiment. In at least one embodiment, any of the exemplary graphics processors may be fabricated using one or more IP cores. In addition to what is illustrated, other logic and circuits may be included in at least one embodiment, including additional graphics processors/cores, peripheral interface controllers, or general-purpose processor cores. In at least one embodiment, the exemplary graphics processors are for use within an SoC.

FIG. 34A illustrates an exemplary graphics processor 3410 of an SoC integrated circuit that may be fabricated using one or more IP cores, in accordance with at least one embodiment. FIG. 34B illustrates an additional exemplary graphics processor 3440 of an SoC integrated circuit that may be fabricated using one or more IP cores, in accordance with at least one embodiment. In at least one embodiment, graphics processor 3410 of FIG. 34A is a low power graphics processor core. In at least one embodiment, graphics processor 3440 of FIG. 34B is a higher performance graphics processor core. In at least one embodiment, each of graphics processors 3410, 3440 can be variants of graphics processor 1010 of FIG. 10.

In at least one embodiment, graphics processor 3410 includes a vertex processor 3405 and one or more fragment processor(s) 3415A-3415N (e.g., 3415A, 3415B, 3415C, 3415D, through 3415N-1, and 3415N). In at least one embodiment, graphics processor 3410 can execute different shader programs via separate logic, such that vertex processor 3405 is optimized to execute operations for vertex shader programs, while one or more fragment processor(s) 3415A-3415N execute fragment (e.g., pixel) shading operations for fragment or pixel shader programs. In at least one embodiment, vertex processor 3405 performs a vertex processing stage of a 3D graphics pipeline and generates primitives and vertex data. In at least one embodiment, fragment processor(s) 3415A-3415N use primitive and vertex data generated by vertex processor 3405 to produce a framebuffer that is displayed on a display device. In at least one embodiment, fragment processor(s) 3415A-3415N are optimized to execute fragment shader programs as provided for in an OpenGL API, which may be used to perform similar operations as a pixel shader program as provided for in a Direct 3D API.

In at least one embodiment, graphics processor 3410 additionally includes one or more MMU(s) 3420A-3420B, cache(s) 3425A-3425B, and circuit interconnect(s) 3430A-3430B. In at least one embodiment, one or more MMU(s) 3420A-3420B provide for virtual to physical address mapping for graphics processor 3410, including for vertex processor 3405 and/or fragment processor(s) 3415A-3415N, which may reference vertex or image/texture data stored in memory, in addition to vertex or image/texture data stored in one or more cache(s) 3425A-3425B. In at least one embodiment, one or more MMU(s) 3420A-3420B may be synchronized with other MMUs within a system, including one or more MMUs associated with one or more application processor(s) 1005, image processors 1015, and/or video processors 1020 of FIG. 10, such that each processor 1005-1020 can participate in a shared or unified virtual memory system. In at least one embodiment, one or more circuit interconnect(s) 3430A-3430B enable graphics processor 3410 to interface with other IP cores within an SoC, either via an internal bus of an SoC or via a direct connection.

In at least one embodiment, graphics processor 3440 includes one or more MMU(s) 3420A-3420B, caches 3425A-3425B, and circuit interconnects 3430A-3430B of graphics processor 3410 of FIG. 34A. In at least one embodiment, graphics processor 3440 includes one or more shader core(s) 3455A-3455N (e.g., 3455A, 3455B, 3455C, 3455D, 3455E, 3455F, through 3455N-1, and 3455N), which provides for a unified shader core architecture in which a single core or type or core can execute all types of programmable shader code, including shader program code to implement vertex shaders, fragment shaders, and/or compute shaders. In at least one embodiment, a number of shader cores can vary. In at least one embodiment, graphics processor 3440 includes an inter-core task manager 3445, which acts as a thread dispatcher to dispatch execution threads to one or more shader cores 3455A-3455N and a tiling unit 3458 to accelerate tiling operations for tile-based rendering, in which rendering operations for a scene are subdivided in image space, for example to exploit local spatial coherence within a scene or to optimize use of internal caches.

In at least one embodiment, the graphics processor 3410 and/or the graphics processor 3440 may be used to implement the system 100 (see FIG. 1) and/or the inference pipeline 500 (see FIG. 5). For example, the graphics processor 3410 and/or the graphics processor 3440 may be used to implement the processing system 104, the requestor device(s) 102, the receiver device(s) 106, and/or the optional data storage units 108. In at least one embodiment, the graphics processor 3410 and/or the graphics processor 3440 may be used to implement at least one of the CPU(s) 116, at least one of the GPU(s) 118, and/or at least one of the DPU(s) 130. In at least one embodiment, at least a portion of the system(s) depicted in FIGS. 34A and 34B is used to implement one or more systems, techniques, functions, and/or processes described in connection with FIGS. 1-5. For example, in at least one embodiment, at least one component shown or described with respect to FIGS. 34A and 34B is used to process data (e.g., data having a DICOM format) in accordance with one or more techniques, functions, and/or processes described with respect to any of FIGS. 1-5.

FIG. 35A illustrates a graphics core 3500, in accordance with at least one embodiment. In at least one embodiment, graphics core 3500 may be included within graphics processor 2910 of FIG. 29. In at least one embodiment, graphics core 3500 may be a unified shader core 3455A-3455N as in FIG. 34B. In at least one embodiment, graphics core 3500 includes a shared instruction cache 3502, a texture unit 3518, and a cache/shared memory 3520 that are common to execution resources within graphics core 3500. In at least one embodiment, graphics core 3500 can include multiple slices 3501A-3501N or partition for each core, and a graphics processor can include multiple instances of graphics core 3500. Slices 3501A-3501N can include support logic including a local instruction cache 3504A-3504N, a thread scheduler 3506A-3506N, a thread dispatcher 3508A-3508N, and a set of registers 3510A-3510N. In at least one embodiment, slices 3501A-3501N can include a set of additional function units ("AFUs") 3512A-3512N, floating-point units ("FPUs") 3514A-3514N, integer arithmetic logic units ("ALUs") 3516-3516N, address computational units ("ACUs") 3513A-3513N, double-precision floating-point units ("DPFPUs") 3515A-3515N, and matrix processing units ("MPUs") 3517A-3517N.

In at least one embodiment, FPUs 3514A-3514N can perform single-precision (32-bit) and half-precision (16-bit) floating point operations, while DPFPUs 3515A-3515N perform double precision (64-bit) floating point operations. In at least one embodiment, ALUs 3516A-3516N can perform variable precision integer operations at 8-bit, 16-bit, and 32-bit precision, and can be configured for mixed precision operations. In at least one embodiment, MPUs 3517A-3517N can also be configured for mixed precision matrix operations, including half-precision floating point and 8-bit integer operations. In at least one embodiment, MPUs 3517-3517N can perform a variety of matrix operations to accelerate CUDA programs, including enabling support for accelerated general matrix to matrix multiplication ("GEMM"). In at least one embodiment, AFUs 3512A-3512N can perform additional logic operations not supported by floating-point or integer units, including trigonometric operations (e.g., Sine, Cosine, etc.).

FIG. 35B illustrates a general-purpose graphics processing unit ("GPGPU") 3530, in accordance with at least one embodiment. In at least one embodiment, GPGPU 3530 is highly-parallel and suitable for deployment on a multi-chip module. In at least one embodiment, GPGPU 3530 can be configured to enable highly-parallel compute operations to be performed by an array of GPUs. In at least one embodiment, GPGPU 3530 can be linked directly to other instances of GPGPU 3530 to create a multi-GPU cluster to improve execution time for CUDA programs. In at least one embodiment, GPGPU 3530 includes a host interface 3532 to enable a connection with a host processor. In at least one embodiment, host interface 3532 is a PCIe interface. In at least one embodiment, host interface 3532 can be a vendor specific communications interface or communications fabric. In at least one embodiment, GPGPU 3530 receives commands from a host processor and uses a global scheduler 3534 to distribute execution threads associated with those commands to a set of compute clusters 3536A-3536H. In at least one embodiment, compute clusters 3536A-3536H share a cache memory 3538. In at least one embodiment, cache memory 3538 can serve as a higher-level cache for cache memories within compute clusters 3536A-3536H.

In at least one embodiment, GPGPU 3530 includes memory 3544A-3544B coupled with compute clusters 3536A-3536H via a set of memory controllers 3542A-3542B. In at least one embodiment, memory 3544A-3544B can include various types of memory devices including DRAM or graphics random access memory, such as synchronous graphics random access memory ("SGRAM"), including graphics double data rate ("GDDR") memory.

In at least one embodiment, compute clusters 3536A-3536H each include a set of graphics cores, such as graphics core 3500 of FIG. 35A, which can include multiple types of integer and floating point logic units that can perform computational operations at a range of precisions including suited for computations associated with CUDA programs. For example, in at least one embodiment, at least a subset of floating point units in each of compute clusters 3536A-3536H can be configured to perform 16-bit or 32-bit floating point operations, while a different subset of floating point units can be configured to perform 64-bit floating point operations.

In at least one embodiment, multiple instances of GPGPU 3530 can be configured to operate as a compute cluster. In at least one embodiment, compute clusters 3536A-3536H may implement any technically feasible communication techniques for synchronization and data exchange. In at least one embodiment, multiple instances of GPGPU 3530 communicate over host interface 3532. In at least one embodiment, GPGPU 3530 includes an I/O hub 3539 that couples GPGPU 3530 with a GPU link 3540 that enables a direct connection to other instances of GPGPU 3530. In at least one embodiment, GPU link 3540 is coupled to a dedicated GPU-to-GPU bridge that enables communication and synchronization between multiple instances of GPGPU 3530. In at least one embodiment GPU link 3540 couples with a high speed interconnect to transmit and receive data to other GPGPUs 3530 or parallel processors. In at least one embodiment, multiple instances of GPGPU 3530 are located in separate data processing systems and communicate via a network device that is accessible via host interface 3532. In at least one embodiment GPU link 3540 can be configured to enable a connection to a host processor in addition to or as an alternative to host interface 3532. In at least one embodiment, GPGPU 3530 can be configured to execute a CUDA program.

In at least one embodiment, the graphics core 3500 and/or the GPGPU 3530 may be used to implement the system 100 (see FIG. 1) and/or the inference pipeline 500 (see FIG. 5). For example, the graphics core 3500 and/or the GPGPU 3530 may be used to implement the processing system 104, the requestor device(s) 102, the receiver device(s) 106, and/or the optional data storage units 108. In at least one embodiment, the graphics core 3500 and/or the GPGPU 3530 may be used to implement at least one of the CPU(s) 116, at least one of the GPU(s) 118, and/or at least one of the DPU(s) 130. In at least one embodiment, the at least one of the memory 3544A-3544B may be used to implement the CPU memory 120, the GPU memory 122, the DPU memory 132, and/or the optional data storage units 108. In at least one embodiment, at least a portion of the system(s) depicted in FIGS. 35A and 35B is used to implement one or more systems, techniques, functions, and/or processes described in connection with FIGS. 1-5. For example, in at least one embodiment, at least one component shown or described with respect to FIGS. 35A and 35B is used to process data (e.g., data having a DICOM format) in accordance with one or more techniques, functions, and/or processes described with respect to any of FIGS. 1-5.

FIG. 36A illustrates a parallel processor 3600, in accordance with at least one embodiment. In at least one embodiment, various components of parallel processor 3600 may be implemented using one or more integrated circuit devices, such as programmable processors, application specific integrated circuits ("ASICs"), or FPGAs.

In at least one embodiment, parallel processor 3600 includes a parallel processing unit 3602. In at least one embodiment, parallel processing unit 3602 includes an I/O unit 3604 that enables communication with other devices, including other instances of parallel processing unit 3602. In at least one embodiment, I/O unit 3604 may be directly connected to other devices. In at least one embodiment, I/O unit 3604 connects with other devices via use of a hub or switch interface, such as memory hub 3605. In at least one embodiment, connections between memory hub 3605 and I/O unit 3604 form a communication link. In at least one embodiment, I/O unit 3604 connects with a host interface 3606 and a memory crossbar 3616, where host interface 3606 receives commands directed to performing processing operations and memory crossbar 3616 receives commands directed to performing memory operations.

In at least one embodiment, when host interface 3606 receives a command buffer via I/O unit 3604, host interface 3606 can direct work operations to perform those commands to a front end 3608. In at least one embodiment, front end 3608 couples with a scheduler 3610, which is configured to distribute commands or other work items to a processing array 3612. In at least one embodiment, scheduler 3610 ensures that processing array 3612 is properly configured and in a valid state before tasks are distributed to processing array 3612. In at least one embodiment, scheduler 3610 is implemented via firmware logic executing on a microcontroller. In at least one embodiment, microcontroller implemented scheduler 3610 is configurable to perform complex scheduling and work distribution operations at coarse and fine granularity, enabling rapid preemption and context switching of threads executing on processing array 3612. In at least one embodiment, host software can prove workloads for scheduling on processing array 3612 via one of multiple graphics processing doorbells. In at least one embodiment, workloads can then be automatically distributed across processing array 3612 by scheduler 3610 logic within a microcontroller including scheduler 3610.

In at least one embodiment, processing array 3612 can include up to "N" clusters (e.g., cluster 3614A, cluster 3614B, through cluster 3614N). In at least one embodiment, each cluster 3614A-3614N of processing array 3612 can execute a large number of concurrent threads. In at least one embodiment, scheduler 3610 can allocate work to clusters 3614A-3614N of processing array 3612 using various scheduling and/or work distribution algorithms, which may vary depending on a workload arising for each type of program or computation. In at least one embodiment, scheduling can be handled dynamically by scheduler 3610, or can be assisted in part by compiler logic during compilation of program logic configured for execution by processing array 3612. In at least one embodiment, different clusters 3614A-3614N of processing array 3612 can be allocated for processing different types of programs or for performing different types of computations.

In at least one embodiment, processing array 3612 can be configured to perform various types of parallel processing operations. In at least one embodiment, processing array 3612 is configured to perform general-purpose parallel compute operations. For example, in at least one embodiment, processing array 3612 can include logic to execute processing tasks including filtering of video and/or audio data, performing modeling operations, including physics operations, and performing data transformations.

In at least one embodiment, processing array 3612 is configured to perform parallel graphics processing operations. In at least one embodiment, processing array 3612 can include additional logic to support execution of such graphics processing operations, including, but not limited to texture sampling logic to perform texture operations, as well as tessellation logic and other vertex processing logic. In at least one embodiment, processing array 3612 can be configured to execute graphics processing related shader programs such as, but not limited to vertex shaders, tessellation shaders, geometry shaders, and pixel shaders. In at least one embodiment, parallel processing unit 3602 can transfer data from system memory via I/O unit 3604 for processing. In at least one embodiment, during processing, transferred data can be stored to on-chip memory (e.g., a parallel processor memory 3622) during processing, then written back to system memory.

In at least one embodiment, when parallel processing unit 3602 is used to perform graphics processing, scheduler 3610 can be configured to divide a processing workload into approximately equal sized tasks, to better enable distribution of graphics processing operations to multiple clusters 3614A-3614N of processing array 3612. In at least one embodiment, portions of processing array 3612 can be configured to perform different types of processing. For example, in at least one embodiment, a first portion may be configured to perform vertex shading and topology generation, a second portion may be configured to perform tessellation and geometry shading, and a third portion may be configured to perform pixel shading or other screen space operations, to produce a rendered image for display. In at least one embodiment, intermediate data produced by one or more of clusters 3614A-3614N may be stored in buffers to allow intermediate data to be transmitted between clusters 3614A-3614N for further processing.

In at least one embodiment, processing array 3612 can receive processing tasks to be executed via scheduler 3610, which receives commands defining processing tasks from front end 3608. In at least one embodiment, processing tasks can include indices of data to be processed, e.g., surface (patch) data, primitive data, vertex data, and/or pixel data, as well as state parameters and commands defining how data is to be processed (e.g., what program is to be executed). In at least one embodiment, scheduler 3610 may be configured to fetch indices corresponding to tasks or may receive indices from front end 3608. In at least one embodiment, front end 3608 can be configured to ensure processing array 3612 is configured to a valid state before a workload specified by incoming command buffers (e.g., batch-buffers, push buffers, etc.) is initiated.

In at least one embodiment, each of one or more instances of parallel processing unit 3602 can couple with parallel processor memory 3622. In at least one embodiment, parallel processor memory 3622 can be accessed via memory crossbar 3616, which can receive memory requests from processing array 3612 as well as I/O unit 3604. In at least one embodiment, memory crossbar 3616 can access parallel processor memory 3622 via a memory interface 3618. In at least one embodiment, memory interface 3618 can include multiple partition units (e.g., a partition unit 3620A, partition unit 3620B, through partition unit 3620N) that can each couple to a portion (e.g., memory unit) of parallel processor memory 3622. In at least one embodiment, a number of partition units 3620A-3620N is configured to be equal to a number of memory units, such that a first partition unit 3620A has a corresponding first memory unit 3624A, a second partition unit 3620B has a corresponding memory unit 3624B, and an Nth partition unit 3620N has a corresponding Nth memory unit 3624N. In at least one embodiment, a number of partition units 3620A-3620N may not be equal to a number of memory devices.

In at least one embodiment, memory units 3624A-3624N can include various types of memory devices, including DRAM or graphics random access memory, such as SGRAM, including GDDR memory. In at least one embodiment, memory units 3624A-3624N may also include 3D stacked memory, including but not limited to high bandwidth memory ("HBM"). In at least one embodiment, render targets, such as frame buffers or texture maps may be stored across memory units 3624A-3624N, allowing partition units 3620A-3620N to write portions of each render target in parallel to efficiently use available bandwidth of parallel processor memory 3622. In at least one embodiment, a local instance of parallel processor memory 3622 may be excluded in favor of a unified memory design that utilizes system memory in conjunction with local cache memory.

In at least one embodiment, any one of clusters 3614A-3614N of processing array 3612 can process data that will be written to any of memory units 3624A-3624N within parallel processor memory 3622. In at least one embodiment, memory crossbar 3616 can be configured to transfer an output of each cluster 3614A-3614N to any partition unit 3620A-3620N or to another cluster 3614A-3614N, which can perform additional processing operations on an output. In at least one embodiment, each cluster 3614A-3614N can communicate with memory interface 3618 through memory crossbar 3616 to read from or write to various external memory devices. In at least one embodiment, memory crossbar 3616 has a connection to memory interface 3618 to communicate with I/O unit 3604, as well as a connection to a local instance of parallel processor memory 3622, enabling processing units within different clusters 3614A-3614N to communicate with system memory or other memory that is not local to parallel processing unit 3602. In at least one embodiment, memory crossbar 3616 can use virtual channels to separate traffic streams between clusters 3614A-3614N and partition units 3620A-3620N.

In at least one embodiment, multiple instances of parallel processing unit 3602 can be provided on a single add-in card, or multiple add-in cards can be interconnected. In at least one embodiment, different instances of parallel processing unit 3602 can be configured to interoperate even if different instances have different numbers of processing cores, different amounts of local parallel processor memory, and/or other configuration differences. For example, in at least one embodiment, some instances of parallel processing unit 3602 can include higher precision floating point units relative to other instances. In at least one embodiment, systems incorporating one or more instances of parallel processing unit 3602 or parallel processor 3600 can be implemented in a variety of configurations and form factors, including but not limited to desktop, laptop, or handheld personal computers, servers, workstations, game consoles, and/or embedded systems.

FIG. 36B illustrates a processing cluster 3694, in accordance with at least one embodiment. In at least one embodiment, processing cluster 3694 is included within a parallel processing unit. In at least one embodiment, processing cluster 3694 is one of processing clusters 3614A-3614N of FIG. 36. In at least one embodiment, processing cluster 3694 can be configured to execute many threads in parallel, where the term "thread" refers to an instance of a particular program executing on a particular set of input data. In at least one embodiment, single instruction, multiple data ("SIMD") instruction issue techniques are used to support parallel execution of a large number of threads without providing multiple independent instruction units. In at least one embodiment, single instruction, multiple thread ("SIMT") techniques are used to support parallel execution of a large number of generally synchronized threads, using a common instruction unit configured to issue instructions to a set of processing engines within each processing cluster 3694.

In at least one embodiment, operation of processing cluster 3694 can be controlled via a pipeline manager 3632 that distributes processing tasks to SIMT parallel processors. In at least one embodiment, pipeline manager 3632 receives instructions from scheduler 3610 of FIG. 36 and manages execution of those instructions via a graphics multiprocessor 3634 and/or a texture unit 3636. In at least one embodiment, graphics multiprocessor 3634 is an exemplary instance of a SIMT parallel processor. However, in at least one embodiment, various types of SIMT parallel processors of differing architectures may be included within processing cluster 3694. In at least one embodiment, one or more instances of graphics multiprocessor 3634 can be included within processing cluster 3694. In at least one embodiment, graphics multiprocessor 3634 can process data and a data crossbar 3640 can be used to distribute processed data to one of multiple possible destinations, including other shader units. In at least one embodiment, pipeline manager 3632 can facilitate distribution of processed data by specifying destinations for processed data to be distributed via data crossbar 3640.

In at least one embodiment, each graphics multiprocessor 3634 within processing cluster 3694 can include an identical set of functional execution logic (e.g., arithmetic logic units, load/store units ("LSUs"), etc.). In at least one embodiment, functional execution logic can be configured in a pipelined manner in which new instructions can be issued before previous instructions are complete. In at least one embodiment, functional execution logic supports a variety of operations including integer and floating point arithmetic, comparison operations, Boolean operations, bit-shifting, and computation of various algebraic functions. In at least one embodiment, same functional-unit hardware can be leveraged to perform different operations and any combination of functional units may be present.

In at least one embodiment, instructions transmitted to processing cluster 3694 constitute a thread. In at least one embodiment, a set of threads executing across a set of parallel processing engines is a thread group. In at least one embodiment, a thread group executes a program on different input data. In at least one embodiment, each thread within a thread group can be assigned to a different processing engine within graphics multiprocessor 3634. In at least one embodiment, a thread group may include fewer threads than a number of processing engines within graphics multiprocessor 3634. In at least one embodiment, when a thread group includes fewer threads than a number of processing engines, one or more of processing engines may be idle during cycles in which that thread group is being processed. In at least one embodiment, a thread group may also include more threads than a number of processing engines within graphics multiprocessor 3634. In at least one embodiment, when a thread group includes more threads than a number of processing engines within graphics multiprocessor 3634, processing can be performed over consecutive clock cycles. In at least one embodiment, multiple thread groups can be executed concurrently on graphics multiprocessor 3634.

In at least one embodiment, graphics multiprocessor 3634 includes an internal cache memory to perform load and store operations. In at least one embodiment, graphics multiprocessor 3634 can forego an internal cache and use a cache memory (e.g., L1 cache 3648) within processing cluster 3694. In at least one embodiment, each graphics multiprocessor 3634 also has access to Level 2 ("L2") caches within partition units (e.g., partition units 3620A-3620N of FIG. 36A) that are shared among all processing clusters 3694 and may be used to transfer data between threads. In at least one embodiment, graphics multiprocessor 3634 may also access off-chip global memory, which can include one or more of local parallel processor memory and/or system memory. In at least one embodiment, any memory external to parallel processing unit 3602 may be used as global memory. In at least one embodiment, processing cluster 3694 includes multiple instances of graphics multiprocessor 3634 that can share common instructions and data, which may be stored in L1 cache 3648.

In at least one embodiment, each processing cluster 3694 may include an MMU 3645 that is configured to map virtual addresses into physical addresses. In at least one embodiment, one or more instances of MMU 3645 may reside within memory interface 3618 of FIG. 36. In at least one embodiment, MMU 3645 includes a set of page table entries ("PTEs") used to map a virtual address to a physical address of a tile and optionally a cache line index. In at least one embodiment, MMU 3645 may include address translation lookaside buffers ("TLBs") or caches that may reside within graphics multiprocessor 3634 or L1 cache 3648 or processing cluster 3694. In at least one embodiment, a physical address is processed to distribute surface data access locality to allow efficient request interleaving among partition units. In at least one embodiment, a cache line index may be used to determine whether a request for a cache line is a hit or miss.

In at least one embodiment, processing cluster 3694 may be configured such that each graphics multiprocessor 3634 is coupled to a texture unit 3636 for performing texture mapping operations, e.g., determining texture sample positions, reading texture data, and filtering texture data. In at least one embodiment, texture data is read from an internal texture L1 cache (not shown) or from an L1 cache within graphics multiprocessor 3634 and is fetched from an L2 cache, local parallel processor memory, or system memory, as needed. In at least one embodiment, each graphics multiprocessor 3634 outputs a processed task to data crossbar 3640 to provide a processed task to another processing cluster 3694 for further processing or to store a processed task in an L2 cache, a local parallel processor memory, or a system memory via memory crossbar 3616. In at least one embodiment, a pre-raster operations unit ("preROP") 3642 is configured to receive data from graphics multiprocessor 3634, direct data to ROP units, which may be located with partition units as described herein (e.g., partition units 3620A-3620N of FIG. 36). In at least one embodiment, PreROP 3642 can perform optimizations for color blending, organize pixel color data, and perform address translations.

FIG. 36C illustrates a graphics multiprocessor 3696, in accordance with at least one embodiment. In at least one embodiment, graphics multiprocessor 3696 is graphics multiprocessor 3634 of FIG. 36B. In at least one embodiment, graphics multiprocessor 3696 couples with pipeline manager 3632 of processing cluster 3694. In at least one embodiment, graphics multiprocessor 3696 has an execution pipeline including but not limited to an instruction cache 3652, an instruction unit 3654, an address mapping unit 3656, a register file 3658, one or more GPGPU cores 3662, and one or more LSUs 3666. GPGPU cores 3662 and LSUs 3666 are coupled with cache memory 3672 and shared memory 3670 via a memory and cache interconnect 3668.

In at least one embodiment, instruction cache 3652 receives a stream of instructions to execute from pipeline manager 3632. In at least one embodiment, instructions are cached in instruction cache 3652 and dispatched for execution by instruction unit 3654. In at least one embodiment, instruction unit 3654 can dispatch instructions as thread groups (e.g., warps), with each thread of a thread group assigned to a different execution unit within GPGPU core 3662. In at least one embodiment, an instruction can access any of a local, shared, or global address space by specifying an address within a unified address space. In at least one embodiment, address mapping unit 3656 can be used to translate addresses in a unified address space into a distinct memory address that can be accessed by LSUs 3666.

In at least one embodiment, register file 3658 provides a set of registers for functional units of graphics multiprocessor 3696. In at least one embodiment, register file 3658 provides temporary storage for operands connected to data paths of functional units (e.g., GPGPU cores 3662, LSUs 3666) of graphics multiprocessor 3696. In at least one embodiment, register file 3658 is divided between each of functional units such that each functional unit is allocated a dedicated portion of register file 3658. In at least one embodiment, register file 3658 is divided between different thread groups being executed by graphics multiprocessor 3696.

In at least one embodiment, GPGPU cores 3662 can each include FPUs and/or integer ALUs that are used to execute instructions of graphics multiprocessor 3696. GPGPU cores 3662 can be similar in architecture or can differ in architecture. In at least one embodiment, a first portion of GPGPU cores 3662 include a single precision FPU and an integer ALU while a second portion of GPGPU cores 3662 include a double precision FPU. In at least one embodiment, FPUs can implement IEEE 754-2008 standard for floating point arithmetic or enable variable precision floating point arithmetic. In at least one embodiment, graphics multiprocessor 3696 can additionally include one or more fixed function or special function units to perform specific functions such as copy rectangle or pixel blending operations. In at least one embodiment one or more of GPGPU cores 3662 can also include fixed or special function logic.

In at least one embodiment, GPGPU cores 3662 include SIMD logic capable of performing a single instruction on multiple sets of data. In at least one embodiment GPGPU cores 3662 can physically execute SIMD4, SIMD8, and SIMD16 instructions and logically execute SIMD1, SIMD2, and SIMD32 instructions. In at least one embodiment, SIMD instructions for GPGPU cores 3662 can be generated at compile time by a shader compiler or automatically generated when executing programs written and compiled for single program multiple data ("SPMD") or SIMT architectures. In at least one embodiment, multiple threads of a program configured for an SIMT execution model can executed via a single SIMD instruction. For example, in at least one embodiment, eight SIMT threads that perform the same or similar operations can be executed in parallel via a single SIMD8 logic unit.

In at least one embodiment, memory and cache interconnect 3668 is an interconnect network that connects each functional unit of graphics multiprocessor 3696 to register file 3658 and to shared memory 3670. In at least one embodiment, memory and cache interconnect 3668 is a crossbar interconnect that allows LSU 3666 to implement load and store operations between shared memory 3670 and register file 3658. In at least one embodiment, register file 3658 can operate at a same frequency as GPGPU cores 3662, thus data transfer between GPGPU cores 3662 and register file 3658 is very low latency. In at least one embodiment, shared memory 3670 can be used to enable communication between threads that execute on functional units within graphics multiprocessor 3696. In at least one embodiment, cache memory 3672 can be used as a data cache for example, to cache texture data communicated between functional units and texture unit 3636. In at least one embodiment, shared memory 3670 can also be used as a program managed cached. In at least one embodiment, threads executing on GPGPU cores 3662 can programmatically store data within shared memory in addition to auto-matically cached data that is stored within cache memory 3672.

In at least one embodiment, a parallel processor or GPGPU as described herein is communicatively coupled to host/processor cores to accelerate graphics operations, machine-learning operations, pattern analysis operations, and various general purpose GPU (GPGPU) functions. In at least one embodiment, a GPU may be communicatively coupled to host processor/cores over a bus or other inter-connect (e.g., a high speed interconnect such as PCIe or NVLink). In at least one embodiment, a GPU may be integrated on a same package or chip as cores and commu-nicatively coupled to cores over a processor bus/intercon-nect that is internal to a package or a chip. In at least one embodiment, regardless of a manner in which a GPU is connected, processor cores may allocate work to a GPU in a form of sequences of commands/instructions contained in a WD. In at least one embodiment, a GPU then uses dedicated circuitry/logic for efficiently processing these commands/instructions.

In at least one embodiment, the parallel processor 3600 may be used to implement the system 100 (see FIG. 1) and/or the inference pipeline 500 (see FIG. 5). For example, the parallel processor 3600 may be used to implement one or more of the processing system 104, the requestor device(s) 102, the receiver device(s) 106, and/or the optional data storage units 108. In at least one embodiment, the parallel processor 3600 may be used to implement at least one of the CPU(s) 116, at least one of the GPU(s) 118, and/or at least one of the DPU(s) 130. In at least one embodiment, the parallel processor memory 3622 may be used to imple-ment the CPU memory 120, the GPU memory 122, the DPU memory 132, and/or the optional data storage units 108. In at least one embodiment, at least a portion of the system(s) depicted in FIGS. 36A-36C is used to implement one or more systems, techniques, functions, and/or processes described in connection with FIGS. 1-5. For example, in at least one embodiment, at least one component shown or described with respect to FIGS. 36A-36C is used to process data (e.g., data having a DICOM format) in accordance with one or more techniques, functions, and/or processes described with respect to any of FIGS. 1-5.

General Computing

The following figures set forth, without limitation, exem-plary software constructs within general computing that can be used to implement at least one embodiment.

FIG. 37 illustrates a software stack of a programming platform, in accordance with at least one embodiment. In at least one embodiment, a programming platform is a plat-form for leveraging hardware on a computing system to accelerate computational tasks. A programming platform may be accessible to software developers through libraries, compiler directives, and/or extensions to programming lan-guages, in at least one embodiment. In at least one embodi-ment, a programming platform may be, but is not limited to, CUDA, Radeon Open Compute Platform ("ROCm"), OpenCL (OpenCL™ is developed by Khronos group), SYCL, or Intel One API.

In at least one embodiment, a software stack 3700 of a programming platform provides an execution environment for an application 3701. In at least one embodiment, appli-cation 3701 may include any computer software capable of being launched on software stack 3700. In at least one embodiment, application 3701 may include, but is not limited to, an artificial intelligence ("AI")/machine learning ("ML") application, a high performance computing ("HPC") application, a virtual desktop infrastructure ("VDI"), or a data center workload.

In at least one embodiment, application 3701 and soft-ware stack 3700 run on hardware 3707. Hardware 3707 may include one or more GPUs, CPUs, FPGAs, AI engines, and/or other types of compute devices that support a pro-gramming platform, in at least one embodiment. In at least one embodiment, such as with CUDA, software stack 3700 may be vendor specific and compatible with only devices from particular vendor(s). In at least one embodiment, such as in with OpenCL, software stack 3700 may be used with devices from different vendors. In at least one embodiment, hardware 3707 includes a host connected to one more devices that can be accessed to perform computational tasks via application programming interface ("API") calls. A device within hardware 3707 may include, but is not limited to, a GPU, FPGA, AI engine, or other compute device (but may also include a CPU) and its memory, as opposed to a host within hardware 3707 that may include, but is not limited to, a CPU (but may also include a compute device) and its memory, in at least one embodiment.

In at least one embodiment, software stack 3700 of a programming platform includes, without limitation, a num-ber of libraries 3703, a runtime 3705, and a device kernel driver 3706. Each of libraries 3703 may include data and programming code that can be used by computer programs and leveraged during software development, in at least one embodiment. In at least one embodiment, libraries 3703 may include, but are not limited to, pre-written code and sub-routines, classes, values, type specifications, configuration data, documentation, help data, and/or message templates. In at least one embodiment, libraries 3703 include functions that are optimized for execution on one or more types of devices. In at least one embodiment, libraries 3703 may include, but are not limited to, functions for performing mathematical, deep learning, and/or other types of opera-tions on devices. In at least one embodiment, libraries 3803 are associated with corresponding APIs 3802, which may include one or more APIs, that expose functions imple-mented in libraries 3803.

In at least one embodiment, application 3701 is written as source code that is compiled into executable code, as dis-cussed in greater detail below in conjunction with FIG. 42.

Executable code of application 3701 may run, at least in part, on an execution environment provided by software stack 3700, in at least one embodiment. In at least one embodiment, during execution of application 3701, code may be reached that needs to run on a device, as opposed to a host. In such a case, runtime 3705 may be called to load and launch requisite code on a device, in at least one embodiment. In at least one embodiment, runtime 3705 may include any technically feasible runtime system that is able to support execution of application S01.

In at least one embodiment, runtime 3705 is implemented as one or more runtime libraries associated with corresponding APIs, which are shown as API(s) 3704. One or more of such runtime libraries may include, without limitation, functions for memory management, execution control, device management, error handling, and/or synchronization, among other things, in at least one embodiment. In at least one embodiment, memory management functions may include, but are not limited to, functions to allocate, deallocate, and copy device memory, as well as transfer data between host memory and device memory. In at least one embodiment, execution control functions may include, but are not limited to, functions to launch a function (sometimes referred to as a "kernel" when a function is a global function callable from a host) on a device and set attribute values in a buffer maintained by a runtime library for a given function to be executed on a device.

Runtime libraries and corresponding API(s) 3704 may be implemented in any technically feasible manner, in at least one embodiment. In at least one embodiment, one (or any number of) API may expose a low-level set of functions for fine-grained control of a device, while another (or any number of) API may expose a higher-level set of such functions. In at least one embodiment, a high-level runtime API may be built on top of a low-level API. In at least one embodiment, one or more of runtime APIs may be language-specific APIs that are layered on top of a language-independent runtime API.

In at least one embodiment, device kernel driver 3706 is configured to facilitate communication with an underlying device. In at least one embodiment, device kernel driver 3706 may provide low-level functionalities upon which APIs, such as API(s) 3704, and/or other software relies. In at least one embodiment, device kernel driver 3706 may be configured to compile intermediate representation ("IR") code into binary code at runtime. For CUDA, device kernel driver 3706 may compile Parallel Thread Execution ("PTX") IR code that is not hardware specific into binary code for a specific target device at runtime (with caching of compiled binary code), which is also sometimes referred to as "finalizing" code, in at least one embodiment. Doing so may permit finalized code to run on a target device, which may not have existed when source code was originally compiled into PTX code, in at least one embodiment. Alternatively, in at least one embodiment, device source code may be compiled into binary code offline, without requiring device kernel driver 3706 to compile IR code at runtime.

In at least one embodiment, the software stack 3700 may be used to implement the system 100 (see FIG. 1) and/or the inference pipeline 500 (see FIG. 5). For example, the software stack 3700 may be executed by the processing system 104, the requestor device(s) 102, the receiver device(s) 106, and/or the optional data storage units 108. In at least one embodiment, the software stack 3700 may include at least a portion of one or more of the CPU application 142A, the GPU application 142B, and/or the DPU application 142C. In at least one embodiment, the hardware 3707 may include at least one of the CPU(s) 116, at least one of the GPU(s) 118, at least one of the DPU(s) 130, the CPU memory 120, the GPU memory 122, the DPU memory 132, and/or the optional data storage units 108. In at least one embodiment, at least a portion of the system(s) depicted in FIG. 37 is used to implement one or more systems, techniques, functions, and/or processes described in connection with FIGS. 1-5. For example, in at least one embodiment, at least one component shown or described with respect to FIG. 37 is used to process data (e.g., data having a DICOM format) in accordance with one or more techniques, functions, and/or processes described with respect to any of FIGS. 1-5.

FIG. 38 illustrates a CUDA implementation of software stack 3700 of FIG. 37, in accordance with at least one embodiment. In at least one embodiment, a CUDA software stack 3800, on which an application 3801 may be launched, includes CUDA libraries 3803, a CUDA runtime 3805, a CUDA driver 3807, and a device kernel driver 3808. In at least one embodiment, CUDA software stack 3800 executes on hardware 3809, which may include a GPU that supports CUDA and is developed by NVIDIA Corporation of Santa Clara, CA.

In at least one embodiment, application 3801, CUDA runtime 3805, and device kernel driver 3808 may perform similar functionalities as application 3701, runtime 3705, and device kernel driver 3706, respectively, which are described above in conjunction with FIG. 37. In at least one embodiment, CUDA driver 3807 includes a library (libcuda.so) that implements a CUDA driver API 3806. Similar to a CUDA runtime API 3804 implemented by a CUDA runtime library (cudart), CUDA driver API 3806 may, without limitation, expose functions for memory management, execution control, device management, error handling, synchronization, and/or graphics interoperability, among other things, in at least one embodiment. In at least one embodiment, CUDA driver API 3806 differs from CUDA runtime API 3804 in that CUDA runtime API 3804 simplifies device code management by providing implicit initialization, context (analogous to a process) management, and module (analogous to dynamically loaded libraries) management. In contrast to high-level CUDA runtime API 3804, CUDA driver API 3806 is a low-level API providing more fine-grained control of a device, particularly with respect to contexts and module loading, in at least one embodiment. In at least one embodiment, CUDA driver API 3806 may expose functions for context management that are not exposed by CUDA runtime API 3804. In at least one embodiment, CUDA driver API 3806 is also language-independent and supports, e.g., OpenCL in addition to CUDA runtime API 3804. Further, in at least one embodiment, development libraries, including CUDA runtime 3805, may be considered as separate from driver components, including user-mode CUDA driver 3807 and kernel-mode device driver 3808 (also sometimes referred to as a "display" driver).

In at least one embodiment, CUDA libraries 3803 may include, but are not limited to, mathematical libraries, deep learning libraries, parallel algorithm libraries, and/or signal/image/video processing libraries, which parallel computing applications such as application 3801 may utilize. In at least one embodiment, CUDA libraries 3803 may include mathematical libraries such as a cuBLAS library that is an implementation of Basic Linear Algebra Subprograms ("BLAS") for performing linear algebra operations, a cuFFT library for computing fast Fourier transforms ("FFTs"), and a cuRAND library for generating random numbers, among others. In at least one embodiment, CUDA libraries 3803 may include deep learning libraries such as a cuDNN library of primitives for deep neural networks and a TensorRT platform for high-performance deep learning inference, among others.

In at least one embodiment, the CUDA software stack 3800 may be used to implement the system 100 (see FIG. 1) and/or the inference pipeline 500 (see FIG. 5). For example, the CUDA software stack 3800 may be executed by the processing system 104, the requestor device(s) 102, the receiver device(s) 106, and/or the optional data storage units 108. In at least one embodiment, the CUDA software stack 3800 may include at least a portion of one or more of the CPU application 142A, the GPU application 142B, and/or the DPU application 142C. In at least one embodiment, the hardware 3809 may include at least one of the CPU(s) 116, at least one of the GPU(s) 118, at least one of the DPU(s) 130, the CPU memory 120, the GPU memory 122, the DPU memory 132, and/or the optional data storage units 108. In at least one embodiment, at least a portion of the system(s) depicted in FIG. 38 is used to implement one or more systems, techniques, functions, and/or processes described in connection with FIGS. 1-5. For example, in at least one embodiment, at least one component shown or described with respect to FIG. 38 is used to process data (e.g., data having a DICOM format) in accordance with one or more techniques, functions, and/or processes described with respect to any of FIGS. 1-5.

FIG. 39 illustrates a ROCm implementation of software stack 3700 of FIG. 37, in accordance with at least one embodiment. In at least one embodiment, a ROCm software stack 3900, on which an application 3901 may be launched, includes a language runtime 3903, a system runtime 3905, a thunk 3907, a ROCm kernel driver 3908, and a device kernel driver 3909. In at least one embodiment, ROCm software stack 3900 executes on hardware 3910, which may include a GPU that supports ROCm and is developed by AMD Corporation of Santa Clara, CA.

In at least one embodiment, application 3901 may perform similar functionalities as application 3701 discussed above in conjunction with FIG. 37. In addition, language runtime 3903 and system runtime 3905 may perform similar functionalities as runtime 3705 discussed above in conjunction with FIG. 37, in at least one embodiment. In at least one embodiment, language runtime 3903 and system runtime 3905 differ in that system runtime 3905 is a language-independent runtime that implements a ROCr system runtime API 3904 and makes use of a Heterogeneous System Architecture ("HAS") Runtime API. HAS runtime API is a thin, user-mode API that exposes interfaces to access and interact with an AMD GPU, including functions for memory management, execution control via architected dispatch of kernels, error handling, system and agent information, and runtime initialization and shutdown, among other things, in at least one embodiment. In contrast to system runtime 3905, language runtime 3903 is an implementation of a language-specific runtime API 3902 layered on top of ROCr system runtime API 3904, in at least one embodiment. In at least one embodiment, language runtime API may include, but is not limited to, a Heterogeneous compute Interface for Portability ("HIP") language runtime API, a Heterogeneous Compute Compiler ("HCC") language runtime API, or an OpenCL API, among others. HIP language in particular is an extension of C++ programming language with functionally similar versions of CUDA mechanisms and, in at least one embodiment, a HIP language runtime API includes functions that are similar to those of CUDA runtime API 3804 discussed above in conjunction with FIG. 38, such as functions for memory management, execution control, device management, error handling, and synchronization, among other things.

In at least one embodiment, thunk (ROCt) 3907 is an interface that can be used to interact with underlying ROCm driver 3908. In at least one embodiment, ROCm driver 3908 is a ROCK driver, which is a combination of an AMDGPU driver and a HAS kernel driver (amdkfd). In at least one embodiment, AMDGPU driver is a device kernel driver for GPUs developed by AMD that performs similar functionalities as device kernel driver 3706 discussed above in conjunction with FIG. 37. In at least one embodiment, HAS kernel driver is a driver permitting different types of processors to share system resources more effectively via hardware features.

In at least one embodiment, various libraries (not shown) may be included in ROCm software stack 3900 above language runtime 3903 and provide functionality similarity to CUDA libraries 3803, discussed above in conjunction with FIG. 38. In at least one embodiment, various libraries may include, but are not limited to, mathematical, deep learning, and/or other libraries such as a hipBLAS library that implements functions similar to those of CUDA cuBLAS, a rocFFT library for computing FFTs that is similar to CUDA cuFFT, among others.

In at least one embodiment, the ROCm software stack 3900 may be used to implement the system 100 (see FIG. 1) and/or the inference pipeline 500 (see FIG. 5). For example, the ROCm software stack 3900 may be executed by the processing system 104, the requestor device(s) 102, the receiver device(s) 106, and/or the optional data storage units 108. In at least one embodiment, the ROCm software stack 3900 may include at least a portion of one or more of the CPU application 142A, the GPU application 142B, and/or the DPU application 142C. In at least one embodiment, the hardware 3909 may include at least one of the CPU(s) 116, at least one of the GPU(s) 118, at least one of the DPU(s) 130, the CPU memory 120, the GPU memory 122, the DPU memory 132, and/or the optional data storage units 108. In at least one embodiment, at least a portion of the system(s) depicted in FIG. 39 is used to implement one or more systems, techniques, functions, and/or processes described in connection with FIGS. 1-5. For example, in at least one embodiment, at least one component shown or described with respect to FIG. 39 is used to process data (e.g., data having a DICOM format) in accordance with one or more techniques, functions, and/or processes described with respect to any of FIGS. 1-5.

FIG. 40 illustrates an OpenCL implementation of software stack 3700 of FIG. 37, in accordance with at least one embodiment. In at least one embodiment, an OpenCL software stack 4000, on which an application 4001 may be launched, includes an OpenCL framework 4005, an OpenCL runtime 4006, and a driver 4007. In at least one embodiment, OpenCL software stack 4000 executes on hardware 4008 that is not vendor-specific. As OpenCL is supported by devices developed by different vendors, specific OpenCL drivers may be required to interoperate with hardware from such vendors, in at least one embodiment.

In at least one embodiment, application 4001, OpenCL runtime 4006, device kernel driver 4007, and hardware 4008 may perform similar functionalities as application 3701, runtime 3705, device kernel driver 3706, and hardware 3707, respectively, that are discussed above in conjunction with FIG. 37. In at least one embodiment, application 4001 further includes an OpenCL kernel 4002 with code that is to be executed on a device.

In at least one embodiment, OpenCL defines a "platform" that allows a host to control devices connected to a host. In at least one embodiment, an OpenCL framework provides a platform layer API and a runtime API, shown as platform API 4003 and runtime API 4005. In at least one embodiment, runtime API 4005 uses contexts to manage execution of kernels on devices. In at least one embodiment, each identified device may be associated with a respective context, which runtime API 4005 may use to manage command queues, program objects, and kernel objects, share memory objects, among other things, for that device. In at least one embodiment, platform API 4003 exposes functions that permit device contexts to be used to select and initialize devices, submit work to devices via command queues, and enable data transfer to and from devices, among other things. In addition, OpenCL framework provides various built-in functions (not shown), including math functions, relational functions, and image processing functions, among others, in at least one embodiment.

In at least one embodiment, a compiler 4004 is also included in OpenCL framework 4005. Source code may be compiled offline prior to executing an application or online during execution of an application, in at least one embodiment. In contrast to CUDA and ROCm, OpenCL applications in at least one embodiment may be compiled online by compiler 4004, which is included to be representative of any number of compilers that may be used to compile source code and/or IR code, such as Standard Portable Intermediate Representation ("SPIR-V") code, into binary code. Alternatively, in at least one embodiment, OpenCL applications may be compiled offline, prior to execution of such applications.

In at least one embodiment, the OpenCL software stack 4000 may be used to implement the system 100 (see FIG. 1) and/or the inference pipeline 500 (see FIG. 5). For example, the OpenCL software stack 4000 may be executed by the processing system 104, the requestor device(s) 102, the receiver device(s) 106, and/or the optional data storage units 108. In at least one embodiment, the OpenCL software stack 4000 may include at least a portion of one or more of the CPU application 142A, the GPU application 142B, and/or the DPU application 142C. In at least one embodiment, the hardware 4008 may include at least one of the CPU(s) 116, at least one of the GPU(s) 118, at least one of the DPU(s) 130, the CPU memory 120, the GPU memory 122, the DPU memory 132, and/or the optional data storage units 108. In at least one embodiment, at least a portion of the system(s) depicted in FIG. 40 is used to implement one or more systems, techniques, functions, and/or processes described in connection with FIGS. 1-5. For example, in at least one embodiment, at least one component shown or described with respect to FIG. 40 is used to process data (e.g., data having a DICOM format) in accordance with one or more techniques, functions, and/or processes described with respect to any of FIGS. 1-5.

FIG. 41 illustrates software that is supported by a programming platform, in accordance with at least one embodiment. In at least one embodiment, a programming platform 4104 is configured to support various programming models 4103, middlewares and/or libraries 4102, and frameworks 4101 that an application 4100 may rely upon. In at least one embodiment, application 4100 may be an AI/ML application implemented using, for example, a deep learning framework such as MXNet, PyTorch, or TensorFlow, which may rely on libraries such as cuDNN, NVIDIA Collective Communications Library ("NCCL"), and/or NVIDA Developer Data Loading Library ("DALI") CUDA libraries to provide accelerated computing on underlying hardware.

In at least one embodiment, programming platform 4104 may be one of a CUDA, ROCm, or OpenCL platform described above in conjunction with FIG. 38, FIG. 39, and FIG. 40, respectively. In at least one embodiment, programming platform 4104 supports multiple programming models 4103, which are abstractions of an underlying computing system permitting expressions of algorithms and data structures. Programming models 4103 may expose features of underlying hardware in order to improve performance, in at least one embodiment. In at least one embodiment, programming models 4103 may include, but are not limited to, CUDA, HIP, OpenCL, C++ Accelerated Massive Parallelism ("C++ AMP"), Open Multi-Processing ("OpenMP"), Open Accelerators ("OpenACC"), and/or Vulcan Compute.

In at least one embodiment, libraries and/or middlewares 4102 provide implementations of abstractions of programming models 4104. In at least one embodiment, such libraries include data and programming code that may be used by computer programs and leveraged during software development. In at least one embodiment, such middlewares include software that provides services to applications beyond those available from programming platform 4104. In at least one embodiment, libraries and/or middlewares 4102 may include, but are not limited to, cuBLAS, cuFFT, cuRAND, and other CUDA libraries, or rocBLAS, rocFFT, rocRAND, and other ROCm libraries. In addition, in at least one embodiment, libraries and/or middlewares 4102 may include NCCL and ROCm Communication Collectives Library ("RCCL") libraries providing communication routines for GPUs, a MIOpen library for deep learning acceleration, and/or an Eigen library for linear algebra, matrix and vector operations, geometrical transformations, numerical solvers, and related algorithms.

In at least one embodiment, application frameworks 4101 depend on libraries and/or middlewares 4102. In at least one embodiment, each of application frameworks 4101 is a software framework used to implement a standard structure of application software. An AI/ML application may be implemented using a framework such as Caffe, Caffe2, TensorFlow, Keras, Py Torch, or MxNet deep learning frameworks, in at least one embodiment.

In at least one embodiment, the system of FIG. 41 may be used to implement the system 100 (see FIG. 1) and/or the inference pipeline 500 (see FIG. 5). For example, the programming platform 4104, the programming models 4103, the frameworks 4101, and/or the middlewares and/or libraries 4102 may be used to implement at least a portion of one or more of the CPU application 142A, the GPU application 142B, and/or the DPU application 142C. In at least one embodiment, at least a portion of the system(s) depicted in FIG. 41 is used to implement one or more systems, techniques, functions, and/or processes described in connection with FIGS. 1-5. For example, in at least one embodiment, at least one component shown or described with respect to FIG. 41 is used to process data (e.g., data having a DICOM format) in accordance with one or more techniques, functions, and/or processes described with respect to any of FIGS. 1-5.

FIG. 42 illustrates compiling code to execute on one of programming platforms of FIGS. 37-40, in accordance with at least one embodiment. In at least one embodiment, a compiler 4201 receives source code 4200 that includes both host code as well as device code. In at least one embodiment, complier 4201 is configured to convert source code 4200 into host executable code 4202 for execution on a host and device executable code 4203 for execution on a device. In at least one embodiment, source code 4200 may either be compiled offline prior to execution of an application, or online during execution of an application.

In at least one embodiment, source code 4200 may include code in any programming language supported by compiler 4201, such as C++, C, Fortran, etc. In at least one embodiment, source code 4200 may be included in a single-source file having a mixture of host code and device code, with locations of device code being indicated therein. In at least one embodiment, a single-source file may be a .cu file that includes CUDA code or a .hip.cpp file that includes HIP code. Alternatively, in at least one embodiment, source code 4200 may include multiple source code files, rather than a single-source file, into which host code and device code are separated.

In at least one embodiment, compiler 4201 is configured to compile source code 4200 into host executable code 4202 for execution on a host and device executable code 4203 for execution on a device. In at least one embodiment, compiler 4201 performs operations including parsing source code 4200 into an abstract system tree (AST), performing optimizations, and generating executable code. In at least one embodiment in which source code 4200 includes a single-source file, compiler 4201 may separate device code from host code in such a single-source file, compile device code and host code into device executable code 4203 and host executable code 4202, respectively, and link device executable code 4203 and host executable code 4202 together in a single file, as discussed in greater detail below with respect to FIG. 31.

In at least one embodiment, host executable code 4202 and device executable code 4203 may be in any suitable format, such as binary code and/or IR code. In a case of CUDA, host executable code 4202 may include native object code and device executable code 4203 may include code in PTX intermediate representation, in at least one embodiment. In a case of ROCm, both host executable code 4202 and device executable code 4203 may include target binary code, in at least one embodiment.

In at least one embodiment, at least a portion of the system(s) depicted in FIG. 42 is used to implement one or more systems, techniques, functions, and/or processes described in connection with FIGS. 1-5. For example, in at least one embodiment, at least one component shown or described with respect to FIG. 42 is used to process data (e.g., data having a DICOM format) in accordance with one or more techniques, functions, and/or processes described with respect to any of FIGS. 1-5.

At least one embodiment of the disclosure can be described in view of the following clauses:

1. A system comprising: first memory; a network interface to obtain input data having a first format, convert the input data to obtain converted input data having a second format, and store the converted input data directly to the first memory; and at least one parallel processing unit to perform at least one operation on the converted input data.

2. The system of clause 1, wherein the at least one operation comprises at least one transformation operation.

3. The system of clause 2, wherein the at least one transformation operation comprises at least one of normalizing intensity values, normalizing spatial dimensions, scaling pixel size from non-isotropic to isotropic, or performing histogram normalization.

4. The system of any one of clauses 1-3, wherein the at least one operation comprises one or more inference operations.

5. The system of any one of clauses 1-4, further comprising: an imaging device to capture imaging data and transmit the imaging data to the network interface, the network interface obtaining the input data from the imaging data.

6. The system of clause 5, wherein the imaging device is medical imaging device and the first format is specified by a Digital Imaging and Communications in Medicine ("DICOM") standard.

7. The system of clause 6, wherein the at least one operation comprises one or more inference operations to obtain a diagnostic result.

8. The system of any one of clauses 1-7, further comprising: second memory, the network interface to obtain the input data by loading the input data from the second memory.

9. The system of any one of clauses 1-8, wherein the network interface comprises one or more data processing units to convert the input data, and the system further comprises: one or more central processing units that are different from the at least one parallel processing unit and the one or more data processing units, the one or more central processing units not to process the input data or the converted input data before the at least one parallel processing unit performs the at least one operation on the converted input data.

10. The system of any one of clauses 1-9, wherein converting the input data to obtain the converted input data comprises performing an alignment transformation operation on the input data.

11. A method comprising: obtaining input data having a first format; converting the input data to converted input data having a second format, the second format being different from the first format; storing the converted input data directly to memory accessible by at least one parallel processing unit; and processing the converted input data stored in the memory using the at least one parallel processing unit.

12. The method of clause 11, wherein processing the converted input data comprises performing at least one transformation operation on the converted input data to produce transformed information, and performing at least one inference operation on the transformed information.

13. The method of clause 12, wherein the at least one transformation operation comprises at least one of normalizing intensity values, normalizing spatial dimensions, scaling pixel size from non-isotropic to isotropic, or performing histogram normalization.

14. The method of clause 12 or 13, wherein the input data comprises imaging data.

15. The method of clause 14, wherein the imaging data comprises a sinogram.

16. The method of clause 14 or 15, wherein the imaging data is medical data having a format specified by a Digital Imaging and Communications in Medicine ("DICOM") standard.

17. The method of any one of clauses 11-16, wherein the memory is a first memory, obtaining the input data comprises loading the input data from a second memory, and the first memory is different from the second memory.

18. The method of any one of clauses 11-17, wherein obtaining the input data comprises at least one of receiving the input data from an Ethernet network, receiving the input data from an Infiniband network, or reading the input data from an emulated storage device.

19. The method of any one of clauses 11-18, wherein processing the converted input data comprises performing at least one transformation operation on the converted input data to produce transformed information, constructing a volume from the transformed information, and performing at least one inference operation on the volume.

20. A processor comprising one or more circuits to: obtain input data having a first format; convert the input data to a second format; and store the converted input data in a location accessible by at least one parallel processing unit operable to perform at least one operation on the converted input data.

21. The processor of clause 20, wherein the one or more circuits are to obtain the input data from an imaging device operable to capture imaging data and transmit the imaging data to a network interface comprising the processor.

22. The processor of clause 21, wherein the imaging device is medical imaging device and the first format is specified by a Digital Imaging and Communications in Medicine ("DICOM") standard.

23. The processor of any one of clauses 20-22, wherein the one or more circuits are to obtain the input data by reading the input data from a memory.

24. The processor of any one of clauses 20-23, wherein converting the input data comprises performing an alignment transformation operation on the input data.

Other variations are within spirit of present disclosure. Thus, while disclosed techniques are susceptible to various modifications and alternative constructions, certain illustrated embodiments thereof are shown in drawings and have been described above in detail. It should be understood, however, that there is no intention to limit disclosure to specific form or forms disclosed, but on contrary, intention is to cover all modifications, alternative constructions, and equivalents falling within spirit and scope of disclosure, as defined in appended claims.

Use of terms "a" and "an" and "the" and similar referents in context of describing disclosed embodiments (especially in context of following claims) are to be construed to cover both singular and plural, unless otherwise indicated herein or clearly contradicted by context, and not as a definition of a term. Terms "comprising," "having," "including," and "containing" are to be construed as open-ended terms (meaning "including, but not limited to,") unless otherwise noted. term "connected," when unmodified and referring to physical connections, is to be construed as partly or wholly contained within, attached to, or joined together, even if there is something intervening. Recitation of ranges of values herein are merely intended to serve as a shorthand method of referring individually to each separate value falling within range, unless otherwise indicated herein and each separate value is incorporated into specification as if it were individually recited herein. In at least one embodiment, use of term "set" (e.g., "a set of items") or "subset" unless otherwise noted or contradicted by context, is to be construed as a nonempty collection comprising one or more members. Further, unless otherwise noted or contradicted by context, term "subset" of a corresponding set does not necessarily denote a proper subset of corresponding set, but subset and corresponding set may be equal.

Conjunctive language, such as phrases of form "at least one of A, B, and C," or "at least one of A, B and C," unless specifically stated otherwise or otherwise clearly contradicted by context, is otherwise understood with context as used in general to present that an item, term, etc., may be either A or B or C, or any nonempty subset of set of A and B and C. For instance, in illustrative example of a set having three members, conjunctive phrases "at least one of A, B, and C" and "at least one of A, B and C" refer to any of following sets: {A}, {B}, {C}, {A, B}, {A, C}, {B, C}, {A, B, C}. Thus, such conjunctive language is not generally intended to imply that certain embodiments require at least one of A, at least one of B and at least one of C each to be present. In addition, unless otherwise noted or contradicted by context, term "plurality" indicates a state of being plural (e.g., "a plurality of items" indicates multiple items). In at least one embodiment, a number of items in a plurality is at least two, but can be more when so indicated either explicitly or by context. Further, unless stated otherwise or otherwise clear from context, phrase "based on" means "based at least in part on" and not "based solely on."

Operations of processes described herein can be performed in any suitable order unless otherwise indicated herein or otherwise clearly contradicted by context. In at least one embodiment, a process such as those processes described herein (or variations and/or combinations thereof) is performed under control of one or more computer systems configured with executable instructions and is implemented as code (e.g., executable instructions, one or more computer programs or one or more applications) executing collectively on one or more processors, by hardware or combinations thereof. In at least one embodiment, code is stored on a computer-readable storage medium. In at least one embodiment, in form of a computer program comprising a plurality of instructions executable by one or more processors. In at least one embodiment, a computer-readable storage medium is a non-transitory computer-readable storage medium that excludes transitory signals (e.g., a propagating transient electric or electromagnetic transmission) but includes non-transitory data storage circuitry (e.g., buffers, cache, and queues) within transceivers of transitory signals. In at least one embodiment, code (e.g., executable code or source code) is stored on a set of one or more non-transitory computer-readable storage media having stored thereon executable instructions (or other memory to store executable instructions) that, when executed (i.e., as a result of being executed) by one or more processors of a computer system, cause computer system to perform operations described herein. A set of non-transitory computer-readable storage media, in at least one embodiment, comprises multiple non-transitory computer-readable storage media and one or more of individual non-transitory storage media of multiple non-transitory computer-readable storage media lack all of code while multiple non-transitory computer-readable storage media collectively store all of code. In at least one embodiment, executable instructions are executed such that different instructions are executed by different processors— in at least one embodiment, a non-transitory computer-readable storage medium store instructions and a main central processing unit ("CPU") executes some of instructions while a graphics processing unit ("GPU") executes other instructions. In at least one embodiment, different components of a computer system have separate processors and different processors execute different subsets of instructions.

Accordingly, in at least one embodiment, computer systems are configured to implement one or more services that singly or collectively perform operations of processes described herein and such computer systems are configured with applicable hardware and/or software that enable performance of operations. Further, a computer system that implements at least one embodiment of present disclosure is a single device and, in another embodiment, is a distributed computer system comprising multiple devices that operate differently such that distributed computer system performs operations described herein and such that a single device does not perform all operations.

Use of any and all examples, or exemplary language (e.g., "such as") provided herein, is intended merely to better illuminate embodiments of disclosure and does not pose a limitation on scope of disclosure unless otherwise claimed. No language in specification should be construed as indicating any non-claimed element as essential to practice of disclosure.

All references, including publications, patent applications, and patents, cited herein are hereby incorporated by reference to same extent as if each reference were individually and specifically indicated to be incorporated by reference and were set forth in its entirety herein.

In description and claims, terms "coupled" and "connected," along with their derivatives, may be used. It should be understood that these terms may be not intended as synonyms for each other. Rather, in particular examples, "connected" or "coupled" may be used to indicate that two or more elements are in direct or indirect physical or electrical contact with each other. "Coupled" may also mean that two or more elements are not in direct contact with each other, but yet still co-operate or interact with each other.

Unless specifically stated otherwise, it may be appreciated that throughout specification terms such as "processing," "computing," "calculating," "determining," or like, refer to action and/or processes of a computer or computing system, or similar electronic computing device, that manipulate and/or transform data represented as physical, such as electronic, quantities within computing system's registers and/or memories into other data similarly represented as physical quantities within computing system's memories, registers or other such information storage, transmission or display devices.

In a similar manner, term "processor" may refer to any device or portion of a device that processes electronic data from registers and/or memory and transform that electronic data into other electronic data that may be stored in registers and/or memory. As non-limiting examples, "processor" may be a CPU or a GPU. A "computing platform" may comprise one or more processors. As used herein, "software" processes may include, in at least one embodiment, software and/or hardware entities that perform work over time, such as tasks, threads, and intelligent agents. Also, each process may refer to multiple processes, for carrying out instructions in sequence or in parallel, continuously or intermittently. Terms "system" and "method" are used herein interchangeably insofar as system may embody one or more methods and methods may be considered a system.

In at least one embodiment, an arithmetic logic unit is a set of combinational logic circuitry that takes one or more inputs to produce a result. In at least one embodiment, an arithmetic logic unit is used by a processor to implement mathematical operation such as addition, subtraction, or multiplication. In at least one embodiment, an arithmetic logic unit is used to implement logical operations such as logical AND/OR or XOR. In at least one embodiment, an arithmetic logic unit is stateless, and made from physical switching components such as semiconductor transistors arranged to form logical gates. In at least one embodiment, an arithmetic logic unit may operate internally as a stateful logic circuit with an associated clock. In at least one embodiment, an arithmetic logic unit may be constructed as an asynchronous logic circuit with an internal state not maintained in an associated register set. In at least one embodiment, an arithmetic logic unit is used by a processor to combine operands stored in one or more registers of the processor and produce an output that can be stored by the processor in another register or a memory location.

In at least one embodiment, as a result of processing an instruction retrieved by the processor, the processor presents one or more inputs or operands to an arithmetic logic unit, causing the arithmetic logic unit to produce a result based at least in part on an instruction code provided to inputs of the arithmetic logic unit. In at least one embodiment, the instruction codes provided by the processor to the ALU are based at least in part on the instruction executed by the processor. In at least one embodiment combinational logic in the ALU processes the inputs and produces an output which is placed on a bus within the processor. In at least one embodiment, the processor selects a destination register, memory location, output device, or output storage location on the output bus so that clocking the processor causes the results produced by the ALU to be sent to the desired location.

In present document, references may be made to obtaining, acquiring, receiving, or inputting analog or digital data into a subsystem, computer system, or computer-implemented machine. In at least one embodiment, process of obtaining, acquiring, receiving, or inputting analog and digital data can be accomplished in a variety of ways such as by receiving data as a parameter of a function call or a call to an application programming interface. In some implementations, process of obtaining, acquiring, receiving, or inputting analog or digital data can be accomplished by transferring data via a serial or parallel interface. In another implementation, process of obtaining, acquiring, receiving, or inputting analog or digital data can be accomplished by transferring data via a computer network from providing entity to acquiring entity. References may also be made to providing, outputting, transmitting, sending, or presenting analog or digital data. In various examples, process of providing, outputting, transmitting, sending, or presenting analog or digital data can be accomplished by transferring data as an input or output parameter of a function call, a parameter of an application programming interface or interprocess communication mechanism.

Although discussion above sets forth example implementations of described techniques, other architectures may be used to implement described functionality, and are intended to be within scope of this disclosure. Furthermore, although specific distributions of responsibilities are defined above for purposes of discussion, various functions and responsibilities might be distributed and divided in different ways, depending on circumstances.

Furthermore, although subject matter has been described in language specific to structural features and/or methodological acts, it is to be understood that subject matter claimed in appended claims is not necessarily limited to specific features or acts described. Rather, specific features and acts are disclosed as exemplary forms of implementing the claims.

What is claimed is:

1. A system comprising:
   first memory;
   at least one graphics processing unit (GPU);

a network interface to obtain input data having a first format, the network interface to convert the input data to obtain converted input data having a multi-dimensional second format compatible with the at least one GPU, and store the converted input data directly to the first memory, the at least one GPU to be separate from the network interface, to access the converted input data stored in the first memory by the network interface, and to perform at least one operation on the converted input data; and one or more central processing units that are different from the at least one GPU and the network interface.

2. The system of claim 1, wherein the at least one operation comprises at least one transformation operation.

3. The system of claim 2, wherein the at least one transformation operation comprises at least one of normalizing intensity values, normalizing spatial dimensions, scaling pixel size from non-isotropic to isotropic, or performing histogram normalization.

4. The system of claim 1, wherein the at least one operation comprises one or more inference operations.

5. The system of claim 1, further comprising:

an imaging device to capture imaging data and transmit the imaging data to the network interface, the network interface obtaining the input data from the imaging data.

6. The system of claim 5, wherein the imaging device is a medical imaging device and the first format is specified by a Digital Imaging and Communications in Medicine ("DICOM") standard.

7. The system of claim 6, wherein the at least one operation comprises one or more inference operations to obtain a diagnostic result.

8. The system of claim 1, further comprising:

second memory, the network interface to obtain the input data by loading the input data from the second memory.

9. The system of claim 1, wherein the network interface comprises one or more data processing units to convert the input data, the one or more central processing units are different from the one or more data processing units, and the one or more central processing units are not to process the input data or the converted input data before the at least one GPU performs the at least one operation on the converted input data.

10. The system of claim 1, wherein converting the input data to obtain the converted input data comprises performing an alignment transformation operation on the input data.

11. A method comprising:

obtaining input data having a first format;

converting with at least one network interface the input data to obtain converted input data having a multi-dimensional second format compatible with at least one graphics processing unit (GPU), the multi-dimensional second format being different from the first format;

using the at least one network interface to store the converted input data directly to memory accessible by the at least one GPU that is separate from the at least one network interface and one or more central processing units that are different from the network interface; and processing the converted input data stored in the memory using the at least one GPU.

12. The method of claim 11, wherein processing the converted input data comprises performing at least one transformation operation on the converted input data to produce transformed information, and performing at least one inference operation on the transformed information.

13. The method of claim 12, wherein the at least one transformation operation comprises at least one of normalizing intensity values, normalizing spatial dimensions, scaling pixel size from non-isotropic to isotropic, or performing histogram normalization.

14. The method of claim 12, wherein the input data comprises imaging data.

15. The method of claim 14, wherein the imaging data comprises a sinogram.

16. The method of claim 14, wherein the imaging data is medical data having a format specified by a Digital Imaging and Communications in Medicine ("DICOM") standard.

17. The method of claim 11, wherein the memory is a first memory, obtaining the input data comprises loading the input data from a second memory, and the first memory is different from the second memory.

18. The method of claim 11, wherein obtaining the input data comprises at least one of receiving the input data from an Ethernet network, receiving the input data from an Infiniband network, or reading the input data from an emulated storage device.

19. The method of claim 11, wherein processing the converted input data comprises performing at least one transformation operation on the converted input data to produce transformed information, constructing a volume from the transformed information, and performing at least one inference operation on the volume.

20. A network interface comprising:

at least one processor comprising one or more circuits to:

obtain input data having a first format;

convert the input data by the one or more circuits of the at least one processor of the network interface into a multi-dimensional second format compatible with at least one graphics processing unit (GPU) that is different from one or more central processing units, which are different from the network interface; and store the converted input data in a location accessible by the at least one GPU that is separate from the network interface and operable to perform at least one operation on the converted input data.

21. The network interface of claim 20, wherein the one or more circuits are to obtain the input data from an imaging device operable to capture imaging data and transmit the imaging data to the network interface.

22. The network interface of claim 21, wherein the imaging device is medical imaging device and the first format is specified by a Digital Imaging and Communications in Medicine ("DICOM") standard.

23. The network interface of claim 20, wherein the one or more circuits are to obtain the input data by reading the input data from a memory.

24. The network interface of claim 20, wherein converting the input data comprises performing an alignment transformation operation on the input data.

25. The network interface of claim 20, wherein the multi-dimensional second format is a tensor format, a TensorFlow tensor format, a PyTorch tensor format, or a CuPy array format.

26. The system of claim 1, wherein the one or more central processing units are not to process the input data or the converted input data before the at least one GPU performs the at least one operation on the converted input data.

27. The system of claim 1, wherein the multi-dimensional second format is a tensor format, a TensorFlow tensor format, a PyTorch tensor format, or a CuPy array format.

28. The method of claim 11, wherein the multi-dimensional second format is a tensor format, a TensorFlow tensor format, a PyTorch tensor format, or a CuPy array format.

\* \* \* \* \*